United States Patent
Takayanagi et al.

(10) Patent No.: US 7,396,844 B1
(45) Date of Patent: *Jul. 8, 2008

(54) BENZAMIDINE DERIVATIVES

(75) Inventors: Masaru Takayanagi, Kawasaki (JP);
Kazuyuki Sagi, Kawasaki (JP);
Tadakiyo Nakagawa, Kawasaki (JP);
Masahiro Yamanashi, Kawasaki (JP);
Takashi Kayahara, Kawasaki (JP);
Shunji Takehana, Kawasaki (JP);
Yumiko Fukuda, Kawasaki (JP);
Mitsuo Takahashi, Kawasaki (JP);
Masataka Shoji, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,492

(22) Filed: Jul. 19, 1999

Related U.S. Application Data

(63) Continuation of application No. PCT/JP98/00176, filed on Jan. 19, 1998.

(30) Foreign Application Priority Data

| Jan. 17, 1997 | (JP) | ................................ P9-006783 |
| Jul. 18, 1997 | (JP) | ................................ P9-194602 |
| Dec. 2, 1997 | (JP) | ................................ P9-331887 |

(51) Int. Cl.
*A61K 31/155* (2006.01)
*C07D 207/14* (2006.01)
*C07D 221/02* (2006.01)
*C07C 249/02* (2006.01)

(52) U.S. Cl. .................. 514/359; 546/239; 548/400; 564/305; 564/309

(58) Field of Classification Search ............... 546/216, 546/192, 229, 236, 237, 239, 329; 514/327, 514/315, 359, 256, 277; 548/400, 339.5
See application file for complete search history.

(56) References Cited

U.S. PATENT DOCUMENTS

| 4,018,933 | A | * | 4/1977 | Schorr et al. | ................. 424/271 |
| 5,518,735 | A | | 5/1996 | Stuerzebecher et al. | |
| 6,410,538 | B2 | * | 6/2002 | Nakagawa et al. | ..... 514/252.01 |
| 6,710,056 | B2 | * | 3/2004 | Sugiki et al. | ................. 514/311 |
| 6,812,231 | B2 | * | 11/2004 | Nakagawa et al. | ........... 514/256 |

FOREIGN PATENT DOCUMENTS

| EP | 0 672 658 | | 9/1995 |
| EP | 0672658 | * | 9/1995 |
| JP | 7-330695 | * | 9/1995 |
| WO | WO 96/28427 | | 9/1996 |
| WO | WO 97/24118 | | 7/1997 |

OTHER PUBLICATIONS

Patani et. al., "Bioisosterism: A Rational Approach in Drug Design", Chem. Rev. 1996, 96, p. 3170.*
R. R. Tidwell, et al., Thrombosis Research 19, pp. 339-349, "Strategies for Anticoagulation With Synthetic Protease Inhibitors. Xa Inhibitors Versus Thrombin Inhibitors," 1980.
David J. Robison, et al., The Journal of Biological Chemistry, vol. 255, No. 5, pp. 2014-2021, "Active Site of Bovine Factor Xa," Mar. 10, 1980.
Takayasu Nagahara, et al., Journal of Medicinal Chemistry, pp. 1200-1207, "Dibasic (Amidinoaryl) Propanoic Acid Derivatives as Novel Blood Coagulation Factor Xa Inhibitors," 1994.
J.M. Herbert, et al., "DX 9065A, a Novel, Synthetic, Selective and Orally Active Inhibitor of Factor Xa: In Vitro and in Vivo Studies,"The Journal of Pharmacology and Experimental Therapeutics, vol. 276, No. 3, 1996, pp. 1030-1038.

(Continued)

*Primary Examiner*—Rita Desai
(74) *Attorney, Agent, or Firm*—Oblon, Spivak, McClelland, Maier & Neustadt, P.C.

(57) ABSTRACT

Benzamidine derivatives of the following formulae or analogs thereof, i.e., pharmaceutically acceptable salts thereof, are provided. These compounds or salts thereof have a blood-coagulation inhibiting effect based on an excellent effect of inhibiting the action of activated blood coagulation factor X, and they are useful as anticoagulants

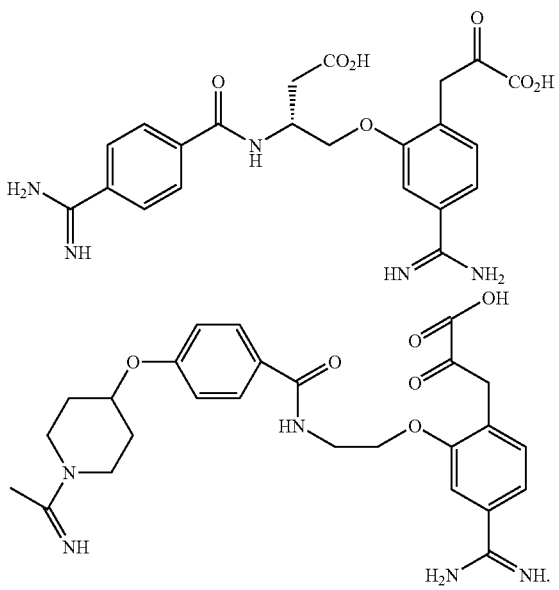

32 Claims, No Drawings

OTHER PUBLICATIONS

G.P. Vlasuk, et al., "Comparison of the In Vivo Anticoagulant Properties of Standard Heparin and the Highly Selective Factor Xa Inhibitors Antistasin and Tick Anticoagulant Peptide (TAP) in a Rabbit Model of Venous Thrombosis," Thrombosis and Haemostasis, vol. 65(3), 1991, pp. 257-262.

P.C. Wong, et al. "Antithrombotic Actions of Selective Inhibitors of Blood Coagulation Factor Xa in Rat Models of Thrombosis," Thrombosis Research, vol. 83, No. 2, 1996, pp. 117-126.

Q. Han, et al., "Design, Synthesis, and Biological Evaluation of Potent and Selective Amidino Bicyclic Factor Xa Inhibitors," J. Med. Chem., vol. 43, 2000, pp. 4398-4415.

K. Sato, et al., "Antithrombotic effect of YM-75466 is separated from its effect on bleeding time and coagulation time," European Journal of Pharmacology, vol. 352, 1998, pp. 59-63.

D.J.P. Pinto, et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa[1]," J. Med. Chem, vol. 44, 2001, pp. 566-578.

M.R. Wiley, et al., "Structure-Based Design of Potent, Amidine-Derived Inhibitors of Factor Xa: Evaluation of Selectivity, Anticoagulant Activity, and Antithrombotic Activity," J. Med. Chem., vol. 43, 2000, pp. 883-899.

J. Hirsh, et al., "Guide to Anticoagulant Therapy Part 2: Oral Anticoagulants," Circulation, vol. 89, No. 3, Mar. 1994, pp. 1469-1480.

J. Hirsh, et al., "Guide to Anticoagulant Therapy Part 1: Heparin," Circulation, vol. 89, No. 3, Mar. 1994, pp. 1449-1468.

B. Kaiser, "Factor Xa Versus Factor IIa Inibitors," Clin. Appl. Thrombosis/Hemostasis, vol. 3(1), 1997, pp. 16-24.

B. Tatlisumak, et al., "Hematologic disorders associated with ischemic stroke," Journal of Neurological Sciences, vol. 140, 1996, pp. 1-11.

H. Kawai, et al., "Effects of a Thrombin Inhibitor, Argatroban, on Ischemic Brain Damage in the Rat Distal Middle Cerebral Artery Occlusion Model," The Journal of Pharmacology and Experimental Therapeutics, vol. 278, No. 2, 1996, pp. 780-785.

F.A. Spencer, et al., "Novel Inhibitors of Factor X for Use in Cardiovascular Diseases," Current Cardiology Reports, vol. 2, 2000, pp. 395-404.

* cited by examiner

BENZAMIDINE DERIVATIVES

This application is a Continuation of application international application PCT/JP98/00176, filed on Jan. 19, 1998.

BACKGROUND OF THE INVENTION

1. Field of the Invention

The present invention relates to new benzamidine derivatives which can be orally administered to exhibit a strong anticoagulant effect by reversibly inhibiting the activated blood coagulation factor X, anticoagulants containing them as active ingredients, and agents for preventing and treating diseases caused by thrombi or emboli. These diseases include, for example, cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; disseminated intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

2. Description of the Background

As the habit of life is being westernized and people of advanced ages are increasing, thrombotic and embolismic patients such as those suffering from myocardial infarction, cerebral thrombosis and peripheral thrombosis are increasing in number year by year, and the treatment of these diseases is becoming more and more important in the society. Anticoagulation treatment bears the internal treatments for the remedy and prevention of thrombosis, like thrombolytic therapy and antiplatelet therapy.

Thrombin inhibitors were developed as thrombus-formation inhibitors in the prior art. However, it has been known that since thrombin not only controls the activation of fibrinogen to form fibrin, which is the last step of the coagulation reactions, but also deeply related to the activation and aggregation of blood platelets, the inhibition of the action of thrombin causes a danger of causing hemorrhage. In addition, when thrombin inhibitors are orally administered, the bioavailability thereof is low. At present, no thrombin inhibitor which can be orally administered is available on the market.

Since the activated blood coagulation factor X is positioned at the juncture of an extrinsic coagulation cascade reaction and an intrinsic coagulation cascade reaction and in the upstream of thrombin, it is possible to inhibit the coagulation system more efficiently and specifically, than the thrombin inhibition, by factor X inhibition (THROMBOSIS RESEARCH, Vol. 19, pages 339 to 349; 1980).

SUMMARY OF THE INVENTION

The object of the present invention is to provide compounds having an excellent effect of inhibiting the effect of activated blood coagulation factor X.

Another object of the present invention is to provide compounds having an effect of specifically inhibiting the effect of activated blood coagulation factor X, which can be orally administered.

DETAINED DESCRIPTION OF THE PREFERRED EMBODIMENTS

Still another object of the present invention is to provide a blood-coagulation inhibitor or an agent for preventing or treating thrombosis or embolism, which contains one of the above-described compounds.

After intensive investigations made under these circumstances, the inventors have found that specified new benzamidine derivatives have an excellent effect of inhibiting activated blood coagulation factor X and are usable for preventing and treating various diseases caused by thrombi and emboli. The present invention has been completed on the basis of this finding. Namely, the present invention relates to benzamidine derivatives of following general formula (1) or pharmaceutically acceptable salts thereof and blood coagulation inhibitors containing them as the active ingredients:

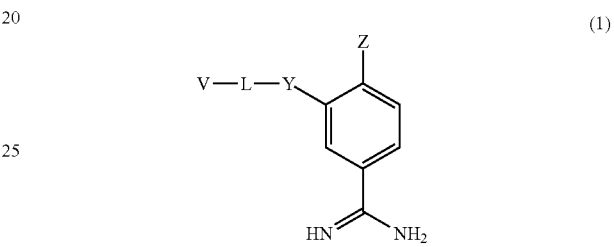

(1)

wherein L represents an organic group of any of the following formulae (2) to (5):

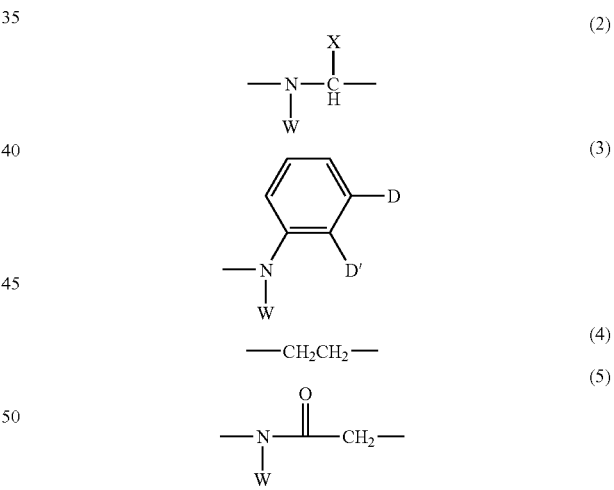

W in above formulae (2), (3) and (5) represents a hydrogen atom, an alkyl group having 1 to 6 carbon atoms, an aryl group having 4 to 10 carbon atoms, an aralkyl group having 5 to 12 carbon atoms or a carboxyalkylsulfonyl group having 2 to 4 carbon atoms; one of D and D' in formula (3) represents a bond to Y in general formula (1) and the other represents a hydrogen atom;

X in formula (2) represents a hydrogen atom, carboxyl group, methoxycarbonyl group, ethoxycarbonyl group or methyl, ethyl or benzyl group which may have a substituent which is selected from among carboxyl group, alkoxycarbonyl groups having 2 to 10 carbon atoms, alkylsulfonyloxy groups having 1 to 6 carbon atoms, piperidyloxy group, amidinopiperidyloxy group, iminoalkylpiperidyloxy groups having 7 to 10 carbon atoms, alkoxycarbonylpiperidyloxy groups having 8 to 14 carbon atoms, piperidylalkyl groups having 6 to 8 carbon atoms, iminoalkylpiperidylalkyl groups having 8 to 11 carbon atoms, alkoxycarbonylpiperidylalkyl groups having 9 to 15 carbon atoms, pyrrolidyloxy group, iminoalkylpyrrolidyloxy groups having 6 to 9 carbon atoms, alkoxycarbonylpyrrolidyloxy groups having 7 to 13 carbon atoms, amidino group, hydroxyl group, halogeno groups, indolyl group and alkyl groups having 1 to 5 carbon atoms; and X and W in formula (2) may be bonded together to form a ring and, in this case, —W—X— represents an ethylene group, trimethylene group or tetramethylene group;

when L is an organic group of formula (2) or (3), V represents a hydrogen atom, a phenyl or benzoyl group having a substituent, a benzenesulfonyl, 2-naphthalenesulfonyl, camphorsulfonyl, cinnamoyl, piperidinecarbonyl, phenylacetyl, quinuclidinylaminoacetyl, quinuclidiniumylacetyl, indolecarbonyl, pyridinecarbonyl, phenylthiocarbonyl or benzimidoyl group which may have a substituent, or an alkanesulfonyl group having 1 to 6 carbon atoms, which may have a substituent;

when L is an organic group of formula (4), V represents a benzoyl group having a substituent, a 2-naphthalenesulfonyl, camphorsulfonyl, cinnamoyl, piperidinecarbonyl, phenylacetyl, quinucidinylaminoacetyl, quinuclidiniumylacetyl, indolecarbonyl, phenylthiocarbonyl or benzimidoyl group which may have a substituent, or an alkanesulfonyl group having 1 to 6 carbon atoms, which may have a substituent; when L is an organic group of formula (5), V represents an aryl group having 4 to 10 carbon atoms, which may have a substituent;

when L is an organic group of any of formulae (2) to (5) and V has a substituent, the substituent is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, acyl groups having 1 to 8 carbon atoms, which may be substituted by an alkoxyl group having 1 to 3 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, acylpiperidyloxy groups having 6 to 9 carbon atoms, which may be substituted with an amino group, iminoalkylpiperidyloxy groups having 7 to 10 carbon atoms, alkoxycarbonylpiperidyloxy groups having 8 to 14 carbon atoms, pyrrolidyloxy group, iminoalkylpyrrolidyloxy groups having 6 to 9' carbon atoms, alkoxycarbonylpyrrolidyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups hang 6 to 9 carbon atoms, benzylsulfonylamino group, piperidylalkyl groups having 6 to 9 carbon atoms, iminoalkylpiperidylalkyl groups having 8 to 12 carbon atoms, piperidylidenealkyl groups having 6 to 9 carbon atoms, iminoalkylpiperididenealkyl groups having 8 to 12 carbon atoms, guanidino group, phosphono group, dialkoxyphosphoryl groups having 2 to 9 carbon atoms, monoalkoxyhydroxyphosphoryl groups having 1 to 4 carbon atoms, aminoethyloxy group, dialkylaminosulfonyl groups having 3 to 6 carbon atoms and dialkylguadinino groups having 2 to 4 carbon atoms;

when L is an organic group of formulae (2) to (4), alternatively, V represents an organic group of following formula (6):

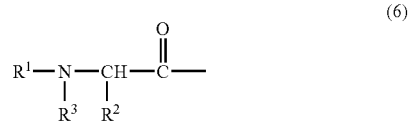

wherein $R^1$ represents a hydrogen atom, an alkoxycarbonyl group or methyl group, $R^2$ represents a hydrogen atom, or methyl group, butyl group, benzyl group, aminobutyl group, hydroxycarbonylethyl group, hydroxycarbonylpropyl group or imidazolylmethyl group, and $R^3$ represents a hydrogen atom or pyridyl group;

Y represents a group of any of the following formulae (7), (8), (9), (10) and (11):

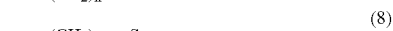

n in formulae (7) and (8) represents an integer of 1 to 3, and

Z represents a hydrogen atom, an alkyl group having 1 to 6 carbon atoms, a halogeno group or a group of any of following formulae (12-1), (12-2) and (12-3):

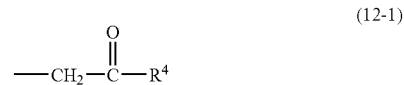
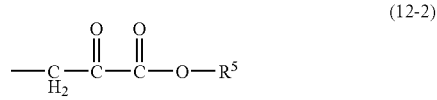
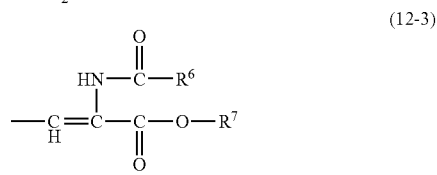

wherein $R^4$ represents a carboxyl group or an aryl group having 4 to 10 carbon atoms, $R^5$ represents an alkyl group having 1 to 6 carbon atoms, $R^6$ represents a hydrogen atom, an alkyl group having 1 to 6 carbon atoms or an alkoxyl group having 1 to 7 carbon atoms, and $R^7$ represents a hydrogen atom or an alkyl group having 1 to 6 carbon atoms.

BEST MODE FOR CARRYING OUT THE INVENTION

In the compounds of general formula (1), the following compounds are preferred: The benzamidine derivatives of general formula. (1) or pharmaceutically acceptable salts thereof, wherein L represents an organic group of any of formulae (2) to (5); W in above formula (2) represents a hydrogen atom, an alkyl group having 1 to 6 carbon atoms, an aryl group having 4 to 10 carbon atoms, an aralkyl group having 5 to 12 carbon atoms; and W in formulae (3) and (5) represents a hydrogen atom; D in formula (3) represents a bond to Y in general formula (1) and D' represents a hydrogen atom;

X represents a hydrogen atom, carboxyl group, methoxycarbonyl group, ethoxycarbonyl group or methyl, ethyl or benzyl group which may have a substituent which is selected from among carboxyl group, alkoxycarbonyl groups having 2 to 7 carbon atoms, alkylsulfonyloxy groups having 1 to 6 carbon atoms, piperidyloxy group, iminoalkylpiperidyloxy groups having 7 to 10 carbon atoms, alkoxycarbonylpiperidyloxy groups having 8 to 14 carbon atoms, piperidylalkyl groups having 6 to 8 carbon atoms, iminoalkylpiperidylalkyl groups having 8 to 11 carbon atoms, alkoxycarbonylpiperidylalkyl groups having 9 to 15 carbon atoms, pyrrolidyloxy group, iminoalkylpyrrolidyloxy groups having 6 to 9 carbon atoms, alkoxycarbonylpyrrolidyloxy groups having 7 to 13 carbon atoms, amidino group, hydroxyl group, halogeno groups, indolyl group and alkyl groups having 1 to 3 carbon atoms; and X and W in formula (2) may be bonded together to form a ring and, in this case, —W—X— represents an ethylene group, trimethylene group or tetramethylene group;

when L is an organic group of formula (2) or (3), V represents a hydrogen atom, a benzoyl group having a substituent, a benzenesulfonyl, 2-naphthalenesulfonyl, camphorsulfonyl, cinnamoyl, piperidinecarbonyl, phenylacetyl, quinuclidinylaminoacetyl, quinuclidiniumylacetyl, indolecarbonyl, phenylthiocarbonyl or benzimidoyl group which may have a substituent, or an alkanesulfonyl group having 1 to 6 carbon atoms, which may have a substituent;

when L is an organic group of formula (4), V represents a benzoyl group having a substituent, a 2-naphthalenesulfonyl, camphorsulfonyl, cinnamoyl, piperidinecarbonyl, phenylacetyl, quinudidinylaminoacetyl, quinuclidiniumylacetyl, indolecarbonyl, phenylthiocarbonyl or benzimidoyl group which may have a substituent, or an alkanesulfonyl group having 1 to 6 carbon atoms, which may have a substituent;

when L is an organic group of formula (5), V represents an aryl group having 4 to 10 carbon atoms, which may have a substituent;

when L is an organic group of any of formulae (2) to (5) and V has a substituent, the substituent is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 7 to 10 carbon atoms, alkoxycarbonylpiperidyloxy groups having 8 to 14 carbon atoms, pyrrolidyloxy group, iminoalkylpyrrolidyloxy groups having 6 to 9 carbon atoms, alkoxycarbonylpyrrolidyloxy groups having 7 to 13 carbon atoms, hydroxycarbonylalkyl groups having 3 to 7 carbon atoms alkoxycarbonylalkyl groups having 4 to 8 carbon atoms, hydroxycarbonylalkenyl groups having 2 to 7 carbon atoms, alkoxycarbonylalkenyl groups having 3 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, benzylsulfonylamino group, piperidylalkyl groups having 6 to 9 carbon atoms, iminoalkylpiperidylalkyl groups having 8 to 12 carbon atoms, piperididenealkyl groups having 6 to 9 carbon atoms, iminoalkylpiperididenealkyl groups having 8 to 12 carbon atoms, guanidino group, phosphono group, dialkoxyphosphoryl groups having 2 to 9 carbon atoms, monoalkoxyhydroxyphosphoryl groups having 1 to 4 carbon atoms and aminoethyloxy group.

When L is an organic group of formulae (2) to (4), alternatively, V represents an organic group of formula (6);

Y represents a group of any of formulae (7), (8), (9), (10) and (11), and n in formula (7) represents 1 or 2, and n in formula (8) represents 1, and Z represents a hydrogen atom, an alkyl group having 1 to 6 carbon atoms, a halogeno group or a group of formula (12-1) wherein $R^4$ represents a carboxyl group or an aryl group having 4 to 10 carbon atoms.

In this connections, preferred benzamidine derivatives or pharmaceutically acceptable salts thereof are those of general formula (1) wherein when V has a substituent, the substituent is selected from among carboxyl group, methoxycarbonyl group, ethoxycarbonyl group, carbamoyl group, amidino group, acetyl group, bromine atom, amino group, methylamino group, t-butoxycarbonylamino group, aminomethyl group, (methylamino)methyl group, (N-t-butoxycarbonyl-N-methylamino)methyl group, 4-piperidyloxy group, 1-acetimidoyl-4-piperidyloxy group, 3-pyrrolidyloxy group, 1-t-butoxycarbonyl-3-pyrrolidyloxy group, 2-carboxylethenyl group, 2-(ethoxycarbonyl)ethenyl group, dimethylcarbamoyl group, N-ethyl-N-methylcarbamoyl group, 2-imidazolinyl group, 1-piperidinecarbonyl group, N,N-dimethylamidino group, 2-(tetrahydropyrimidinyl) group, 1-pyrrolidinecarbonyl group, 2-(4-pyridyl)vinyl group, 1-pyrrole group, cyclohexyloxy group, diethylamino group, 2-(4-pyridyl)ethyl group, isopropyl group, 1-pyrrolidyl group, benzoyl group, benzenesulfonyl group, benzyl group, 4-pyridyl group, dimethylamino group, 1-piperidinyl group, phenoxy group, 1-piperazinecarbonyl group, 1-acetimidoyl-4-piperazinecarbonyl group, (4-pyridyl)amino group, methylcarbamoyl group, phenyl group, cyclohexyl group, 1-piperazinesulfonyl group, 1-acetimidoyl-4-piperazinesulfonyl group, 4-(pyridyl)methyl group, 4-piperidylidenemethyl group, 4-piperidylmethyl group, 1-acetimidoyl-4-piperidylidenemethyl group, 1-acetimidoyl-4-piperidylmethyl group, 2-imidazolyl group, 1-phenoxycarbonyl-4-piperidyloxy group, monoethoxyhydroxyphosphoryl group, diethoxyphosphoryl group, chlorine atom, 1-(aminoacetyl)-4-piperidyloxy group, trifluoromethyl group, benzylsulfonylamino group, guanidino group, phosphono group and aminoethyloxy group.

In this connections, preferred benzamidine derivatives or pharmaceutically acceptable salts thereof are those of general formula (1) wherein W is hydrogen atom, methyl group or benzyl group.

In this connections, preferred benzamidine derivatives or pharmaceutically acceptable salts thereof are those of general formula (1) wherein when X has a substituent, the substituent is selected from among carboxyl group, methoxycarbonyl group, ethoxycarbonyl group, ethanesulfonyloxy group, butanesulfonyloxy group, 4-piperidyloxy group, 1-acetimidoyl-4-piperidyloxy group, 1-benzyloxycarbonyl-4-piperidyloxy group, 4-piperidylmethyl group, (1-acetimidoyl-4 piperidyl)methyl group, 1-acetimidoyl-3-pyrrolidyloxy group, isopropyl group, 3-indolyl group and iodine atom.

In this connections, preferred benzamidine derivatives or pharmaceutically acceptable salts thereof are those of general formula (1) wherein Z is any of hydrogen atom, iodine atom, methyl group, 2-carboxy-2-oxoethyl group and 2-(2-furyl)-2-oxoethyl group.

Alternatively, preferred benzamidine derivatives or pharmaceutically acceptable salts thereof are those of general formula (1) wherein L represents an organic group of formula (2) wherein W represents a hydrogen atom, an alkyl group having 1 to 6 carbon atoms, an aryl group having 4 to 10 carbon atoms or an aralkyl group having 5 to 12 carbon atoms;

X represents a hydrogen atom, carboxyl group, methoxycarbonyl group, ethoxycarbonyl group or methyl, ethyl or benzyl group which may have a substituent which is selected from among carboxyl group, alkoxycarbonyl groups having 2 to 7 carbon atoms, alkylsulfonyloxy groups having 1 to 6 carbon atoms, piperidyloxy group, iminoalkylpiperidyloxy groups having 7 to 10 carbon atoms, alkoxycarbonylpiperidyloxy groups having 8 to 14 carbon atoms, piperidylalkyl groups having 6 to 8 carbon atoms, iminoalkylpiperidylalkyl groups having 8 to 11 carbon atoms, alkoxycarbonylpiperidylalkyl groups having 9 to 15 carbon atoms, pyrrolidyloxy group, iminoalkylpyrrolidyloxy groups having 6 to 9 carbon atoms and alkoxycarbonylpyrrolidyloxy groups having 7 to 13 carbon atoms, V represents a hydrogen atom, a benzoyl group having a substituent, a benzenesulfonyl, 2-naphthalenesulfonyl, camphorsulfonyl, cinnamoyl, piperidinecarbonyl, phenylacetyl, quinuclidinylaminoacetyl or quinuclidiniumylacetyl group which may have a substituent, or an alkanesulfonyl group having 1 to 6 carbon atoms, which may have a substituent;

when V has a substituent, the substituent is selected from among carboxyl group, alkoxycarbonyl groups having 2 to 7 carbon atoms, aminoalkyl groups having 1 to 3 carbon atoms, alkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 7 to 10 carbon atoms, alkoxycarbonylpiperidyloxy groups having 8 to 14 carbon atoms, pyrrolidyloxy group, iminoalkylpyrrolidyloxy groups having 6 to 9 carbon atoms, alkoxycarbonylpyrrolidyloxy groups having 7 to 13 carbon atoms, hydroxycarbonylalkyl groups having 3 to 7 carbon atoms, alkoxycarbonylalkyl groups having 4 to 8 carbon atoms, hydroxycarbonylalkenyl groups having 3 to 7 carbon atoms and alkoxycarbonylalkenyl groups having 4 to 8 carbon atoms; or V represents an organic group of formula (6) wherein $R^1$ represents a hydrogen atom, an alkoxycarbonyl, group or methyl group, $R^2$ represents methyl group, butyl group, benzyl group, aminobutyl group, hydroxycarbonylethyl group, hydroxycarbonylpropyl group or imidazolylmethyl group, and $R^3$ represents a hydrogen atom;

Y represents a group of any of formulae (7), (8), (9), (10) and (11), and n in formula (7) represents 1 or 2, and n in formula (8) represents 1, and Z represents a hydrogen atom, an alkyl group having 1 to 6 carbon atoms, a halogeno group or a group of formula (12-1) wherein $R^4$ represents a carboxyl group or an aryl group having 4 to 10 carbon atoms.

In this connections, preferred benzamidine derivatives or pharmaceutically acceptable salts thereof are those of general formula (1) wherein when V has a substituent, the substituent is selected from among carboxyl group, methoxycarbonyl group, ethoxycarbonyl group, aminocarbonyl group, amidino group, acetyl group, bromine atom, amino group, methylamino group, t-butoxycarbonylamino group, aminomethyl group, (methylamino)methyl group, (N-t-butoxycarbonyl-N-methylamino)methyl group, 4-piperidyloxy group, 1-acetimidoyl-4-piperidyloxy group, 3-pyrrolidyloxy group, 1-t-butoxycarbonyl-3-pyrrolidyloxy group, 2-carboxylethenyl group and 2-(ethoxycarbonyl)ethenyl group.

In this connections, preferred benzamidine derivatives or pharmaceutically acceptable salts thereof are those of general formula (1) wherein W is hydrogen atom, methyl group or benzyl group.

In this connections, preferred benzamidine derivatives or pharmaceutically acceptable salts thereof are those of general formula (1) wherein when X has a substituent, the substituent is selected from among carboxyl group, methoxycarbonyl group, ethoxycarbonyl group, ethanesulfonyloxy group, butanesulfonyloxy group, 4-piperidyloxy group, 1-acetimidoyl-4-piperidyloxy group, 1-benzyloxycarbonyl-4-piperidyloxy group, 4-piperidylmethyl group, (1-acetimidoyl-4-piperidyl)methyl group and 1-acetimidoyl-3-pyrrolidyloxy group.

In this connections, preferred benzamidine derivatives or pharmaceutically acceptable salts thereof are those of general formula (1) wherein Z is any of hydrogen atom, iodine atom, methyl group, 2-carboxy-2-oxoethyl group and 2-(2-furyl)-2-oxoethyl group.

Alternatively, preferred benzamidine derivatives or pharmaceutically acceptable salts thereof are those of general formula (1) wherein L represents an organic group of formula (2) or (4), W in formula (2) represents a hydrogen atom or an alkyl group having 1 to 6 carbon atoms;

X represents a hydrogen atom, a carboxyalkyl group having 2 or 3 carbon atoms or an alkoxycarbonylalkyl group having 3 to 6 carbon atoms, V represents a benzoyl, pyridinecarbonyl or piperidinecarbonyl group having a substituent which is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylaminoalkyl groups having 2 to 7 carbon atoms, N-alkyl-N-alkoxycarbonylaminoalkyl groups having 4 to 10 carbon atoms, piperidyloxy group, iminoalkylpiperidyloxy groups having 7 to 10 carbon atoms, alkoxycarbonylpiperidyloxy groups having 8 to 14 carbon atoms, pyrrolidyloxy group, iminoalkylpyrrolidyloxy groups having 6 to 9 carbon atoms, alkoxycarbonylpyrrolidyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, benzylsulfonylamino group, piperidylalkyl groups having 6 to 9 carbon atoms, iminoalkylpiperidylalkyl groups having 8 to 12 carbon atoms, piperididenealkyl groups having 6 to 9 carbon atoms, iminoalkylpiperididenealkyl groups having 8 to 12 carbon atoms, guanidino group, phosphono group, dialkoxyphosphoryl groups having 2 to 9 carbon atoms, monoalkoxyhydroxyphosphoryl groups having 1 to 4 carbon atoms, aminoethyloxy group, dialkylaminosulfonyl groups having 3 to 6 carbon atoms and dialkylguadinino groups having 2 to 4 carbon atoms;

Y represents a group of formulae (7) wherein n represents an integer of 1; and

Z represents a hydrogen atom or a group of any of following formulae (12-2-1) and (12-3):

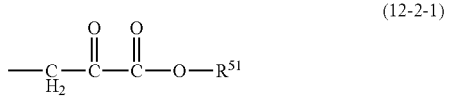

(12-2-1)

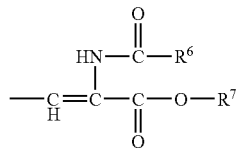

(12-3)

wherein $R^{51}$ represents a hydrogen atom or an alkyl group having 1 to 6 carbon atoms, $R^6$ represents a hydrogen atom, an alkyl group having 1 to 6 carbon or an alkoxyl group having 1 to 7 carbon atoms, and $R^7$ represents a hydrogen atom or an alkyl group having 1 to 6 carbon atoms.

In this connections, preferred benzamidine derivatives or pharmaceutically acceptable salts thereof are those of general formula (1) wherein L represents an organic group of formula (2).

In this connections, preferred benzamidine derivatives or pharmaceutically acceptable salts thereof are those of general formula (1) wherein L represents an organic group of formula (2), W in formula (2) represents a hydrogen atom or an alkyl group having 1 to 6 carbon atoms;

X represents a hydrogen atom, a carboxyalkyl group having 2 or 3 carbon atoms or an alkoxycarbonylalkyl group having 3 to 6 carbon atoms, V represents a benzoyl, pyridinecarbonyl or piperidinecarbonyl group having a substituent which is selected from among carbamoyl group, mono- or dialkylcarbamoyl groups having 2 to 7 carbon atoms, amidino group, mono- or dialkylamidino groups having 2 to 7 carbon atoms, acyl groups having 2 to 8 carbon atoms, dialkylamino groups having 2 to 6 carbon atoms, arylamino groups having 4 to 6 carbon atoms, dialkylaminoalkyl groups having 3 to 7 carbon atoms, piperidyloxy group, iminoalkylpiperidyloxy groups having 7 to 10 carbon atoms, pyrrolidyloxy group, iminoalkylpyrrolidyloxy groups having 6 to 9 carbon atoms, aryl groups having 4 to 10 carbon atoms, arylalkenyl groups having 6 to 12 carbon atoms, alkoxyl groups having 1 to 10 carbon atoms, alkyl groups having 3 to 8 carbon atoms, arylsulfonyl groups having 4 to 10 carbon atoms, iminoalkylpiperazinecarbonyl groups having 7 to 10 carbon atoms, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperididenealkyl groups having 6 to 9 carbon atoms, iminoalkylpiperididenealkyl groups having 8 to 12 carbon atoms and guanidino group.

In this connections, preferred benzamidine derivatives or pharmaceutically acceptable salts thereof are those of general formula (1) wherein L represents an organic group of formula (2) wherein W represents a hydrogen atom or methyl group, X represents a hydrogen atom, a carboxyalkyl group having 2 or 3 carbon atoms or an alkoxycarbonylalkyl group having 3 to 6 carbon atoms, V represents 1-(pyridyl)-piperidine-4-carbonyl group or benzoyl group having a substituent which is selected from among dialkylcarbamoyl groups having 3 to 7 carbon atoms, dialkylamidino groups having 3 to 7 carbon atoms, benzoyl group, dialkylamino groups having 2 to 6 carbon atoms, pyridylamino group, iminoalkylpiperidyloxy groups having 7 to 10 carbon atoms, iminoalkylpyrrolidyloxy groups having 6 to 9 carbon atoms, pyridylalkyl groups having 6 or 7 carbon atoms, iminoalkylpiperidylalkyl groups having 8 to 12 carbon atoms, iminoalkylpiperididenealkyl groups having 8 to 12 carbon atoms and guanidino group;

Y represents a group of formulae (7) wherein a represents an integer of 1; and

Z represents a hydrogen atom or a group of formula (12-2-1).

In this connections, preferred benzamidine derivatives or pharmaceutically acceptable salts thereof are those of general formula (1) wherein L represents an organic group of formula (2) wherein W represents a hydrogen atom; X represents a hydrogen atom, a carboxyalkyl group having 2 or 3 carbon atoms or an alkoxycarbonylalkyl group having 3 to 6 carbon atoms, V represents 1-(4-pyridyl)-piperidine-4-carbonyl group or benzoyl group having a substituent at the p-position, which substituent is selected from among dimethylcarbamoyl group, (pyrrolidine-1-yl)carbonyl group, N,N-dimethylamidino group, (pyrrolidine-1-yl)(imino)methyl group, benzoyl group, 1-pyrrolidyl group, 4-pyridylamino group, 1-acetimidoyl-4-piperidyloxy group, 4-pyridylethyl group and guanidino group;

Y represents a group of formula (7) wherein n represents an integer of 1; and

Z represents a group of formula (12-2-1).

Alternatively, preferred benzamidine derivatives or pharmaceutically acceptable salts thereof are those of general formula (1)

wherein L represents an organic group of formula (2) wherein W represents a hydrogen atom, X represents a carboxyalkyl group having 2 or 3 carbon atoms or alkoxycarbonylalkyl group having 3 to 6 carbon atoms, V represents a benzoyl, pyridinecarbonyl or piperidinecarbonyl group having a substituent at the m- or p-position, which substituent is selected from among mono- or dialkylamidino groups having 2 to 7 carbon atoms, pyridyl group, carboxyl group, amidino group, dialkylaminocarbonyl groups having 3 to 6 carbon atoms, dialkylaminosulfonyl groups having 3 to 6 carbon atoms, imidazoline-2-yl-amino group, pyrrolidyl group, piperidyloxy group and iminoalkylpiperidyloxy groups having 7 to 10 carbon atoms;

Y represents a group of formula (7) wherein n represents an integer of 1; and

Z represents a group of any one of formulae (12-2-1) and (12-3).

In this connections, preferred benzamidine derivatives or pharmaceutically acceptable salts thereof are those of general formula (1) wherein Z is 2-acetamido-2-ethoxycarbonylethenyl group, 2-acetamido-2-methoxycarbonylethenyl group, 2-acetamido-2-carboxyethenyl group or 2-carboxy-2-oxoethyl group.

In this connections, preferred benzamidine derivatives or pharmaceutically acceptable salts thereof are those of general formula (1) wherein X represents ethoxycarbonylmethyl group or carboxymethyl group.

In this connections, preferred benzamidine derivatives or pharmaceutically acceptable salts thereof are those of general formula (1) wherein V represents benzoyl, pyridinecarbonyl or piperidinecarbonyl group having a substituent at the p-position, which substituent is selected from among amidino group, carboxyl group, dimethylaminocarbonyl group, 1-pyrrolidylcarbonyl, 4-piperidyloxy group and 1-acetimidoyl-4-piperidyloxy group.

Alternatively, preferred benzamidine derivatives or pharmaceutically acceptable salts thereof are those of general formula (1) wherein L represents an organic group of formula (2) wherein:

W represents a hydrogen atom;

X represents a benzyl group having a substituent which is selected from among carboxyl group, alkoxycarbonyl groups having 2 to 7 carbon atoms, alkylsulfonyloxy groups having 1 to 6 carbon atoms, piperidyloxy group, iminoalkylpiperidyloxy groups having 7 to 10 carbon atoms, alkoxycarbonylpiperidyloxy groups having 8 to 14 carbon atoms, piperidylalkyl groups having 6 to 8 carbon atoms, iminoalkylpiperidylalkyl groups having 8 to 11 carbon atoms, alkoxycarbonylpiperidylalkyl groups having 9 to 15 carbon atoms, pyrrolidyloxy group, iminoalkylpyrrolidyloxy groups having 6 to 9 carbon atoms, alkoxycarbonylpyrrolidyloxy groups having 7 to 13 carbon atoms, amidino group, benzyloxycarbonyl group, hydroxyl group, halogeno groups, amidinopiperidyloxy group and alkyl groups having 1 to 3 carbon atoms;

V represents a hydrogen atom, 2-naphthalenesulfonyl, camphorsulfonyl, cinnamoyl, piperidinecarbonyl, phenylacetyl, quinuclidinylaminoacetyl, quinuclidiniumylacetyl, indolecarbonyl, phenylthiocarbonyl, pyridinecarbonyl, piperidinecarbonyl or benzimidoyl group, or an alkanesulfonyl or benzenesulfonyl group which may have a substituent selected from among carboxyl group, alkoxycarbonyl groups having 2 to 7 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, phosphono group, dialkoxyphosphoryl groups having 2 to 9 carbon atoms and monoalkoxyhydroxyphosphoryl groups having 1 to 4 carbon toms;

Y represents a group of formula (7) wherein n represents an integer of 1, and

Z represents a hydrogen atom, an alkyl group having 1 to 6 carbon atoms, a halogeno group or a group of any of formulae (12-1), (12-1) and (12-3).

In this connections, preferred benzamidine derivatives or pharmaceutically acceptable salts thereof are those of general formula (1) wherein:

X represents a benzyl group having a substituent selected from among carboxyl group, alkoxycarbonyl groups having 2 to 7 carbon atoms, alkylsulfonyloxy groups having 1 to 6 carbon atoms, piperidyloxy group, iminoalkylpiperidyloxy groups having 7 to 10 carbon atoms, alkoxycarbonylpiperidyloxy groups having 8 to 14 carbon atoms, piperidylalkyl groups having 6 to 8 carbon atoms, iminoalkylpiperidylalkyl groups having 8 to 11 carbon atoms, alkoxycarbonylpiperidylalkyl groups having 9 to 15 carbon atoms, pyrrolidyloxy group, iminoalkylpyrrolidyloxy groups having 6 to 9 carbon atoms and alkoxycarbonylpyrrolidyloxy groups having 7 to 13 carbon atoms, and V represents a hydrogen atom, a benzenesulfonyl, 2-naphthalenesulfonyl, camphorsulfonyl, cinnamoyl, piperidinecarbonyl, phenylacetyl, quinuclidinylaminoacetyl or quinuclidiniumylacetyl group or an alkanesulfonyl group having 1 to 6 carbon atoms;

Y represents a group of formula (7) wherein n represents an integer of 1, and

Z represents a hydrogen atom or a group of formula (12-1).

More concretely, preferred compounds are those described in the Examples, which by no means limit them. Particularly preferred benzamidine derivatives are those selected from the group consisting of (3R)-3-(4-amidinobenzoylamino)-4-[5-amidino-2-(2-carboxy-2-oxoethyl)phenoxy]butanoic acid, (3R)-4-[5-amidino-2-(2-carboxy-2-oxoethyl)phenoxy]-3-(4-dimethylcarbamoylbenzoylamino)butanoic acid, (3R)-4-[5-amidino-2-(2-carboxy-2-oxoethyl)phenoxy]-3-(4-carboxybenzoylamino)butanoic acid, (3R)-4-[5-amidino-2-(2-carboxy-2-oxoethyl)phenoxy]-3-[4-(pyrrolidine-1-carbonyl)benzoylamino]butanoic acid, (3R)-4-[5-amidino-2-(2-carboxy-2-oxoethyl)phenoxy]-3-[4-(1-(1-iminoethyl)piperidyl-4-oxy)benzoylamino]butanoic acid and (3R)-4-[5-amidino-2-(2-carboxy-2-oxoethyl)phenoxy]-3-[4-(pyrrolidine-1-sulfonyl)benzoylamino]butanoic acid, and pharmaceutically acceptable salts thereof.

Compounds of Examples 79, 213 and 206 are preferred. Compound of Example 193, (3R)-4-[5-amidino-2-(2-carboxy-2-oxoethyl)phenoxy]-3-[4-(pyrrolidine-1-carbonyl)benzoylamino]butanoic acid of Example 191 and compounds of Examples 215, 205 and 7 are also preferred.

The amidino group of the compounds of general formula (1) may be protected by a suitable protecting group.

The alkyl groups in the present invention may be branched or have a ring. For example, the alkyl groups include cyclohexylmethyl group or the like. The term "aryl" herein involves not only aromatic cyclic hydrocarbon groups but also heterocyclic aromatic groups having one to three hetero atoms selected from among O, N and S. Examples of the aryl groups include phenyl, pyridyl, imidazolyl and pyrrolyl groups. An example of the arylalkenyl groups is 2-(4-pyridyl)

vinyl group. The dialkylamidino groups include N,N-dialkylamidino groups and N,N'-dialkylamidino groups. The two alkyl groups in the dialkylcarbamoyl, dialkylamidino, dialkylamino, dialkylaminoalkyl, dialkylaminosulfonyl and dialkylguanidino groups may be bonded together to form a ring. In those groups, one of CH$_2$'s may be replaced by O, NH or S, and CH$_2$—CH$_2$ may be replaced by CH═CH. For example, the dialkylcarbamoyl groups include pyrrolidine-1-carbonyl group, the dialkylamidino groups include 2-imidazoline-2-yl group and (pyrrolidine-1-yl)(imino)methyl group, and dialkylguanidino groups include imidazolinne-2-amino group. The acyl groups include not only alkylcarbonyl groups but also arylcarbonyl groups. For example, acyl groups having 1 to 8 carbon atoms include benzoyl group. The alkoxyl groups include not only alkyloxy groups but also aryloxy and aralkyloxy groups. For example, the alkoxyl groups include cyclohexyloxy and phenoxy groups, and the alkoxycarbonyl groups include benzyloxycarbonyl group.

The term "aryl" herein indicates not only aromatic hydrocarbon ring groups but also aromatic heterocyclic ring groups. For instance, the arylalkenyl groups include 2-(4-pyridyl)vinyl group. The dialkylamidino groups include N,N-dialkylamidino groups and N,N'-dialkylamidino groups. The two alkyl groups in the dialkylcarbamoyl, dialkylamidino, dialkylamino and dialkylaminoalkyl groups may be bonded together to form a ring. For instance, the dialkylcarbamoyl groups include, for example, 1-pyrrolidinecarbonyl group; and the dialkylamidino groups include, for example, 2-imidazoline-2-yl group. The alkoxyl groups include not only alkyloxy groups but also aryloxy groups. For instance, examples of the alkoxycarbonylpiperidyloxy groups include, for example, 1-phenoxycarbonyl-4-piperidyloxy group.

The compounds of the present invention may have an asymmetric carbon atom. Those compounds include mixtures of various stereoisomers such as geometrical isomers, tautomers and optical isomers, and those isolated therefrom.

The description will be made on typical processes for producing the compounds (1) of the present invention.

[Process for Producing Compounds of General Formula (1) Wherein L is Represented by Formula (2)]

A benzonitrile derivative (14) can be obtained by reacting an aminoalkyl halide (13), in which nitrogen is protected with, for example, benzyloxycarbonyl group or t-butoxycarbonyl group, with 3-cyanophenol in the presence of a base such as potassium carbonate in a solvent such as dimethylformamide. The protective group on the nitrogen of the obtained benzonitrile derivative (14) can be removed with an acidic solution such as 4 N hydrogen chloride solution in dioxane to obtain an amine (15).

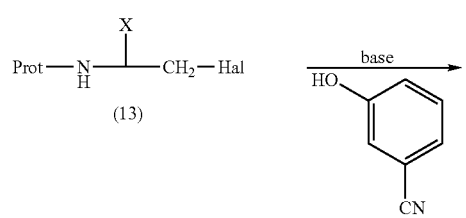

wherein Prot represents a protective group such as Boc group or Z group, and Hal represents a halogen atom.

When a compound of general formula (1) wherein V represents a benzoyl group having a substituent, cinnamoyl, piperidinecarbonyl or phenylacetyl group which may have a substituent or an organic group of the above formula (6) is to be produced, the amine (15) is reacted with an acylating agent in the presence of a base such as diisopropylethylamine in a solvent such as dichloromethane to obtain an amide (16).

When a compound of general formula (1) wherein V represents an alkanesulfonyl, benzenesulfonyl or naphthalenesulfonyl group which may have a substituent, the amine (15) is reacted with a sulfonylating agent in the presence of a base such as triethylamine in a solvent such as dimethylformamide to obtain an amide (16).

When a compound of general formula (1) wherein W does not represent a hydrogen atom but represents an organic group, the amide (16) is reacted with a base such as sodium hydride in a solvent such as dimethylformamide, and then the reaction product is reacted with an alkylating agent to obtain an amide (17) having W on nitrogen.

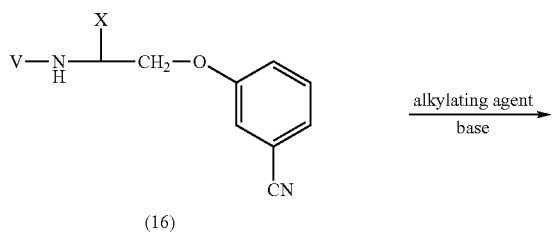

(16)

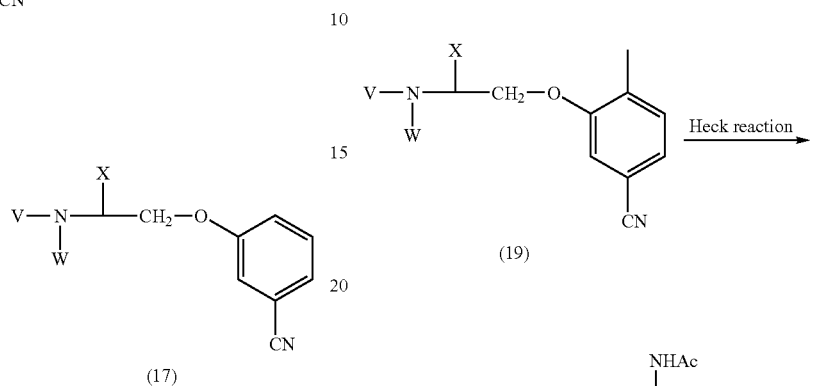

The cyano group of the amide (17) thus obtained can be converted into amidino group by reacting it with an alcohol such as ethanol containing a hydrogen halide such as hydrogen chloride and then reacting the product with ammonia. Thus, a benzamidine derivative (18) of general formula (1) wherein Y is represented by the above formula (7) and Z is a hydrogen atom can be obtained.

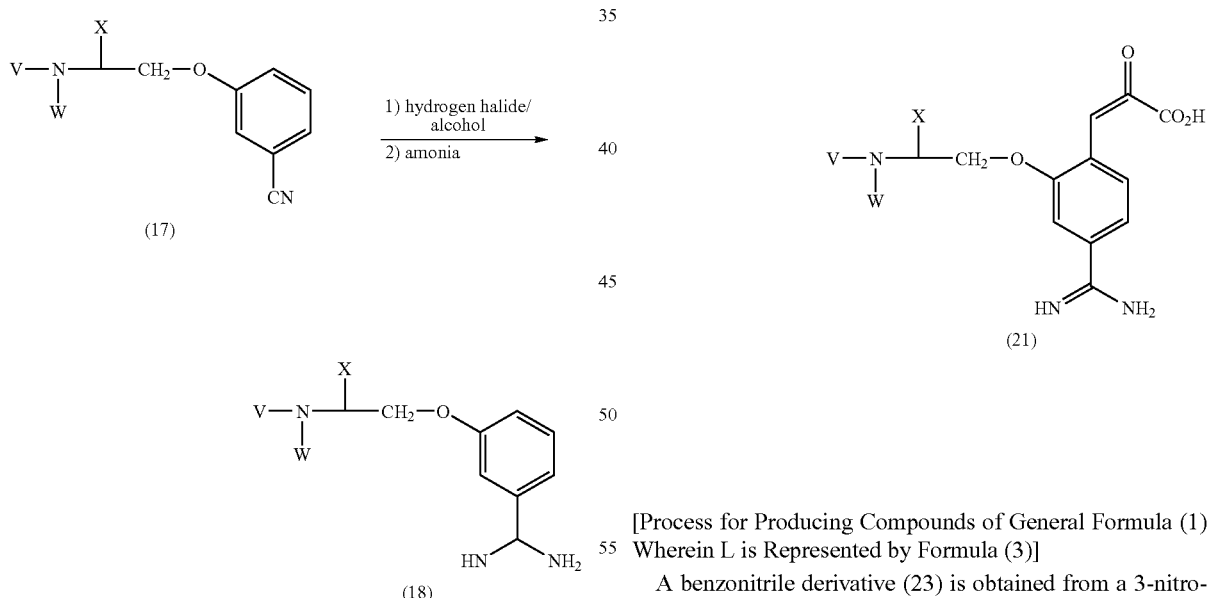

When a compound of general formula (1) wherein Z is 2-oxo-2-carboxyethyl group is to be produced, 5-cyano-2-iodophenol used as the starting material is converted into a 4-iodobenzonitrile derivative (19) in the same manner as in the production of compound (16) described above, and then this compound is condensed with methyl 2-acetylaminoacrylate by, for example, Heck reaction to obtain an acrylic acid derivative (20). Then the cyano group is converted into amidino group as mentioned above, and the both the ester part and enamino part on the substituent at the 4-position are simultaneously hydrolyzed to obtain a benzamidine derivative (21) of general formula (1) wherein Y is represented by above formula (7) and Z represents 2-oxo-2-carboxyethyl group.

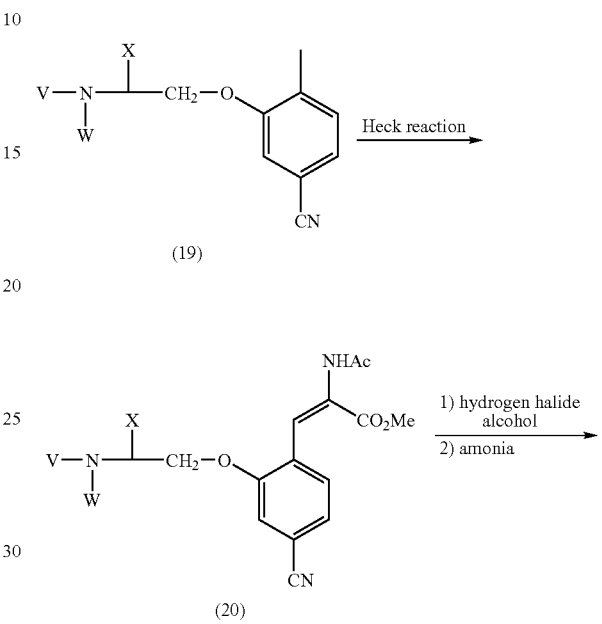

[Process for Producing Compounds of General Formula (1) Wherein L is Represented by Formula (3)]

A benzonitrile derivative (23) is obtained from a 3-nitrophenylalkyl halide (22) in the same manner as in the production of compound (14) described above, and then this derivative (23) is reacted with, for example, zinc in a solvent such as acetic acid to obtain an amine (24). The amine (24) is acylated or sulfonylated in the same manner as in the production of compound (16) described above and then the cyano group is converted into amidino group also in the same manner as that described above to obtain a benzamidine derivative of general formula (1) wherein Y is represented by the above formula (7) and Z is hydrogen atom.

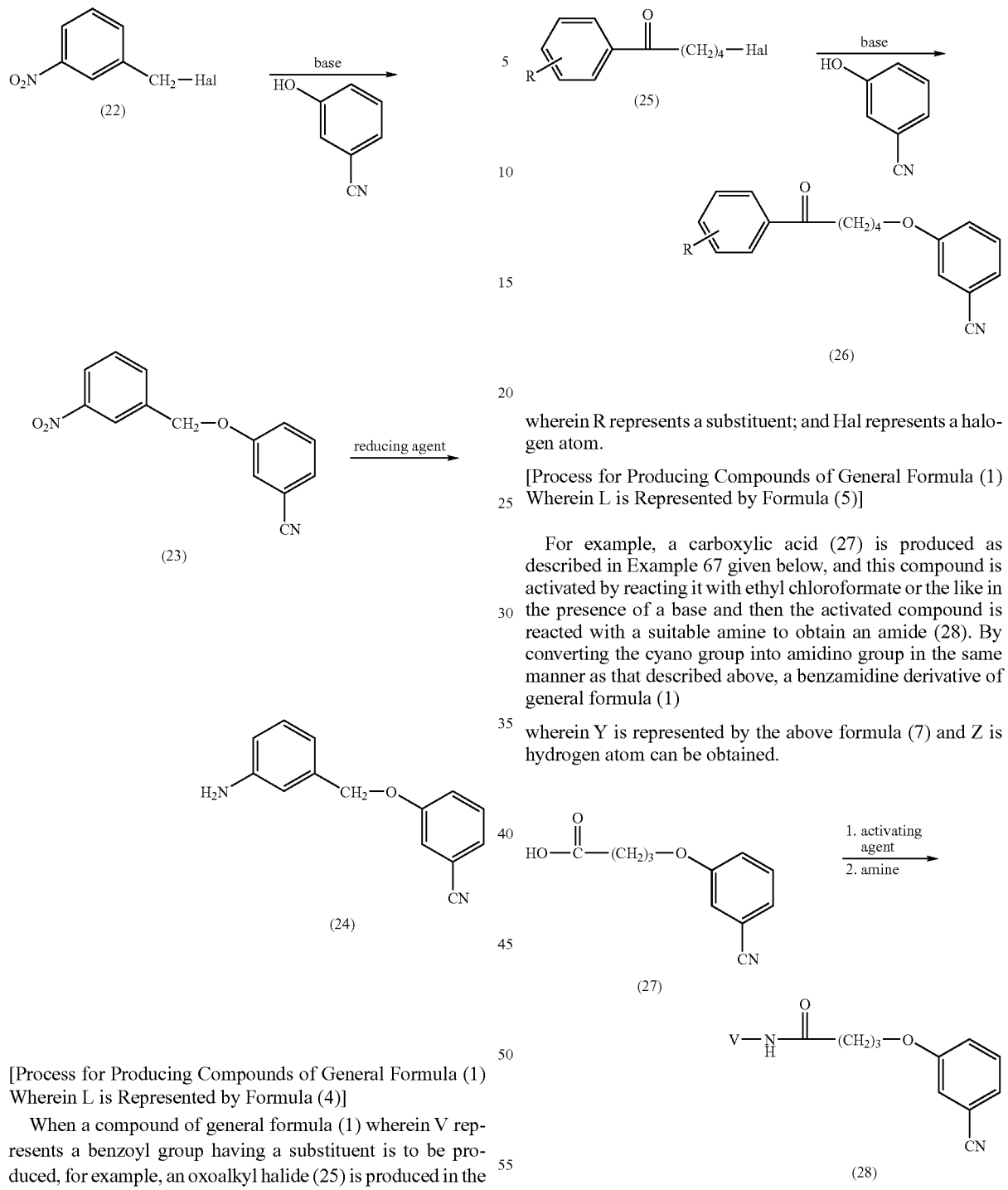

wherein R represents a substituent; and Hal represents a halogen atom.

[Process for Producing Compounds of General Formula (1) Wherein L is Represented by Formula (5)]

For example, a carboxylic acid (27) is produced as described in Example 67 given below, and this compound is activated by reacting it with ethyl chloroformate or the like in the presence of a base and then the activated compound is reacted with a suitable amine to obtain an amide (28). By converting the cyano group into amidino group in the same manner as that described above, a benzamidine derivative of general formula (1) wherein Y is represented by the above formula (7) and Z is hydrogen atom can be obtained.

[Process for Producing Compounds of General Formula (1) Wherein L is Represented by Formula (4)]

When a compound of general formula (1) wherein V represents a benzoyl group having a substituent is to be produced, for example, an oxoalkyl halide (25) is produced in the same manner as that in Example 63 given below, and then a benzonitrile derivative (26) is obtained in the same manner as in the production of compound (14) described above. In this case, the ketone of the oxoalkyl halide (25) may be protected by converting it into, for example, an acetal prior to the reaction. By converting the cyano group of the benzonitrile derivative (26) into amidino group in the same manner as that described above, a benzamidine derivative of general formula (1) wherein Y is represented by the above formula (7) and Z is hydrogen atom can be obtained.

The benzamidine derivatives of the present invention can be produced also by a process comprising the following steps:

A benzonitrile derivative (30) can be obtained by reacting an aminoalkyl alcohol (29), in which nitrogen is protected with, for example, benzyloxycarbonyl group or t-butoxycarbonyl group, and 3-cyano-5-iodophenol with, for example, an azodicarbonyl compound such as diethyl diazocarboxylate in the presence of, for example, triphenylphosphine in a solvent such as THF. The protective group on the nitrogen of the obtained benzonitrile derivative (30) can be removed with an acidic solution such as 4 N hydrogen chloride solution in dioxane to obtain an amine (31).

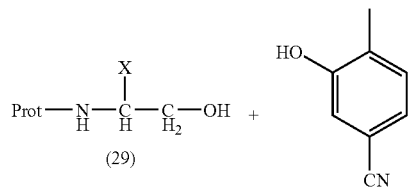

(29)

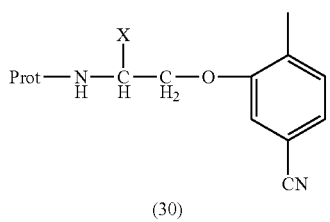

(30)

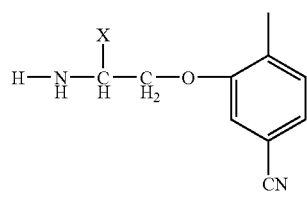

(31)

wherein Prot represents a protective group such as Boc group or Z group, and X represents a carboxyalkyl group having 2 or 3 carbon atoms or an alkoxycarbonylalkyl group having 3 to 6 carbon atoms.

Then amine (31) is condensed with a carboxylic acid (32) in the presence of a condensing agent and a base such as triethylamine in a solvent such as dichloromethane to obtain an amide (33).

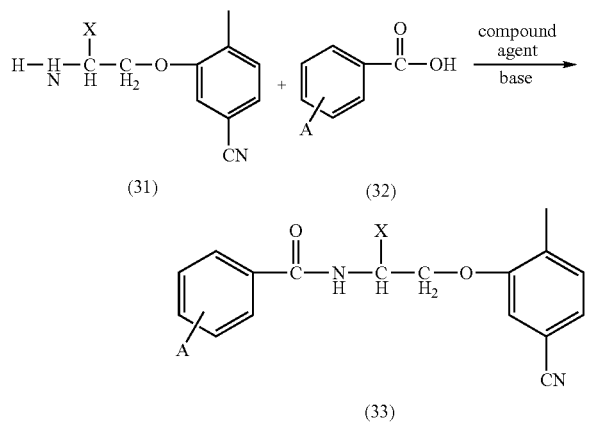

wherein A represents a substituent.

Thus obtained amide (33) is condensed with an acrylic acid derivative such as methyl 2-acetamidoacrylate by, for example, Heck reaction in a solvent such as acetonitrile to obtain an acrylic acid derivative (34).

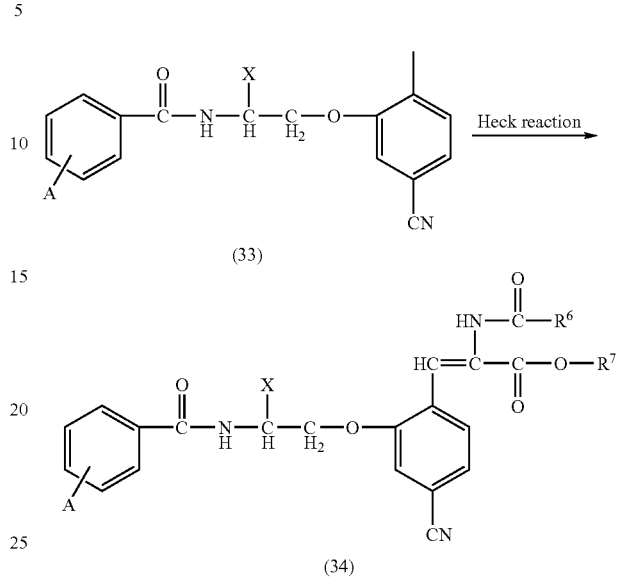

The cyano group can be converted into amidino group by reacting acrylic acid derivative (34) with an alcohol such as ethanol containing a hydrogen halide such as hydrogen chloride and then reacting the product with an ammonium salt such as ammonium carbonate. By these steps, benzamidine derivative (35) of general formula (1) wherein Z is represented by formula (12-3) given above can be obtained.

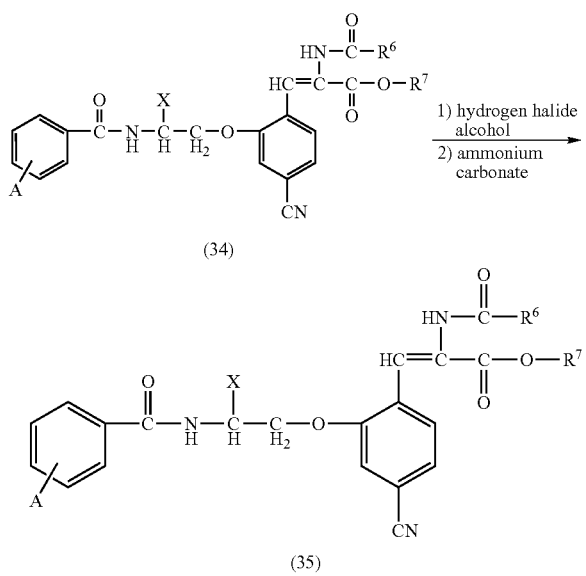

Benzamidine derivatives (36) of general formula (1) wherein Z represents 2-carboxy-2-oxoethyl group can be produced by simultaneously hydrolyzing the ester part and enamino part in the substituent at the 4-position of benzamidine derivative (35) wherein Z is the same as above thereof in an aqueous solution of a hydrogen halide such as hydrogen chloride.

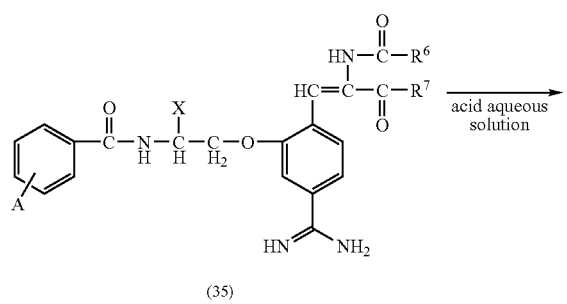

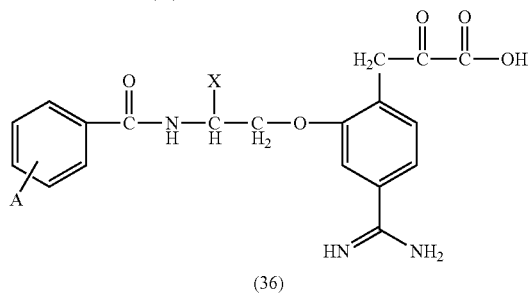

The compounds of general formula (1) and salts thereof produced as described above can be isolated by the purification by a well-known method such as extraction, concentration, concentration under reduced pressure, extraction with a solvent, crystallization, recrystallization, redissolution and chromatography.

The salts of benzamidine derivatives of general formula (1) are pharmaceutically acceptable ones such as salts of them with mineral acids, e.g. hydrochloric acid, hydrobromic acid, sulfuric acid, nitric acid and phosphoric acid; and organic acids, e.g. formic acid, acetic acid, lactic acid, salicylic acid, mandelic acid, citric acid, oxalic acid, maleic acid, fumaric acid, tartaric acid, tannic acid, malic acid, touenesulfonic acid, methanesulfonic acid and benzenesulfonic acid.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary pharmaceutical preparation materials by an ordinary method. For example, the tablets are prepared by mixing the benzamidine derivative, the active ingredient of the present invention, with any of known pharmaceutic acids such as inert diluents, e.g. lactose, calcium carbonate and calcium phosphate, binders, e.g. acacia, corn starch and gelatin, extending agents, e.g. alginic acid, corn starch and pre-gelatinized starch, sweetening agents, e.g. sucrose, lactose and saccharin, corrigents, e.g. peppermint and cherry, and lubricants, e.g. magnesium stearate, talc and carboxymethyl cellulose.

When the benzamidine derivatives of general formula (1) are used as the anticoagulants, they can be administered either orally or parenterally. The dose which varies depending on the age, body weight and conditions of the patient and the administration method is usually 0.01 to 1,000 mg, preferably 0.1 to 50 mg, per day for adults in the oral administration, and 1 μg to 100 mg, preferably 0.01 to 10 mg, in the parenteral administration.

The following Examples will further illustrate the present invention, which are only preferred embodiments of the invention and which by no means limit the invention.

In the Examples, NMR spectra of the compounds of formula (1) wherein Z represents 2-carboxy-2-oxoethyl group in DMSO-d6 are those of a mixture of keto- and enol-forms.

Example 1

Synthesis of N-[2-(3-amidinophenoxy)ethyl]-4-amidinobenzthioamide bistrifluoroacetate Step 1

Synthesis of t-butyl(2-bromoethyl)carbamate 9.22 g (45 mmol) of 2-bromoethylamine hydrobromide was dissolved in 100 ml of dichloromethane. 7.64 g (35 mmol) of di-t-butyl dicarbonate, 10.0 g (99 mmol) of triethylamine and 100 mg (0.82 mmol) of 4-(dimethylamino)pyridine were added to the resultant solution, and the obtained mixture was stirred overnight. After the treatment with dichloromethane as the extractant in an ordinary manner, the title compound was obtained.

Yield: 5.99 g (26.7 mmol) (76%).

H-NMR (CDCl3) δ 1.45 (1H, s), 3.46 (2H, dt), 3.51 (2H, t), 4.95 (1H, br).

Step 2

Synthesis of 3-[2-(t-butoxycarbonylamino)ethoxy]benzonitrile 5.85 g (29 mmol) of t-butyl(2-bromoethyl)carbamate was dissolved in 100 ml of dimethylformamide. 2.38 g (26.4 mmol) of 3-hydroxybenzonitrile, 3.04 g (53 mmol) of potassium carbonate and 4.31 g (53 mmol) of sodium iodide were added to the solution, and the obtained mixture was stirred at 50° C. for 6 hours. After the treatment with ethyl acetate as the extractant in an ordinary manner, the crude product was obtained. After the purification by silica gel column chromatography, the title compound was obtained.

Yield: 3.33 g (13.3 mmol) (51%).

H-NMR (CDCl3) δ 1.44 (1H, s), 3.55 (2H, t), 4.05 (2H, t), 4.95 (1H, brs), 7.12 (1H, d), 7.14 (1H, s), 7.26 (1H, d), 7.38 (1H, t).

Step 3

Synthesis of 3-(2-aminoethoxy)benzonitrile 1.41 g of 3-[2-(t-butoxycarbonylamino)ethoxy]benzonitrile was dissolved in 20 ml of 4 N solution of hydrogen chloride in dioxane, and the solution was stirred at room temperature for 2 hours. The solvent was evaporated. The residue was suspended in dichloromethane, and the obtained suspension was filtered to obtain hydrochloride of the title compound.

Yield: 0.89 g (83%).

The hydrochloride was dissolved in 1 N aqueous sodium hydroxide solution. After treatment with ethyl acetate as the extractant in an ordinary manner the title compound was obtained H-NMR (CDCl3) δ 3.10 (2H, t), 4.00 (2H, t) 7.15 (1H, d), 7.17 (1H, s), 7.25 (1H, d), 7.37 (1H, t).

Step 6

Synthesis of N-[2-(3-cyanophenoxy)ethyl]-4-cyanobenzamide 1.13 g (7.68 mmol) of 4-cyanobenzoic acid and 1.6 ml (14.1 mmol) of N-methylmorpholine were dissolved in 30 ml of dimethylformamide. 0.67 ml (7.05 mmol) of ethyl chloroformate was added to the solution under cooling with ice/water. After stirring for 5 minutes, 1.27 g (6.41 mmol) of 3-(2-aminoethoxy)benzonitrile was added to the reaction mixture, and the obtained mixture was stirred at room temperature for one hour. After the treatment with ethyl acetate as the extractant in an ordinary manner, the title compound was obtained.

Yield: 1.29 g (4.43 mmol) (69%).

MS (FAB, m/z) 292 (MH+)

H-NMR (CDCl3) δ 3.91 (2H, dt), 4.19 (2H, t), 6.78 (1H, br), 7.14 (1H, d), 7.17 (1H, s), 7.28 (1H, d), 7.39 (1H, t), 7.75 (2H, d), 7.90 (2H, d)

Step 5

Synthesis of N-[2-(3-cyanophenoxy)ethyl]-4-cyanobenzthioamide 1.46 g (5.00 mmol)) of N-[2-(3-cyanophenoxy)ethyl]-4-cyanobenzamide was dissolved in 50 ml of toluene. 3.03 g (7.5 mmol) of 2,4-bis(4-methoxyphenyl)-1,3-dithia-2,4-diphosphetane-2,4-disulfide was added to the solution, and the obtained mixture was heated under reflux for 4 hours. The precipitate was removed by the filtration, and the solvent was evaporated under reduced pressure. The residue was purified by the silica gel column chromatography, and the title compound was obtained.

Yield: 1.16 g (3.77 mmol) (75%).

H-NMR (CDCl3) δ3.85 (2H, dt), 4.30 (2H, t), 7.15 (1H, d), 7.17 (1H, s), 7.24 (1H, d), 7.39 (1H, t), 7.65 (2H, d), 7.81 (2H, d), 8.02 (1H, br).

Step 6

Synthesis of N-[2-(3-amidinophenoxy)ethyl]-4-amidinobenzthioamide bistrifluoroacetate 1.16 g (3.77 mmol) of N-[2-(3-cyanophenoxy)ethyl]-4-cyanobenzthioamide was dissolved in 18 ml of 4 N solution of hydrogen chloride in dioxane. 2 ml of ethanol containing 30% (w/v) of hydrogen chloride was added to the obtained solution. After stirring at room temperature for 96 hours, the solvent was evaporated under reduced pressure. The residue was dissolved in 20 ml of 10% (w/v) solution of ammonia in ethanol, and the obtained solution was stirred at room temperature for 24 hours. The solvent was evaporated, and the residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 909 mg (1.59 mmol) (42%).

MS (ESI, m/z) 342 (MH+)

H-NMR (DMSO-d6) δ 4.12 (2H, dt), 4.41 (2H, t), 7.35 (1H, d), 7.40 (1H, d), 7.41 (1H, s), 7.55 (1H, t), 7.82 (2H, d), 7.88 (2H, d), 9.20 (2H, br), 9.30 (4H, br), 9.39 (2H, br), 9.47 (1H, t).

Example 2

Synthesis of N-[2-(3-amidinophenoxy)ethyl]-4-carbamoylbenzamide trifluoroacetate

Step 1

Synthesis of benzyl-N-(2-bromoethyl)carbamate 10 g (49 mmol) of 2-bromoethylamine hydrobromide and 15 ml of triethylamine were dissolved in dichloromethane. 7.8 ml (49 mmol) of benzyl chloroformate was added to the obtained solution under cooling with ice, and they were stirred at room temperature. The reaction mixture was treated with dichloromethane as the extractant in an ordinary manner to obtain a crude product, which was purified by the silica gel column chromatography to obtain the title compound.

Yield: 10.6 g (41 mmol) (84%)

H-NMR (CDCl3) δ 3.45 (2H, t), 3.60 (2H, dt), 5.10 (2H, s), 5.20 (1H, brs), 7.30-7.38 (5H, m)

Step 2

Synthesis of 3-(2-aminoethoxy)benzonitrile hydrobromide 8 g of benzyl-N-(2-bromoethyl)carbamate, 3.7 g of 3-hydroxybenzonitrile, 4.3 g of calcium carbonate, 5.1 g of potassium iodide and 1.1 g of tetrabutylammonium iodide were stirred in dimethylformamide at 60° C. After the treatment with ethyl acetate as the extractant in an ordinary manner, the product was purified by the silica gel column chromatography to obtain 3-[2-(benzyloxycarbonylamino)ethoxy]benzonitrile. Acetic acid containing 20% of hydrogen bromide was added to the product under cooling with ice, and the resultant mixture was stirred at room temperature for 2 hours. The solvent was evaporated, and the residue was washed with ethyl acetate to obtain the title compound.

Yield: 4 g

H-NMR (DMSO-d6) δ 3.25 (2H, m), 4.25 (2H, t), 7.35 (1H, d), 7.45 (1H, d), 7.50 (1H, s), 7.55 (1H, t), 8.00 (3H, br)

Step 3

Synthesis of methyl 4-[N-[2-(3-cyanophenoxy)ethyl]carbamoyl]benzoate 1.50 g (6.2 mmol) of 3-(2-aminoethoxy)benzonitrile hydrobromide and 3 ml of triethylamine were stirred in 15 ml of dimethylformamide under cooling with ice. 1.23 g (6.2 mmol) of monomethyl terephthalate chloride was slowly added thereto, and they were stirred for 3 hours. The temperature was elevated to the room temperature, and the reaction liquid was diluted with 1 N hydrochloric acid. After the extraction with ethyl acetate, the organic layer was washed with a saturated aqueous sodium hydrogencarbonate solution and then with saturated aqueous NaCl solution, and then dried over anhydrous magnesium sulfate. The solvent was evaporated to obtain the title compound.

Yield: 1.4 g (4.3 mmol) (70%).

H-NMR (CDCl3) δ 53.90 (2H, dt), 3.93 (3H, s), 4.20 (2H, t), 6.60 (1H, br), 7.16 (1H, d), 7.17 (1H, s), 7.27 (1H, d), 7.39 (1H, t), 7.84 (2H, d), 8.12 (2H, d)

Step 4

Synthesis of
N-[2-(3-cyanophenoxy)ethyl]-4-carbamoylbenzamide 100 mg (0.31 mmol) of methyl 4-[N-[2-(3-cyanophenoxy)ethyl)carbamoyl]benzoate was stirred in 100 ml of 28% aqueous ammonia overnight. The reaction liquid was evaporated under reduced pressure, and 1 N hydrochloric acid was added to the residue. After the extraction with ethyl acetate, the organic layer was washed with saturated aqueous NaCl solution and then dried over anhydrous magnesium sulfate. The solvent was evaporated to obtain the title compound.

Yield: 98 mg (0.32 mmol) (100%).

H-NMR (DMSO-d6) δ 3.62 (2H, dt), 4.20 (2H, t), 7.32 (1H, d), 7.40 (1H, d), 7.44-7.52 (3H, m), 7.88-7.96 (4H, m), 8.06 (1H, br), 8.80 (1H, t)

Step 5

Synthesis of
N-[2-(3-amidinophenoxy)ethyl]-4-carbamoylbenzamide trifluoroacetate The title compound was obtained from 95 mg of N-[2-(3-cyanophenoxy)ethyl]-4-carbamoylbenzamide in the same manner as that of step 6 in Example 1.

Yield: 40.3 mg (0.09 mmol) (30%).

MS (ESI, m/z) 327 (MH+)

H-NMR (DMSO-d6) δ 3.70 (2H, dt), 4.20 (2H, t), 7.32-7.40 (3H, m), 7.48 (1H, br), 7.54 (1H, t), 7.89-7.97 (4H, m), 8.60 (1H, br), 8.84 (1H, brt), 9.06 (2H, brs), 9.28 (2H, brs).

Example 3

Synthesis of N-[2-(3-amidinophenoxy)ethyl]-4-(N,N-dimethylcarbamoyl)benzamide trifluoroacetate

Step 1

Synthesis of
4-[N-[2-(3-cyanophenoxy)ethyl]carbamoyl]benzoic acid 310 mg (1 mmol) of methyl 4-[N-[2-(3-cyanophenoxy)ethyl]carbamoyl]benzoate was stirred in 15 ml of ethanol and 15 ml of THF. 3 ml of 1 N aqueous sodium hydroxide solution was added thereto and they were stirred at room temperature overnight. The reaction liquid was distilled under reduced pressure and then 1 N hydrochloric acid was added to the residue. After the extraction with ethyl acetate, the extract was washed with a saturated aqueous NaCl solution and then dried over anhydrous magnesium sulfate. The solvent was evaporated to obtain the title compound.

Yield: 299 mg (0.96 mmol) (96%).

H-NMR (DMSO-d6) δ 3.65 (2H, dt), 4.20 (2H, t), 7.32 (1H, d), 7.40 (1H, d), 7.44-7.52 (2H, m), 7.94 (2H, d); 8.02 (2H, d), 8.85 (1H, brt)

Step 2

Synthesis of N-[2-(3-cyanophenoxy)ethyl]-4-(N,N-dimethylcarbamoyl)benzamide 140 mg (0.45 mmol) of 4-[N-[2-(3-cyanophenoxy)ethyl]carbamoyl]benzoic acid was stirred in dimethylformamide. 50 mg (0.5 mmol) of triethylamine and 48 mg (0.45 mmol) of ethyl chloroformate were added thereto under cooling with ice, and they were stirred for 5 minutes to obtain the acid anhydride. Then 1 ml (excess amount) of 50% aqueous dimethylamine solution was added to the acid anhydride. The temperature was elevated to room temperature, and the reaction mixture was stirred for 2 hours and then diluted with 1 N hydrochloric acid. After the extraction with ethyl acetate, the organic layer was washed with saturated aqueous sodium hydrogencarbonate solution and then with saturated aqueous NaCl solution. The product was dried over anhydrous magnesium sulfate and the solvent was evaporated to obtain the title compound.

Yield: 102 mg (0.30 mmol) (67%).

H-NMR (CDCl3) δ 2.90 (3H, br), 3.10 (3H, br), 3.90 (2H, dt), 4.20 (2H, t), 6.80 (1H, br), 7.16 (1H, d), 7.17 (1H, s), 7.26 (1H, d), 7.39 (1H, t), 7.45 (2H, d), 7.80 (2H, d)

Step 3

Synthesis of N-[2-(3-amidinophenoxy)ethyl]-4-(N,N-dimethylcarbamoyl)benzamide trifluoroacetate 100 mg (0.32 mmol) of N-[2-(3-cyanophenoxy)ethyl]-4-N,N-dimethylcarbamoyl)benzamide was stirred in 5 ml of dioxane containing 4 N hydrogen chloride. 0.5 ml of ethanol was added to the resultant mixture and they were stirred at room temperature for 2 days. The solvent was evaporated under reduced pressure, and the residue was stirred in 10 ml of ethanol. 80 mg of ammonium carbonate was added to the resultant mixture, and they were stirred at room temperature for 5 days. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 95 mg (0.2 mmol) (63%).

MS (ESI, m/z) 355 (MH+)

H-NMR (DMSO-d6) δ 2.85 (3H, br), 3.00 (3H, br), 3.65 (2H, dt), 4.22 (2H, t), 7.31-7.41 (3H, m), 7.48 (2H, d), 7.54 (1H, t), 7.91 (2H, d), 8.80 (1H, t), 9.05 (2H, br), 9.30 (2H, br).

Example 4

Synthesis of N-[2-(3-amidinophenoxy)ethyl]-4-(N-methyl-N-ethylcarbamoyl)benzamide trifluoroacetate

Step 1

Synthesis of N-[2-(3-cyanophenoxy)ethyl]-4-(N-methyl-N-ethylcarbamoyl)benzamide 258 mg (0.83 mmol) of 4-[N-[2-(3-cyanophenoxy)ethyl]carbamoyl]benzoic acid, 53 mg (0.9 mmol) of N-ethyl-N-methylamine, 129 mg (0.83 mmol) of 1-hydroxybenzotriazole (hydrous, 87%) and 159 mg (0.83 mmol) of 1-(3-dimethylaminopropyl)-3-ethylcarbodiimide hydrochloride were stirred in 10 ml of dichloro ee at room temperature overnight. The resultant mixture was diluted with 1 N hydrochloric acid. After the extraction with dichloromethane, the organic layer was washed with 1 N aqueous sodium hydroxide solution and then with saturated aqueous NaCl solution and dried over anhydrous magnesium-sulfate. The solvent was evaporated to obtain the title compound.

Yield: 288 mg (0.82 mmol) (99%)

H-NMR (CDCl3) δ 1.00-1.30 (3H, m), 2.82-3.62 (5H, m), 3.83 (2H, dt), 4.20 (2H, t), 7.12-7.41 (7H, m), 7.78 (2H, d)

Step 2

Synthesis of N-[2-(3-amidinophenoxy)ethyl]-4-(N-methyl-N-ethylcarbamoyl)benzamide trifluoroacetate The title compound was obtained from 280 mg (0.8 mmol) of N-[2-(3-cyanophenoxy)ethyl]-4-(N-methyl-N-ethylcarbamoyl)benzamide in the same manner as that of step 3 in Example 3.

Yield: 242 mg (0.5 mmol) (63%).
MS (ESI, m/z) 369 (MH+)
H-NMR (DMSO-d6) δ 1.00-1.20 (3H, brm), 2.80-3.00 (3H, br), 3.10-3.50 (2H, m), 3.70 (2H, dt), 4.20 (2H, t), 7.34 (1H, d), 7.39 (1H, d), 7.40 (1H, s), 7.43-7.50 (2H, br), 7.54 (1H, t), 7.91 (2H, d), 8.80 (1H, br), 9.10 (2H, br), 9.30 (2H, br).

Example 5

Synthesis of N-[2-(3-amidinophenoxy)ethyl]-4-(2-imidazoline-2-yl)benzamide bistrifluoroacetate Step 1

Synthesis of ethyl 4-ethoxycarbonimidoylbenzoate hydrochloride 5.16 g (29 mmol) of ethyl 4-cyanobenzoate was stirred in 50 ml of 4N solution of hydrogen chloride in dioxane. 5 ml of ethanol was added to the resultant mixture, and they were stirred at room temperature for 4 days. The solvent was evaporated, and the residue was washed with ethyl acetate and dried to obtain the title compound.

Yield: 3.24 g (12.6 mmol) (43%).
H-NMR (DMSO-d6) δ 1.35 (3H, t), 1.50 (3H, t), 4.40 (2H, q), 4.65 (2H, q), 8.18 (2H, d), 8.25 (2H, d)

Step 2

Synthesis of ethyl 4-(2-imidazoline-2-yl)benzoate 2.96 g (11.5 mmol) of ethyl 4-ethoxycarbonimidoylbenzoate hydrochloride and 690 mg (11.5 mmol) of ethylenediamine were stirred in 100 ml of ethanol at 60° C. for 4 hours. The solvent was evaporated. 1 N aqueous sodium hydroxide solution was added to the residue. After the extraction with dichloromethane followed by the washing with saturated Aqueous NaCl solution and drying over anhydrous magnesium sulfate, the solvent was evaporated to obtain the title compound.

Yield: 2.15 g (9.85 mmol) (86%)
H-NMR (CDCl3) δ 1.40 (3H, t), 3.80 (4H, br), 4.40 (2H, q), 7.80 (2H, d), 8.02 (2H, d)

Step 3

Synthesis of 4-(2-imidazoline-2-yl)benzoic acid hydrochloride 1 g (4.58 mmol) of ethyl 4-(2-imidazoline-2-yl)benzoate was heated under reflux in 4 ml of hydrochloric acid and 8 ml of acetic acid. The solvent was evaporated to obtain the title compound.

Yield: 1.04 g (4.59 mmol) (100%)
H-NMR (DMSO-d6) δ 4.00 (4H, s), 8.20 (4H, s), 11.00 (2H, br).

Step 4

Synthesis of N-[2-(3-amidinophenoxy)ethyl]-4-(2-imidazoline-2-yl)benzamide bistrifluoroacetate 400 mg (1.76 mmol) of 4-(2-imidazolinne-2-yl)benzoic acid hydrochloride, 428 mg (1.76 mmol) of 3-(2-aminoethoxy)benzonitrile hydrobromide, 301 mg (1.94 mmol) of 1-hydroxybenzotriazole (hydrous, 87%), 372 mg (1.94 mmol) of 1-(3-dimethylaminopropyl)-3-ethylcarbodiimide hydrochloride and 200 mg (2.00 mmol) of triethylamine were stirred in dimethylformamide at room temperature overnight. The solvent was evaporated under reduced pressure, and the residue was treated by the reversed-phase medium pressure liquid chromatography with silica gel, containing octadodecyl group chemically bonded thereto, as the filler. After the elution with a mixed solvent of methanol and water, the solvent was evaporated from the fraction of the intended product, and the residue was washed with ethyl acetate to obtain 400 mg of the condensate. 100 mg of the condensate was treated in the same manner as that of step 3 in Example 3 to obtain the title compound.

Yield: 117 mg (0.2 mmol)
MS (ESI, m/z) 352 (MH+)
H-NMR (DMSO-d6) δ 3.70 (2H, dt), 4.00 (4H, s), 4.22 (2H, t), 7.30-7.42 (3H, m), 7.55 (1H, t), 8.02 (2H, d), 8.10 (2H, d), 9.05 (1H, t), 9.20-9.35 (4H, br), 10.7 (2H, s)

Example 6

Synthesis of N-[2-(3-amidinophenoxy)ethyl]-4-(1-piperidinecarbonyl)benzamide trifluoroacetate Step 1

Synthesis of 4-(1-piperidinecarbonyl)benzoic acid 6 ml of piperidine was stirred in dichloromethane at 0° C., and a solution of 3 g (15 mmol) of monomethyl terephthalate chloride in dichloromethane was added to the resultant mixture. The temperature was elevated to room temperature, and they were stirred for 2 hours and then diluted with 1 N hydrochloric acid. After the extraction with dichloromethane, the organic layer was washed with saturated aqueous sodium hydrogencarbonate solution and then with saturated aqueous NaCl solution, and dried over anhydrous magnesium sulfate. The solvent was evaporated, and the residue was stirred in ethanol. 30 ml of 1 N aqueous sodium hydroxide solution was added to the resultant mixture, and they were stirred at room temperature overnight. The solvent was evaporated, and the reaction liquid was concentrated and then diluted with 1 N hydrochloric acid. After the extraction with ethyl acetate, the organic layer was washed with saturated aqueous NaCl solution and dried over anhydrous magnesium sulfate. The solvent was evaporated to obtain the title compound.

Yield: 2.81 g (12 mmol) (80%)
H-NMR (CDCl3) δ 1.45-1.75 (6H, br), 3.33 (2H, br), 3.75 (2H, br), 7.50 (2H, d), 8.15 (2H, d)

Step 2

Synthesis of N-[2-((3-amidinophenoxy)ethyl)-4-(1-piperidinecarbonyl)benzamide trifluoroacetate N-[2-(3-cyanophenoxy)ethyl]-4-((1-piperidinecarbonyl)benzamide was obtained from 300 mg (1.29 mmol) of 4-(1-piperidinecarbonyl)benzoic acid, 255 mg (1.29 mmol) of 3-(2-aminoethoxy)benzonitrile hydrochloride, 200 mg (1.29 mmol) of 1-hydroxybenzotriazole (hydrous, 87%), 247 mg (1.29 mmol) of 1-(3-dimethylaminopropyl)-3-ethylcarbodiimide hydrochloride and 130.5 mg (1.29 mmol) of triethylamine in the same manner as that of step 1 in Example 4. The whole amount of this product was treated in the same manner as that of step 3 in Example 3 to obtain the title compound.

Yield: 370 mg (0.73 mmol) (56%)

MS (ESI, m/z) 395 (MH+)

H-NMR (DMSO-d6) δ 1.40-1.65 (6H, br), 3.25 (2H, br), 3.60 (2H, br), 3.65 (2H, dt), 4.25 (2H, t), 7.34 (1H, d), 7.39 (1H, d), 7.40 (1H, s), 7.45 (2H, d), 7.54 (1H, t), 7.91 (2H, d)

Example 7

Synthesis of N-[2-(3-amidinophenoxy)ethyl]-4-(N,N-dimethylamidino)benzamide bistrifluoroacetate Step 1

Synthesis of ethyl 4-(N,N-dimethylamidino)benzoate 1 g (3.9 mmol) of ethyl 4-ethoxycarbonimidoylbenzoate hydrochloride was stirred in a mixture of 3 ml of ethanol and 10 ml of 50% aqueous dimethylamine solution overnight. Then the solvent was evaporated, and 10 ml of dioxane containing 4 N hydrogen chloride and 1 ml of ethanol were added to the residue. After stirring at room temperature for 5 days, the solvent was evaporated. 1 N sodium hydroxide was added to the residue. After the extraction with dichloromethane, the organic layer was washed with saturated Aqueous NaCl solution and dried over anhydrous magnesium sulfate. The solvent was evaporated to obtain the title compound.

Yield: 671 mg (3.05 mmol) (78%)

H-NMR (CDCl3) δ 1.40 (3H, t), 2.95 (6H, s), 4.30 (1H, br), 4.40 (2H, q), 7.40 (2H, d), 8.10 (2H, d).

Step 2

Synthesis of N-[2-(3-cyanophenoxy)ethyl]-4-(N,N-dimethylamidino)benzamide trifluoroacetate 670 mg (3.0 mmol) of ethyl 4-(N,N-dimethylamidino)benzoate was heated under reflux in 20 ml of 6 N hydrochloric acid. The solvent was evaporated. 10 ml of dichloromethane, 600 mg (3.0 mmol) of 3-(2-aminoethoxy)benzonitrile hydrochloride, 575 mg (3.0 mmol) of 1-(3-dimethylaminopropyl)-3-ethylcarbodiimide hydrochloride, 405 mg (3.0 mmol) of 1-hydroxybenzotriazole and 303 mg (3.0 mmol)) of triethylamine were added to the residue, and they were stirred at room temperature for 5 days. 1 N aqueous sodium hydroxide solution was added to the reaction mixture. After the extraction with dichloromethane, the organic layer was washed with saturated NaCl solution and dried over anhydrous magnesium sulfate. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 716 mg (1.59 mmol) (53%).

H-NMR (DMSO-d6) δ 2.98 (3H, s), 3.22 (3H, s), 3.65 (2H, dt), 4.22 (2H, t), 7.30-7.53 (4H, m), 7.70 (2H, d), 8.05 (2H, d), 8.92 (1H, br), 9.00 (1H, s), 9.40 (1H, s)

Step 3

Synthesis of N-[2-(3-amidinophenoxy)ethyl]-4-(N,N-dimethylamidino)benzamide bistrifluoroacetate The title compound was obtained from 506 mg (1.1 mmol) of N-[2-(3-cyanophenoxy)ethyl]-4-(N,N-dimethylamidino) benzamide trifluoroacetate in the same manner as that of step 3 in Example 3.

Yield: 389 mg (0.67 mmol) (61%).

MS (ESI, m/z) 354 (MH+)

H-NMR (DMSO-d6) δ 2.95 (3H, s), 3.22 (3H, s), 3.70 (2H, dt), 4.22 (2H, t), 7.34 (1H, d), 7.38-7.44 (2H, m), 7.54 (1H, t), 7.70 (2H, d), 8.07 (2H, d), 9.00-9.42 (7H, m).

Example 8

Synthesis of N-[2-(3-amidinophenoxy)ethyl]-4-(1,4,5,6-tetrahydropyrimidine-2-yl)benzamide bistrifluoroacetate Step 1

Synthesis of N-[2-(3-cyanophenoxy)ethyl]-4-(1,4,5,6-tetrahydropyrimidine-2-yl)benzamide trifluoroacetate 10 g (68 mmol) of 4-cyanobenzoic acid was stirred in 100 ml of dioxane containing 4 N hydrogen chloride and 10 ml of ethanol for 2 days. The solvent was evaporated, and the residue was washed with ethyl acetate to obtain 10.9 g of a mixture of 4-ethoxycarbonimidoylbenzoic acid and its ester. A portion (500 mg) of the mixture and 162 mg (2.18 mmol) of propylenediamine were stirred in 15 ml of ethanol at 60° C. for 2 hours. The solvent was evaporated. Concentrated hydrochloric acid was added to the residue, and they were stirred at 60° C. for 5 hours. The solvent was evaporated, and the residue was washed with ethyl acetate to obtain 290 mg (1.2 mmol) of crude 4-(1,4,5,6-tetrahydropyrimidine-2-yl)benzoic acid. 238 mg (1.2 mmol) of 3-(2-aminoethoxy)benzonitrile hydrochloride, 230 mg (1.2 mmol) of 1-(3-dimethylaminopropyl)-3-ethylcarbodiimide hydrochloride, 186 mg (1.2 mmol) of 1-hydroxybenzotriazole (hydrous, 87%), 122 mg (1.2 mmol) of triethylamine and 10 ml of dimethylformamide were added to the crude product, and they were stirred at room temperature for 4 days. The solvent was evaporated under reduced pressure, and 1 N aqueous sodium hydroxide solution was added to the residue. After the extraction with dichloromethane, the organic layer was washed with saturated aqueous NaCl solution and dried over anhydrous magnesium sulfate. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 125 mg.

H-NMR (DMSO-d6) δ 2.00 (2H, m), 3.50 (4H, br), 3.65 (2H, dt), 4.20 (2H, t), 7.32 (1H, d), 7.41 (1H, d), 7.44-7.52 (2H, m), 7.81 (2H, d), 8.04 (2H, d), 8.94 (1H, t), 10.00 (2H, s)

Step 2

Synthesis of N-[2-(3-amidinophenoxy)ethyl]-4-(1,4,5,6-tetrahydropyrimidine-2-yl)benzamide bistrifluoroacetate The title compound was obtained from 117 mg (0.25 mmol) of N-[2-(3-cyanophenoxy)ethyl]-4-(1,4,5,6-tetrahydropyrimidine-2-yl)benzamide in the same manner as that of step 3 in Example 3.
Yield: 37 mg (0.06 mmol) (24%).
MS (ESI, m/z) 366 (MH+)
H-NMR (DMSO-d6) δ 2.00 (2H, br), 3.50 (4H, br), 3.70 (2H, dt), 4.25 (2H, t), 7.30-7.45 (3H, m), 7.55 (1H, t), 7.82 (2H, d), 8.06 (2H, d), 9.03 (1H, br), 9.30 (2H, br), 9.40 (2H, br), 10.1 (2H, br).

Example 9

Synthesis of N-[2-(3-amidinophenoxy)ethyl]-4-(1-pyrrolidinecarbonyl)benzamide trifluoroacetate Step 1

Synthesis of N-[2-(3-cyanophenoxy)ethyl]-4-(1-pyrrolidinecarbonyl)benzamide

The title compound was obtained from 245 mg (0.79 mmol) of 4-[N-[2-(3-cyanophenoxy)ethyl]carbamoyl]benzoic acid, 62 mg (0.87 mmol) of pyrrolidine, 123 mg (0.79 mmol) of 1-hydroxybenzotriazole (hydrous, 87%) and 151 mg (0.79 mmol) of 1-(3-dimethylaminopropyl)-3-ethylcarbodiimide hydrochloride in the same manner as that of step 1 in Example 4.
Yield: 277 mg (0.76 mmol (96%)
H-NMR (CDCl3) δ 1.80-2.00 (4H, m), 3.30-3.70 (4H, m), 3.85 (2H, dt), 4.20 (2H, t), 7.14-7.28 (4H, m), 7.38 (1H, t), 7.48 (2H, d), 7.79 (2H, d)

Step 2

Synthesis of N-[2-(3-amidinophenoxy)ethyl]-4-(1-pyrrolidinecarbonyl)benzamide trifluoroacetate The title compound was obtained from 270 mg (0.74 mmol) of N-[2-(3-cyanophenoxy)ethyl]-4-(1-pyrrolidinecarbonyl)benzamide in the same manner as that of step 3 in Example 3.
Yield: 238 mg (0.48 mmol) (65%).
MS (ESI, m/z) 381 (MH+)
H-NMR (DMSO-d6) δ 1.75-1.90 (4H, m), 3.30-3.50 (4H, m), 3.70 (2H, dt), 4.20 (2H, t), 7.34 (1H, d), 7.39 (1H, d), 7.40 (1H, s), 7.54 (1H, t), 7.59 (2H, d), 7.91 (2H, d), 8.80 (1H, t), 9.10 (2H, br), 9.30 (2H, br).

Example 10

Synthesis of N-[2-(3-amidinophenoxy)ethyl]-4-[(E)-2-(pyridine-4-yl)vinyl]benzamide bistrifluoroacetate 412 mg (1.44 mmol) of methyl 4-(diethoxyphosphorylmethyl)benzoate was dissolved in 50 ml of tetrahydrofuran. 63 mg (1.44 mmol) of sodium hydride was added to the obtained solution under cooling with ice. After stirring for 30 minutes, the temperature was elevated to room temperature and the resultant mixture was stirred for 30 minutes. 154 mg (1.44 mmol) of pyridine-4-aldehyde was added to the mixture. After stirring for 20 hours, the reaction liquid was diluted with water and then extracted with ethyl acetate. The organic layer was washed with water and then with a saturated aqueous common salt solution. After drying over anhydrous magnesium sulfate, the solvent was evaporated, and 5 ml of concentrated hydrochloric acid was added to the residue. After stirring at 60° C. for 22 hours, the solvent was evaporated and the obtained residue was dissolved in 10 ml of dichloromethane. 0.58 ml (4.17 mmol) of triethylamine, 176 mg (0.92 mmol) of 1-(3-dimethylaminopropyl)-3-ethylcarbodiimide hydrochloride, 124 mg (0.92 mmol) of 1-hydroxybenzotriazole and 182 mg (0.83 mmol) of 3-(2-aminoethoxy)benzonitrile hydrochloride were added to the obtained solution, and the resultant mixture was stirred for 18 hours. The reaction liquid was diluted with water. After the extraction with ethyl acetate, the organic layer was washed with water, 1 N aqueous sodium hydroxide solution and saturated Aqueous NaCl solution successively and then dried over anhydrous magnesium sulfate. The solvent was evaporated, and the residue was treated in the same manner as that of step 6 in Example 1 to obtain the title compound.
Yield: 150 mg (0.24 mmol) (47%)
MS (ESI, m/z) 387 (MH+)
H-NMR (DMSO-d6) δ 3.70 (2H, dt), 4.26 (2H, t), 7.32-7.50 (3H, m), 7.54 (1H, dd), 7.66-7.84 (5H, m), 7.95 (2H, d), 8.64 (2H, d), 8.82-8.90 (1H, m), 9.18 (2H, br), 9.39 (2H, br).

Example 11

Synthesis of N-[2-(3-amidinophenoxy)ethyl]-4-(1H-pyrrole-1-yl)benzamide trifluoroacetate 210 mg(1 of 4-(1H-pyrrole-1-yl)benzoic acid was dissolved in 10 ml of dichloromethane. 0.47 ml (3.36 mmol) of triethylamine, 236 mg (1.24 mmol) of 1-(3-dimethylaminopropyl)-3-ethylcarbodiimide hydrochloride, 167 mg (1.24 mmol) of 1-hydroxybenzotriazole and 222 mg (1.12 mmol) of 3-(2-aminoethoxy)benzonitrile hydrochloride was added to the solution, and they were stirred for 18 hours. The reaction liquid was diluted with water. After the extraction with ethyl acetate, the organic layer was washed successively with water, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.
Yield: 243 mg (0.53 mmol) (47%).
MS (ESI, m/z) 349 (MH+)
H-NMR (DMSO-d6) δ 3.69 (4H, q), 3.63 (2H, dt), 4.24 (2H, t), 6.31 (2H, dd), 7.30-7.44 (3H, m), 7.45-7.60 (3H, m), 7.69 (2H, d), 7.95 (2H, d), 8.77 (1H, br), 9.12 (2H, br), 9.28 (2H, br).

Example 12

Synthesis of N-[2-(3-amidinophenoxy)ethyl]-4-cyclohexyloxybenzamide trifluoroacetate Step 1

Synthesis of ethyl 4-cyclohexyloxybenzoate 822 mg (4.95 mmol) of ethyl 4-hydroxybenzoate was dissolved in 20 ml of tetrahydrofuran. 545 mg (5.45 mmol) of cyclohexanol, 1.56 g (5.94 mmol) of triphenylphosphine and 202 mg (1.50 mmol) of diethyl azodicarboxylate were added to the solution, and they were stirred for 22 hours. The reaction liquid was diluted with water. After the extraction with ethyl acetate, the organic layer was washed with 1 N sodium hydroxide and then with saturated aqueous NaCl solution, and dried over anhydrous magnesium sulfate. The solvent was evaporated, and the residue was purified by the silica gel column chromatography to obtain the title compound.

Yield: 640 mg (2.58 mmol) (52%).

H-NMR (CDCl3) δ 1.32-1.44 (3H, m), 1.37 (3H, t), 1.48-1.63 (3H, m), 1.74-1.87 (2H, m), 1.93-2.20 (2H, m)-4.28-4.40 (1H, m), 4.34 (2H, q), 6.90 (2H, d), 7.97 (2H, d)

Step 2

Synthesis of N-[2-(3-amidinophenoxy)ethyl]-4-cyclohexyloxybenzamide trifluoroacetate 3 ml of 1 N sodium hydroxide and 10 ml of ethanol were added to 237 mg (0.95 mmol) of ethyl 4-cyclohexyloxybenzoate, and they were stirred for 20 hours. The reaction liquid was acidified with 1 N hydrochloric acid. After the extraction with ethyl acetate, the organic layer was dried over anhydrous magnesium sulfate. The solvent was evaporated, and the residue was dissolved in 10 ml of dichloromethane. 0.73 ml (5.25 mmol) of triethylamine, 200 mg (1.05 mmol) of 1-(3-dimethylaminopropyl)-3-ethylcarbodiimide hydrochloride, 141 mg (1.05 mmol) of 1-hydroxybenzotriazole and 188 mg (0.95 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 162 mg (0.77 mmol) (34%).

MS (ESI, m/z) 382 (MH+)

H-NMR (DMSO-d6) δ 1.30-1.58 (6H, m), 1.64-1.75 (2H, m), 1.88-1.98 (2H, m), 3.67 (2H, dt), 4.20 (2H, t), 4.37-4.48 (2H, m), 6.98 (2H, d), 7.33 (1H, d), 7.39 (2H, br), 7.53 (1H, dd), 7.81 (2H, d), 8.56 (1H, br), 9.08 (2H, br), 9.26 (2H, br).

Example 13

Synthesis of N-[2-(3-amidinophenoxy)ethyl]-4-diethylaminobenzamide trifluoroacetate 210 mg (1.09 mmol) of 4-diethylaminobenzoic acid was dissolved in 10 ml of dichloromethane. 0.76 ml (5.45 mmol) of triethylamine, 229 mg (1.20 mmol) of 1-(3-dimethylaminopropyl)-3-ethylcarbodiimide hydrochloride, 162 mg (1.20 mmol) of 1-hydroxybenzotriazole and 215 mg (1.09 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 410 mg (0.88 mmol) (80%).

MS (ESI, m/z) 355 (MH+)

H-NMR (DMSO-d6) δ 1.10 (6H, t), 3.38 (4H, q), 3.63 (2H, dt), 4.18 (2H, t), 6.66 (2H, d), 7.32-7.40 (3H, m), 7.53 (1H, dd), 7.71 (2H, d), 8.31 (1H, br), 9.04 (2H, br), 9.28 (2H, br)

Example 14

Synthesis of N-[2-(3-amidinophenoxy)ethyl]-4-[2-(pyridine-4-yl)ethyl]benzamide bistrifluoroacetate 50 mg (0.08 mmol) of N-[2-(3-amidinophenoxy)ethyl]-4-[(E)-2-(pyridine-4-yl)vinyl]benzamide bistrifluoroacetate was dissolved in 5 ml of methanol. 50 mg of palladium/carbon was added to the solution, and they were stirred in the presence of hydrogen for 20 hours. After the filtration through Celite, the solvent was evaporated. The residue wasp purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 7 mg (0.01 mmol) (14%).

MS (ESI, m/z) 389 (MH+)

H-NMR (DMSO-d6) δ 3.06 (2H, dt), 3.18 (2H, dt), 3.66 (2H, dt), 4.22 (2H, t), 7.29-7.45 (5H, m), 7.54 (1H, dd), 7.80 (4H, dd), 8.66-8.80 (3H, m), 9.30 (2H, br).

Example 15

Synthesis of N-[2-(3-amidinophenoxy)ethyl]-4-nitrobenzamide trifluoroacetate

MS (ESI, m/z) 329 (MH+)

190 mg (1.14 mmol) of 4-nitrobenzoic acid was dissolved in 10 ml of dichloromethane. 0.47 ml (3.42 mmol) of triethylamine, 239 mg (1.25 mmol) of 1-(3-dimethylaminopropyl)-3-ethylcarbodiimide hydrochloride, 169 mg (1.25 mmol) of 1-hydroxybenzotriazole and 225 mg (1.14 mmol) of 3-(2-aminoethoxy)benzonitrile hydrochloride were added to the solution, and they were stirred for 20 hours. The reaction liquid was diluted with water. After the extraction with ethyl acetate, the organic layer was washed with water, 1 N sodium hydroxide and saturated aqueous NaCl solution successively, and dried over anhydrous magnesium sulfite. The solvent was evaporated, and the residue was treated in the same manner as that of step 6 in Example 1 to obtain the title compound.

Yield: 290 mg (0.66 mmol) (58%).

MS (ESI, m/z) 329 (MH+)

H-NMR (DMSO-d6) δ 3.71 (2H, dt), 4.25 (2H, t), 7.34 (1H, dd), 7.40 (2H, br), 7.54 (1H, t), 8.09 (2H, d), 8.33 (2H, d), 9.10 (1H, br), 9.14 (2H, br), 9.28 (2H, br).

Example 16

Synthesis of N-[2-(3-amidinophenoxy)ethyl]-4-trifluoromethylbenzamide trifluoroacetate 194 mg (1.02 mmol) of 4-trifluoromethylbenzoic acid was dissolved in 10 ml of dichloromethane. 0.43 ml (3.06 mmol) of triethylamine, 215 mg (1.12 mmol) of 1-(3-dimethylaminopropyl)-3-ethylcarbodiimide hydrochloride, 152 mg (1.12 mmol) of 1-hydroxybenzotriazole and 203 mg (1.02 mmol) of 3-(2-aminoethoxy)benzonitrile hydrochloride were added to the solution, and they were stirred for 20 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 240 mg (0.56 mmol) (51%).
MS (ESI, m/z) 352 (MH+)
H-NMR (DMSO-d6) δ 3.69 (2H, dt), 4.24 (2H, t), 7.34 (1H, dd), 7.40 (2H, br), 7.54 (1H, dd), 7.86 (2H, d), 8.06 (2H, d), 8.99 (1H, br), 9.12 (2H, br), 9.28 (2H, br).

Example 17

Synthesis of N-[2-(3-amidinophenoxy)ethyl]-4-isopropylbenzamide trifluoroacetate Step 1

Synthesis of N-[2-(3-cyanophenoxy)ethyl]-4-isopropylbenzamide 283 mg (1.73 mmol) of 4-isopropylbenzoic acid was dissolved in 10 ml of dichloromethane. 1.2 ml (8.65 mmol) of triethylamine, 363 mg (1.90 mmol) of 1-(3-dimethylaminopropyl)-3-ethylcarbodiimide hydrochloride, 256 mg (190 mmol) of 1-hydroxybenzotriazole and 342 mg (1.24 mmol) of 3-(2-aminoethoxy)benzonitrile hydrochloride were added to the solution, and they were stirred for 18 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was purified by the silica gel column chromatography to obtain the title compound.

Yield: 440 mg (1.43 mmol) (83%).
H-NMR (CDCl3) δ 2.96 (6H, s), 3.62 (2H, dt), 4.17 (2H, t), 6.70 (2H, d), 7.32-7.43 (3H, m), 7.54 (1H, t), 7.74 (2H, d), 8.36 (1H, t), 9.05 (2H, br), 9.28 (2H, br)

Step 2

Synthesis of N-[2-(3-amidinophenoxy)ethyl]-4-isopropylbenzamide trifluoroacetate The title compound was obtained from 440 mg (1.43 mmol) of N-[2-(3-cyanophenoxy)ethyl]-4-isopropylbenzamide in the same manner as that of step 6 in Example 1.

Yield: 170 mg (0.39 mmol) (27%).
MS (ESI, m/z) 326 (MH+)
H-NMR (DMSO-d6) δ 1.20 (3H, s), 1.22 (3H, s), 2.83+3.03 (1H, m), 3.66 (2H, dt), 4.21 (2H, t), 7.33 (2H, d), 7.36-7.42 (2H, m), 7.53 (1H, dd), 7.79 (2H, d), 8.65 (1H, br), 9.16 (2H, br), 9.28 (2H, br).

Example 18

Synthesis of N-[2-(3-amidinophenoxy)ethyl]-4-(pyrrolidine-1-yl)benzamide trifluoroacetate Step 1

Synthesis of ethyl 4-(pyrrolidine-1-yl)benzoate 1.69 g (10.2 mmol) of ethyl 4-aminobenzoate was dissolved in 10 ml of benzene. 2.18 g (10.1 mmol) of 1,4-dibromobutane and 3.53 ml (20.2 mmol) of diisopropylethylamine were added to the solution, and they were heated under reflux for 48 hours. The reaction solution was diluted with water. After the extraction with ethyl acetate, the organic layer was washed with water and then with saturated Aqueous NaCl solution and dried over anhydrous magnesium sulfate. The solvent was evaporated to obtain the crude title compound.

Yield: 1.0 g (4.56 mmol) (46%).
H-NMR (CDCl3) δ 1.37 (3H, t), 1.92-2.18 (4H, m), 3.21-3.47 (3H, m), 4.31 (2H, q), 6.50 ((2H, d), 7.91 (2H, d).

Step 2

Synthesis of N-[2-(3-amidinophenoxy)ethyl]-4-(pyrrolidine-1-yl)benzamide trifluoroacetate 5 ml of concentrated hydrochloric acid was added to 343 mg (1.56 mmol) of ethyl 4-(pyrrolidine-1-yl)benzoate, and they were stirred at 60° C. for 20 hours. The solvent was evaporated and the residue was dissolved in 10 ml of dichloromethane. 1.09 ml (7.80 mmol) of triethylamine, 329 mg (1.72 mmol) of 1-(3-dimethylaminopropyl)-3-ethylcarbodiimide hydrochloride, 233 mg (1.72 mmol) of 1-hydroxybenzotriazole and 308 mg (1.56 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N aqueous sodium hydroxide solution and saturated aqueous NaCl solution successively, and dried over anhydrous magnesium sulfate. The solvent was evaporated, and the residue was treated in the same manner as that of step 6 in Example 1 to obtain the title compound.

Yield: 220 mg (0.43 mmol) (30%).
MS (ESI, m/z) 352 (MH+)
H-NMR (DMSO-d6) δ 1.96 (4H, t), 3.27 (4H, t), 3.62 (2H, dt), 4.20 (2H, t), 6.52 (2H, d), 7.38-7.39 (3H, m), 7.53 (1H, dd), 7.74 (2H, d), 8.38 (1H, br), 9.29 (2H, br), 9.37 (2H, br).

Example 19

Synthesis of 1-benzoyl-N-[2-(3-amidinophenoxy)ethyl]piperidine-4-carboxyamide trifluoroacetate Step 1

Synthesis of N-[2-(3-cyanophenoxy)ethyl]piperidine-4-carboxyamide 2.54 g (11.1 mmol) of (t-butoxycarbonyl)piperidine-4-carbxylic acid, 2.00 g (10.1 mmol) of 3-(2-aminoethoxy)benzonitrile, 1.4 ml (10.1 mmol) of triethylamine, 1.50 g (11.1 mmol) of 1-hydroxybenzotriazole and 2.13 g (11.1 mmol) of 1-(3-dimethylaminopropyl)-3-ethylcarbodiimide hydrochloride were stirred in 15 ml of dimethylformamide at room temperature overnight. After the treatment with ethyl acetate as the extractant in an ordinary manner, crude 1-(t-butoxycarbonyl)-N-[2-(3-cyanophenoxy)ethyl]piperidine-4-carboxyamide was obtained. This crude product was stirred in a liquid mixture of 5 ml (20.1 mmol) of dioxane containing 4 N hydrogen chloride and 10 ml of dioxane at room temperature for 4 hours. The solvent was evaporated, and 1 N aqueous sodium hydroxide solution was added to the residue. After the treatment with ethyl acetate as the extractant in an ordinary manner, the title compound was obtained.

Yield: 1.73 g (6.34 mmol) (63%).
MS (ESI, m/z) 274 (MH+)

H-NMR (CDCl3) δ 1.64 (2H, ddd), 1.84 (2H, d), 2.14 (2H, s), 2.28 (1H, tt), 2.64 (2H, ddd), 3.16 (2H, dt), 3.70 (2H, t), 4.06 (2H, t), 6.00 (1H, brs), 7.14 (1H, d), 7.15 (1H, s), 7.26 (1H, d), 7.38 (1H, t)

Step 2

Synthesis of 1-benzoyl-N-[2-(3-cyanophenoxy) ethyl]piperidine-4-carboxyamide 175 mg (1.43 mmol) of benzoic acid, 430 mg (1.58 mmol) of N-[2-(3-cyanophenoxy)ethyl]piperidine-4-carboxyamide, 0.22 ml (1.58 mmol) of triethylamine, 213 mg (158 mmol) of 1-hydroxybenzotriazole and 303 mg (1.58 mmol) of 1-(3-dimethylaminopropyl)-3-ethylcarbodiimide hydrochloride were stirred in 10 ml of dimethylformamide at room temperature overnight. After the treatment with ethyl acetate as the extractant in an ordinary manner, the title compound was obtained.

Yield: 458 mg (1.21 mmol) (85%).
MS (ESI, m/z) 378 (MH+)
H-NMR (CDCl3) δ 1.60-2.00 (5H, m), 2.38-2.40 (2H, m), 2.80-3.01 (2H, m), 3.62 (2H, t), 4.02 (2H, t), 6.40 (1H, brs), 7.15 (2H, brs), 7.25 (1H, d), 7.32-7.40 (6H, m)

Step 3

Synthesis of 1-benzoyl-N-[2-(3-amidinophenoxy) ethyl]piperidine-4-carboxyamide trifluoroacetate 458 mg (1.21 mmol) of 1-benzoyl-N-[2-(3-cyanophenoxy) ethyl]piperidine-4-carboxyamide was stirred in 10 ml of dioxane containing 4 N hydrogen chloride. 3.5 ml of ethanol containing 30% (w/v) of hydrogen chloride was added to the resultant mixture. After the stirring at room temperature for 3 days, the solvent was evaporated under reduced pressure. The residue was dissolved in 15 ml of 10% (w/v) solution of ammonia in ethanol, and the obtained solution was stirred at room temperature for 2 days. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 514 mg (1.01 mmol) (84%).
MS (ESI, m/z) 395 (MH+)
H-NMR (DMSO-d6) δ 1.52 (2H, t), 1.60-1.80 (2H, m), 2.38-2.42 (1H, m), 2.80-3.10 (2H, m), 3.45 (2H, t), 3.50-3.64 (1H, m), 4.08 (2H, t), 4.20-4.50 (1H, m), 7.28 (1H, d), 7.30-7.48 (5H, m), 7.30-7.48 (5H, m), 7.51 (1H, t), 8.12 (1H, t), 9.22 (4H, d).

Example 20

Synthesis of 1-benzenesulfonyl-N-[2-(3-amidinophenoxy)ethyl]piperidine-4-carboxyamide trifluoroacetate Step 1

Synthesis of 1-benzenesulfonyl-N-[2-(3-cyanophenoxy)ethyl]piperidine-4-carboxyamide 430 mg (1.58 mmol) of N-[2-(3-cyanophenoxy)ethyl]piperidine-4-carboxyamide was dissolved in 10 ml of dimethylformamide. 0.2 ml (1.43 mmol) of triethylamine and 253 mg (1.43 mmol) of benzenesulfonyl chloride were added to the solution at 0° C., and they were stirred for 13 hours. After the treatment with ethyl acetate as the extractant in an ordinary manner, the title compound was obtained.

Yield: 568 mg (1.37 mmol) (96%).
MS (ESI, m/z) 414 (MH+)
H-NMR (CDCl3) δ 1.80 (2H, dd), 1.90 (2H, td), 2.05 (1H, d), 2.40 (2H, td), 3.62 (2H, t), 3.76 (2H, dt), 4.05 (2H, t), 6.00 (1H, brs), 7.10 (2H, t), 7.23 (2H, d), 7.40 (2H, t), 7.58 (3H, td), 7.78 (2H, d)

Step 2

Synthesis of 1-benzenesulfonyl-N-[2-(3-amidinophenoxy)ethyl]piperidine-4-carboxyamide trifluoroacetate 568 mg (1.37 mmol) of 1-benzenesulfonyl-N-[2-(3-cyanophenoxy)ethyl]piperidine-4-carboxyamide was stirred in 10 ml of dioxane containing 4 N hydrogen chloride. 3.5 ml of ethanol containing 30% (w/v) of hydrogen chloride was added to the resultant mixture. After the stirring at room temperature for 3 days, the solvent was evaporated under reduced pressure. The residue was dissolved in 15 ml of 10% (w/v) solution of ammonia in ethanol, and the obtained solution was stirred at room temperature for 2 days. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 533 mg (0.98 mmol) (72%).
MS (ESI, m/z) 430 (MH+)
H-NMR (DMSO-d6) δ 1.52 (2H, t), 1.72 (2H, d), 2.05-2.18 (1H, m), 2.30 (2H, t), 3.42 (2H, t), 3.60 (2H, d), 4.05 (2H, t), 7.26 (1H, d), 7.34 (1H, s), 7.38 (1H, d), 7.50 (1H, t), 7.62 (1H, d), 7.63-7.77 (5H, m), 8.00 (1H, t), 9.22 (4H, d).

Example 21

Synthesis of 1-benzyl-N-[2-(3-amidinophenoxy) ethyl]-piperidine-4-carboxyamide bistrifluoroacetate 430 mg (1.58 mmol) of N-[2-(3-cyanophenoxy)ethyl]piperidine-4-carboxyamide was dissolved in 10 ml of dimethylformamide. 540 mg (3.93 mmol) of potassium carbonate and 0.16 ml (1.31 mmol) of benzyl bromide were added to the solution, and they were stirred at 50° C. for 13 hours. After the treatment with ethyl acetate as the extractant in an ordinary manner, crude 1-benzyl-N-[2-(3-cyanophenoxy)ethyl]piperidine-4-carboxyamide was obtained. The crude product was stirred in 10 ml of dioxane containing 4 N hydrogen chloride. 3.5 ml of ethanol containing 30% (w/v) of hydrogen chloride was added to the resultant mixture. After the stirring at room temperature for 3 days, the solvent was evaporated under reduced pressure. The residue was dissolved in 20 ml of 10% (w/v) solution of ammonia in ethanol, and the obtained solution was stirred at room temperature for 2 days. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 532 mg (0.875 mmol) (67%).
MS (ESI, m/z) 381 (MH+)
H-NMR (DMSO-d6) δ 1.70 (2H, t), 1.90 (2H, t), 2.40 (1H, t), 2.90 (2H, t), 3.20-3.40 (2H, m), 3.42 (2H, t), 4.08 (2H, t), 4.15 (2H, brs), 7.28 (1H, d), 7.33 (1H, s), 7.34 (1H, d), 7.40-7.60 (5H, m), 8.26 (1H, brs), 9.30 (4H, d), 9.63-9.80 (1H, m).

Example 22

Synthesis of N-[2-(3-amidinophenoxy)ethyl]-4-(piperidine-1-yl)benzamide trifluoroacetate Step 1

Synthesis of ethyl 4-(piperidine-1-yl)benzoate 2.16 g (13.1 mmol) of ethyl 4-aminobenzoate was dissolved in 20 ml of benzene. 2.97 g (13.0 mmol) of 1,5-dibromopentane and 4.53 ml (26.0 mmol) of diisopropylethylamine were added to the solution, and they were heated under reflux for 48 hours. The reaction liquid was diluted with water. After the extraction with ethyl acetate, the organic layer was washed with water and then with saturated aqueous NaCl solution, and dried over anhydrous magnesium sulfate. The solvent was evaporated to obtain the crude title compound.

Yield: 1.5 g (6.44 mmol) (49%).
H-NMR (CDCl3) δ 1.37 (3H, t), 1.52-1.77 (6H, m), 3.26-3.37 (4H, m), 4.32 (2H, q), 6.85 (2H, d), 7.91 (2H, d)

Step 2

Synthesis of N-[2-(3-amidinophenoxy)ethyl]-4-(piperidine-1-yl)benzamide trifluoroacetate 5 ml of concentrated hydrochloric acid was added to 311 mg (1.33 mmol) of ethyl 4-(piperidine-1-yl)benzoate, and they were stirred at 60° C. for 20 hours. The solvent was evaporated, and the residue was dissolved in 10 ml of dichloromethane. 0.93 ml (6.65 mmol) of triethylamine, 279 mg (1.46 mmol) of 1-(3-dimethylaminopropyl)-3-ethylcarbodiimide hydrochloride, 199 mg (1.46 mmol) of 1-hydroxybenzotriazole and 264 mg (1.33 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 310 mg (0.65 mmol) (48%).
MS (ESI, m/z) 367 (MH+)
H-NMR (DMSO-d6) δ 1.58 (6H, br), 3.28 (4H, br). 3.62 (2H, dt), 4.18 (2H, t), 6.94 (2H, d), 7.30-7.41 (3H, m), 7.53 (1H, dd), 7.73 (2H, d), 8.42 (1H, br), 9.03 (2H, br), 9.28 (2H, br).

Example 23

Synthesis of N-[2-(3-amidinophenoxy)ethyl]-1H-indole-5-carboxyamide trifluoroacetate 237 mg (1.47 mmol) of 1H-indole-5-carboxylic acid was dissolved in 5 ml of dichloromethane. 1.02 ml (7.35 mmol) of triethylamine, 309 mg (1.62 mmol) of 1-(3-dimethylaminopropyl)-3-ethylcarbodiimide hydrochloride, 219 mg (1.62 mmol) of 1-hydroxybenzotriazole and 291 mg (1.47 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 160 mg (0.29 mmol) (20%).
MS (ESI, m/z) 323 (MH+)
H-NMR (DMSO-d6) δ 3.68 (2H, dt), 4.23 (2H, t), 6.52 (1H, br), 7.26-7.63 (8H, m), 8.14 (1H, br), 8.50-8.59 (1H, m), 9.12 (1H, br), 9.20 (1H, br), 9.20 (2H, br).

Example 24

Synthesis of N-[2-(3-amidinophenoxy)ethyl]-1-(4-pyridyl)piperidine-4-carboxyamide bistrifluoroacetate Step 1

Synthesis of ethyl 1-(4-pyridyl)piperidine-4-carboxylate 4.0 g (26.6 mmol) of 4-chloropyridine hydrochloride, 4.2 g (26.6 mmol) of ethyl piperidine-4-carboxylate and 7.4 ml (53.2 mmol) of triethylamine were stirred in 100 ml of xylene at 130° C. for 24 hours. After the treatment with ethyl acetate as the extractant in an ordinary manner, the title compound was obtained.

Yield: 2.95 g (12.6 mmol) (47%).
MS (ESI, m/z) 235 (MH+)
H-NMR (CDCl3) δ 1.25 (3H, t), 1.71-1.85 (2H, m), 2.00 (2H, d), 2.50-2.60 (1H, m), 2.90 (2H, t), 3.81 (2H, d), 4.20 (2H, q), 6.66 (2H, d), 8.26 (2H, d)

Step 2

Synthesis of 1-(4-pyridyl)piperidine-4-carboxylic acid hydrochloride 2.95 g (12.6 mmol) of ethyl 1-(4-pyridyl)piperidine-4-carboxylate was stirred in 100 ml of dioxane. 50 ml of 1 N aqueous hydrochloric acid solution was added thereto, and the resultant mixture was stirred at 95° C. for 20 hours. The solvent was evaporated under reduced pressure to obtain the title compound.

Yield: 3.21 g (11.5 mmol) (91%).
MS (ESI, m/z) 207 (MH+)
H-NMR (DMSO-d6) δ 1.54 (2H, t), 1.90 (2H, d), 2.60-2.70 (1H, m), 3.30 (2H, t), 4.10 (2H, d), 7.19 (2H, d), 8.20 (2H, d).

Step 3

Synthesis of N-[2-(3-cyanophenoxy)ethyl]-1-(4-pyridyl)piperidine-4-carboxyamide 412 mg (1.48 mmol) of 1-(4-pyridyl)-piperidine-4-carboxylic acid hydrochloride, 350 mg (1.77 mmol) of 3-(2-aminoethoxy)benzonitrile, 0.25 ml (1.77 mmol) of triethylamine, 240 mg (1.77 mmol) of 1-hydroxybenzotriazole and 340 mg (1.77 mmol) of 1-(3-dimethylaminopropyl)-3-ethylcarbodiimide hydrochloride were stirred together in 3 ml of dimethylformamide at room temperature overnight. After the treatment with ethyl acetate as the extractant in an ordinary manner; the title compound was obtained.

Yield: 470 mg (1.34 mmol) (91%)

MS (ESI, m/z) 351 (MH+)

H-NMR (DMSO-d6) δ 1.52 (2H, dd), 1.68 (2H, d), 2.38-2.45 (1H, m), 2.80 (2H, t), 3.40 (2H, dd), 3.90 (2H, d), 4.08 (2H, t), 6.80 (2H, d), 7.31 (1H, d), 7.40 (1H, d), 7.42 (1H, s), 7.51 (1H, t), 8.09 (1H, t), 8.13 (2H, d).

Step 4

Synthesis of N-[2-(3-amidinophenoxy)ethyl]-1-(4-pyridyl)piperidine-4-carboxyamide bistrifluoroacetate 10 ml of ethanol containing 30% (w/v) of hydrogen chloride was added to 460 mg (1.31 mmol) of N-[2-(3-cyanophenoxy)ethyl]-1-(4-pyridyl)piperidine-4-carboxyamide, and the resultant mixture was stirred at room temperature for 7 days. The solvent was evaporated under reduced pressure, and the residue was dissolved in 10 ml of 10% (w/v) solution of ammonia in ethanol. The obtained solution was stirred at room temperature for 31 hours. The solvent was evaporated, and the obtained residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 402 mg (0.675 mmol) (52%).

MS (ESI, m/z) 368 (MH+)

H-NMR (DMSO-d6) δ 1.57 (2H, dd), 1.82 (2H, dd), 2.51-2.60 (1H, m), 3.10 (2H, t), 3.40 (2H, t), 4.09 (2H, t), 4.23 (2H, d), 7.18 (2H, d), 7.25 (1H, d), 7.20 (1H, s), 7.40 (1H, d), 7.57 (1H, t), 8.02 (2H, t), 9.17 (4H, t).

Example 25

Synthesis of 4-benzoyl-N-[2-(3-amidinophenoxy)ethyl]benzamide trifluoroacetate 257 mg (1.14 mmol) of 4-benzoylbenzoic acid was dissolved in 10 ml of dichloromethane. 0.48 ml (3.42 mmol) of triethylamine, 240 mg (1.25 mmol) of 1-(3-dimethylaminopropyl)-3-ethylcarbodiimide hydrochloride, 169 mg (1.25 mmol) of 1-hydroxybenzotriazole and 226 mg (1.14 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 20 mg (0.04 mmol) (4%)

MS (ESI, m/z) 388 (MH+)

H-NMR (DMSO-d6) δ 3.68 (2H, dt), 4.13 (2H, t), 7.27-7.44 (4H, m), 7.54 (1H, dd), 7.57 (1H, d), 7.59 (2H, d), 7.75 (2H, d), 7.81 (2H, d), 8.01 (1H, d), 8.91 (1H, t), 9.10 (2H, br), 9.29 (2H, br).

Example 26

Synthesis of N-[2-(3-amidinophenoxy)ethyl]-4-dimethylaminobenzamide trifluoroacetate 204 mg (1.24 mmol) of 4-dimethylaminobenzoic acid was dissolved in 10 ml of dichloromethane. 0.52 ml (3.72 mmol) of triethylamine, 260 mg (1.36 mmol) of 1-(3-dimethylaminopropyl)-3-ethylcarbodiimide hydrochloride, 184 mg (1.36 mmol) of 1-hydroxybenzotriazole and 246 mg (1.24 mmol) of 3-(2-aminoethoxy)benzonitrile hydrochloride were added to the solution, and they were stirred for 18 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 300 mg (0.68 mmol) (55%).

MS (ESI, m/z) 327 (MH+)

H-NMR (DMSO-d6) δ 2.96 (6H, s), 3.62 (2H, dt), 4.17 (2H, t), 6.70 (2H, d), 7.32-7.43 (3H, m), 7.54 (1H, dd), 7.74 (2H, d), 8.36 (1H, t), 9.05 (2H, br), 9.28 (2H, br).

Example 27

Synthesis of N-[2-(3-amidinophenoxy)ethyl]-3-(2-aminoethoxy)benzamidine tristrifluoroacetate 10 ml of ethanol containing 30% (w/v) of hydrogen chloride was added to 1.75 g (8.84 mmol) of 3-(2-aminoethoxy)benzonitrile, and the resultant mixture was stirred at room temperature for 22 hours. The solvent was evaporated under reduced pressure, and the residue was dissolved in 10 ml of 10% (w/v) solution of ammonia in ethanol. The obtained solution was stirred at room temperature for 31 hours. The solvent was evaporated, and the obtained residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 134 mg (0.195 mmol) (2.2%).

MS (ESI, m/z) 342 (MH+)

H-NMR (DMSO-d6) δ 3.20-3.23 (2H, m), 3.81-3.85 (2H, t), 4.24 (2H, dd), 4.38 (2H, dd), 7.25-7.40 (4H, m), 7.50-7.60 (4H, m), 8.18 (2H, brs), 9.60 (4H, t).

Example 28

Synthesis of N-[2-(3-amidinophenoxy)ethyl]-4-benzylbenzamide trifluoroacetate 780 mg (3.45 mmol) of 4-benzoylbenzoic acid was dissolved in 10 ml of acetic acid. 100 mg of palladium/carbon and 0.1 ml of concentrated sulfuric acid were added to the solution. The resultant mixture was stirred in the presence of hydrogen under medium pressure for 18 hours. The solvent was evaporated, and the residue was diluted with water. After the extraction with ethyl acetate, the organic layer was washed with water and dried over anhydrous magnesium sulfate. The solvent was evaporated, and the residue was dissolved in 10 ml of dichloromethane. 073 ml (5.2 mmol) of triethylamine, 220 mg (1.15 mmol) of 1-(3-dimethylaminopropyl)-3-ethylcarbodimide hydrochloride, 155 mg (1.15 mmol) of 1-hydroxybenzotriazole and 206 mg (1.04 mmol) of 3-(2-aminoethoxy)benzonitrile hydrochloride were added to the solution. The resultant mixture was stirred for 18 hours, and the mixture was diluted with water. After the extraction with ethyl acetate, the organic layer was successively washed with water, 1 N aqueous sodium hydroxide solution and saturated Aqueous NaCl solution. After drying over anhydrous magnesium sulfate, the solvent was evaporated, and the residue was treated in the same manner as that of step 6 in Example 1 to obtain the title compound.

Yield: 150 mg (0.31 mmol) (9%)
MS (ESI, m/z) 374 (MH+)
H-NMR (DMSO-d6) δ 3.65 (2H, dt), 3.99 (2H, s), 4.20 (2H, t), 7.15-7.41 (10H, m), 7.53 (1H, dd), 7.78 (2H, d), 8.66 (1H, t), 9.14 (2H, br), 9.27 (2H, br).

Example 29

Synthesis of N-[2-(3-amidinophenoxy)ethyl]-4-(piperazine-1-carbonyl)benzamide bistrifluoroacetate and ethyl 4-[N-[2-(3-amidinophenoxy)ethyl]carbamoyl]benzoate bistrifluoroacetate Step 1

Synthesis of t-butyl 4-(4-methoxycarbonylbenzoyl) piperazine-1-carboxylate 4.93 g (26.5 mmol) of t-butyl piperazine-1-carboxylate and 4.8 ml (34.5 mmol) of triethylamine were stirred in 50 ml of dimethylformamide under cooling with ice. 5.25 g (26.5 mmol) of monomethyl terephthalate chloride was slowly added to the resultant mixture, and they were stirred for 16 hours. The temperature was elevated to room temperature, and the reaction liquid was diluted with 1 N hydrochloric acid. After the extraction with ethyl acetate followed by the treatment in an ordinary manner, the title compound was obtained.

Yield: 7.08 g (20.3 mmol) (77%)
MS (ESI, m/z) 349 (MH+)
H-NMR (CDCl3) δ 1.47 (9H, s), 3.25-3.60 (6H, m), 3.60-3.80 (2H, m), 3.94 (3H, s), 7.46 (2H, d), 8.09 (2H, d)

Step 2

Synthesis of t-butyl 4-(4-carboxybenzoyl)piperazine-1-carboxylate 7.08 g (20.3 mmol) of t-butyl 4-(4-methoxycarbonylbenzoyl)piperazine-1-carboxylate was stirred in 40 ml of methanol and 40 ml of THF. 51 ml (51 mmol) of 1 N aqueous sodium hydroxide solution was added to the resultant solution, and they were stirred at 80° C. for 20 minutes. The reaction liquid was evaporated under reduced pressure and 1 N hydrochloric acid was added to the residue. After the extraction with ethyl acetate followed with the treatment in an ordinary manner, the title compound was obtained.

Yield: 6.78 g (20.3 mmol) (100%)
MS (ESI, m/z) 335 (MH+)
H-NMR (CDCl3) δ 1.41 (9H, s), 3.20-3.50 (6H, m), 3.52-3.70 (2H, m), 7.49 (2H, d), 8.01 (2H, d)

Step 3

Synthesis of t-butyl 4-[4-[N-[2-(3-cyanophenoxy) ethyl]carbamoyl]benzoyl]piperazine-1-carboxylate 1.60 g (4.8 mmol) of t-butyl 4-(4-carboxybenzoyl)piperazine-1-carboxylate, 1.58 g (8.0 mmol) of 3-(2-aminoethoxy) benzonitrile, 1.67 ml (12 mmol) of triethylamine, 650 mg (4.8 mmol) of 1-hydroxybenzotriazole and 920 mg (4.8 mmol) of 1-(3-dimethylaminopropyl)-3-ethylcarbodiimide hydrochloride were stirred in 20 ml of dimethylformamide at room temperature overnight. After the treatment with ethyl acetate as the extractant in an ordinary manner, the title compound was obtained.

Yield: 1.44 g (3.02 mmol) (63%).
MS (ESI, m/z) 479 (MH+)
H-NMR (CDCl3) δ 1.47 (9H, s), 3.20-3.60 (6H, m), 3.62-3.80 (2H, m), 3.91 (2H, t), 4.20 (2H, t), 6.60 (1H, brs), 7.15 (1H, d), 7.18 (1H, s), 7.28 (1H, d), 7.39 (1H, t), 7.49 (2H, d), 7.82 (2H, d)

Step 4

Synthesis of N-[2-(3-amidinophenoxy)ethyl]-4-(piperazine-1-carbonyl)benzamide bistrifluoroacetate and ethyl 4-[N-[2-(3-amidinophenoxy)ethyl]carbamoyl]benzoate bistrifluoroacetate 1.44 g (3.02 mmol) of t-butyl 4-[4-[N-[2-(3-cyanophenoxy)ethyl]carbamoyl]benzoyl]piperazine-1-carboxylate was stirred in 5 ml of dioxane containing 4 N hydrogen chloride. 5 ml of 30% (w/v) solution of hydrogen chloride in ethanol was added to the resultant mixture and they were stirred at room temperature for 3 days. The solvent was evaporated under reduced pressure. The residue was dissolved in 5 ml of 10% (w/v) solution of ammonia in ethanol, and the solution was stirred at room temperature for 22 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

N-[2-(3-Amidinophenoxy)ethyl]-4-(piperazine-1-carbonyl)benzamide bistrifluoroacetate Yield: 145 mg (0.23 mmol) (7.7%)
MS (ESI, m/z) 396 (MH+)
H-NMR (DMSO-d6) δ 3.10-3.23 (6H, m), 3.40-3.80 (2H, m), 3.65 (2H, t), 4.23 (2H, t), 7.33 (1H, d), 7.38 (2H, d), 7.50 (1H, d), 7.55 (2H, d), 7.95 (2H, d), 8.86 (1H, t), 9.00 (2H, brs), 9.20 (4H, d).

Ethyl 4-[N-[2-(3-amidinophenoxy)ethyl]carbamoyl]benzoate bistrifluoroacetate

MS (FAB, m/z) 356 (MH+)
H-NMR (DMSO-d6) δ 1.34 (3H, t), 3.68 (2H, dt), 4.23 (2H, t), 4.38 (2H, q), 7.35-7.40 (3H, m), 7.51 (1H, t), 7.97 (2H, d), 8.02 (2H, d), 8.92 (1H, t), 9.10 (2H, br), 9.26 (2H, br).

Example 30

Synthesis of 4-(4-acetimidoylpiperazine-1-carbonyl)-N-[2-(3-amidinophenoxy)ethyl]benzamide bistrifluoroacetate 597 mg (1.51 mmol) of N-[2-(3-amidinophenoxy)ethyl]-4-(piperazine-1-carbonyl)benzamide bistrifluoroacetate was dissolved in 12 ml of ethanol. 1 ml (7.8 mmol) of triethylamine and 380 mg (0.764 mmol) of ethyl acetimidate hydrochloride were added to the solution, and they were stirred at room temperature for 2 days. The solvent was evaporated.

The residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 23.3 mg (0.035 mmol) (2.3%).

MS (ESI, m/z) 437 (MH+)

H-NMR (DMSO-d6) δ 2.30 (3H, brs), 3.10-3.25 (2H, m), 3.40-3.80 (8H, m), 4.24 (2H, t), 7.30 (1H, d), 7.39 (2H, d), 7.52 (1H, d), 7.55 (2H, d), 7.95 (2H, d), 8.70 (1H, t), 8.87 (2H, brs), 9.22 (4H, d).

Example 31

Synthesis of N-[2-(3-amidinophenoxy)ethyl]-4-aminobenzamide bistrifluoroacetate

Step 1

Synthesis of N-[2-(3-cyanophenoxy)ethyl]-4-aminobenzamide 4.00 g (20.4 mmol) of 3-(2-aminoethoxy)benzonitrile hydrochloride was dissolved in 50 ml of dimethylformamide. 6.2 ml (43.8 mmol) of triethylamine, 2.00 g (14.6 mmol) of p-aminobenzoic acid, 1.98 g (14.6 mmol) of 1-hydroxybenzotriazole and 2.80 g (14.6 mmol) of 1-(3-dimethylaminopropyl)-3-ethylcarbodiimide hydrochloride were added to the solution at 0° C., and they were stirred at room temperature overnight. After the treatment with ethyl acetate as the extractant in an ordinary manner, the product was purified by the silica gel chromatography to obtain the title compound.

Yield: 1.69 g (6.01 mmol) (29%)

MS (ESI, m/z) 282 (MH+)

H-NMR (DMSO-d6) δ 3.58 (2H, q), 4.15 (2H, t), 5.61 (2H, br), 6.54 (2H, d), 7.32 (1H, d), 7.38 (1H, d), 7.44 (1H, s), 7.58 (2H, d), 7.95 (1H, s), 8.19 (1H, t)

Step 2

Synthesis of N-[2-(3-amidinophenoxy)ethyl]-4-aminobenzamide bistrifluoroacetate

The title compound was obtained from 110 mg (0.39 mmol) of N-[2-(3-cyanophenoxy)ethyl]-4-aminobenzamide in the same manner as that of step 6 in Example 1.

Yield: 45.5 mg (0.087 mmol) (22%).

MS, (ESI, m/z) 299 (MH+)

H-NMR (DMSO-d6) δ 3.21 (2H, br), 4.38 (2H, dd), 7.19 (1H, s), 7.34 (1H, d), 7.36 (1H, s), 7.42-7.60 (5H, m), 8.42 (3H, br), 9.34 (2H, br), 9.54 (2H, br).

Example 32

Synthesis of N-[2-(3-amidinophenoxy)ethyl]-4-(phenylmethanesulfonylamino)benzamide trifluoroacetate

Step 1

Synthesis of N-[2-(3-cyanophenoxy)ethyl]-4-(phenylmethanesulfonylamino)benzamide 670 mg (2.38 mmol) of 4-amino-N-[2-(3-cyanophenoxy)ethyl]benzamide was dissolved in 10 ml of dimethylformamide. 0.42 ml (2.38 mmol) of diisopropylethylamine and 454 mg (2.38 mmol) of α-toluenesulfonyl chloride were added to the solution at 0° C., and they were stirred for 13 hours. After the treatment with ethyl acetate as the extractant in an ordinary manner, the title compound was obtained.

Yield: 200 g (0.46 mmol) (19%).

MS (ESI, m/z) 436 (MH+)

H-NMR (CDCl3) δ 3.70 (2H, t), 4.10 (2H, t), 4.79 (2H, s), 7.10-7.19 (2H, m), 7.20-7.28 (2H, m), 7.30-7.40 (5H, m), 7.48 (2H, d), 7.51 (2H, d)

Step 2

Synthesis of N-[2-(3-amidinophenoxy)ethyl]-4-(phenylmethanesulfonylamino)benzamide trifluoroacetate 10 ml of 30% (w/v) solution of hydrogen chloride in ethanol was added to 261 mg (0.6 mmol) of N-[2-(3-cyanophenoxy)ethyl]-4-(phenylmethanesulfonylamino)benzamide, and they were stirred at room temperature for 3 days. The solvent was evaporated under reduced pressure. The residue was dissolved in 10 ml of 10% (w/v) solution of ammonia in ethanol, and the solution was stirred at room temperature for 31 hours. The solvent 110 was evaporated. The residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the intended compound.

Yield: 71.7 mg (0.127 mmol) (21%).

MS (ESI, m/z) 453 (MH+)

H-NMR (DMSO-d6) δ 3.69 (2H, t), 4.19 (2H, t), 4.53 (2H, s), 7.20-7.40 (11H, m), 7.84 (2H, d), 8.64 (1H, t), 9.10 (4H, d).

Example 33

Synthesis of N-[2-(3-amidinophenoxy)ethyl]-4-phenoxybenzamide trifluoroacetate 296 mg (1.4 mmol) of 4-phenoxybenzoic acid was dissolved in 10 ml of dichloromethane. 0.56 ml (4.2 mmol) of triethylamine, 295 mg (1.5 mmol) of 1-(3-dimethylaminopropyl)-3-ethylcarbodiimide hydrochloride, 208 mg (1.5 mmol) of 1-hydroxybenzotriazole and 277 mg (1.4 mmol) of 3-(2-aminoethoxy)benzonitrile hydrochloride were added to the solution, and they were stirred for 16 hours. The reaction liquid was diluted with water. After the extraction with ethyl acetate, the organic layer was washed with water, 1 N sodium hydroxide and saturated aqueous NaCl solution successively, and dried over anhydrous magnesium sulfate. The solvent was evaporated, and the residue was treated in the same manner as that of step 6 in Example 1 to obtain the title compound.

Yield: 360 mg (0.74 mmol) (53%).

MS (ESI, m/z) 376 (MH+)

H-NMR (DMSO-d6) δ 3.67 (2H, dt), 4.21 (2H, t), 7.01 (2H, d), 7.07 (2H, d), 7.18 (1H, d), 7.30-7.48 (5H, m), 7.53 (1H, dd), 7.88 (2H, d), 8.70 (1H, t), 9.23 (2H, br), 9.29 (2H, br).

Example 34

Synthesis of N-[2-(3-amidinophenoxy)ethyl]-2-[N-methyl-N-(pyridine-4-yl)amino)]acetamide bistrifluoroacetate

Step 1

Synthesis of ethyl [N-methyl-N-(pyridine-4-yl)amino]acetate 17 g (113 mmol) of 4-chloropyridine, 17 g (111 mmol) of ethyl (methylamino)acetate and 47 ml (333 mmol) of triethylamine were stirred in 350 ml of xylene at 130° C. for 24 hours. After the treatment with ethyl acetate as the extractant in an ordinary manner, the title compound was obtained.
Yield: 1.28 g (6.59 mmol) (6%)
H-NMR (CDCl3) δ 1.26 (3H, t), 3.09 (2H, s), 4.17 (3H, s), 4.24 (2H, q), 6.49 (2H, d), 8.25 (2H, d).

Step 2

Synthesis of [N-methyl-N-(pyridine-4-yl)amino]acetic acid hydrochloride 1.28 g (6.60 mmol) of ethyl [N-methyl-N-(pyridine-4-yl)amino]acetate was stirred in 30 ml of dioxane. 26 ml of 1 N hydrochloric acid was added to the resultant mixture, and they were stirred at 95° C. for 20 hours. The solvent was evaporated under reduced pressure to obtain the title compound.
Yield: 1.24 g (5.19 mmol) (79%).
H-NMR (DMSO-d6) δ 3.19 (3H, s), 4.48 (2H, s), 7.03 (2H, brs), 8.30 (2H, brs)

Step 3

Synthesis of N-[2-(3-amidinophenoxy)ethyl]-2-[N-methyl-N-(pyridine-4-yl)amino]acetamide bistrifluoroacetate 300 mg (1.26 mmol) of [N-methyl-N-(pyridine-4-yl)amino]acetic acid hydrochloride, 300 mg (1.51 mmol) of 3-(2-aminoethoxy)benzonitrile, 0.21 ml (1.51 mmol) of triethylamine, 205 mg (1.51 mmol) of 1-hydroxybenzotriazole and 290 mg (1.51 mmol) of 1-(3-dimethylaminopropyl)-3-ethylcarbodiimide hydrochloride were stirred in 1.3 ml of dimethylformamide at room temperature overnight. After the treatment with ethyl acetate as the extractant in an ordinary manner, the crude product was obtained. The crude product was stirred in 2 ml of dioxane containing 4 N hydrogen chloride. 2 ml of ethanol containing 30% (w/v) of hydrogen chloride was added to the reaction mixture. After stirring at room temperature for 7 days, the solvent was evaporated under reduced pressure. The residue was dissolved in 2 ml of 10% (w/v) solution of ammonia in ethanol. The solution was stirred at room temperature for 31 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 185 mg (0.281 mmol) (22%)
MS (ESI, m/z) 328 (MH+)
H-NMR (DMSO-d6) δ 3.24 (3H, s), 3.50 (2H, t), 4.10 (2H, t), 4.30 (2H, s), 6.99 (2H, brs), 7.31 (1H, d), 7.33 (1H, s), 7.40 (1H, d), 7.57 (1H, t), 8.25 (2H, brs), 8.56 (1H, t), 9.38 (4H, d).

Example 35

Synthesis of N-[2-(3-amidinophenoxy)ethyl]-4-[(Pyridine-4-yl)amino]benzamide, bistrifluoroacetate

Step 1

Synthesis of ethyl 4-[(pyridine-4-yl)amino]benzoate 4.57 g (31 mmol) of 4-chloropyridine and 5.03 g (31 mmol) of ethyl 4-aminobenzoate were dissolved in 100 ml of xylene. 12.7 ml (92 mmol) of triethylamine was added to the obtained solution and the resultant mixture was heated under reflux for 50 hours. The solvent was evaporated, and the residue was diluted with water. After the extraction with dichloromethane followed by washing with saturated Aqueous NaCl solution and drying over anhydrous magnesium sulfate, the solvent was evaporated and the residue was purified by the silica gel column chromatography to obtain the title compound.
Yield: 360 mg (1.49 mmol) (5%)
H-NMR (CDCl3) δ 1.40 (3H, t), 4.37 (2H, q), 6.95 (2H, dd), 7.19 (2H, dd), 8.03 (2H, dd), 8.38 (2H, dd).

Step 2

Synthesis of N-[2-(3-cyanophenoxy)ethyl]-4-[(pyridine-4-yl)amino]benzamide 180 mg (0.743 mmol) of ethyl 4-[(pyridine-4-yl)amino]benzoate was dissolved in 5 ml of concentrated hydrochloric acid, and the solution was stirred at 70° C. for 15 hours. The solvent was evaporated, and the residue was dissolved in 5 ml of dichloromethane. 0.23 ml (1.64 mmol) of triethylamine, 156 mg (0.82 mmol) of 1-(3-dimethylaminopropyl)-3-ethylcarbodiimide hydrochloride, 208 mg (0.82 mmol) of 1-hydroxybenzotriazole and 199 mg (0.82 mmol) of 3-(2-aminoethoxy)benzonitrile hydrobromide were added to the solution, and they were stirred for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was purified by the silica gel column chromatography to obtain the title compound.
Yield: 99 mg (0.27 mmol) (37%)
H-NMR (CD3OD) δ 3.78 (2H, dt), 4.23 (2H, t), 7.06 (1H, dd), 7.25-7.40 (6H, m), 7.85 (2H, dd), 8.19 (2H, dd)

Step 3

Synthesis of N-[2-(3-amidinophenoxy)ethyl]-4-[(pyridine-4-yl)amino]benzamide bistrifluoroacetate The title compound was obtained from 95 mg (0.27 mmol) of n-[2-(3-cyanophenoxy)ethyl]-4-[(pyridine-4-yl)amino]benzamide in the same manner as that of step 6 in Example 1.
Yield: 51 mg (0.08 mmol) (32%)
MS (ESI, m/z) 376 (MH+)
H-NMR (DMSO-d6) δ 3.68 (2H, dt), 4.24 (2H, t), 7.24 (2H, d), 7.30-7.37 (2H, m), 7.39-7.48 (3H, m), 7.53 (1H, dd), 7.98 (2H, d), 8.12-8.26 (1H, m), 8.34 (2H, d), 8.80-8.89 (1H, m), 9.16 (2H, br), 9.33 (2H, br).

Example 36

Synthesis of N-[2-(3-amidinophenoxy)ethyl]-4-(N-methylcarbamoyl)benzamide trifluoroacetate

Step 1

Synthesis of N-[2-(3-cyanophenoxy)ethyl]-4-(N-methylcarbamoyl)benzamide

The title compound was obtained from 150 mg (0.48 mmol) of 4-[N-[2-(3-cyanophenoxy)ethyl]carbamoyl]benzoic acid, 52 mg (0.48 mmol) of ethyl chloroformate, 0.5 ml (excess) of triethylamine and 30 ml of 40% aqueous monomethylamine solution in the same manner as that of step 2 in Example 3.

Yield: 87 mg (0.27 mmol) (56%)

H-NMR (CDCl3) δ3.05 (3H, d), 3.90 (2H, dt), 4.20 (2H, t), 6.20 (1H, br), 6.61 (1H, br), 7.15 (1H, d), 7.17 (1H, s), 7.27 (1H, d), 7.39 (1H, t), 7.83 (4H, s)

Step 2

Synthesis of N-[2-(3-amidinophenoxy)ethyl]-4-(N-methylcarbamoyl)benzamide trifluoroacetate The title compound was obtained from 83 mg (0.26 mmol) of [N-[2-(3-cyanophenoxy)ethyl]-4-(N-methylcarbamoyl)benzamide in the same manner as that of step 3 in Example 3.

Yield: 68 mg (0.15 mmol) (58%)

MS (ESI, m/z) 341 (MH+)

H-NMR (DMSO-d6) δ 2.80 (3H, d), 3.70 (2H, dt), 4.20 (2H, t), 7.34 (1H, d), 7.39 (1H, d), 7.40 (1H, s), 7.54 (1H, t), 7.88-7.94 (4H, m), 8.54 (1H, d), 8.82 (1H, t), 9.05 (2H, br), 9.28 (2H, br).

Example 37

Synthesis of N-[2-(3-amidinophenoxy)ethyl]-4-phenylbenzamide trifluoroacetate 132 mg (0.67 mmol) of 4-phenylbenzoic acid was dissolved in 10 ml of dichloromethane. 0.28 ml (2.0 mmol) of triethylamine, 141 mg (0.73 mmol) of 1-(3-dimethylaminopropyl)-3-ethylcarbodiimide hydrochloride, 59 mg (0.59 mmol) of 1-hydroxybenzotriazole and 132 mg (0.67 mmol) of 3-(2-aminoethoxy)benzonitrile hydrochloride were added to the solution, and they were stirred for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.

Yield: 30 mg (0.08 mmol) (8%)

MS (ESI, m/z) 360 (MH+)

H-NMR (DMSO-d6) δ 3.89 (2H, dt), 4.25 (2H, t), 7.31-7.45 (3H, m), 7.48 (2H, d), 7.52 (1H, d), 7.54 (1H, dd), 7.73 (2H, d), 7.78 (2H, d), 7.98 (2H, d), 8.82 (1H, t), 9.15 (2H, br), 9.33 (2H, br):

Example 38

Synthesis of N-[2-(3-amidinophenoxy)ethyl]-4-cyclohexylbenzamide trifluoroacetate 0.10 ml (0.67 mmol) of ethyl chloroformate was added to 136 mg (0.67 mmol) of 4-cyclohexylbenzoic acid, 5 ml of dimethylformamide and 0.07 ml (1.34 mmol) of N-methylmorpholine, and they were stirred for 30 minutes. 132 mg (0.67 mmol) of 3-(2-aminoethoxy)benzonitrile hydrochloride was added to the resultant mixture. The temperature was elevated to room temperature, and they were stirred for one hour. The reaction liquid was diluted with water. After the extraction with ethyl acetate, the organic layer was successively washed with water, 1 N hydrochloric acid and saturated aqueous NaCl solution, and then dried over anhydrous magnesium sulfate. The solvent was evaporated, and the residue was treated in the same manner as that of step 6 in Example 1 to obtain the title compound.

Yield: 40 mg (0.08 mmol) (12%)

MS (ESI, m/z) 366 (MH+)

H-NMR (DMSO-d6) δ 1.18-1.51 (5H, m), 1.45 (9H, s), 1.65-1.78 (5H, m), 2.52-2.63 (1H, m), 3.65 (2H, dt), 4.21 (2H, t), 7.25-7.37 (3H, m), 7.39 (2H, d), 7.54 (1H, dd), 7.79 (2H, d), 8.68 (1H, t), 9.15 (2H, br), 9.34 (2H, br).

Example 39

Synthesis of N-[2-(3-amidinophenoxy)ethyl]-4-(piperazine-1-sulfonyl)benzamide bistrifluoroacetate

Step 1

Synthesis of t-butyl 4-(4-methoxycarbonylbenzenesulfonyl)piperazine-1-carboxylate 10.67 g (57.3 mmol) of t-butyl piperazine-1-carboxylate was dissolved in 180 ml of dimethylformamide. 10 ml (57.3 mmol) of diisopropylethylamine and a solution of 17.3 g (57.3 mmol) of 4-iodobenzenesulfonyl chloride in 20 ml of dimethylformamide were added to the solution at 0° C., and the resultant mixture was stirred for 5 hours. After the treatment with ethyl acetate as the extractant in an ordinary manner, crude t-butyl 4-(4-iodobenzenesulfonyl)piperazine-1-carboxylate was obtained. This crude product was dissolved in 150 ml of dimethylformamide. 750 mg (3.5 mmol) of palladium (II) acetate, 55 ml (1.39 mol) of methanol and 19 ml (139 mmol) of triethylamine were added to the solution, and the resultant mixture was stirred under heating at 90° C. in the presence of carbon monoxide for 23 hours. After the treatment with ethyl acetate as the extractant in an ordinary manner, the crude title compound was obtained. This product was then purified by the silica gel column chromatography.

Yield: 4.30 g (11.2 mmol) (20%)

H-NMR (CDCl3) δ 1.42 (9H, s), 2.98 (4H, t), 3.51 (4H, t), 3.97 (3H, s), 7.82 (2H, d), 8.20 (2H, d).

Step 2

Synthesis of t-butyl 4-(4-carboxybenzenesulfonyl)piperazine-1-carboxylate 4.30 g (11.2 mmol) of t-butyl 4-(4-methoxycarbonylbenzenesulfonyl)-piperazine-1-carboxylate was stirred in 15 ml of methanol and 15 ml of THF. 17 ml of 1 N aqueous sodium hydroxide solution was added to the resultant mixture, and they were stirred at 60° C. overnight. The reaction liquid was evaporated under reduced pressure, and 1 N hydrochloric acid was added to the residue. After the treatment with ethyl acetate as the extractant in an ordinary manner, the title compound was obtained.

Yield: 1.41 g (3.8 mmol) (34%)
MS (ESI, m/z) 398 (M+Na+).
H-NMR (CDCl3) δ 1.41 (9H, s), 3.02 (4H, t), 3.52 (4H, t), 7.84 (2H, d), 8.24 (2H, d)

Step 3

Synthesis of t-butyl 4-[4-[N-[-2-(3-cyanophenoxy)ethyl]carbamoyl]benzenesulfonyl]piperazine-1-carboxylate 1.41 g (3.79 mmol) of t-butyl (4-carboxybenzenesulfonyl)piperazine-1-carboxylate was stirred in dimethylformamide. 1.3 ml (9.25 mmol) of triethylamine and 0.38 ml (3.95 mmol) of ethyl chloroformate were added to the resultant mixture. After stirring for 5 minutes followed by the addition of 1.02 g (4.61 mmol) of 3-(2-aminoethoxy)benzonitrile, the temperature was elevated to room temperature and they were stirred for 2 hours. After the dilution with 1 N hydrochloric acid and extraction with ethyl acetate, the product was treated in an ordinary manner to obtain the title compound.

Yield: 1.88 g (3.66 mmol) (97%)
MS (ESI, m/z) 537 (M+Na+)
H-NMR (CDCl3) δ 1.40 (9H, s), 2.97 (4H, t), 3.49 (4H, t), 3.91 (2H, dd), 4.19 (2H, t), 7.03 (1H, t), 7.14 (1H, d), 7.17 (1H, s), 7.27 (1H, d), 7.38 (1H, d), 7.78 (2H, d), 7.98 (2H, d)

Step 4

Synthesis of N-[2-(3-amidinophenoxy)ethyl]-4-(piperazine-1-sulfonyl)benzamide bistrifluoroacetate 1.88 g (3.66 mmol) of t-butyl [4-[N-[2-(3-cyanophenoxy)ethyl]carbamoyl]benzenesulfonyl]piperazine-1-carboxylate was stirred in 0.92 ml (3.66 mmol) of dioxane containing 4 N hydrogen chloride. 4 ml of ethanol containing 30% (w/v) of hydrogen chloride was added to the reaction mixture. After stirring at room temperature for 6 days, the solvent was evaporated under reduced pressure. The residue was dissolved in 5 ml of 10% (w/v) ammonia solution in ethanol. The solution was stirred at room temperature for 17 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 736 mg (1.12 mmol) (31%)
MS (ESI, m/z) 432 (MH+)
H-NMR (DMSO-d6) δ 3.12 (4H, d), 3.20 (4H, d), 3.70 (2H, dd), 4.22 (2H, t), 7.32 (1H, d), 7.38 (1H, s), 7.40 (1H, d), 7.54 (1H, t), 7.90 (2H, d), 8.14 (2H, d), 8.60 (1H, brs), 8.95 (1H, brs), 9.15 (4H, d).

Example 40

Synthesis of 4-(4-acetimidoylpiperazine-1-sulfonyl)-N-[2-(3-amidinophenoxy)ethyl]benzamide bistrifluoroacetate 240 mg (0.364 mmol) of N-[2-(3-amidinophenoxy)ethyl]-4-(piperazine-1-sulfonyl)benzamide bistrifluoroacetate was dissolved in 3 ml of ethanol. 0.27 ml (1.89 mmol) of triethylamine and 95 mg (0.764 mmol) of ethyl acetimidate hydrochloride were added to the solution, and they were stirred at room temperature for 6 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid; the fraction of the intended product was freeze-dried to obtain the title compound.

Yield: 113 mg (0.161 mmol) (44%)
MS (ESI, m/z) 473 (MH+)
H-NMR (DMSO-d6) δ 2.18 (3H, s), 3.05-3.18 (4H, m), 3.58-3.68 (4H, m), 3.75 (2H, t), 4.44 (2H, t), 7.31 (1H, d), 7.39 (1H, s), 7.41 (1H, d), 7.54 (1H, t), 7.88 (2H, d), 8.12 (2H, d), 8.68 (1H, s), 9.05 (1H, t), 9.28 (4H, d).

Example 41

Synthesis of N-[2-(3-amidinophenoxy)ethyl]-4-[(pyridine-4-yl)methyl]benzamide bistrifluoroacetate

Step 1

Synthesis of 4-(4-iodobenzyl)pyridine 5.0 g (30 mmol) of 4-benzylpyridine was dissolved in 30 ml of acetic acid. 3.53 ml (65 mmol) of concentrated sulfuric acid, 2.99 g (11.8 mmol) of iodine and 1.17 g (5.9 mmol) of sodium iodate were added to the solution, and the resultant mixture was stirred at 70° C. for 20 hours. After cooling, 0.15 g of sodium metaperiodate was added to the reaction mixture. After the distillation under reduced pressure, water was added to the residue, which was washed with dichloromethane. After the addition of 1 N aqueous sodium hydroxide solution followed by the extraction with dichloromethane twice, the solvent was evaporated. The residue was purified by the silica gel column chromatography to obtain the title compound.

Yield: 2.7 g (9.2 mmol) (31%)
H-NMR (CDCl3) δ 3.91 (2H, s), 6.92 (2H, d), 7.07 (2H, d), 7.64 (2H, d), 8.50 (2H, d)

Step 2

Synthesis of methyl 4-[(pyridine-4-yl)methyl]benzoate 1.03 g (3.49 mmol) of 4-(4-iodobenzyl)pyridine was dissolved in 15 ml of dimethylformamide. 39 mg (0.18 mmol) of palladium acetate, 0.97 ml (6.98 mmol) of triethylamine and 2.82 ml (69.8 mmol) of methanol were added to the solution, and the resultant mixture was stirred in the presence of carbon monoxide at 70° C. for 6 hours. The reaction solution was diluted with water. After the extraction with ethyl acetate, the organic layer was washed with water and then with a saturated Aqueous NaCl solution. The solvent was evaporated, and the residue was purified by the silica gel column chromatography to obtain the title compound.

Yield: 630 mg (2.78 mmol) (79%)
H-NMR (CDCl3) δ 3.91 (3H, s), 4.02 (2H, s), 7.08 (2H, d), 7.24 (2H, d), 7.98 (2H, d), 8.51 (2H, dd).

Step 3

Synthesis of N-[2-(3-cyanophenoxy)ethyl]-4-[(pyridine-4-yl)methyl]benzamide 262 mg (1.15 mmol) of methyl 4-[(pyridine-4-yl)methyl]benzoate was dissolved in 5 ml of concentrated hydrochloric acid. The solution was stirred at 70° C. for 15 hours. The solvent was evaporated, and the residue was dissolved in 5 ml of dichloromethane. 0.24 ml (1.73 mmol) of triethylamine, 243 mg (1.27 mmol) of 1-(3-dimethylaminopropyl)-3-ethylcarbodiimide hydrochloride, 172 mg (1.27 mmol) of 1-hydroxybenzotriazole and 308 mg (1.27 mmol) of 3-(2-aminoethoxy)benzonitrile hydrochloride were added to the solution, and they were stirred for 15 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was purified by the silica gel column chromatography to obtain the title compound.

Yield: 320 mg (0.90 mmol) (78%)

H-NMR (CDCl3) δ 3.89 (2H, dt), 4.02 (2H, s), 4.18 (2H, t), 6.46-6.57 (1H, m), 7.16 (2H, br), 7.25 (2H, d), 7.27 (2H, d), 7.39 (1H, dd), 7.74 (2H, d), 8.51 (2H, dd)

Step 4

Synthesis of N-[2-(3-amidinophenoxy)ethyl]-4-[(pyridine-4-yl)methyl]benzamide bistrifluoroacetate The title compound was obtained from 218 mg (0.61 mmol) of N-[2-(3-cyanophenoxy)ethyl]-4-[(pyridine-4-yl)methyl]benzamide in the same manner as that of step 6 in Example 1.

Yield: 170 mg (0.45 mmol) (74%)

MS (ESI, m/z) 375 (MH+)

H-NMR (DMSO-d6) δ 3.65 (2H, dt), 4.20 (2H, s), 4.21 (2H, t), 7.22-7.43 (5H, m), 7.47 (1H, dd), 7.60 (2H, d), 7.83 (2H, dd), 8.65 (3H, br), 9.08 (2H, r), 9.28 (2H, br).

Example 42

Synthesis of N-[2-(3-amidinophenoxy)ethyl]-4-[(piperidine-4-ylidene)methyl]benzamide bistrifluoroacetate

Step 1

Synthesis of methyl 4-(diethoxyphosphorylmethyl)benzoate 6.64 g (40 mmol) of triethyl phosphite was added to 2.29 g (10 mmol) of methyl 4-(bromomethyl)benzoate, and the resultant mixture was stirred at 150° C. for 19 hours. The mixture was purified by the silica gel column chromatography to obtain the title compound.

Yield: 2.6 g (9 mmol) (90%).

H-NMR (CDCl3) δ 1.25 (6H, t), 3.20 (2H, d), 4.02 (4H, dq), 7.39 (2H, d), 8.00 (2H, d)

Step 2

Synthesis of methyl 4-[[1-(t-butoxycarbonyl)piperidine-4-ylidene]methyl]benzoate 2.7 ml (20.0 mmol) of triethylamine, 1.84 g (8.45 mmol) of di-t-butyl carbonate and 30 ml of dichloromethane were added to 1.0 g (5.0 mmol) of 4-piperidone, and the resultant mixture was stirred for 19 hours. The reaction solution was diluted with water. After the extraction with dichloromethane, the organic layer was washed with 1 N aqueous hydrochloric acid solution and then with a saturated Aqueous NaCl solution, and then dried over anhydrous magnesium sulfate. The solvent was evaporated under reduced pressure to obtain 1-t-butoxycarbonyl-4-piperidone. Separately, 80 ml of tetrahydrofuran and methyl 4-(diethoxyphosphorylmethyl)benzoate were added to 241 mg (6.0 mmol) of sodium hydride under cooling with ice, and the resultant mixture was stirred for 30 minutes and then at room temperature for 30 minutes. Crude 1-t-butoxycarbonyl-4-piperidone obtained as described above was added to the mixture, and they were stirred for 20 hours. The reaction solution was diluted with water. After the extraction with ethyl acetate, the organic layer was washed with water and then with a saturated Aqueous NaCl solution, and then dried over anhydrous magnesium sulfate. The solvent was evaporated and the residue was purified by the silica gel column chromatography to obtain the title compound.

Yield: 1.26 g (3.8 mmol) (76%).

H-NMR (CDCl3) δ 1.48 (9H, s), 2.38 (2H, dd), 2.44 (2H, dd), 3.42 (2H, dd), 3.53 (2H, dd), 3.89 (3H, s), 6.39 (1H, br), 7.24 (2H, d), 7.98 (2H, d).

Step 3

Synthesis of N-[2-(3-cyanophenoxy)ethyl]-4-[(1-t-butoxycarbonylpiperidine-4-ylidene)methyl]benzamide 6 ml of 1 N sodium hydroxide and 18 ml of ethanol were added to 331 mg (1.0 mmol) of methyl 4-[(1-t-butoxycarbonylpiperidine-4-ylidene)methyl]benzoate, and they were stirred for 18 hours. The reaction liquid was acidified with 1 N hydrochloric acid. After the extraction with ethyl acetate, the organic layer was dried over anhydrous magnesium sulfate. The solvent was evaporated. 5 ml of dimethylformamide, 0.22 ml (2.0 mmol) of N-methylmorpholine and 0.10 ml (1.0 mmol) of ethyl chloroformate were added to the residue under cooling with ice, and they were stirred for 30 minutes. 243 mg (1.0 mmol) of 3-(2-aminoethoxy)benzonitrile hydrobromide was added to the resultant mixture at that temperature. The temperature was elevated to room temperature, and they were stirred for one hour. The reaction liquid was diluted with water. After the extraction with ethyl acetate, the organic layer was successively washed with water, 1 N hydrochloric acid and saturated aqueous NaCl solution, and then dried over anhydrous magnesium sulfate. The solvent was evaporated, and the residue was purified by the silica gel column chromatography to obtain the title compound.

Yield: 309 mg (0.67 mmol) (67%)

H-NMR (CDCl3) δ 1.48 (9H, s), 2.35 (2H, dd), 2.44 (2H, dd), 3.41 (2H, dd), 3.52 (2H, dd), 3.89 (2H, dt), 4.18 (2H, t), 6.37 (1H, br), 6.51-6.60 (1H, m), 7.17 (1H, br), 7.23-7.29 (1H, m), 7.39 (1H, dt), 7.74 (2H, d)

Step 4

Synthesis of N-[2-(3-amidinophenoxy)ethyl]-4-[(piperidine-4-ylidene)methyl]benzamide bistrifluoroacetate The title compound was obtained from 230 mg (0.50 mmol) of N-[2-(3-cyanophenoxy)ethyl]-4-[(1-t-butoxycarbonylpiperidine-4-ylidene)methyl]benzamide in the same manner as that of step 6 in Example 1.

Yield: 190 mg (0.31 mmol) (63%)
MS (ESI, m/z) 379 (MH+)
H-NMR (DMSO-d6) δ 2.42-2.68 (4H, m), 2.99-3.24 (4H, m), 3.68 (2H, dt), 4.22 (2H, t), 6.53 (1H, s), 7.24-7.43 (6H, m), 7.56 (1H, t), 7.88 (2H, d), 8.77 (3H, br), 9.17 (2H, br), 9.30 (2H, br).

Example 43

Synthesis of N-[2-(3-amidinophenoxy)ethyl]-4-[(piperidine-4-yl)methyl]benzamide bistrifluoroacetate Step 1

Synthesis of N-[2-(3-cyanophenoxy)ethyl]-4-[(1-t-butoxycarbonylpiperidine-4-yl)]methyl]benzamide 95 mg of 10% palladium/carbon and 20 ml of methanol were added to 434 mg (1.31 mmol) of methyl 4-[(1-butoxycarbonylpiperidine-4-ylidene)methyl]benzoate, and the resultant mixture was stirred in the presence of hydrogen for 15 hours. After the filtration through Celite, the solvent was evaporated. 4 ml of 1 N aqueous sodium hydroxide solution and 6 ml of ethanol were added to the residue, and the resultant mixture was stirred for 18 hours. The reaction liquid was acidified with 1 N aqueous hydrochloric acid. After the extraction with ethyl acetate, the extract was dried over anhydrous magnesium sulfate and the solvent was evaporated. 5 ml of dimethylformamide, 0.22 ml (2.00 mmol) of N-methylmorpholine and 0.10 ml (1.0 mmol) of ethyl chloroformate were added to the residue under cooling with ice. After stirring for 30 minutes, 243 mg (1.0 mmol) of 3-(2-aminoethoxy) benzonitrile hydrobromide was added at that temperature. The resultant mixture was stirred at room temperature for 1 hour. The reaction liquid was diluted with water. After the extraction with ethyl acetate, the organic layer was washed with water, 1 N aqueous hydrochloric acid solution and saturated aqueous common salt solution successively, and then dried over anhydrous magnesium sulfate. The solvent was evaporated, and the residue was purified by the silica gel column chromatography to obtain the title compound.

Yield: 296 mg (0.64 mmol) (49%).
H-NMR (CDCl3) δ 1.10-1.19 (2H, m), 1.45 (9H, s), 1.58-1.78 (3H, m), 2.59 (2H, d), 2.61-2.69 (2H, m), 3.89 (2H, dt), 4.00-4.13 (2H, m), 4.18 (2H, t), 6.46-6.55 (1H, m), 7.17 (2H, br), 7.18 (2H, d), 7.27 (1H, dt), 7.71 (2H, d).

Step 2

Synthesis of N-[2-(3-amidinophenoxy)ethyl]-4-[(piperidine-4-yl)methyl]benzamide bistrifluoroacetate The title compound was obtained from 230 mg (0.50 mmol) of N-[2-(3-cyanophenoxy)ethyl]-4-[(1-t-butoxycarbonylpiperidine-4-yl)methyl]benzamide in the same manner as that of step 6 in Example 1.

Yield: 190 mg (0.31 mmol) (63%)
MS (ESI, m/z) 381 (MH+)
H-NMR (DMSO-d6) δ 1.21-1.41 (2H, m), 1.62-1.74 (2H, m), 1.77-1.93 (1H, m), 2.59 (2H, d), 2.70-2.89 (2H, m), 3.05-3.32 (2H, m), 3.66 (2H, dt), 4.21 (2H, t), 7.28 (2H, d), 7.30-7.36 (1H, m), 7.37-7.43 (2H, m), 7.54 (1H, dd), 7.81 (2H, d), 8.18-8.36 (1H, m), 8.51-8.64 (2H, m), 8.68 (1H, t), 9.22 (2H, br), 9.29 (2h, br).

Example 44

Synthesis of N-[2-(3-amidinophenoxy)ethyl]-4-[(1-acetimidoylpiperidine-4-ylidene)methyl]benzamide bistrifluoroacetate 9.9 mg (0.02 mmol) of N-[2-(3-amidinophenoxy)ethyl]-4-[(piperidine-4-ylidene)methyl]benzamide bistrifluoroacetate was dissolved in 2 ml of ethanol. 0.02 ml (0.15 mmol) of triethylamine and 4 mg (0.03 mmol) of ethyl acetimidate hydrochloride were added to the solution, and they were stirred for 15 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 8.4 mg (0.01 mmol) (79%)
MS (ESI, m/z) 420 (MH+)
H-NMR (DMSO-d6) δ 2.31 (3H, s), 2.54-2.68 (3H, m), 2.68-2.75 (1H, m), 3.55-3.66 (4H, m), 3.67 (2H, dt), 4.22 (2H, t), 6.50 (H, br), 7.29-7.44 (5H, m), 7.53 (1H, dd), 7.86 (2H, d), 8.56 (1H, br), 8.74 (1H, t), 9.16 (1H, br), 9.20 (2H, br), 9.28 (2H, br).

Example 45

Synthesis of N-[2-(3-amidinophenoxy)ethyl]-4-[(1-acetimidoylpiperidine-4-yl)methyl]benzamide bistrifluoroacetate 10 mg (0.02 mmol) of N-[2-(3-amidinophenoxy)ethyl]-4-[(piperidine-4-ylidene)methyl]benzamide bistrifluoroacetate was dissolved in 2 ml of ethanol. Then the same procedure as that of Example 44 was repeated except that 0.02 ml (0.15 mmol) of triethylamine and 4 mg (0.03 mmol) of ethyl acetimidate hydrochloride were used to obtain the title compound.

Yield: 6 mg (0.01 mmol) (56%)
MS (ESI, m/z) 422 (MH+)
H-NMR (DMSO-d6) δ 1.21-1.35 (2H, m), 1.59-1.62 (2H, m), 1.83-2.00 (1H, m), 2.24 (3H, s), 2.59 (2H, d), 2.94-3.20 (2H, m), 3.66 (2H, dt), 3.80-3.92 (1H, m), 3.96-4.08 (2H, m), 4.21 (2H, t), 7.24-7.43 (5H, m), 7.53 (1H, dd), 7.81 (2H, d), 8.48 (1H, br), 8.68 (1H, t), 9.03 (1H, br), 9.15 (2H, br), 9.28 (2H, br).

Example 46

Synthesis of N-[2-(3-amidinophenoxy)ethyl]-4-(2-1H-imidazolyl)benzamide bistrifluoroacetate Step 1

Synthesis of ethyl 4-(2-1H-imidazolyl)benzoate 500 mg (2.3 mmol) of ethyl 4-(2-imidazoline-2-yl)benzoate and 500 mg of 10% palladium/carbon were heated in 20 ml of toluene under reflux in argon atmosphere for 9 hours. The reaction liquid was diluted with ethyl acetate and filtered through Celite. The filtrate was concentrated to obtain the title compound.

Yield: 332 mg (1.5 mmol) (67%)
H-NMR (CDCl3) δ 1.40 (3H, t), 4.40 (2H, q), 7.20 (2H, s), 7.90 (2H, d), 8.10 (2H, d).

Step 2

Synthesis of 4-(2-1H-imidazolyl)benzoic acid hydrochloride 160 mg (0.74 mmol) of ethyl 4-(2-1H-imidazolyl)benzoate was heated under reflux in 4 ml of hydrochloric acid and 8 ml of acetic acid Three hours after, the solvent was evaporated to obtain the title compound.

Yield: 157 mg (0.70 mmol) (94%)

H-NMR (DMSO-d6) δ 7.82 (2H, s), 8.15 (2H, d), 8.25 (2H, d)

Step 3

Synthesis of N-[2-(3-amidinophenoxy)ethyl]-4-(2-1H-imidazolyl)benzamide bistrifluoroacetate 155 mg (0.7 mmol) of 4-(2-1H-imidazolyl)benzoic acid hydrochloride, 195 mg (0.8 mmol) of 3-(2-aminoethoxy)benzonitrile hydrobromide, 153 mg (0.8 mmol) of 1-(3-dimethylaminopropyl)-3-ethylcarbodiimide hydrochloride, 124 mg (0.8 mmol) of 1-hydroxybenzotriazole hydrate (hydrous, 87%) and 300 mg (3.0 mmol) of triethylamine were stirred in dichloromethane at a temperature ranging from room temperature to 40° C. for 2 days. The solvent was evaporated. 1 N aqueous sodium hydroxide solution was added to the residue. After the extraction with ethyl acetate followed by the washing with saturated aqueous NaCl solution and drying over anhydrous magnesium sulfate, the solvent was evaporated. The residue was suspended in chloroform. After the filtration, the filter cake was treated in the same manner as that of step 6 in Example 1 to obtain the title compound.

Yield: 78 mg (0.14 mmol) (20%).

MS (ESI, m/z) 350 (MH+)

H-NMR (DMSO-d6) δ 3.70 (2H, dt), 4.23 (2H, t), 7.34 (1H, d), 7.40 (1H, d), 7.41 (1H, s), 7.54 (1H, t), 7.72 (2H, s), 8.06 (2H, d), 8.16 (2H, d), 8.96 (1H, t), 9.16 (2H, br), 9.32 (2H, br).

Example 47

Synthesis of N-[2-(3-amidinophenoxy)ethyl]-4-acetylbenzamide trifluoroacetate 223 mg (1.36 mmol) of 4-acetylbenzoic acid was dissolved in 10 ml of dichloromethane. 0.95 ml (6.80 mmol) of triethylamine, 286 mg (1.50 mmol) of 1-(3-dimethylaminopropyl)-3-ethylcarbodiimide hydrochloride, 202 mg (1.50 mmol) of 1-hydroxybenzotriazole and 269 mg (1.36 mmol) of 3-(2-aminoethoxy)benzonitrile hydrochloride were added to the solution, and they were stirred for 16 hours. The reaction liquid was diluted with water. After the extraction with ethyl acetate, the organic layer was washed successively with water, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.

Yield: 188 mg (0.58 mmol) (43%)

MS (ESI, m/z) 326 (MH+)

H-NMR (DMSO-d6) δ 2.62 (3H, s), 3.70 (2H, dt), 4.24 (2H, t), 7.31-7.42 (3H, m), 7.53 (1H, dd), 8.00 (4H, dd), 8.93 (1H, br), 9.11 (2H, br), 9.28 (2H, br).

Example 48

Synthesis of N-[2-(3-amidinophenoxy)ethyl]-4-chlorobenzamide trifluoroacetate 205 mg (1.02 mmol) of 3-(2-aminoethoxy)benzonitrile hydrochloride was dissolved in 10 ml of dichloromethane. 0.44 ml (3.12 mmol) of triethylamine and 217 mg (1.04 mmol) of 4-chlorobenzoyl chloride were added to the solution under cooling with ice. After stirring for 30 minutes, the temperature was elevated to room temperature, and they were stirred for 3 hours. The reaction liquid was diluted with water. After the extraction with ethyl acetate, the organic layer was successively washed with 1 N hydrochloric acid, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.

Yield: 170 mg (0.39 mmol) (38%)

MS (ESI, m/z) 317 (MH+)

H-NMR (DMSO-d6) δ 3.69 (2H, dt), 4.24 (2H, t), 7.34 (1H, dd), 7.40 (2H, br), 7.54 (1H, dd), 7.86 (2H, d), 8.06 (2H, d), 8.99 (1H, br), 9.12 (2H, br), 9.28 (2H, br).

Example 49

Synthesis of N-[2-(3-amidinophenoxy)ethyl]-4-guanidnobenzamide bistrifluoroacetate

Step 1

Synthesis of 3-hydroxybenzamidine hydrochloride 5 g (42 mmol) of 3-hydroxybenzonitrile was dissolved in 50 ml of ethanol containing 30% (w/v) of hydrogen chloride, and the solution was stirred at room temperature overnight. The solvent was evaporated, and the residue was dissolved in 50 ml of 30% (w/v) solution of ammonia in ethanol. The obtained solution was stirred at room temperature overnight, and the solvent was evaporated to obtain the title compound.

Yield 4.4 g (25.5 mmol) (61%).

Step 2

Synthesis of N-t-butoxycarbonyl-3-hydroxybenzamidine 1 g (5.8 mmol) of 3-hydroxybenzamidine hydrochloride, 1.27 g (5.8 mmol)) of di-t-butyl dicarbonate, 24 mg (0.2 mmol) of 4-(dimethylamino)pyridine and 1.30 g (12.8 mmol) of triethylamine were dissolved in 20 ml of dimethylformamide, and the obtained solution was stirred at room temperature overnight. The reaction liquid was poured into water. After the extraction with ethyl acetate, the organic layer was extracted with 1 N aqueous sodium hydroxide solution. The aqueous layer was made weakly alkaline with concentrated hydrochloric acid and then treated with ethyl acetate as the extractant in an ordinary manner to obtain the title compound.

Yield: 458 mg (1.94 mmol) (33%)

H-NMR (DMSO-d6) δ 1.45 (9H, s), 6.95 (1H, d), 7.25 (1H, t), 7.35 (1H, d), 7.38 (1H, s), 8.90 (2H, br), 9.65 (1H, br).

Step 3

Synthesis of 3-(2-aminoethoxy)benzamidine dihydrochloride

N-t-Butoxycarbonyl-3-[2-(t-butoxycarbonylamino) ethoxy]benzamidine was obtained from N-t-butoxycarbonyl-3-hydroxybenzamidine and t-butyl-N-(2-bromoethyl)carbamate in the same manner as that of step 2 in Example 1. This product was not purified and treated in the same manner as that of step 3 in Example 1 to obtain the title compound.

H-NMR (DMSO-d6) δ 3.20 (2H, t), 4.35 (2H, t), 7.34 (1H, d), 7.44-7.60 (3H, m), 8.36 (3H, br), 9.28 (2H, r), 9.50 (2H, br).

Step 4

Synthesis of N-[2-(3-amidinophenoxy)ethyl]-4-guanidinobenzamide bistrifluoroacetate 152 mg (0.7 mmol) of 4-guanidinobenzoic acid hydrochloride, 166 mg (0.66 mmol) of 3-(2-aminoethoxy)benzamidine dihydrochloride, 142 mg (1.4 mmol) of triethylamine, 110 mg (0.7 mmol) of 1-hydroxybenzotriazole (hydrous, 87%) and 134 mg (0.7 mmol) of 1-(3-dimethylaminoproyl)-3-ethylcarbodiimide hydrochloride were stirred in 3 ml of dimethylformamide at room temperature overnight. The solvent was evaporated under reduced pressure, and the obtained residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 172 mg (0.3 mmol) (46%).

MS (ESI, m/z) 341 (MH+)

H-NMR (DMSO-d6) δ 3.65 (2H, dt), 4.20 (2H, t), 7.28-7.42 (5H, m), 7.53 (1H, t), 7.70 (4H, brs), 7.93 (2H, d), 8.78 (1H, t), 9.20 (2H, br), 9.30 (2H, br), 10.15 (1H, s).

Example 50

Synthesis of N-[2-(3-amidinophenoxy)ethyl]-4-(1-phenoxycarbonyl-4-piperidyloxy)benzamide trifluoroacetate N-[2-(3-cyanophenoxy)ethyl]-4-(1-t-butoxycarbonyl-4-piperidyloxy)benzamide was reacted with dioxane containing 4 N hydrogen chloride and ethanol to obtain ethyl 3-[2-[4-(4-piperidyloxy)benzoylamino]ethoxy]benzimidate dihydrochloride. 96.4 mg (0.221 mmol) of this compound was reacted with 70.0 mg (0.447 mmol) of phenyl chloroformate and 742 mg (6.07 mmol) of diisopropylethylamine in 15 ml of dichloromethane. After converting the product into the amidine compound with ethanol containing 10% (w/v) of ammonia in an ordinary manner, the product was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 54.5 mg (0.0885 mmol) (40.0%)

MS (ESI, m/z) 503 (MH+)

H-NMR (DMSO-d6) δ 1.60-2.07 (4H, m), 3.23-4.85 (6H, m), 4.10-4.21 (2H, m), 4.63-4.80 (1H, m), 7.03-7.58 (11H, m), 7.82 (2H, d), 8.55 (1H, t), 9.05 (2H, brs), 9.23 (2H, brs).

Example 51

Synthesis of (3S)-3-(4-amidinobenzoylamino)-4-(3-amidinophenoxy)butyric acid bistrifluoroacetate and ethyl (3S)-3-(4-amidinobenzoylamino)-4-(3-amidinophenoxy)butyrate bistrifluoroacetate

Step 1

Synthesis of benzyl (3S)-3-t-butoxycarbonylamino-4-(3-cyanophenoxy)butyrate 970 mg (3.0 mmol)) of β-benzyl N-t-butoxycarbonyl-L-aspartate and 0.42 ml (3.0 mmol) of triethylamine were dissolved in 15 ml of tetrahydrofuran. 0.29 ml (3.0 mmol) of ethyl chloroformate was added to the solution under cooling with ice, and they were stirred for 20 minutes. The precipitate thus formed was removed by the suction filtration. 3 g of ice and 227 mg (6.0 mmol) of sodium borohydride were added to the filtrate under cooling with ice, and they were stirred for 1.5 hours. 10 ml of 1 N aqueous hydrogen chloride solution was added to the reaction mixture, and they were stirred at room temperature for additional one hour. After the treatment with ethyl acetate as the extractant in an ordinary manner, an oily residue was obtained, which was dissolved in 12 ml of tetrahydrofuran. 288 mg (2.41 mmol) of 3-cyanophenol, 690 mg (2.63 mmol) of triphenylphosphine and 1.05 g (2.41 mmol) of diethyl azodicarboxylate (40% solution in toluene) were added to the solution, and they were stirred at room temperature overnight. The solvent was evaporated, and the residue was purified by the silica gel column chromatography to obtain the title compound.

Yield: 455 mg (1.11 mmol) (37%)

H-NMR (CDCl3) δ 1.46 (9H, s), 2.79 (2H, d), 4.00 (1H, dd), 4.06 (1H, dd), 4.41 (1H, br), 5.13 (2H, s), 5.56 (1H, br), 7.05-7.18 (4H, m), 7.21-7.38 (5H, m)

Step 2

Synthesis of benzyl (3S)-3-(4-cyanobenzoylamino)-4-(3-cyanophenoxy)butyrate 455 mg (1.1 mmol)) of benzyl (3S)-t-butoxycarbonylamino-4-(3-cyanophenoxy)butyrate was dissolved in 5 ml of 4 N solution of hydrogen chloride in dioxane. The solution was stirred at 0° C. for 6 hours. The solvent was evaporated, and the oily residue was dissolved in 5 ml of dichloromethane. 276 mg (1.67 mmol) of 4-cyanobenzoyl chloride and 0.31 ml (2.22 mmol) of triethylamine were added to the solution under cooling with ice, and they were stirred at room temperature overnight. After the treatment with ethyl acetate as the extractant in an ordinary manner, the crude product was obtained, which was purified by the silica gel column chromatography to obtain the title compound.

Yield: 260 mg (0.59 mmol) (53%).

H-NMR (CDCl3) δ 2.86 (1H, dd), 2.95 (1H, dd), 4.12 (1H, dd), 4.20 (1H, dd), 4.85 (1H, br), 5.16 (2H, s), 7.09 (1H, d), 7.11 (1H, dd), 7.24-7.40 (7H, m), 7.72 (2H, d), 7.83 (2H, d)

Step 3

Synthesis of ethyl (3S)-3-(4-amidinobenzoylamino)-4-(3-amidinophenoxy)butyrate bistrifluoroacetate 260 mg (0.59 mmol) of benzyl (3S)-3-(4-cyanobenzoylamino)-4-(3 cyanophenoxy)butyrate was added to 5 ml of ethanol containing 30% (w/v) of hydrogen chloride, and they were stirred at room temperature overnight. Then, the solvent was evaporated under reduced pressure, and the residue was dissolved in 5 ml of 10% (w/v) solution of ammonia in ethanol at room temperature. The solution was stirred at room temperature for two nights. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 113 mg (0.176 mmol) (30.0%)
MS (ESI, m/z) 412 (MH+)
H-NMR (DMSO-d6) δ 1.15 (3H, t), 2.82 (2H, d), 4.07 (2H, q), 4.12 (1H, dd), 4.24 (1H, dd), 4.72 (1H, br), 7.33 (1H, d), 7.39 (1H, s), 7.40 (1H, d), 7.54 (1H, dd), 7.91 (2H, d), 8.02 (2H, d), 8.84 (1H, d), 9.16 (2H, s), 9.28 (4H, s), 9.42 (2H, s).

Step 4

Synthesis of (3S)-3-(4-amidinobenzoylamino)-4-(3-amidinophenoxy)butyric acid bistrifluoroacetate 338 mg (0.528 mmol) of ethyl (3S)-3-(4-amidinobenzoylamino)-4-(3-amidinophenoxy)butyrate bistrifluoroacetate was dissolved in 10 ml of concentrated hydrochloric acid, and the solution was stirred at 40° C. for 6 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 41 mg (0.067 mmol) (13%)
MS (ESI, m/z) 384 (MH+)
H-NMR (DMSO-d6) δ 2.74 (2H, d), 4.13 (1H, dd), 4.24 (1H, dd), 4.69 (1H, ddt), 7.35 (1H, d), 7.40 (1H, d), 7.41 (1H, s), 7.55 (1H, dd), 7.91 (2H, d), 8.03 (2H, d), 8.81 (1H, d), 9.20 (2H, s), 9.28 (2H, s), 9.33 (2H, s), 9.43 (2H, s).

Example 52

Synthesis of ethyl (3R)-4-(3-amidinophenoxy)-3-[4-(piperidine-4-yl)methylbenzoylamino]butyrate bistrifluoroacetate

Step 1

Synthesis of benzyl (3R)-3-t-butoxycarbonylamino-4-(3-cyanophenoxy)butyrate 3.23 g (10.0 mmol) of β-benzyl N-t-butoxycarbonyl-D-aspartate and 1.39 ml (10.0 mmol) of triethylamine were dissolved in 50 ml of tetrahydrofuran. 0.96 ml (10.0 mmol) of ethyl chloroformate was added to the solution under cooling with ice, and they were stirred for 20 minutes. The precipitate thus formed was removed by the suction filtration. 5 g of ice and 0.76 g (20.0 mmol) of sodium borohydride were added to the filtrate under cooling with ice, and they were stirred for 1.5 hours. 20 ml of 1 N aqueous hydrogen chloride solution was added to the reaction mixture, and they were stirred at room temperature for additional one hour. After the treatment with ethyl acetate as the extractant in an ordinary manner, an oily product was obtained, which was dissolved in 36 ml of tetrahydrofuran. 0.96 g (8.04 mmol) of 3-cyanophenol, 2.30 g (8.77 mmol) of triphenylphosphine and 3.50 g (8.04 mmol) of diethyl azodicarboxylate (40% solution in toluene) were added to the solution, and they were stirred at room temperature overnight. The solvent was evaporated, and the residue was purified by the silica gel column chromatography to obtain the title compound.

Yield: 1.80 g (4.38 mmol) (44%)
H-NMR (CDCl3) δ 1.46 (9H, s), 2.79 (2H, d), 4.00 (1H, dd), 4.06 (1H, dd), 4.41 (1H, br), 5.13 (2H, s), 5.56 (1H, br), 7.05-7.18 (4H, m), 7.21-7.38 (5H, m)

Step 2

Synthesis of benzyl (3R)-3-amino-4-(3-cyanophenoxy)butyrate hydrochloride

The title compound was obtained by removing t-butoxycarbonyl group in an ordinary manner from benzyl (3R)-3-t-butoxycarbonylamino-4-(3-cyanophenoxy)butyrate in dioxane containing 4 N hydrogen chloride.

Step 3

Synthesis of ethyl (3R)-4-(3-amidinophenoxy)-3-[4-(piperidine-4-yl)methylbenzoylamino]butyrate bistrifluoroacetate 95 mg of palladium/carbon and 20 ml of methanol were added to 334 mg (1.00 mmol) of methyl 4-[1-(t-butoxycarbonyl)piperidine-4-ylidene]methyl benzoate, and they were stirred in the presence of hydrogen for 15 hours. After the filtration through Celite, the solvent was evaporated. 4 ml of 1 N sodium hydroxide and 6 ml of ethanol were added to the residue, and they were stirred for 18 hours. The reaction liquid was acidified with 1 N hydrochloric acid. After the extraction with ethyl acetate followed by drying over anhydrous magnesium sulfate, the solvent was evaporated. The residue was dissolved in 5 ml of dichloromethane. 0.46 ml (3.27 mmol) of triethylamine, 209 mg (1.50 mmol) of 1-(3-dimethylaminopropyl)-3-ethylcarbodiimide hydrochloride, 147 mg (1.09 mmol) of 1-hydroxybenzotriazole and 306 mg (0.99 mmol) of benzyl (3R)-3-amino-4-(3-cyanophenoxy) butyrate were added to the solution, and they were stirred for 16 hours. The reaction liquid was diluted with water. After the extraction with ethyl acetate, the organic layer was washed successively with water, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.

Yield: 105 mg (0.22 mmol) (22%)
MS (ESI, m/z) 464 (MH+)
H-NMR (DMSO-d6) δ 1.15 (3H, t), 1.22-1.40 (2H, m), 1.62-1.74 (2H, m), 1.78-1.90 (1H, m), 2.56-2.65 (2H, m), 2.69-2.90 (4H, m), 3.16-3.31 (2H, m), 4.01-4.16 (3H, m), 4.18-4.27 (1H, m), 4.64-4.78 (1H, m), 7.27-7.45 (6H, m), 7.78 (2H, d), 8.28 (1H, br), 8.47-8.65 (2H, m), 9.16 (4H, br), 9.29 (2H, br).

Example 53

Synthesis of (3R)-4-(3-amidinophenoxy)-3-[4-(1-piperidine-4-yl)methylbenzoylamino]butyric acid bistrifluoroacetate The title compound was obtained from 30 mg (0.05 mmol) of (3R)-4-(3-amidinophenoxy)-3-[4-(1-piperidine-4-yl)methylbenzoylamino]butyrate bistrifluoroacetate in the same manner as that of step 4 in Example 51.

Yield: 17 mg (0.22 mmol) (62%).
MS (ESI, m/z) 439 (MH+)
H-NMR (DMSO-d6) δ 1.26-1.45 (2H, m), 1.61-1.73 (2H, m), 1.74-1.89 (1H, m), 2.58 (2H, d), 2.67-2.85 (4H, m), 3.24-3.36 (2H, m), 4.10 (1H, dd), 4.24 (1H, dd), 4.68 (1H, ddt), 7.27 ((2H, d), 7.33 (1H, d), 7.43 (2H, br), 8.28 (1H, br), 8.47-8.65 (2H, m), 9.16 (4H, br), 9.29 (2H, br).

Example 54

Synthesis of ethyl (3R)-3-[(biphenyl-4-carbonyl)amino]-4-(3-amidinophenoxy)butyrate trifluoroacetate

Step 1

Synthesis of 4-phenyl benzoyl chloride 10 ml of thionyl chloride as added to 1.05 g (5.3 mmol) of 4-phenylbenzoic acid, and they were heated under reflux for 3 hours. The solvent was evaporated to obtain the crude product.

Step 2

Synthesis of benzyl (3R)-3-[(biphenyl-4-carbonyl)amino]-4-(3-cyanophenoxy)butyrate 310 mg (1.0 mmol) of benzyl (3R)-3-amino-4-(3-cyanophenoxy)butyrate hydrochloride was dissolved in 10 ml of dimethylformamide. 0.18 ml (1.3 mmol) of triethylamine was added to the solution. 282 mg (1.3 mmol) of 4-phenylbenzoyl chloride was added to the resultant mixture under cooling with ice, and they were stirred for 30 minutes. The temperature was elevated to room temperature, and the reaction mixture was stirred for additional 2 hours. The reaction liquid was diluted with water. After the extraction with ethyl acetate, the organic layer was successively washed with water, 1 N hydrochloric acid, saturated aqueous sodium hydrogencarbonate solution and saturated aqueous NaCl solution, and then dried over anhydrous magnesium sulfate. The solvent was evaporated, and the residue was purified by the silica gel column chromatography to obtain the title compound.

Yield: 220 mg (0.45 mmol) (45%)
H-NMR (CDCl3) δ 2.93 (2H, dt), 4.19 (2H, dt), 4.83-4.97 (1H, m), 7.14 (2H, dd), 7.24-7.29 (2H, m), 7.33-7.51 (8H, m), 7.59-7.68 (4H, m), 7.83 (2H, d)

Step 3

Synthesis of ethyl (3R)-3-[(biphenyl-4-carbonyl)amino]-4-(3-amidinophenoxy)butyrate trifluoroacetate The title compound was obtained from 220 mg (0.45 mmol) of benzyl (3R)-[(biphenyl-4-carbonyl)amino]-4-(3-cyanophenoxy)butyrate in the same manner as that of step 6 in Example 1.

Yield: 115 mg (0.21 mmol) (46%).
MS (ESI, m/z) 446 (MH+)
H-NMR (DMSO-d6) δ 1.16 (3H, t), 2.80 (2H, d), 4.07 (2H, q), 4.08-4.17 (1H, m), 4.20-4.29 (1H, m), 4.64-4.68 (1H, m), 7.29-7.59 (7H, m), 7.74 (2H, d), 7.78 (2H, d), 7.93 (2H, d), 8.62 (1H, d), 9.11 (2H, br), 9.29 (2H, br).

Example 55

Synthesis of (3R)-3-[(biphenyl-4-carbonyl)amino]-4-(3-amidinophenoxy)butyric acid trifluoroacetate 120 mg (0.18 mmol) of ethyl (3R)-3-[(biphenyl-4-carbonyl)amino]-4-(3-amidinophenoxy)butyrate trifluoroacetate was dissolved in 5 ml of concentrated hydrochloric acid, and the solution was stirred at 60° C. for 19 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 14 mg (0.03 mmol) (15%)
MS (ESI, m/z) 418 (MH+)
H-NMR (DMSO-d6) δ 2.71 (2H, d), 4.09-4.20 (1H, m), 4.21-4.30 (1H, m), 4.63-4.75 (1H, m), 7.33-7.59 (7H, m), 7.74 (2H, d), 7.78 (2H, d), 7.95 (2H, d), 8.61 (1H, d), 9.22 (4H, br).

Example 56

Synthesis of (3R)-4-(3-amidinophenoxy)-3-[(4-dimethylcarbamoylbenzoyl)amino]butyric acid trifluoroacetate

Step 1

Synthesis of 4-dimethylcarbamoylbenzoic acid

A solution of 5 g (25.2 mmol) of methyl 4-chlorocarbonyl benzoate in 20 ml of dioxane was added to 30 ml of 50% aqueous dimethylamine solution under cooling with ice. After stirring for 30 minutes, 50 ml of 1 N aqueous sodium hydroxide solution was added to the resultant mixture, and they were stirred at room temperature for 2 days. The reaction liquid was washed with ethyl acetate and made acidic with hydrochloric acid. After the extraction with ethyl acetate, the extract was washed with saturated Aqueous NaCl solution and then dried over anhydrous magnesium sulfate. The solvent was evaporated, and the residue was washed with hexane and dried to obtain the title compound.

Yield: 2.58 g (13.4 mmol) (53%)
H-NMR (CDCl3) δ 2.85 (3H, br), 2.95 (3H, br), 7.50 (2H, d), 7.97 (2H, d).

Step 2

Synthesis of benzyl (3R)-4-(3-cyanophenoxy)-3-[(4-dimethylcarbamoylbenzoyl)amino]butyrate 1N Aqueous sodium hydroxide solution was added to benzyl (3R)-4-(3-cyanophenoxy)-3-aminobutyrate hydrochloride. Ethyl acetate was added as the extractant to the resultant mixture. After the treatment in an ordinary manner, benzyl (3R)-4-(3-cyanopheoxy)-3-aminobutyrate was obtained. 300 mg (0.97 mmol) of this compound, 193 mg (1 mmol) of 4-dimethylcarbamoylbenzoic acid, 192 mg (1 mmol) of 1-(3-dimethylaminopropyl)-3-ethylcarbodiimide hydrochloride and 155 mg (1 mmol) of 1-hydroxybenzotriazole were stirred in 10 ml of dichloromethane at room temperature overnight. 1 N aqueous hydrochloric acid solution was added to the reaction liquid. After the extraction with dichloromethane, the organic layer was washed with 1 N aqueous sodium hydroxide solution and saturated aqueous common salt solution and then dried over anhydrous magnesium sulfate. The solvent was evaporated, and the residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 178 mg (0.37 mmol) (37%).

H-NMR (DMSO-d6) δ 2.82 (2H, d), 2.90 (3H, br), 3.00 (3H, br), 4.05-4.25 (2H, m), 4.70 (1H, m), 5.10 (2H, s), 7.26-7.35 (6H, m), 7.38-7.51 (5H, m), 7.84 (2H, d), 8.64 (1H, d).

Step 3

Synthesis of (3R)-4-(3-amidinophenoxy)-[(4-dimethylcarbamoylbenzoyl)amino]butylic acid trifluoroacetate 178 mg (0.38 mmol) of benzyl (3R)-4-(3-cyanophenoxy)-3-[(4-dimethylcarbamoylbenzoyl)amino]butyrate was stirred in 6 ml of dioxane containing 4 N hydrogen chloride. 1 ml of ethanol was added to the resultant mixture. After stirring at room temperature for 6 days, the solvent was evaporated under reduced pressure. The residue was stirred in 10 ml of ethanol and then 60 mg of ammonium carbonate was added thereto. After stirring at room temperature for 2 days, the solvent was evaporated. 15 ml of concentrated hydrochloric acid was added to the residue and the resultant mixture was stirred at 40° C. overnight. The solvent was evaporated, and the obtained residue was purified by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 108 mg (0.21 mmol) (55%).

MS (ESI, m/z) 413 (MH+)

H-NMR (DMSO-d6) δ 2.80 (2H, d), 3.00 (3H, br), 3.10 (3H, br), 4.15-4.35 (2H, m), 4.75 (1H, m), 7.40-7.49 (3H, m), 7.54-7.64 (3H, m), 7.96 (2H, d), 8.70 (1H, d), 9.15 (2H, br), 9.35 (2H, br).

Example 57

Synthesis of (3R)-4-(3-amidinophenoxy)-3-[(4-guanidinobenzoyl)amino]butyric acid bistrifluoroacetate Step 1

Synthesis of benzyl (3R)-4-(3-cyanophenoxy)-3-[(4-guanidinobenzoyl)amino]butyrate trifluoroacetate 247 mg (0.8 mmol) of benzyl (3R)-4-(3-cyanophenoxy)-3-aminobutyrate, 138 mg (0.64 mmol) of 4-guanidinobenzoic acid monohydrochloride, 100 mg (0.64 mmol) of 1-hydroxybenzotriazole (hydrous, 87%) and 123 mg (0.64 mmol) of 1-(3-dimethylaminopropyl)-3-ethylcarbodiimide hydrochloride were stirred together in 5 ml of dimethylformamide at room temperature for 3 days. The solvent was evaporated under reduced pressure. 1 N aqueous sodium hydroxide solution was added to the residue. After the extraction with dichloromethane, the organic layer was washed with saturated aqueous NaCl solution and then dried over anhydrous magnesium sulfate. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 123 mg (0.21 mmol) (33%)

H-NMR (CD3OD) δ 2.90 (2H, m), 4.20 (2H, m), 4.85 (1H, m), 5.15 (2H, s), 7.20-7.38 (10H, m), 7.41 (1H, t), 7.82 (2H, d)

Step 2

Synthesis of (3R)-4-(3-amidinophenoxy)-3-[(4-guanidinobenzoyl)amino]butyric acid bistrifluoroacetate The title compound was obtained from 178 mg (0.3 mmol) of benzyl (3R)-4-(3-cyanophenoxy)-3-[(4-guanidinobenzoyl)amino]butyrate trifluoroacetate in the same manner as that of step 3 in Example 56.

Yield: 111 mg (0.18 mmol) (60%).

MS (ESI, m/z) 399 (MH+)

H-NMR (DMSO-d6) δ2.75 (2H, d), 4.05-4.25 (2H, m), 4.70 (1H, m), 7.30-7.43 (5H, m), 7.53 (1H, t), 7.68 (4H, s), 7.92 (2H, d), 8.58 (1H, d), 9.13 (2H, s), 9.30 (2H, s), 10.13 (1H, s).

Example 58

Synthesis of (3R)-4-(3-amidinophenoxy)-3-[4-(pyrrolidine-1-yl)benzoylamino]butyric acid trifluoroacetate 505 mg (1.23 mmol) of benzyl (3R)-3-(t-butoxycarbonyl)amino-4-(3-cyanophenoxy)butyrate was dissolved in 5 ml of 4 N dioxane hydrochloride and 2.5 ml of dioxane, and the solution was stirred for 15 hours. The solvent was evaporated, and the residue was dissolved in 10 ml of dichloromethane. 334 mg (1.00 mmol) of 4-(pyrrolidine-1-yl)benzoic acid, 0.86 ml (6.15 mmol) of triethylamine, 258 mg (1.35 mmol) of 1-(3-dimethylaminopropyl)-3-ethylcarbodiimide hydrochloride and 183 mg (1.35 mmol) of 1-hydroxybenzotriazole were added to the solution, and they were stirred at room temperature for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated. 5 ml of 4 N dioxane hydrochloride and 1 ml of ethanol were added to the residue, and they were stirred for 96 hours. The solvent was evaporated under reduced pressure, and the residue was dissolved in 10 ml of 10% (w/v) solution of ammonia in ethanol. The solution was stirred for 24 hours. The solvent was evaporated under reduced pressure. 5 ml of concentrated hydrochloric acid was added to the residue, and they were stirred at 50° C. for 15 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 170 mg (0.32 mmol) (24%)
MS (ESI, m/z) 411 (MH+)
H-NMR (DMSO-d6) δ 1.87-2.03 (4H, m), 2.70 (2H, d), 3.20-3.35 (4H, m), 4.04 (1H, dd), 4.21 (1H, dd), 4.63 (1H, ddt), 6.53 (2H, d), 7.32-7.45 (3H, m), 7.53 (1H, dd), 7.72 (2H, d), 8.11 (1H, d), 9.06 (2H, br), 9.27 (2H, br).

Example 59

Synthesis of ethyl (3R)-4-(3-amidinophenoxy)-3-[4-(pyrrolidine-1-yl)benzoylamino]butyrate trifluoroacetate 5.1 g (12.4 mmol) of benzyl (3R)-3-(t-butoxycarbonyl)amino-4-(3-cyanophenoxy)butyrate was dissolved in 20 ml of 4 N dioxane hydrochloride and 10 ml of dioxane, and the solution was stirred for 15 hours. The solvent was evaporated, and the residue was dissolved in 10 ml of dichloromethane. 2.61 g (13.7 mmol) of 4-(pyrrolidine-1-yl)benzoic acid, 8.63 ml (62 mmol) of triethylamine, 2.61 g (13.7 mmol) of 1-(3-dimethylaminopropyl)-3-ethylcarbodiimide hydrochloride and 1.85 mg (13.7 mmol) of 1-hydroxybenzotriazole were added to the solution, and they were stirred at room temperature for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was treated in the same manner as that of step 6 in Example 1 to obtain the title compound.

Yield: 800 mg (1.45 mmol) (28%).
MS (ESI, m/z) 439 (MH+)
H-NMR (DMSO-d6) δ 1.14 (3H, t), 1.86-2.01 (4H, m), 2.70 (2H, d), 3.18-3.33 (4H, m), 4.02 (1H, dd), 4.10 (1H, q), 4.21 (1H, dd), 4.63 (1H, ddt), 6.53 (2H, d), 7.35-7.51 (3H, m), 7.53 (1H, dd), 7.72 (2H, d), 8.11 (1H, d), 9.04 (2H, br), 9.28 (2H, br).

Example 60

Synthesis of (3R)-3-(4-carbamoylbenzoylamino)-4-(3-amidinophenoxy)butyric acid bistrifluoroacetate Step 1

Synthesis of benzyl (3R)-3-(4-cyanobenzoylamino)-4-(3-cyanophenoxy)butyrate 1.8 g (4.38 mmol) of benzyl (3R)-3-t-butoxycarbonylamino-4-(3-cyanophenoxy)butyrate was dissolved in 20 ml of 4 N solution of hydrogen chloride in dioxane, and the solution was stirred at 0° C. for 6 hours. The solvent was evaporated, and the oily residue was dissolved in 5 ml of dichloromethane. 1.09 g (6.58 mmol) of 4-cyanobenzoyl chloride and 1.22 ml (8.76 mmol) of triethylamine were added to the solution under cooling with ice, and they were stirred at room temperature overnight. After the treatment with ethyl acetate as the extractant in an ordinary manner, the crude product was obtained, which was purified by the silica gel column chromatography to obtain the title compound.

Yield: 1.21 g (2.75 mmol) (63%).

H-NMR (CDCl3) δ 2.86 (1H, dd), 2.95 (1H, dd), 4.12 (1H, dd), 4.20 (1H, dd), 4.85 (1H, br), 5.16 (2H, s), 7.09 (1H, d), 7.11 (1H, dd), 7.24-7.40 (7H, m), 7.72 (2H, d), 7.83 (2H, d)

Step 2

Synthesis of (3R)-3-(4-carbamoylbenzoylamino)-4-(3-amidinophenoxy)butyric acid bistrifluoroacetate Benzyl (3R)-3-(4-cyanobenzoylamino)-4-(3-cyanophenoxy)butyrate was added to ethanol containing 30% (w/v) of hydrogen chloride, and they were stirred at room temperature overnight. Then the reaction mixture was dissolved in 10% (w/v) solution of ammonia in ethanol at room temperature. The solution was stirred at room temperature for two nights. The solvent was evaporated, and the residue was dissolved in concentrated hydrochloric acid, and they were stirred at 40° C. for 6 hours. Hydrogen chloride was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

MS (ESI, m/z) 385 (MH+)
H-NMR (DMSO-d6) δ 2.75 (2H, d), 4.12 (1H, dd), 4.23 (1H, dd), 4.68 (1H, br), 7.35 (1H, d), 7.40 (1H, d), 7.42 (1H, s), 7.53 (1H, t), 7.89 (2H, d), 7.96 (2H, d), 8.09 (2H, br), 8.66 (1H, d), 9.24 (2H, br), 9.29 (2H, br).

Example 61

Synthesis of ethyl (3R)-4-(3-amidinophenoxy)-3-[(4-dimethylamino)benzoylamino]butyrate trifluoroacetate, and (3R)-4-(3-amidinophenoxy)-3-[(4-dimethylamino)benzoylamino]butyric acid trifluoroacetate 700 mg (1.70 mmol) of benzyl (3R)-3-(t-butoxycarbonyl)amino-4-(3-cyanophenoxy)butyrate was dissolved in 5 ml of 4 N dioxane hydrochloride and 2.5 ml of dioxane, and the solution was stirred for 15 hours. The solvent was evaporated, and the residue was dissolved in 10 ml of dichloromethane. 282 mg (1.71 mmol) of 4-dimethylaminobenzoic acid, 1.19 ml (8.55 mmol) of triethylamine, 748 mg (1.88 mmol) of 1-(3-dimethylaminopropyl)-3-ethylcarbodiimide hydrochloride and 254 mg (1.88 mmol) of 1-hydroxybenzotriazole were added to the solution, and they were stirred at room temperature for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was treated in the same manner as that of step 3 in Example 56 to obtain the title compound. In this case, however, the solution of ammonium carbonate in ethanol was replaced with ethanol containing 10% of ammonia. Ethyl (3R)-4-(3-amidinophenoxy)-3-[4-(dimethylamino)benzoylamino]butyrate trifluoroacetate:

Yield: 10 mg (0.02 mmol) (1%)
MS (ESI, m/z) 413 (MH+)
H-NMR (DMSO-d6) δ 1.14 (3H, t), 2.78 (2H, d), 2.97 (6H, s), 4.06 (2H, q), 4.10 (2H, dd), 4.23 (2H, dd), 4.68 (2H, dd), 6.69 (2H, d), 7.30-7.42 (3H, m), 7.53 (1H, dd), 7.71 (2H, d), 8.18 (2H, d), 9.10 (2H, br), 9.28 (2H, br).

(3R)-4-(3-Amidinophenoxy)-3-[4-(dimethylamino)benzoylamino]butyric acid trifluoroacetate Yield: 70 mg (0.14 mmol) (8%)
MS (ESI, m/z) 385 (MH+)
H-NMR (DMSO-d6) δ 2.69 (2H, d), 2.97 (6H, s), 4.04 (2H, dd), 4.22 (2H, dd), 4.64 (2H, q), 6.70 (2H, d), 7.33-7.44 (3H, m), 7.53 (1H, dd), 7.72 (2H, d), 8.14 (2H, d), 9.09 (2H, br), 9.25 (2H, br).

Example 62

Synthesis of (3R)-4-(3-amidinophenoxy)-3-[4-(1-acetimidoyl-4-piperidyloxy)benzoylamino]butylic acid bistrifluoroacetate

Step 1

Synthesis of ethyl 4-(1-t-butoxycarbonyl-4-piperidyloxy)benzoate 1.76 g (9.3 mmol) of 1-t-butoxycarbonyl-4-hydroxypiperidine, obtained by t-butoxycarbonylating 4-hydroxypiperidine with di-t-butyl dicarbonate by an ordinary method, 1.7 g (10.2 mmol) of ethyl 4-hydroxybenzoate and 2.44 g (9.3 mmol) of triphenylphosphine were dissolved in 40 ml of tetrahydrofuran. 1.62 g (9.3 mmol) of diethyl azodicarboxylate was added to the solution at room temperature and the resultant mixture was stirred overnight. The reaction mixture was treated with ethyl acetate as the extractant in an ordinary manner to obtain a crude product, which was purified by the silica gel column chromatography to obtain the title compound.

Yield: 1.57 g (4.5 mmol) (44%)
H-NMR (CDCl3) δ 1.38 (3H, t), 1.50 (9H, s), 1.70-1.80 (2H, m), 1.90-2.00 (2H, m), 3.30-3.41 (2H, m), 3.63-3.75 (2H, m), 4.35 (2H, q), 4.55 (1H, m), 6.90 (2H, d), 8.00 (2H, d).

Step 2

Synthesis of 4-(1-t-butoxycarbonyl-4-piperidyloxy)benzoic acid 847 mg (2.43 mmol) of ethyl (1-t-butoxycarbonyl-4-piperidyloxy)benzoate was dissolved in 50 ml of ethanol. 5 ml of 1 N aqueous sodium hydroxide solution was added to the solution, and they were stirred at room temperature for 3 days. The reaction liquid was concentrated and then treated with ethyl acetate as the extractant in an ordinary manner to obtain the title compound.

Yield: 697 mg (2.2 mmol) (92%)
H-NMR (CDCl3) δ 1.50 (9H, s), 1.70-2.00 (4H, m), 3.30-3.40 (2H, m), 3.65-3.75 (2H, m), 4.60 (1H, s), 6.95 (2H, d), 8.05 (2H, d).

Step 3

Synthesis of benzyl (3R)-4-(3-cyanophenoxy)-3-[4-(1-t-butoxycarbonyl-4-piperidyloxy)benzoylamino]butyrate 1.46 g (3.56 mmol) of benzyl (3R)-3-(t-butoxycarbonyl)amino-4-(3-cyanophenoxy)butyrate was dissolved in 10 ml of 4 N dioxane hydrochloride and 5 ml of dioxane, and the solution was stirred for 15 hours. The solvent was evaporated, and the residue was dissolved in 20 ml of dichloromethane. 1.14 g (3.56 mmol) of 4-(1-t-butoxycarbonyl-4-piperidyloxy)benzoic acid, 2.48 ml (17.8 mmol) of triethylamine, 748 mg (3.92 mmol) of 1-(3-dimethylaminopropyl)-3-ethylcarbodiimide hydrochloride and 529 mg (3.92 mmol) of 1-hydroxybenzotriazole were added to the solution, and they were stirred for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated, and the residue was treated by the silica gel column chromatography to obtain the title compound.

Yield: 1.0 g (1.63 mmol) (46%).
H-NMR (CDCl3) δ 1.45 (9H, s), 1.68-1.81 (2H, m), 1.84-1.97 (2H, m), 2.88 (2H, dt), 3.27-3.40 (2H, m), 3.61-3.73 (2H, m), 4.04-4.23 (2H, m), 4.46-4.58 (1H, m), 4.77-4.90 (1H, m), 5.13 (2H, s), 6.89 (2H, d), 7.02-7.13 (3H, m), 7.27-7.37 (6H, m), 7.68 (2H, d)

Step 4

Synthesis of (3R)-4-(3-amidinophenoxy)-3-[4-(1-acetimidoyl-4-piperidyloxy)benzoylamino]butylic acid trifluoroacetate 10 ml of 4 N dioxane hydrochloride and 2 ml of ethanol were added to 1.0 g (1.63 mmol) of benzyl (3R)-4-(3-cyanophenoxy)-3-[4-(1-t-butoxycarbonyl-4-piperidyloxy)benzoylamino]butyrate, and they were stirred for 48 hours. The solvent was evaporated, and the residue was dissolved in 10 ml of 10% (w/v) solution of ammonia in ethanol. The solution was stirred for 24 hours. The solvent was evaporated, and the residue was dissolved in 10 ml of ethanol. 1.0 g (8.16 mmol) of ethyl acetimidate hydrochloride and 1.1 ml (8.16 mmol) of triethylamine were added to the solution, and they were stirred for 24 hours. The solvent was evaporated, and the residue was dissolved in 10 ml of concentrated hydrochloric acid, and they were stirred at 40° C. for 18 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 600 mg (0.85 mmol) (52%)
MS (ESI, m/z) 482 (MH+)
H-NMR (DMSO-d6) δ 1.66-1.85 (2H, m), 2.02-2.16 (2H, m), 2.29 (3H, s), 2.71 (2H, d), 3.43-3.56 (3H, m), 4.00-4.13 (2H, m), 4.18-4.30 (2H, m), 4.58-4.63 (2H, m), 4.76-4.86 (1H, m), 7.07 (2H, d), 7.32-7.50 (3H, m), 7.54 (1H, dd), 7.84 (2H, d), 8.39 (1H, d), 8.60 (1H, br), 9.09 (2H, br), 9.14 (1H, br), 9.28 (2H, br).

Example 63

Synthesis of 3-[5-(4-amidinophenyl)-5-oxopentyl]oxybenzamidine bistrifluoroacetate

Step 1

Synthesis of 4-(5-chloro-1-oxopentyl)benzonitrile 1 g (6.9 mmol) of 4-acetylbenzonitrile was dissolved in 8 ml of tetrahydrofuran. 9 ml of lithium bis(trimethylsilyl)amide (1 M solution in hexane) was gradually added to the solution at −70° C. and they were stirred for 30 minutes. 1.43 g (7 mmol) of 1-chloro-3-iodopropane dissolved in 6 ml of tetrahydrofuran was added thereto, and the resultant mixture was stirred at room temperature overnight. The reaction liquid was poured into water. After the extraction with ethyl acetate, the extract was washed with 1 N hydrochloric acid and saturated aqueous common salt solution, and then dried over powdery magnesium sulfate. The solvent was evaporated, and the residue was purified by the silica gel chromatography to obtain the title compound.

Yield: 59.3 mg (0.27 mmol) (3.9%)

H-NMR (CDCl3) δ 1.82-1.95 (4H, m), 3.03 (2H, t), 3.60 (2H, t), 7.80 (2H, d), 8.05 (2H, d).

Step 2

Synthesis of
3-[5-(4-cyanophenyl)-5-oxopentyl]oxybenzonitrile 53 mg (0.24 mmol) of 4-(5-chloro-1-oxopentyl)benzonitrile was dissolved in 2 ml of dimethylformamide. 33 mg (0.24 mmol) of potassium carbonate, 40 mg of potassium iodide and 29 mg (0.24 mmol) of 3-hydroxybenzonitrile were added to the solution, and they were stirred at 70° C. overnight. 1 N Hydrochloric acid was added to the reaction mixture. After the extraction with ethyl acetate, the extract was washed with 1 N aqueous sodium hydroxide solution and saturated aqueous common salt solution, and then dried over powdery magnesium sulfate. The solvent was evaporated, and the residue was purified by the silica gel chromatography to obtain the title compound.

Yield: 24 mg (0.079 mmol) (33%)

H-NMR (CDCl3) δ 1.82-2.00 (4H, m), 3.08 (2H, t), 4.02 (2H, t), 7.12 (1H, d), 7.14 (1H, s), 7.22 (1H, d), 7.37 (1H, t), 7.79 (2H, d), 8.03 (2H, d).

Step 3

Synthesis of
3-[5-(4-amidinophenyl)-5-oxopentyl)oxybenzamidine
bistrifluoroacetate The title compound was obtained from 43 mg (0.14 mmol) of 3-[5-(4-cyanophenyl)-5-oxopentyl]oxybenzonitrile in the same manner as that of step 6 in Example 1.

Yield: 8.8 g (0.015 mmol) (11%).

MS (ESI, m/z) 339 (MH+)

H-NMR (DMSO-d6) δ 1.78-1.90 (4H, m), 3.20 (2H, t), 4.12 (2H, t), 7.30 (1H, d), 7.37 (1H, s), 7.39 (1H, d), 7.53 (1H, t), 7.94 (2H, d), 8.16 (2H, d), 9.24-9.48 (8H, brm).

Example 64

Synthesis of 4-[4-(3-amidinophenoxy)butyryl]-N,N-dimethylbenzamide trifluoroacetate Step 1

Synthesis of 2-(4-bromophenyl)-2-(3-chloropropyl)-5,5-dimethyl-1,3-dioxane 10 g (38.2 mmol) of 4'-bromo-4-chlorobutyrophenone, 4 g (38.2 mmol) of 2,2-dimethyl-1,3-propanediol and 200 mg (1 mmol) of p-toluenesulfonic acid monohydrate were heated under reflex in benzene for 3 days to conduct the azeotropic dehydration. Saturated aqueous sodium hydrogencarbonate solution was added to the reaction mixture. After the extraction with ethyl acetate, the extract was washed with water and saturated aqueous common salt solution and then dried over anhydrous magnesium sulfate. The solvent was evaporated to obtain the title compound.

Yield: 13.3 g (38 mmol) (100%)

H-NMR (CDCl3) δ 0.60 (3H, s), 1.22 (3H, s), 1.78-2.00 (4H, m), 3.40 (4H, s), 3.50 (1H, t), 7.25 (2H, d), 7.55 (2H, d).

Step 2

Synthesis of 3-[3-[2-(4-bromophenyl)-5,5-dimethyl-1,3-dioxane-2-yl]propoxy]benzonitrile 236 mg (5.9 mmol) of sodium hydride (oily, 60%) was stirred in dimethylformamide. 691 mg (5.8 mmol) of 3-hydroxybenzonitrile was added thereto under cooling with ice. After stirring at room temperature for 30 minutes, a solution of 2 g (5.75 mmol) of 2-(4-bromophenyl)-2-(3-chloropropyl)-5,5-dimethyl-1,3-dioxane in dimethylformamide was added to the reaction mixture, and they were stirred at 100° C. overnight. Water was added to the mixture. After the extraction with ethyl acetate, the organic layer was washed with 1 N aqueous sodium hydroxide solution and saturated aqueous common salt solution and dried over anhydrous magnesium sulfate. The solvent was evaporated to obtain the crude title compound.

Yield: 2.25 g (5.23 mmol) (91%)

H-NMR (CDCl3) δ 0.60 (3H, s), 1.22 (3H, s), 1.80-2.00 (4H, m), 3.40 (4H, s), 3.93 (1H, s), 7.06 (1H, d), 7.08 (1H, s), 7.19 (1H, d), 7.26-7.35 (3H, m), 7.52 (2H, d).

Step 3

Synthesis of 4-[4-(3-cyanophenoxy)butyryl]benzoic acid 500 mg (1.16 mmol) of 3-[3-[2-(4-bromophenyl)-5,5-dimethyl-1,3-dioxane-2-yl]propoxy]benzonitrile, 260 mg (1.4 mmol) of tributylamine and 42 mg (0.06 mmol) of bis(triphenylphosphine)palladium (II) chloride were stirred in 3 ml of 1-butanol and 5 ml of dimethylformamide at 100° C. in carbon monoxide atmosphere overnight. Ether was added to the reaction liquid. After washing with water, 0.5 N hydrochloric acid, saturated sodium hydrogencarbonate solution and saturated aqueous common salt solution, the reaction mixture was dried over anhydrous magnesium sulfate. The solvent was evaporated. 9 ml of 6 N hydrochloric acid solution and 9 ml of acetic acid were added to the residue, and the resultant mixture was heated under reflux for 4 hours. The solvent was evaporated. Saturated aqueous sodium hydrogencarbonate solution was added to the residue. The resultant mixture was washed with ethyl acetate, and the aqueous layer was made acidic with hydrogen chloride. After the extraction with ethyl acetate, the organic layer was washed with saturated aqueous common salt solution and then dried over anhydrous magnesium sulfate. The solvent was evaporated to obtain the crude title compound.

Yield: 247 mg (0.80 mmol) (69%)

H-NMR (DMSO-d6) δ 2.10 (2H, m), 3.25 (2H, t), 4.10 (2H, t), 7.28 (1H, d), 7.36-752 (3H, m), 8.07 (4H, s).

Step 4

Synthesis of 4-[4-(3-cyanophenoxy)butyryl]-N,N-dimethylbenzamide 240 mg (0.78 mmol) of 4-[4-(3-cyanophenoxy)butyryl]benzoic acid, 150 mg (0.78 mmol) of 1-(3-dimethylaminopropyl)-3-ethylcarbodiimide hydrochloride, 121 mg (0.78 mmol) of 1-hydroxybenzotriazole (hydrous, 87%) and 100 mg of 50% aqueous dimethylamine solution were stirred together in 5 ml of dimethylformamide at room temperature overnight. 1 N hydrochloric acid was added to the resultant mixture. After the extraction with dichloromethane, the extract was washed with saturated aqueous sodium hydrogencarbonate solution and then with saturated aqueous NaCl solution, and dried over anhydrous magnesium sulfate. The solvent was evaporated. The residue was purified by the silica gel chromatography with ethyl acetate as the eluent to obtain the title compound.

Yield: 149 mg (0.44 mmol) (57%).
H-NMR (CDCl3) δ 2.25 (2H, m), 2.98 (3H, s), 3.18 (3H, s), 3.20 (2H, t), 4.10 (2H, t), 7.12 (1H, d), 7.14 (1H, s), 7.23 (1H, d), 7.36 (1H, t), 7.51 (2H, d), 8.02 (2H, d).

Step 5

Synthesis of 4-[4-(3-amidinophenoxy)butyryl]-N,N-dimethylbenzamide trifluoroacetate The title compound was obtained from 70 mg (0.21 mmol) of 4-[4-(3-cyanophenoxy)butyryl]-N,N-dimethylbenzamide in the same manner as that of step 3 in Example 3.

Yield: 42 mg (0.09 mmol) (43%).
MS (ESI, m/z) 354 (MH+)
H-NMR (DMSO-d6) δ 2.15 (2H, m), 2.83 (3H, s), 3.00 (3H, s), 3.25 (2h, t), 4.17 (2H, t), 7.30 (1H, d), 7.38 (1H, s), 7.40 (1H, d), 7.50-7.58 (3H, m), 8.04 (2H, d), 9.30 (2H, br), 9.40 (2H br).

Example 65

Synthesis of 4-[4-(3-amidinophenoxy)butyryl]-N,N-dimethylbenzamidine bistrifluoroacetate 70 mg (0.21 mmol) of 4-[4-(3-cyanophenoxy)butyryl]-N,N-dimethylbenzamide was stirred in dichloromethane. 67 mg (0.45 mmol) of trimethyloxonium tetrafluoroborate was added thereto, and they were stirred at room temperature for 2 days. Ethanol was added to the reaction mixture, dichloroethane was evaporated, 71 mg of ammonium carbonate was added to the residue, and the resultant mixture was stirred at room temperature for 4 days. The solvent was evaporated, and dichloromethane was added to the residue. After the extraction with 1 N hydrochloric acid, the aqueous layer was made alkaline with 1 N aqueous sodium hydroxide solution. After the extraction with dichloromethane, the organic layer was washed with saturated aqueous common salt solution and dried over anhydrous magnesium sulfate. The residue was treated in the same manner to obtain the title compound.

Yield: 8 mg (0.014 mmol) (7%)
MS (ESI, m/z) 353 (MH+)
H-NMR (DMSO-d6) δ 2.15 (2H, m), 3.00 (3H, s), 3.22 (3H, s), 3.30 (2H, t), 4.20 (2H, t), 7.29 (1H, d), 7.37 (1H, s), 7.38 (1H, d), 7.54 (1H, t), 7.76 (2H, d), 8.18 (2H, d), 9.03-9.42 (6H, m).

Example 66

Synthesis of 4-[4-(3-amidinophenoxy)butyryl]benzamidine bistrifluoroacetate

Step 1

Synthesis of 4-[4-(3-cyanophenoxy)butyryl]benzonitrile 500 mg (1.16 mmol) of 3-[3-[2-(4-bromophenyl)-5,5-dimethyl-1,3-dioxane-2-yl]propoxy]benzonitrile and 114 mg (1.27 mmol) of copper (1) cyamide were stirred in 1 ml of dimethylformamide at 140° C. overnight. Saturated aqueous sodium hydrogencarbonate solution was added to the resultant mixture. After the extraction with ethyl acetate, the organic layer was washed with saturated aqueous NaCl solution, and then dried over anhydrous magnesium sulfate. The solvent was evaporated. 10 ml of ethanol and 2 ml of 6 N hydrochloric acid were added to the residue, and the resultant mixture was heated under reflux for 5 hours. The solvent was evaporated. 1 N hydrochloric acid was added to the residue. After the extraction with ethyl acetate, the extract was washed with saturated aqueous NaCl solution and then dried over anhydrous magnesium sulfate. The solvent was evaporated. The residue was purified by the silica gel chromatography with ethyl acetate hexane as the extractant to obtain the title compound.

Yield: 50 mg (0.17 mmol) (15%)
H-NMR (CDCl3) δ 2.28 (2H, m), 3.20 (2H, t), 4.10 (2H, t), 7.12 (1H, d), 7.13 (1H, s), 7.24 (1H, d), 7.36 (1H, t), 7.78 (2H, d), 8.07 (2H, d)

Step 2

Synthesis of 4-[4-(3-amidinophenoxy)butyryl]benzamidine bistrifluoroacetate

The title compound was obtained from 50 mg (0.17 mmol) of 4-[4-(3-cyanophenoxy)butyryl]benzonitrile in the same manner as that of step 3 in Example 3.

Yield: 35 mg (0.06 mmol) (35%).
MS (ESI, m/z) 353 (MH+)
H-NMR (DMSO-d6) δ 2.15 (2H, m), 3.30 (2H, t), 4.20 (2H, t), 7.30 (1H, d), 7.37 (1H, s), 7.38 (1H, d), 7.54 (1H, t), 7.95 (2H, d), 8.17 (2H d), 9.18-9.50 (8H, m).

Example 67

Synthesis of 4-(3-amidinophenoxy)-N-(4-amidinophenyl)butyramide bistrifluoroacetate Step 1

Synthesis of ethyl 4-(3-cyanophenoxy)-2-butenoate 1 g (3.9 mmol) of ethyl 4-bromocrotonate, 465 mg (3.9 mmol) of 3-hydroxybenzonitrile, 539 mg (3.9 mmol) of potassium carbonate and 647 mg (3.9 mmol)) of potassium iodide were stirred in N,N-dimethylformamide at room temperature for 3 days. 1 N hydrochloric acid was added to the reaction liquid. After the extraction with ethyl acetate, the extract was washed with 1 N aqueous sodium hydroxide solution and saturated aqueous common salt solution, and dried over anhydrous magnesium sulfate. The solvent was evaporated to obtain the title compound.

Yield: 832 mg (3.6 mmol) (93%)
H-NMR (CDCl3) δ 1.30 (3H, t), 4.20 (2H, q), 4.75 (2H, m), 6.17 (1H, dt), 7.05 (1H, dt), 7.12-7.18 (2H, m), 7.28 (1H, d), 7.40 (1H, t).

Step 2

Synthesis of 4-(3-cyanophenoxy)butylic acid 830 mg (3.6 mmol) of ethyl 4-(3-cyanophenoxy)-2-butenoate and 10 ml of 1 N aqueous sodium hydroxide solution were stirred n 50 ml of ethanol for 6 hours. The reaction liquid was concentrated, 1 N hydrochloric acid was added thereto, and the precipitate thus formed was taken by the filtration. 20 ml of ethanol and 30 mg of 10% palladium/carbon were added to the thus-obtained precipitate, and they were stirred at room temperature in hydrogen atmosphere for 1.5 hours. The reaction liquid was filtered. The filtrate was concentrated and 1 N hydrochloric acid was added thereto. After the extraction with ethyl acetate, the extract was washed with saturated aqueous common salt solution and dried over anhydrous magnesium sulfate. The solvent was evaporated to obtain the title compound.

Yield: 290 mg (1.4 mmol) (39%)

H-NMR (CDCl3) δ 2.15 (2H, m), 2.60 (2H, t), 4.03 (2H, t), 7.09-7.14 (2H, m), 7.24 (2H, d), 7.36 (1H, t).

Step 3

Synthesis of 4-(3-cyanophenoxy)-N-(4-cyanophenyl)butyramide 100 mg (0.49 mmol) of 4-(3-cyanophenoxy)butyric acid and 50 mg (0.49 mmol) of triethylamine were stirred in dimethylformamide under cooling with ice. 53 mg (0.49 mmol) of ethyl chloroformate was added to the resultant mixture. After stirring for 2 minutes, 58 mg (0.49 mmol) of p-aminobenzonitrile was added to the reaction mixture. The temperature was elevated to room temperature, and they were stirred overnight. 1 N hydrochloric acid was added to the reaction mixture. After the extraction with ethyl acetate, the extract was washed with saturated aqueous sodium hydrogencarbonate solution and then with saturated aqueous NaCl solution, and then dried over anhydrous magnesium sulfate. The solvent was evaporated to obtain the crude title compound.

Yield: 113 mg (0.37 mmol) (76%).

H-NMR (CDCl3) δ 2.20 (2H, m), 2.60 (2H, t), 4.05 (2H, t), 7.08-7.14 (2H, m), 7.24 (2H, d), 7.36 (2H, t), 7.49 (1H, br), 7.58-7.68 (4H, m).

Step 4

Synthesis of 4-(3-amidinophenoxy)-N-(4-amidinophenyl)butyramide bistrifluoroacetate The title compound was obtained from 110 mg (0.36 mmol) of 4-(3-cyanophenoxy)-N-(4-cyanophenyl)butyramide in the same manner as that of step 3 in Example 3.

Yield: 5.2 mg (0.009 mmol) (3%).

MS (ESI, m/z) 340 (MH+)

H-NMR (DMSO-d6) δ 2.10 (2H, m), 2.60 (2H, t), 4.15 (2H, t), 7.30 (1H, d), 7.37 (1H, s), 7.39 (1H, d), 7.53 (1H, t), 7.80 (4H, s), 9.00-9.30 (8H, m), 10.45 (1H, s).

Example 68

Synthesis of 3-(3-amidinophenoxy)-N-(4-amidinophenyl)propionamide bistrifluoroacetate Step 1

Synthesis of methyl 3-(3-cyanophenoxy)propionate 24 mg (0.6 mmol) of sodium hydride was stirred in 10 ml of methyl acrylate. 1 g (8.4 mmol) of 3-hydroxybenzonitrile and 2 mg of hydroquinone were added thereto. After heating under reflux for 3 days, acetic acid was added and they were concentrated under reduced pressure. Ethyl acetate was added to the resultant mixture. After washing with water, 1 N aqueous sodium hydroxide solution and saturated Aqueous NaCl solution, the reaction mixture was dried over anhydrous magnesium sulfate. The solvent was evaporated to obtain the title compound.

Yield: 996 mg (4.85 mmol) (58%)

H-NMR (CDCl3) δ 2.80 (2H, t), 3.77 (3H, s), 4.25 (2H, t), 7.14 (1H, d), 7.15 (1H, s), 7.26 (1H, d), 7.37 (1H, t).

Step 2

Synthesis of 3-(3-cyanophenoxy)propionic acid 500 mg (2.4 mmol) of methyl 3-(3-cyanophenoxy)propionate was heated in 40 ml of 6 N hydrochloric acid at 70° C. for 30 minutes. After the extraction with ethyl acetate, the extract was washed with saturated aqueous NaCl solution and then dried on anhydrous magnesium sulfate. The solvent was evaporated to obtain the title compound.

Yield: 476 mg (2.5 mmol) (100%)

H-NMR (DMSO-d6) δ 2.70 (2H, t), 4.23 (2H, t), 7.29 (1H, d), 7.38-7.48 (2H, m), 7.49 (1H, t).

Step 3

Synthesis of 3-(3-cyanophenoxy)-N-(4-cyanophenyl)propionamide

The crude title compound was obtained from 122 mg (0.64 mmol) of 3-(3-cyanophenoxy)propionic acid, 150 mg (1.5 mmol) of N-methylmorpholine, 70 mg (0.64 mmol) of ethyl chloroformate and 82 mg (0.7 mmol) of 4-aminobenzonitrile in the same manner as that of step 3 in Example 67. This crude product was purified by the silica gel chromatography with ethyl acetate/hexane as the eluent.

Yield: 36 mg (0.12 mmol) (19%).

H-NMR (CD3OD) δ 2.90 (2H, t), 4.40 (2H, t), 7.23-7.31 (3H, m), 7.44 (1H, t), 7.65-7.83 (4H, m).

Step 4

Synthesis of 3-(3-amidinophenoxy)-N-(4-amidinophenyl)propionamide bistrifluoroacetate The title compound was obtained from 35 mg (0.12 mmol) of (3-cyanophenoxy)-N-(4-cyanophenyl)propionamide in the same manner as that of step 3 in Example 3.

Yield: 8.4 mg (0.015 mmol) (13%).

MS (ESI, m/z) 326 (MH+)

H-NMR (DMSO-d6) δ 2.90 (2H, t), 4.40 (2H, t), 7.32 (1H, d), 7.37-7.42 (2H, m), 7.54 (1H, t), 7.82 (4H, s), 9.00 (2H, br), 9.20 (4H, br), 9.30 (2H, br), 10.60 (1H, s).

Example 69

Synthesis of N-[3-(3-amidinophenoxymethyl)]phenyl-4-amidinobenzamide bistrifluoroacetate Step 1

Synthesis of 3-(3-nitrobenzyloxy)benzonitrile 1.70 g (10.0 mmol) of 3-nitrobenzyl chloride, 1.48 g (12.4 mmol) of 3-cyanophenol and 3.58 g (25.9 mmol) of potassium carbonate were suspended in 80 ml of dimethylformamide, and the resultant suspension was stirred at 95° C. overnight. After leaving the suspension to cool, 150 ml of water was added to the suspension, and the solid formed was taken by the filtration. The solid was washed with 100 ml of water and then 20 ml of ethyl acetate, and dried under reduced pressure to obtain the title compound.

Yield: 2.32 g (9.12 mmol) (91.2%)

H-NMR (DMSO-d6) δ 5.38 (2H, s), 7.38-7.42 (2H, m), 7.48-7.59 (2H, m), 7.75 (1H, dd), 7.93 (1H, dd), 8.23 (1H, dd), 8.35 (1H, d).

Step 2

Synthesis of 3-[3-aminobenzyloxy]benzonitrile 2.32 g (9.12 mmol) of 3-[3-nitrobenzyloxy]benzonitrile and 4.38 g of zinc were suspended in 50 ml of acetic acid, and the obtained suspension was stirred at 45° C. for 4 hours. The insoluble matter was filtered out, and the filtrate was evaporated. 100 ml of chloroform and 50 ml of 1 N aqueous sodium hydroxide solution were added to the residue. After the separation of the liquids followed by the treatment by an ordinary method, the title compound was obtained.

Yield: 1.42 g (6.33 mmol) (69.4%)

H-NMR (DMSO-d6) δ 5.03 (2H, s), 5.09 (2H, brs), 6.50 (1H, dd), 6.55 (1H, d), 6.63 (1H, d), 7.02 (1H, dd), 7.35 (1H, dd), 7.40 (1H, dd), 7.42 (1H, d), 7.43 (1H, dd).

Step 3

Synthesis of N-[3-(3-amidinophenoxymethyl)phenyl]-4-amidinobenzamide bistrifluoroacetate N-[3-(3-cyanophenoxymethyl)]phenyl-4-cyanobenzamide was obtained by condensing 2.48 g (11.1 mmol) of 3-[3-aminobenzyloxy]benzonitrile and 1.18 g (8.02 mmol) of 4-cyanobenzoic acid in the same manner as that of step 1 in Example 4. The title compound was obtained from this compound in the same manner as that of step 6 in Example 1 without the purification.

Yield: 895 mg (1.45 mmol) (18.1%).

MS (ESI, m/z) 388 (MH+)

H-NMR (DMSO-d6) δ 5.24 (2H, s), 7.22 (1H, d), 7.25-7.32 (6H, m), 7.78 (1H, d), 8.00 (2H, d), 8.20 (2H, d), 9.38 (2H, s), 9.45 (2H, s), 9.62 (2H, s), 9.80 (2H, s), 10.60 (1H, s).

Example 70

Synthesis of N-[(1R)-1-(2-methylpropyl)-2-(3-amidinophenoxy)ethyl]-4-(pyrrolidine-1-yl)benzamide bistrifluoroacetate Step 1

Synthesis of t-butyl [(1R)-2-chloro-1-(2-methylpropyl)ethyl]carbamate

A mixed anhydride was obtained from 5 g (21.6 mmol) of N-t-butoxycarbonyl-D-leucine, 2.44 g (22.5 mol) of ethyl chloroformate and 3.21 g (24.8 mmol) of diisopropylethylamine in 50 ml of THF. After the reduction with 2.12 g of sodium borohydride, crude t-butyl (1R)-2-hydroxy-1-(2-methylpropyl)ethyl carbamate was obtained.

H-NMR (CDCl3) δ 0.92 (3H, d), 0.94 (3H, d), 1.27-1.38 (2H, m), 1.42 (9H, s), 1.60-1.73 (1H, m), 2.68-4.18 (3H, m), 4.67 (1H, d).

Crude t-butyl (1R)-2-hydroxy-1-(2-methylpropyl)ethyl carbamate thus obtained was reacted with 2.47 g (21.6 mmol) of methanesulfonyl chloride and 4.52 g (35.0 mmol) of diisopropylethylamine by an ordinary method to obtain a corresponding mesyl compound, which was reacted with 2.15 g (50.7 mol) of lithium chloride in 120 ml of dimethylformamide to obtain the title compound.

Yield: 2.35 g (9.97 mmol) (46.2%)

H-NMR (CDCl3) δ 0.92 (3H, d), 0.94 (3H, d), 1.27-1.38 (2H, m), 1.42 (9H, s), 1.58-1.73 (1H, m), 2.88-4.18 (3H, m), 4.75 (1H, d).

Step 2

Synthesis of t-butyl (1R)-2-(3-cyanophenoxy)-1-(2-methylpropyl)ethylcarbamate 2.35 g (9.97 mmol) of t-butyl (1R)-2-chloro-1-(2-methylpropyl)ethylcarbamate was reacted with 2.42 g (20.3 mmol)) of 3-cyanophenol and 2.72 g (19.7 mmol) of potassium carbonate in dimethylformamide. After the treatment in an ordinary manner, the title compound was obtained.

Yield: 1.27 g (3.99 mmol) (40.0%)

H-NMR (CDCl3) δ 0.91 (3H, d), 0.94 (3H, d), 1.42 (9H, s), 1.40-1.78 (3H, m), 3.88-4.09 (3H, m), 4.59-4.67 (1H, m), 7.10-7.42 (4H, m).

Step 3

Synthesis of N-[(1R)-2-(3-amidinophenoxy)-1-(2-methylpropyl)ethyl]-4-(pyrrolidine-1-yl)benzamide bistrifluoroacetate The title compound was obtained from 1.27 g (3.99 mmol) of t-butyl (1R)-2-(3-cyanophenoxy)-1-(2-methylpropyl)ethylcarbamate in the same manner as that of Example 59.

Yield: 1.70 mg (0.325 mmol) (8.15%)

H-NMR (DMSO-d6) δ 0.88 (3H, d), 0.91 (3H, d), 1.41-1.78 (3H, m), 1.82-2.01 (4H, m), 1.82-2.01 (4H, m), 3.15-3.30 (4H, m), 3.95 (1H, dd), 4.10 (1H, dd), 4.32-4.42 (1H, d), 6.55 (2H, d), 7.35 (1H, d), 7.38 (1H, dd), 7.40 (1H, d), 7.53 (1H, dd), 7.65 (1H, dd), 7.93 (1H, d), 9.21 (2H, s), 9.27 (2H, s).

Example 71

Synthesis of monoethyl 4-[(1S)-2-(3-amidinophenoxy)-1-[4-(4-piperidyloxy)phenylmethyl]ethyl]sulfamoyl]phenylphosphonate bistrifluoroacetate and diethyl 4-[(1S)-2-(3-amidinophenoxy)-1-[4-(4-piperidyloxy)phenylmethyl]ethyl]sulfamoyl]phenylphosphonate bistrifluoroacetate Step 1

Synthesis of benzyl 4-hydroxypiperidine-1-carboxylate 25.0 g (247 mmol) of 4-hydroxypiperidine was dissolved in 800 ml of dichloromethane. 38 ml (266 mmol) of benzyloxycarbonyl chloride and 75 ml (538 mmol) of triethylamine were added to the solution at 0° C., and they were stirred at room temperature for 15 hours. After the treatment with dichloromethane as the extractant in an ordinary manner, an oily residue was obtained. This residue was subjected to the subsequent reaction without the purification.

Yield: 44.6 g (203 mmol) (82%).

Step 2

Synthesis of methyl (2S)-2-(t-butoxycarbonylamino)-3-(4-hydroxyphenyl)propionate

15.2 g (65.6 mmol) of hydrochloride of methyl ester of L-tyrosine was dissolved in 200 ml of dichloromethane. A solution of 20 ml (143 mmol) of triethylamine and 13.1 g (60.0 mmol) of di-t-butyl dicarbonate in 50 ml of dichloromethane was added to the solution, and they were stirred for 15 hours. After the treatment with dichloromethane as the extractant in an ordinary manner, the oily residue was obtained. This residue was subjected to the subsequent reaction without the purification.

Yield: 19.2 g (65.2 mmol) (99%).

Step 3

Synthesis of methyl (2S)-3-[4-[1-(benzyloxycarbonyl)-4-piperidyloxy]phenyl]-2-(t-butoxycarbonylamino)propionate

18.9 g (86.2 mmol) of benzyl 4-hydroxypiperidine-1-carboxylate, 25.4 g (86.2 mmol) of methyl (2S)-2-(t-butoxycarbonylamino)-3-(4-hydroxyphenyl)propionate and 27.1 g (103.4 mmol) of triphenylphosphine were dissolved in 500 ml of tetrahydrofuran. 37.5 g (86.2 mmol) of diethyl azodicarboxylate was added to the solution at room temperature, and they were stirred for 15 hours. After the treatment with ethyl acetate as the extractant in an ordinary manner, the crude product was obtained, which was purified by the silica gel column chromatography to obtain the title compound.

Yield: 32.1 g (62.6 mmol) (73%).

H-NMR (CDCl3) δ 1.42 (9H, s), 1.70-1.84 (2H, m), 1.86-2.00 (2H, m), 2.91-3.10 (2H, m), 3.38-3.53 (2H, m), 3.70 (3H, s), 3.71-3.82 (2H, m), 4.40-4.44 (1H, m) 4.45-4.60 (1H, m), 4.93-5.00 (1H, m), 5.18 (2H, s), 6.92 (2H, d), 7.02 (2H, d), 7.13-7.21 (5H, m)

Step 4

Synthesis of benzyl 4-[4-(2S)-2-(t-butoxycarbonylamino)-3-hydroxypropyl]phenoxy]piperidine-1-carboxylate

10.4 g of methyl (2S)-3-[4-[1-(benzyloxycarbonyl)-4-piperidyloxy]phenyl]-2-(t-butoxycarbonylamino)propionate was dissolved in 30 ml of tetrahydrofuran and 30 ml of methanol. 2.44 g (64.5 mmol) of sodium borohydride was added to the solution at 0° C. The temperature was elevated to room temperature. After stirring for 15 hours, 0.82 g (21.7 mmol) of sodium borohydride was again added to the reaction mixture. The temperature was elevated to room temperature and the mixture was stirred for additional 2 hours. After the treatment with ethyl acetate as the extractant in an ordinary manner, the crude product was obtained, which was purified by the silica gel column chromatography to obtain the title compound.

Yield: 9.35 g (19.5 mmol) (96%).

H-NMR (CDCl3) δ 1.44 (9H, s), 1.68-1.82 (2H, m), 1.84-1.98 (2H, m), 2.78 (2H, d), 3.29-3.95 (7H, m), 4.40-4.44 (1H, m), 5.14 (2H, s), 6.92 (2H, d), 7.12 (2H, d), 7.28-7.40 (5H, m)

Step 5

Synthesis of benzyl 4-[4-[(2S)-3-chloro-2-(t-butoxycarbonylamino)propyl]phenoxy]piperidine-1-carboxylate

5.5 g (11.3 mmol) of benzyl 4-[4-[(2S)-2-(t-butoxycarbonylamino)-3-hydroxypropyl]phenoxy]piperidine-1-carboxylate was dissolved in 60 ml of dichloromethane. 3.2 ml (22.6 mmol) of triethylamine and 1.95 g (17.0 mmol) of methanesulfonyl chloride were added to the solution at 0° C. After stirring for 4 hours, the reaction mixture was treated with dichloromethane as the extractant in an ordinary manner to obtain an oily residue. The residue thus obtained was dissolved in 120 ml of dimethylformamide. 2.57 g (60.6 mmol) of lithium chloride was added to the solution, and they were stirred at 50° C. for 15 hours. After the treatment with ethyl acetate as the extractant in an ordinary manner, the crude product was obtained, which was purified by the silica gel column chromatography to obtain the title compound.

Yield: 2.60 g (5.16 mmol) (45%).

H-NMR (CDCl3) δ 1.44 (9H, s), 1.63-1.82 (2H, m), 1.83-2.00 (2H, m), 2.91-3.10 (2H, m), 2.83 (2H, d), 3.40-3.54 (3H, m), 3.57-3.63 (1H, m), 3.66-3.80 (3H, m), 4.40-4.52 (1H, m), 5.14 (2H, s), 6.92 (2H, d), 7.16 (2H, d), 7.13-7.21 (5H, m)

Step 6

Synthesis of 3-[(2S)-3-[4-[1-(benzyloxycarbonyl)-4-piperidyloxy]phenyl]-2-(t-butoxycarbonylamino)propoxy]benzonitrile

6.4 g (12.7 mmol) of benzyl 3-[4-[(2S)-3-chloro-2-(t-butoxycarbonylamino)propyl]phenoxy]piperidine-1-carboxylate was dissolved in 70 ml of dimethylformamide. 2.27 g (19.1 mmol) of 3-cyanophenol and 3.51 g (25.4 mmol) of potassium carbonate were added to the solution, and they were stirred at 70° C. for 15 hours. After the treatment with ethyl acetate as the extractant in an ordinary manner, the crude product was obtained, which was purified by the silica gel column chromatography to obtain the title compound.

Yield: 5.0 g (8.54 mmol) (67%).

H-NMR (CDCl3) δ 1.44 (9H, s), 1.66-1.83 (2H, m), 1.84-2.00 (2H, m), 2.50-2.60 (1H, m), 2.82-2.93 (1H, m), 3.40-3.53 (3H, m), 3.58-3.63 (1H, m), 3.65-3.80 (3H, m), 4.40-4.53 (1H, m), 5.14 (2H, s) 6.92 (2H, d), 7.16 (2H, d), 7.13-7.21 (5H, m)

Step 7

Synthesis of 3-[(2S)-3-[4-[1-(benzyloxycarbonyl)-4-piperidyloxy]phenyl]-2-(4-iodobenzenesulfonylamino)propoxy]benzonitrile

25 ml of 4 N solution of hydrogen chloride in dioxane and 12.5 ml of dioxane were added to 2.54 g (4.34 mmol) of 3-[(2S)-3-[4-[1-(benzyloxycarbonyl)-4-piperidyloxy]phenyl]-2-(t-butoxycarbonylamino)propoxy]benzonitrile. After stirring at room temperature for 24 hours, the solvent was evaporated under reduced pressure, and the residue was dissolved in 40 ml of dimethylformamide. 1.77 ml (13.0 mmol) of diisopropylethylamine and 1.97 g (6.51 mmol) of 4-iodobenzenesulfonyl chloride were added to the solution at 0° C. 30 minutes after, the temperature was elevated to room temperature, and the reaction mixture was stirred for 19 hours. After the treatment with ethyl acetate as the extractant in an ordinary manner, the crude product was obtained. The crude product was purified by the silica gel column chromatography to obtain the title compound.

Yield: 2.50 g (3.39 mmol) (78%).

H-NMR (CDCl3) δ 1.62-1.83 (2H, m), 1.63-2.00 (2H, m), 2.62-2.80 (1H, m), 2.83-3.00 (1H, m), 3.40-3.53 (2H, m), 3.62-3.80 (3H, m), 3.81-4.00 (2H, m), 4.40-4.45 (1H, m), 4.40-4.45 (1H, m), 5.14 (2H, s), 5.20-5.36 (1H, m), 6.73 (2H, d), 6.90 (2H, d), 7.01 (2H, d), 7.24-7.44 (9H, m), 7.70 (2H, d)

Step 8

Synthesis of diethyl 4-[(1S)-2-(3-cyanophenoxy)-1-[4-(1-benzyloxycarbonyl-4-piperidyl)oxy]phenylmethyl]ethyl]sulfamoyl]phenylphosphonate 0.59 mol (0.46 mmol) of diethyl phosphonate, 24 mg (0.02 mmol) of tetrakistriphenylphosphine palladium and 20 ml of triethylamine were added to 310 mg (0.42 mmol) of 3-[(2S)-3-[4-[(1-benzyloxycarbonyl-4-piperidyl)oxy]phenyl]-2-(4-iodobenzenesulfonylamino)propoxy]benzonitrile, and they were stirred in the presence of argon at 90° C. for 4 hours. The solvent was evaporated, and the residue was purified by the silica gel column chromatography to obtain the title compound.

Yield: 139 mg (0.18 mmol) (43%)

H-NMR (CDCl3) δ 1.34 (6H, t), 1.68-1.83 (2H, m), 1.84-2.00 (2H, m), 2.76-2.94 (1H, m), 3.40-3.53 (2H, m), 3.70-3.81 (3H, m), 3.82-3.95 (2H, m), 4.04-4.25 (4H, m), 4.38-4.52 (1H, m), 5.14 (2H, s), 6.76 (2H, d), 6.92 (2H, d), 6.95-7.05 (3H, m), 7.32-7.39 (5H, m), 7.42-7.51 (1H, m), 7.63-7.71 (1H, m), 7.84 (2H, d), 7.87 (2H, d).

Step 9

Synthesis of monoethyl 4-[(1S)-2-(3-amidinophenoxy)-1-[4-(4-piperidyloxy)phenylmethyl]ethyl]sulfamoyl]phenylphosphonate bistrifluoroacetate and diethyl 4-[(1S)-2-(3-amidinophenoxy)-1-[4-(4-piperidyloxy)phenylmethyl]ethyl]sulfamoyl]phenylphosphonate bistrifluoroacetate 139 mg (0.18 mmol) of diethyl 4-[(1S)-2-(3-cyanophenoxy)-1-[4-[(1-benzyloxycarbonyl-4-piperidyl)oxy]phenylmethyl]ethyl]sulfamoyl]phenylsulfonate was dissolved in 4.5 ml of 4 N solution of hydrogen chloride in dioxane. 0.5 ml of ethanol containing 30% (w/v) of hydrogen chloride was added to the solution. After stirring at room temperature for 96 hours, the solvent was evaporated under reduced pressure. The residue was dissolved in 24 ml of 10% (w/v) solution of ammonia in ethanol, and the solution was stirred at room temperature for 24 hours. The solvent was evaporated, and 18 ml of acetic acid containing 20% of hydrogen bromide was added to the residue at 0° C. After stirring for one hour, the temperature was elevated to room temperature, and the reaction mixture was stirred for 7 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Monoethyl 4-[(1S)-2-(3-amidinophenoxy)-1-[4-(4-piperidyloxy)phenylmethyl]ethyl]sulfamoyl]phenylphosphonate bistrifluoroacetate Yield: 29 mg (0.03 mmol) (19%)

MS (ESI, m/z) 579 (MH+)

H-NMR (DMSO-d6) δ 1.18 (H, t), 1.68-1.90 (2H, m), 2.00-2.18 (2H, m), 2.56-2.70 (1H, m), 2.80-2.92 (1H, m), 3.01-3.21 (2H, m), 3.21-3.36 (2H, m), 3.64-3.76 (1H, m), 3.82 (2H, q), 3.96 (2H, d), 4.53-4.64 (1H, m), 6.80 (2H, d), 7.03 (2H, d), 7.08 (1H, br), 7.22 (1H, br), 7.37 (1H, dd), 7.46 (1H, dd), 7.68 (2H, d), 7.70 (2H, br), 8.21 (1H, dd), 8.38-8.54 (1H, m), 9.00 (2H, br), 9.33 (2H, br).

Diethyl 4-[(1S)-2-(3-amidinopheoxy)-1-[4-(4-piperidyloxy)phenylmethyl]ethyl]sulfamoyl]phenylphosphonate bistrifluoroacetate Yield: 19 mg (0.02 mmol) (12%)

MS (ESI, m/z) 645 (MH+)

H-NMR (DMSO-d6) δ 1.24 (6H, t), 1.70-1.87 (2H, m), 2.01-2.14 (2H, m), 2.54-2.69 (1H, m), 2.77-2.93 (1H, m), 2.98-3.18 (2H, m), 3.20-3.33 (2H, m), 3.62-3.74 (1H, m), 3.97 (2H, d), 4.04 (4H, dq), 4.53-4.64 (1H, m), 6.80 (2H, d), 7.03 (2H, dd), 7.08 (1H, br), 7.26 (1H, br), 7.37 (1H, dd), 7.48 (1H, dd), 7.74 (2H, d), 7.76 (2H, br), 8.31 (1H, dd), 8.38-8.54 (1H, m), 9.02 (2H, br), 9.27 (2H, br).

Example 72

Synthesis of diethyl 4-[(1S)-2-(3-amidinophenoxy)-1-[4-(1-acetimidoyl-4-piperidyl)oxy]phenylmethyl]ethyl]sulfamoyl]phenylphosphonate bistrifluoroacetate The title compound was obtained from 19 mg (0.02 mmol) of diethyl 4-[(1S)-2-(3-amidinophenoxy)-1-[4-(4-piperidyloxy)phenylmethyl]ethyl]sulfamoyl]phenylphosphonate bistrifluoroacetate in the same manner as that of Example 44.

Yield: 11 mg (0.01 mmol) (55%)

MS (ESI, m/z) 686 (MH+)

H-NMR (DMSO-d6) δ 1.14 (6H, t), 1.60-1.84 (2H, m), 1.93-2.14 (2H, m), 2.28 (3H, s), 2.54-2.71 (1H, m), 2.78-2.93 (1H, m), 3.46-3.60 ((2H, m), 3.62-3.77 (3H, m), 3.80 (4H, q), 3.98 (2H, d), 4.58-4.67 (1H, m), 6.82 (2H, d), 7.05 (2H, d), 7.08 (1H, br), 7.23 (1H, br), 7.35 (1H, d), 7.47 (1H, dd), 7.67 (4H, dd), 8.21 (1H, dd), 8.73 (1H, br), 9.08 (2H, br), 9.10 (1H, br), 9.33 (2H, br).

Example 73

Synthesis of monoethyl 4-[(1S)-2-(3-amidinophenoxy)-1-[4-[(1-acetimidoyl-4-piperidyl)oxy]phenylmethyl]ethyl]sulfamoyl]phenylphosphonate bistrifluoroacetate The title compound was obtained from 29 mg (0.03 mmol) of monoethyl 4-[(1S)-2-(3-amidinophenoxy) 1-[4-(4-piperidyloxy)phenylmethyl]ethyl]sulfamoyl]phenylphosphonate in the same manner as that of Example 44.

Yield: 13 mg (0.01 mmol) (43%)

MS (ESI, m/z) 658 (MH+)

H-NMR (DMSO-d6) δ 1.24 (3H, t), 1.67-1.85 (2H, m), 1.99-2.15 (2H, m), 2.29 (3H, s), 2.56-2.70 (1H, m), 2.79-2.95 (1H, m), 3.47-3.61 (2H, m), 3.62-3.85 (3H, m), 3.97 (2H, d), 4.03 (2, q), 4.59-4.71 (1H, m), 6.82 (2H, d), 7.05 (2H, d), 7.09

(1H, br), 7.27 (1H, br), 7.42 (1H, d), 7.48 (1H, dd), 7.73 (2H, d), 7.76 (2H, br), 8.32 (1H, dd), 8.57 (1H, br), 9.06 (2H, br), 9.13 (1H, br), 9.32 (2H, br).

Example 74

Synthesis of 4-[(1S)-2-(3-amidinophenoxy)-1-[4-[(1-acetimidoyl-4-piperidyl)oxy]phenylmethyl]ethyl]sulfamoyl]phenylphosphonic acid bistrifluoroacetate 1 ml of concentrated hydrochloric acid was added to 8 mg (0.009 mmol) of diethyl [(1S)-2-(3-amidinophenoxy)-1-[4-[(1-acetimidoyl-4-piperidyl)oxy]phenylmethyl]ethyl]sulfamoyl]phenylphosphonate bistrifluoroacetate, and they were stirred at 130° C. for 4 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 3 mg (0.004 mmol) (39%).
MS (ESI, m/z) 630 (MH+)
H-NMR (DMSO-d6) δ 1.62-1.83 (2H, m), 1.94-2.12 (2H, m), 2.28 (3H, s), 2.53-2.70 (1H, m), 278-2.86 (1H, m), 3.48-3.63 (2H, m), 3.65-3.80 (3H, m), 3.95 (2H, d), 4.58-4.70 (1H, m), 6.82 (2H, d), 7.03 (2H, d), 7.07 (1H, br), 7.22 (1H, br), 7.34 (1H, d), 7.46 (1H, dd), 7.66 (2H, d), 7.78 (2H, br), 8.16 (1H, d), 8.66 (1H, br), 9.04 (2H, br), 9.09 (1H, br), 9.30 (2H, br).

Example 75

Synthesis of 4-[(1S)-2-(3-amidinophenoxy)-1-[(4-amidinophenyl)methyl]ethyl]sulfamoyl]benzoic acid bistrifluoroacetate

Step 1

Synthesis of t-butyl [(1S)-2-hydroxy-1-(4-iodobenzyl)ethyl]carbamate 0.56 ml (7.73 mmol) of thionyl chloride was added to 3 ml of methanol under cooling with ice. 450 mg (1.56 mmol) of L-4-iodophenylalanine was added to the resultant mixture, and they were heated under reflux for 2 hours. The solvent was evaporated. 0.52 ml (4.68 mmol) of N-methylmorpholine, 443 mg (2.03 mmol) of di-t-butyl carbonate and 10 ml of dichloromethane were added to the residue, and they were stirred for 19 hours. The reaction liquid was diluted with water. After the extraction with dichloromethane, the organic layer was washed with saturated aqueous sodium hydrogencarbonate solution and then with saturated aqueous NaCl solution, and then dried over anhydrous magnesium sulfate. The solvent was evaporated under reduced pressure. 3 ml of methanol and 3 ml of tetrahydrofuran were added to the residue. 143 mg (3.78 mmol) of sodium borohydride was added to the resultant mixture, and they were stirred for 17 hours. The reaction liquid was slowly poured into 1 N hydrochloric acid. After the extraction with ethyl acetate, the organic layer was successively washed with water. 1 N hydrochloric acid, 1 N sodium hydroxide and saturated aqueous NaCl solution, and dried over anhydrous magnesium sulfate. The solvent was evaporated. The residue was purified by the silica gel column chromatography to obtain the title compound.

Yield: 240 mg (0.64 mmol) (41%)
H-NMR (CDCl3) δ 1.42 (9H, s), 3.48-3.77 (2H, m), 2.59 (2H, d), 3.79-3.91 (2H, m), 4.63-4.78 (1H, m), 6.97 (2H, d), 7.64 (2H, d)

Step 2

Synthesis of t-butyl [(1S)-2-chloro-1-(4-iodobenzyl)ethyl]carbamate 0.27 ml (1.92 mmol) of triethylamine and 165 mg (1.44 mmol) of methanesulfonyl chloride were added to 5 ml of dichloromethane containing 360 mg (0.96 mmol) of t-butyl [(1S)-2-hydroxy-1-(4-iodobenzyl)ethyl]carbamate under cooling with ice. After stirring for 30 minutes, the temperature was elevated to room temperature, and the mixture was stirred for 15 hours. The reaction liquid was diluted with water. After the extraction with dichloromethane, the organic layer was successively washed with 1 N hydrochloric acid, 1 N sodium hydroxide and saturated aqueous NaCl solution, and dried over anhydrous magnesium sulfate. The solvent was evaporated under reduced pressure. 10 ml of dimethylformamide and 203 mg (4.8 mmol) of lithium chloride were added to the residue, and they were stirred at 50° C. for 19 hours. The reaction liquid was diluted with water. After the extraction with ethyl acetate, the organic layer was successively washed with water and saturated aqueous NaCl solution. The solvent was evaporated, and the residue was purified by the silica gel column chromatography to obtain the title compound.
Yield: 237 mg (0.60 mmol) (63%)
H-NMR (CDCl3) δ 1.43 (9H, s), 2.80-2.93 (2H, m), 3.48 (1H, dd), 3.62 (1H, dd), 4.00-4.18 (1H, m), 7.00 (2H, d), 7.63 (2H, d).

Step 3

Synthesis of t-butyl [(1S)-2-(3-cyanophenoxy)-1-(4-iodobenzyl)]ethyl]carbamate 107 mg (0.90 mmol) of 3-cyanophenol and 165 mg (1.2 mmol) of potassium carbonate were added to 237 mg (0.60 mmol) of t-butyl [(1S)-2-chloro-1-(4-iodobenzyl)ethyl]carbamate and 5 ml of dimethylformamide, and they were stirred at 70° C. for 19 hours. The reaction liquid was diluted with water. After the extraction with ethyl acetate, the organic layer was successively washed with water and saturated aqueous NaCl solution. The solvent was evaporated, and the residue was purified by the silica gel column chromatography to obtain the title compound.
Yield: 282 mg (0.59 mmol) (63%)
H-NMR (CDCl3) δ 1.43 (9H, s), 2.93 (2H, d), 3.84-3.94 (2H, m), 4.73-4.89 (1H, d), 6.94 (2H, d), 7.09 (2H, d), 7.13 (1H, d), 7.38 (1H, dd), 7.60 (2H, d).

Step 4

Synthesis of t-butyl 4-[(1S)-2-(3-cyanophenoxy)-1-(4-iodobenzyl)ethyl]sulfamoyl]benzoate 117 mg (0.24 mmol) of t-butyl [(1S)-2-(3-cyanohenoxy)-1-(4-iodobenzyl)ethyl]carbamate was dissolved in 1.3 ml of 4 N solution of hydrogen chloride in dioxane and 0.63 ml of dioxane, and the solution was stirred for 3 hours. The solvent was evaporated, and the residue was dissolved in 5 ml of dimethylformamide. 0.13 ml (0.73 mmol) of diisopropylamine and 135 mg (0.49 mmol) of t-butyl 4-chlorosulfonylbenzoate (obtained by reacting chlorosulfonylbenzoic acid, isobutene and concentrated sulfuric acid in dichloromethane and treating the product by an ordinary method) were added to the solution under cooling, and they were stirred for 30 minutes and then at room temperature for 19 hours. The reaction liquid was diluted with water. After the extraction with ethyl acetate, the organic layer was washed with water and then saturated Aqueous NaCl solution. The solvent was evaporated, and the residue was purified by the silica gel column chromatography to obtain the title compound.

Yield: 50 mg (0.08 mmol) (33%)

H-NMR (CDCl3) δ 1.63 (9H, s), 2.71-2.82 (1H, m), 2.86-2.99 (1H, m), 5.15-5.28 (1H, m), 7.07 (2H, br), 7.20 (2H, d), 7.27 (1H, dd), 7.34 (1H, dd), 7.45 (2H, d), 7.69 (2H, d), 7.98 (2H, d)

Step 5

Synthesis of t-butyl 4-[(1S)-2-(3-cyanophenoxy)-1-(4-cyanobenzyl)ethyl]sulfamoyl]benzoate 50 mg (0.08 mmol) of t-Butyl 4-[(1S)-2-(3-cyanophenoxy)-1-(4-iodobenzyl)ethyl]sulfamoyl]benzoate was dissolved in 0.5 ml of N-methyl-2-pyrrolidone. 11 mg (0.01 mmol) of copper (I) cyamide was added to the solution and they were stirred at 130° C. in the presence of argon for 7 hours. The reaction liquid was treated by the silica gel column chromatography to obtain the purified title compound.

Yield: 21 mg (0.04 mmol) (33%)

H-NMR (CDCl3) δ 1.63 (9H, s), 2.82-3.10 (1H, m), 3.90 (2H, br), 5.06-5.13 (1H, m), 7.01 (2H, br), 7.15 (2H, d), 7.28 (1H, dd), 7.37 (1H, dd), 7.47 (2H, d), 7.74 (2H, d), 7.98 (2H, d)

Step 6

Synthesis of 4-[(1S)-2-(3-amidinophenoxy)-1-[(4-amidinophenyl)methyl]ethyl]sulfamoyl]benzoate bistrifluoroacetate The title compound was obtained from 21 mg (0.04 mmol) of t-butyl 4-[(1S)-2-(3-cyanophenoxy)-1-(4-cyanobenzyl)ethyl]sulfamoyl]benzoate in the same manner as that described above.

Yield: 3 mg (0.004 mmol) (10%).

MS (ESI, m/z) 496 (MH+)

H-NMR (DMSO-d6) δ2.42-2.60 (1H, m), 2.72-2.84 (1H, m), 3.48-3.61 (1H, m), 3.77 (2H, dd), 6.88 (2H, dd), 7.01 (1H, br), 7.08 (2H, d), 7.12 (1H, dd), 7.23 (1H, t), 7.33 (2H, d), 7.38 (1H, br), 7.60 (2H, d), 8.08-8.15 (1H, m), 8.63 (2H, br), 8.73 (1H, br), 8.93 (2H, br), 9.02 (2H, br).

Example 76

Synthesis of N-[2-(3-amidinophenoxy)ethyl]-N-benzyl-4-[(piperidine-4-yl)oxy]benzamide bistrifluoroacetate

Step 1

Synthesis of N-[2-(3-cyanophenoxy)ethyl]-4-(1-t-butoxycarbonyl-4-piperidyloxy)benzamide The title compound was obtained from 211.2 mg (0.65 mmol) of 4-(1-t-butoxycarbonyl-4-piperidyloxy)benzoic acid and 129.2 mg (0.65 mmol) of 3-(2-aminoethoxy)benzonitrile hydrochloride in the same manner as that of step 4 in Example 1.

Yield: 167 mg (0.36 mmol) (55%)

H-NMR (CDCl3) δ 1.50 (9H, s), 1.65-1.80 (2H, m), 1.85-2.00 (2H, m), 3.30-3.40 (2H, m), 3.60-3.75 (2H, m), 3.90 (2H, dt), 4.20 (2H, t), 4.55 (1H, m), 6.45 (1H, t), 6.94 (2H, d), 7.15 (1H, d), 7.17 (1H, s), 7.26 (1H, d), 7.38 (1H, t), 6.74 (2H, d)

Step 2

Synthesis of N-[2-(3-cyanophenoxy)ethyl]-N-benzyl-4-(1-t-butoxycarbonylpiperidine-4-yl)oxybenzamide 236 mg (5.91 mmol) of sodium hydride (oily, 60%) was stirred in dimethylformamide under cooling with ice. A solution of 2.67 g (5.91 mmol) of N-[2-(3-cyanohenoxy)ethyl]-4-(1-t-butoxycarbonylpiperidine-4-yl)oxybenzamide in a small amount of dimethylformamide was added thereto. After the completion of the formation of hydrogen, 1.4 ml (11.8 mmol) of benzyl bromide was added to the resultant mixture, and they were stirred at room temperature for 2 hours. The solvent was evaporated under reduced pressure, and 1 N hydrogen chloride was added to the residue. After the treatment with ethyl acetate as the extractant in an ordinary manner, the crude product was obtained. The crude product was then purified by the silica gel column chromatography to obtain the title compound.

Yield: 2.85 mg (5.26 mmol) (89%)

H-NMR (CDCl3) δ 1.43 (9H, s), 1.72-1.80 (2H, m), 1.85-1.93 (2H, m), 3.23-3.38 (2H, m), 3.60-3.70 (2H, m), 3.72-3.81 (2H, m), 4.15-4.22 (2H, m), 4.47-4.50 (1H, m), 4.77 (2H, brs), 6.88 (1H, d), 7.09 (1H, m), 7.25 (1H, brs), 7.26-7.50 (7H, m), 7.58 (1H, d), 7.68 (1H, t), 8.01 (1H, s)

Step 3

Synthesis of N-[2-(3-amidinophenoxy)ethyl]-N-benzyl-4-[(piperidine-4-yl)oxy]benzamide bistrifluoroacetate 2.85 g (5.26 mmol) of N-[2-(3-cyanophenoxy)ethyl]-N-benzyl-4-(1-t-butoxycarbonylpiperidine-4-yl)oxybenzamide was stirred in 5 ml of dioxane containing 4 N hydrogen chloride. 5 ml of ethanol containing 30% (w/v) of hydrogen chloride was added to the resultant mixture, and they were stirred at room temperature for 5 days. The solvent was evaporated under reduced pressure, and the residue was dissolved in 15 ml of 10% (w/v) solution of ammonia in ethanol. The solution was stirred at room temperature for one day. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 1.25 g (1.78 mmol) (34%).

MS (ESI, m/z) 473 (MH+)

H-NMR (DMSO-d6) δ 1.79-1.83 (2H, m), 2.05-2.11 (2H, m), 3.06-3.11 (2H, m), 3.22-3.27 (2H, m), 3.63-3.68 (2H, m), 4.15-4.29 (2H, m), 4.69-4.77 (3H, m), 7.04 (2H, d), 7.20-7.60 (10H, m), 7.50 (1H, t), 8.60 (2H, brs), 9.26 (4H, d).

Example 77

Synthesis of N-[2-(3-amidinophenxy)ethyl]-N-benzyl-4-(1-acetylpiperidine-4-yl)oxybenzamide trifluoroacetate 180 mg (0.257 mmol) of N-[2-(3-amidinophenoxy)ethyl]-N-benzyl-4-[(piperidine-4-yl)oxy]benzamide bistrifluoroacetate and 0.12 ml (0.848 mmol) of triethylamine were stirred in 1 ml of pyridine under cooling with ice. 0.02 ml (0.283 mmol) of acetyl chloride was slowly added to the resultant mixture, and they were stirred for 3 days. The temperature was elevated to room temperature. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 73.5 mg (0.12 mmol) (46%)
MS (ESI, m/z) 515 (MH+)
H-NMR (DMSO-d6) δ 1.41-1.62 (2H, m), 1.85-2.00 (2H, m), 2.01 (3H, s), 3.23 (2H, dt), 3.60-3.65 (2H, m), 3.80-3.90 (1H, m), 4.20-4.30 (2H, m), 4.60-4.70 (2H, m), 4.75 (2H, brs), 7.03 (2H, d), 7.20-7.43 (10H, m), 7.52 (1H, t), 9.21 (4H, d).

Example 78

Synthesis of N-[2-(3-amidinophenoxy)ethyl]-N-benzyl-4-[1-(aminoacetyl)piperidine-4-yl]oxybenzamide bistrifluoroacetate 40 mg (0.314 mmol) of N-t-butoxycarbonylglycine was stirred in dimethylformamide. 0.1 ml (0.69 mmol) of triethylamine and 0.03 ml (0.314 mmol) of ethyl chloroformate were added thereto under cooling with ice. After stirring for 5 minutes, 220 mg (0.314 mmol) of N-[2-(3-amidinophenoxy)ethyl]-N-benzyl-4-[(piperidine-4-yl)oxy]benzamide bistrifluoroacetate was added to the resultant mixture. The temperature was elevated to room temperature. After stirring for 4 hours, the solvent was evaporated to obtain the crude product, which was stirred in 0.5 ml of dioxane containing 4 N hydrogen chloride for 28 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 61.6 mg (0.0813 mmol) (26%)
MS (ESI, m/z) 530 (MH+)
H-NMR (DMSO-d6) δ 1.50-1.70 (2H, m), 1.91-2.10 (2H, m), 3.05-3.10 (1H, m), 3.20-3.40 (2H, m), 3.52-3.70 (3H, m), 3.80-4.00 (2H, m), 4.23 (2H, m), 4.72 (2H, brs), 7.05 (2H, d), 7.20-7.52 (10H, m), 7.53 (1H, t), 8.03 (3H, brs), 9.28 (4H, d).

Example 79

Synthesis of 3-[4-amidino-2-[2-[4-(1-acetimidoyl-4-piperidyloxy)benzoylamino]ethoxy]phenyl]-2-oxo-propionic acid bistrifluoroacetate

Step 1

Synthesis of 3-hydroxy-4-iodobenzoic acid 30.0 g (217 mmol)) of 3-hydroxybenzoic acid was dissolved in 200 ml of acetic acid. 53.0 g (326 mmol) of iodine monochloride was added to the solution at room temperature. After stirring at 45° C. for 15 hours, the solvent was evaporated under reduced pressure. The residue was washed with 500 ml of 1% aqueous sodium thiosulfate solution twice and 500 ml of water twice, and then dried at 80° C. under reduced pressure to obtain the title compound.

Yield: 17.2 g (65.2 mmol) (30%)
MS (FAB, m/z) 265 (MH+)
H-NMR (DMSO-d6) δ 7.13 (1H, dd), 7.43 (1H, d), 7.80 (1H, d).

Step 2

Synthesis of 3-hydroxy-4-iodobenzonitrile 22.3 g (89.7 mmol) of 3-hydroxy-4-iodobenzoic acid was dissolved in 300 ml of tetrahydrofuran. 19.7 ml (206 mmol) of ethyl chloroformate and 28.7 ml (206 mmol) of triethylamine was added to the solution at 0° C. After stirring for 15 minutes, the obtained triethylamine hydrochloride was taken by the filtration. The filtrate was added to 300 ml of tetrahydrofuran solution, in which ammonia had been bubbled, at 0° C. After stirring at room temperature for 18 hours, the solvent was evaporated under reduced pressure. The residue was dissolved in 450 ml of dioxane. 17.4 ml (117 mmol) of Trifluoromethanesulfonic anhydride and 21.8 ml (269 mmol) of pyridine were added to the solution at 0° C. After stirring at room temperature for 18 hours, the solvent was evaporated under reduced pressure. The residue was treated with chloroform as the extractant by an ordinary method to obtain an oily residue. This residue was dissolved in 180 ml of tetrahydrofuran/methanol (1:1). 90 ml (90.0 mmol) of 1 N aqueous sodium hydroxide solution was added to the solution at room temperature. After stirring under these conditions for 4 hours, the solvent was evaporated under reduced pressure, and the residue was washed with dichloromethane. The residue was acidified with 1 N aqueous hydrogen chloride solution, and treated with ethyl acetate as the extractant by an ordinary method to obtain the crude product, which was purified by the silica gel column chromatography to obtain the title compound.

Yield: 9.29 g (37.9 mmol) (42%)
MS (FAB, m/z) 246 (MH+)
H-NMR (CDCl3) δ 5.63 (1H, br), 6.96 (1H, dd), 7.23 (1H, d), 7.79 (1H, d).

Step 3

Synthesis of 3-(2-aminoethoxy)-4-iodobenzonitrile hydrochloride

The title compound was obtained from 3-hydroxy-4-iodobenzonitrile and t-butyl(2-chloroethyl)carbamate in the same manner as that of steps 2 and 3 in Example 1. t-Butyl(2-chloroethyl)carbamate had been obtained from 2-chloroethylamine hydrochloride in the same manner as that of step 1 in Example 1.

Step 4

Synthesis of N-[2-(5-cyano-2-iodophenoxy)ethyl]-4-(1-t-butoxycarbonyl-4-piperidyloxy)benzamide 2.28 g (7.03 mmol) of 3-(2-aminoethoxy)-4-iodobenzonitrile hydrochloride, 2.90 g (9.02 mmol) of 4-[1-t-butoxycarbonyl-4-piperidyl]oxy]benzoic acid, 11.1 g (85.9 mmol) of diisopropylethylamine, 3.02 (15.8 mmol) of 1-(3-dimethylaminopropyl)-3-ethylcarbodiimide hydrochloride and 0.62 g (5.07 mmol) of 4-dimethylaminopyridine were dissolved in 80 ml of dimethylformamide, and the resultant solution was stirred at room temperature overnight. The solvent was evaporated, and the residue was purified by the silica gel column chromatography to obtain the title compound.

Yield: 2.72 g (4.60 mmol) (65.4%)

H-NMR (CDCl3) δ 1.43 (9H, s)), 1.62-1.82 (2H, m), 1.89-2.00 (2H, m), 3.30-3.40 (2H, m), 3.62-3.78 (2H, m), 3.95 (2H, dt), 4.22 (2H, t), 4.55 (1H, m), 6.64 (1H, t), 6.94 (2H, d), 7.01 (1H, d), 7.03 (1H, dd), 7.78 (2H, d), 7.89 (1H, d).

Step 5

Synthesis of methyl 2-acetylamino-3-[4-cyano-2-[2-[4-(1-t-butoxycarbonyl-4-piperidyloxy)benzoylamino]ethoxy]phenyl]acrylate 2.72 g (4.60 mmol) of N-[2-(5-cyano-2-iodophenoxy)ethyl]-4-(1-t-butoxycarbonyl-4-piperidyloxy)benzamide and 1.32 g (9.22 mmol) of methyl 2-acetaminoacrylate were dissolved in 80 ml of acetonitrile. 272 mg (1.21 mmol) of palladium (II) acetate, 630 mg (2.07 mmol) of tri-o-tolylphosphine and 1.71 g (9.23 mmol) of tributylamine were added to the solution, and they were heated under reflux for 3 days. The solvent was evaporated, and the residue was treated with ethyl acetate as the extractant in an ordinary manner to obtain the crude product, which was purified by the silica gel column chromatography to obtain the title compound.

Yield: 1.12 g (1.85 mmol) (40.2%)

H-NMR (CDCl3) δ 1.45 (9H, s), 1.65-1.80 (2H, m), 1.85-2.00 (2H, m), 2.02 (3H, s), 3.30-3.40 (2H, m), 3.60-3.75 (2H, m), 3.80 (3H, s), 4.35 (2H, t), 4.55 (1H, m), 6.82 (2H, d), 6.99 (1H, t), 7.18-7.22 (2H, m), 7.33 (1H, s), 7.44 (1H, s), 7.69 (2H, d), 7.87 (1H, d).

Step 6

Synthesis of 3-[4-amidino-2-[2-[4-(1-acetimidoyl-4-piperidyloxy)benzoylamino]ethoxy]phenyl]-2-oxo-propionic acid bistrifluoroacetate 1.12 g (1.85 mmol) of methyl 2-acetylamino-3-[4-cyano-3-[2-[4-(1-t-butoxycarbony-4-piperidyloxy)benzoylamino]ethoxy]phenyl]acrylate was dissolved in 50 ml of 4 N solution of hydrogen chloride in dioxane. 5 ml of ethanol was added to the solution, and they were stirred at room temperature for 10 days. The solvent was evaporated. The residue was dissolved in 80 ml of 20% (w/v) solution of ammonia in ethanol, and the solution was stirred at room temperature for 4 days. The solvent was evaporated, and the residue was dissolved in a solution of 2.23 g (18.0 mmol) of ethyl acetimidate hydrochloride and 16.0 g (158 mmol) of triethylamine in 100 ml of ethanol. The solution was stirred at 30° C. for 4 days. The solvent was evaporated, and the obtained crude product was dissolved in 50 ml of a mixed solvent of water and acetonitrile (4:1) containing 0.1% (v/v) of trifluoroacetic acid. The solution was treated by the reversed-phase medium pressure liquid chromatography with silica gel containing octadodecyl group chemically bonded thereto as the filler (LiChroprep RP-18 37×440 mm). After the elution with a mixed solvent of water and acetonitrile containing 0.1% (v/v) of trifluoroacetic acid, the solvent was removed by the freeze-drying. The residue was dissolved in 50 ml of 6 N hydrochloric acid, and the solution was stirred at 80° C. for 2 hours. The solvent was evaporated. The crude product was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 123 mg (0.167 mmol) (9.0%).

MS (ESI, m/z) 510 (MH+)

H-NMR (DMSO-d6) δ 1.65-1.85 (2H, m), 2.02-2.19 (2H, m), 2.25 (3H, s), 3.58-3.82 (6H, m), 4.23 (2H, s, keto form), 4.30 (2H, t), 4.79 (1H, m), 6.80 (1H, s, enol form), 7.07 (2H, d), 7.38-7.47 (2H, m), 7.83 (2H, d), 8.33 (1H, d), 8.55-8.67 (2H, m), 9.05-9.34 (5H, brm), 9.75 (1H, br, enol form)

Example 80

Synthesis of 3-[4-amidino-2-[2-[4-(dimethylcarbamoyl)benzoylamino]ethoxy]phenyl]-2-oxo-propionic acid trifluoroacetate Step 1

Synthesis of N-[2-(2-iodo-5-cyanophenoxy)ethyl]-4-(N,N-dimethylcarbamoyl)benzamide 600 mg (3.1 mmol) of 4-dimethylcarbamoylbenzoic acid and 1.25 g of triethylamine were stirred in dimethylformamide. 336 mg (3.1 mmol) of ethyl chloroformate was added to the resultant mixture, and they were stirred for 5 minutes. 3-(2-aminoethoxy)-4-iodobenzonitrile monohydrochloride was added to the mixture. The temperature was elevated to room temperature. After stirring for 2 hours, 1 N hydrochloric acid was added to the mixture. After extracting with ethyl acetate, the organic layer was washed with saturated aqueous sodium hydrogencarbonate solution and saturated aqueous NaCl a solution, and dried over anhydrous magnesium sulfate. The solvent was evaporated, and the residue was washed with ethyl acetate to obtain the title compound. Further, the residue obtained after the evaporation of the solvent from the wash solution was purified by the silica gel chromatography (ethyl acetate/methanol) to obtain the title compound.

Yield: 983 mg (2.1 mmol) (68%)

H-NMR (DMSO-d6) δ 2.87 (3H, br), 3.00 (3H, br), 3.65 (2H, dt), 4.27 (2H, t), 7.17 (1H, d), 7.47 (2H, d), 7.52 (1H, s), 7.88 (2H, d), 7.98 (1H, d), 8.67 (1H, br)

Step 2

Synthesis of methyl 2-acetylamino-3-[4-cyano-2-[4-(dimethylcarbamoyl)benzoylamino]ethoxy]phenyl]acrylate 968 mg (2.09 mmol) of [2-(2-iodo-5-cyanophenoxy)ethyl]-4-(N,N-dimethylcarbamoyl)benzamide, 600 mg (4.18 mmol) of methyl 2-(acetylamino)acrylate, 93 mg (0.38 mmol) of palladium (II) acetate, 548 mg (1.8 mmol) of tri-o-tolylphosphine and 775 mg (4.18 mmol) of tributylamine were heated under reflux in acetonitrile for 2 days. The solvent was evaporated, and methanol was added to the residue. The resultant mixture was filtered through Celite, and the solvent was evaporated. 1 N hydrochloric acid was added to the residue. After the extraction with ethyl acetate, the organic layer was washed with saturated aqueous NaCl solution, and dried over anhydrous magnesium sulfate. The solvent was evaporated. The residue was purified by the silica gel chromatography (ethyl acetate/methanol) to obtain the title compound.

Yield: 629 mg (1.3 mmol) (62%)

H-NMR (DMSO-d6) δ 1.95 (3H, s), 2.90 (3H, s), 3.00 (3H, s), 3.60-3.70 (5H, m), 4.30 (2H, t), 7.21 (1H, s), 7.43 (1H, d), 7.47 (2H, d), 7.63 (1H, s), 7.67 (1H, d), 7.87 (2H, d), 8.75 (1H, t), 9.65 (1H, s)

Step 3

Synthesis of 3-[4-amidino-2-[2-[4-(dimethylcarbamoyl)benzoylamino]ethoxy]phenyl]-2-oxopropionic acid trifluoroacetate 5 ml of 4 N dioxane hydrochloride and 1 ml of ethanol were added to 620 mg (1.3 mmol) of methyl 2-acetylamino-3-[4-cyano-2-[4-(dimethylcarbamoyl)benzoylamino]ethoxy]phenyl]acrylate, and they were stirred for 96 hours. The solvent was evaporated under reduced pressure, and the residue was dissolved in 10 ml of 10% (w/v) solution of ammonia in ethanol. The solution was stirred for 24 hours. The solvent was evaporated under reduced pressure, and the residue was dissolved in 5 ml of 6 N hydrochloric acid. The solution was stirred at 80° C. for 2 hours. The solvent was evaporated under reduced pressure, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 46 mg (0.08 mmol) (6%)

MS (ESI, m/z) 441 (MH+)

H-NMR (DMSO-d6) δ 2.90 (3H, br), 3.00 (3H, br), 3.70 (2H, dt), 4.28 (2H, t), 4.23 (2H, s, keto form), 6.85 (1H, s, enol form), 7.35-7.50 (4H, m), 7.88 (2H, d), 8.33 (1H, d), 8.83 (1H, t), 9.00 (2H, br), 9.25 (2H, br), 9.75 (1H, enol, s).

Example 81

Synthesis of 3-[4-amidino-2-[2-[4-(4-piperidylmethyl)benzoylamino]ethoxy]phenyl]-2-oxopropionic acid bistrifluoroacetate Step 1

Synthesis of methyl 2-acetylamino-3-[4-cyano-2-[2-[4-[(1-t-butoxycarbonyl-4-piperidyl)methyl]benzoylamino]ethoxy]phenyl]acrylate 4 ml of 1 N sodium hydroxide and 6 ml of ethanol were added to 600 mg (1.80 mmol) of methyl 4-[(1-t-butoxycarbonylpiperidine-4-yl)methyl]benzoate, and they were stirred for 18 hours. The reaction liquid was acidified with 1 N hydrochloric acid. After the extraction with ethyl acetate followed by the drying over anhydrous magnesium sulfate, the solvent was evaporated. The residue was dissolved in 10 ml of dichloromethane. 1.25 ml (9.06 mmol) of triethylamine, 378 mg (1.98 mmol) of 1-(3-dimethylaminopropyl-3-ethylcarbodiimide hydrochloride, 267 mg (1.98 mmol) of 1-hydroxybenzotriazole and 202 mg (1.02 mmol) of 3-(2-aminoethoxy)-4-iodobenzonitrile hydrochloride were added to the residue, and they were stirred for 20 hours. The reaction liquid was diluted with water. After the extraction with ethyl acetate, the organic layer was successively washed with water, 1 N sodium hydroxide and saturated aqueous NaCl solution and then dried over anhydrous magnesium sulfate. The solvent was evaporated. The residue was dissolved in 10 ml of acetonitrile. 478 mg (3.34 mmol) of methyl 2-acetamide acrylate, 41 mg (0.17 mmol) of palladium (II) acetate, 355 mg (1.17 mmol) of tris(2-methylphenyl)phosphine and 618 mg (3.34 mmol) of tributylamine were added to the solution, and they were heated under reflux for 18 hours. The solvent was evaporated, and the reaction liquid was diluted with water. After the extraction with ethyl acetate, the organic layer was successively washed with water, 1 N sodium hydroxide and saturated aqueous NaCl solution, and dried over anhydrous magnesium sulfate. The solvent was evaporated, and the residue was purified by the silica gel column chromatography to obtain the title compound.

Yield: 530 mg (0.85 mmol) (51%)

H-NMR (CDCl3) δ 1.04-1.17 (2H, m), 1.42 (9H, s), 1.58-1.77 (3H, m), 1.98 (3H, s), 2.54 (2H, d), 2.73-2.89 (2H, m), 3.78 (3H, s), 3.89 (2H, dt), 3.96-4.08 (2H, m), 4.31 (2H, t), 6.95-7.03 (1H, m), 7.11 (2H, d), 7.12-7.19 (2H, m), 7.23-7.27 (1H, m), 7.29-7.34 (1H, m), 7.43 (1H, br), 7.63 (2H, d)

Step 2

Synthesis of 3-[4-amidino-2-[2-[4-(4-piperidylmethyl)benzoylamino]ethoxy]phenyl]-2-oxopropionic acid bistrifluoroacetate The title compound was obtained from 530 mg (0.85 mmol) of methyl 2-acetylamino-3-[4-cyano-2-[2-[4-[(1-t-butoxycarbonyl-4-piperidyl)methyl]benzoylamino]ethoxy]phenyl]acrylate in the same manner as that of step 3 in Example 80.

Yield: 150 mg (0.22 mmol) (25%)

MS (ESI, m/z) 467 (MH+)

H-NMR (DMSO-d6) δ 1.23-1.40 (2H, m), 1.62-1.73 (2H, m), 1.76-1.90 (1H, m), 2.59 (2H, d), 2.72-2.91 (2H, m), 3.17-3.30 (2H, m), 3.68 (2H, dt), 4.21 (2H, s keto form), 4.29 (2H, t), 6.82 (1H, s, enol form), 7.27 (2H, d), 7.34-7.49 (2H, m), 7.80 (2H, d), 8.34 (1H, d), 8.66-8.74 (1H, m), 9.12 (2H, br), 9.25 (2H, br), 9.78 (1 h, br, enol form).

Example 82

Synthesis of 3-[4-amidino-2-[2-[4-(pyrrolidine-1-yl)benzoylamino]ethoxy]phenyl]-2-oxopropionic acid trifluoroacetate Step 1

Synthesis of methyl 2-acetylamino-3-[4-cyano-2-[2-[4-(pyrrolidine-1-yl)benzoylamino]ethoxy]phenyl]acrylate 400 mg (2.09 mmol) of 4-(pyrrolidine-1-yl)benzoic acid was dissolved in 10 ml of dichloromethane. 1.25 ml (9.06 mmol) of triethylamine, 439 mg (2.30 mmol) of 1-(3-dimethylaminopropyl)-3-ethylcarbodiimide hydrochloride, 310 mg (2.30 mmol) of 1-hydroxybenzotriazole and 636 mg (2.09 mmol) of 3-(2-aminoethoxy)-4-iodobenzonitrile hydrochloride were added to the solution, and they were stirred for 19 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated. The residue was dissolved in 15 ml of acetonitrile. 503 mg (3.51 mmol) of methyl 2-acetamide acrylate, 43 mg (0.18 mmol) of palladium (II) acetate, 375 mg (1.23 mmol) of tris(2-methylphenyl)phosphine and 649 mg (3.51 mmol) of tributylamine were added to the solution, and they were heated under reflux for 18 hours. The solvent was evaporated, and the reaction liquid was diluted with water. After the extraction with ethyl acetate, the organic layer was successively washed with water, 1 N sodium hydroxide and saturated aqueous NaCl solution, and dried over anhydrous magnesium sulfate. The solvent was evaporated, and the residue was purified by the silica gel column chromatography to obtain the title compound.

Yield: 650 mg (1.37 mmol) (78%)

H-NMR (CDCl3) δ 1.92-2.10 (7H, m), 3.11-3.28 (3H, m), 3.74-3.83 (5H, m), 4.24 (2H, t), 6.45 (2H, d), 6.65-6.73 (1H, m), 7.18 (1H, d), 7.24 (1H, br), 7.31-7.42 (2H, m), 7.61 (2H, d)

Step 2

Synthesis of 3-[4-amidino-2-[2-[4-(pyrrolidine-1-yl)benzoylamino]ethoxy]phenyl]-2-oxopropionic acid trifluoroacetate The title compound was obtained from 650 mg (1.37 mmol) of methyl 2-acetylamino-3-[4-cyano-2-[2-[4-[(pyrrolidine 1-yl)benzoylamino]ethoxy]phenyl]acrylate in the same manner as that of step 3 in Example 80.

Yield: 130 mg (0.24 mmol) (17%)

MS (ESI, m/z) 439 (MH+)

H-NMR (DMSO-d6) δ 1.88-2.04 (4H, m), 3.23-3.35 (4H, m), 3.67 (2H, dt), 4.21 (2H, s, keto form); 4.23 (2H, t), 6.52 (2H, d), 6.82 (1H, s, enol form), 7.31-7.52 (2H, m), 7.72 (2H, d), 8.27-8.39 (2H, m), 9.00 (2H, br), 9.26 (2H, br), 9.78 (1H, br, enol form).

Example 83

Synthesis of (4S)-4-(4-amidinobenzoylamino)-5-(3-amidinophenoxy)pentanoic acid bistrifluoroacetate and ethyl (4S)-(4-amidinobenzoylamino)-5-(3-amidinophenoxy)pentanoate bistrifluoroacetate Step 1

Synthesis of benzyl (4S)-4-t-butoxycarbonylamino-5-(3-cyanophenoxy)pentanoate

The title compound was obtained from 6.75 g (20.0 mmol) of γ-benzyl N-t-butoxycarbonyl-L-glutamate in the same manner as that of step 1 in Example 51.

Yield: 6.90 g (16.3 mmol) (81%)

H-NMR (CDCl3) δ 1.44 (9H, s), 1.69 (2H, br), 2.02 (2H, br), 3.98 (2H, br), 4.83 (1H, br), 5.11 (2H, s), 7.04-7.16 (4H, m), 7.24-7.40 (5H, m)

Step 2

Synthesis of benzyl (4S)-4-(4-cyanobenzoylamino)-5-(3-cyanophenoxy)pentanoate

The title compound was obtained from 6.90 g (16.3 mmol) of benzyl (4S)-4-t-butoxycarbonylamino-5-(3-cyanophenoxy)pentanoate in the same manner as that of step 2 in Example 51.

Yield: 3.56 g (7.85 mmol) (48%)

H-NMR (CDCl3) δ 2.10-2.28 (2H, m), 2, 54 (1H, ddd), 2.69 (1H, ddd), 4.10 (1H, dd), 4.18 (1H, dd), 4.48 (1H, br), 5.12 (2H, s), 7.00 (1H, br), 7.14-7.19 (2H, m), 7.24-7.41 (7H, m), 7.72 (2H, d), 7.87 (2H, d)

Step 3

Synthesis of ethyl (4S)-4-(4-amidinobenzoylamino)-5-(3-amidinophenoxy)pentanoate bistrifluoroacetate The title compound was obtained from 3.56 g (7.85 mmol) of benzyl (4S)-4-(4-cyanobenzoylamino)-5-(3-cyanophenoxy)pentanoate in the same manner as that of step 3 in Example 51.

Yield: 2.19 g (3.35 mmol) (43%)

MS (ESI, m/z) 426 (MH+)

H-NMR (DMSO-d6) δ 1.15 (3H, t), 1.88-1.98 (1H, m), 2.01-2.11 (1H, m), 2.45 (2H, ddd), 4.03 (2H, q), 4.11 (1H, dd), 4.19 (1H, dd), 4.38 (1H, br), 7.34 (1H, d), 7.39 (1H, d), 7.40 (1H, s), 7.54 (1H, dd), 7.91 (2H, d), 8.05 (2H, d), 8.66 (1H, d), 9.17 (2H, s), 9.29 (4H, s), 9.42 (2H, s).

Step 4

Synthesis of (4S)-4-(4-amidinobenzoylamino)-5-(3-amidinophenoxy)pentanoic acid bistrifluoroacetate The title compound was obtained from 1.57 g (2.40 mmol) of ethyl (4S)-4-(4-amidinobenzoylamino)-5-(3-amidinophenoxy)pentanoate bistrifluoroacetate in the same manner as that of step 4 in Example 51.

Yield: 424 mg (0.677 mmol) (28%).

MS (ESI, m/z) 398 (MH+)

H-NMR (DMSO-d6) δ 1.84-1.96 (1H, m), 1.98-2.10 (1H, m), 2.37 (2H, ddd), 4.11 (1H, dd), 4.20 (1H, dd), 4.38 (1H, br), 7.33 (1H, d), 7.39 (1H, d), 7.40 (1H, s), 7.91 (2H, d), 8.05 (2H, d), 8.65 (1H, d), 9.18 (2H, s), 9.26 (2H, s), 9.29 (2H, s), 9.41 (2H, s).

Example 84

Synthesis of (4R)-4-(4-carbamoylbenzoylamino)-5-(3-amidinophenoxy)pentanoic acid bistrifluoroacetate Step 1

Synthesis of benzyl (4R)-4-t-butoxycarbonylamino-5-(3-cyanophenoxy)pentanoate

The title compound was obtained from 3.37 g (10.0 mmol) of γ-benzyl N-t-butoxycarbonyl-D-glutamate in the same manner as that of step 1 in Example 51.

Yield: 3.20 g (7.54 mmol) (75%)

H-NMR (CDCl3) δ 1.44 (9H, s), 1.69 (2H, br), 2.02 (2H, br), 3.98 (2H, br), 4.83 (1H, br), 5.11 (2H, s), 7.04-7.16 (4H, m), 7.24-7.40 (5H, m)

Step 2

Synthesis of benzyl (4R)-4-(4-cyanobenzoylamino)-5-(3-cyanophenoxy)pentanoate

The title compound was obtained from 3.20 g (7.54 mmol) of benzyl (4R)-4-t-butoxycarbonylamino-5-(3-cyanophenoxy)pentanoate in the same manner as that of step 2 in Example 51.

Yield: 2.16 g (4.76 mmol) (63%)

H-NMR (CDCl3) δ 2.10-2.28 (2H, m), 2, 54 (1H, ddd), 2.69 (1H, ddd), 4.10 (1H, dd), 4.18 (1H, dd), 4.48 (1H, br), 5.12 (2H, s), 7.00 (1H, br), 7.14-7.19 (2H, m), 7.24-7.41 (7H, m), 7.72 (2H, d), 7.87 (2H, d)

Step 3

Synthesis of (4R)-4-(4-carbamoylbenzoylamino)-5-(3-amidinophenoxy)pentanoic acid bistrifluoroacetate The title compound was obtained from benzyl (4R)-4-(4-cyanobenzoylamino)-5-(3-cyanophenoxy)pentanoate in the same manner as that of step 2 in Example 60.

MS (ESI, m/z) 399 (MH+)

H-NMR (DMSO-d6) δ 1.90 (1H, br), 2.01 (1H, br), 2.36 (2H, br), 4.08 (1H, dd), 4.17 (1H, dd), 4.36 (1H, br), 7.35 (1H, d), 7.39 (1H, d), 7.41 (1H, s), 7.53 (1H, t), 7.92 (2H, d), 7.96 (2H, d), 8.08 (2H, br), 8.50 (1H, d), 9.14 (2H, br), 9.27 (2H, br).

Example 85

Synthesis of N-[2-(3-amidinophenoxy)ethyl]-N-benzyl-4-(1-acetimidoylpiperidine-4-yl)oxybenzamide bistrifluoroacetate 230 mg (0.34 mmol) of N-[2-(3-amidinophenoxy)ethyl]-N-benzyl-4-(piperidine-4-yl)oxybenzamide bistrifluoroacetate was dissolved in 3 ml of ethanol. 0.25 ml (1.74 mmol) of triethylamine and 87 mg (0.71 mmol) of ethyl acetimidate hydrochloride were added to the solution, and they were stirred at room temperature for 6 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 196 mg (0.269 mmol) (81%)

MS (ESI, m/z) 473 (MH+)

H-NMR (DMSO-d6) δ 1.65-1.80 (2H, m), 2.00-2.10 (2H, m), 2.31 (3H, s), 3.52 (2H, t), 3.57-3.80 (2H, m), 4.12-4.30 (2H, m), 4.60-4.80 (4H, m), 7.01 (2H, d), 7.20-7.40 (10H, m), 7.50 (1H, t), 8.62 (1H, s), 9.17 (1H, s), 9.32 (4H, brs).

Example 86

Synthesis of N-[(1R)-1-benzyl-2-(3-amidinophenoxy)ethyl]-4-(pyrrolidine-1-yl)benzamide bistrifluoroacetate Methyl (2R)-2-(t-butoxycarbonylamino)-3-phenylpropionate was obtained from methyl D-phenylalanine hydrochloride in the same manner as that of step 2 in Example 71. This compound was converted into t-butyl (1R)-1-benzyl-2-hydroxyethylcarbamate in the same manner as that of step 4 in Example 71. This compound was further converted into t-butyl (1R)-1-benzyl-2-(3-cyanophenoxy)ethylcarbamate in the same manner as that of steps 5 and 6 in Example 71. The title compound was obtained from 1.55 (4.40 mmol) of t-butyl (1R)-1-benzyl-2-(3-cyanophenoxy)ethylcarbamate in the same manner as that of Example 59.

Yield: 568 mg (1.02 mmol) (23.2%).

MS (ESI, m/z) 443 (MH+)

H-NMR (DMSO-d6) δ1.82-2.01 (4H, m), 2.92-3.10 (2H, m), 3.18-3.37 (4H, m), 4.05 (1H, dd), 4.19 (1H, dd), 4.42-4.57 (1H, m), 6.53 (2H, d), 7.15-7.42 (8H, m), 7.55 (1H, dd), 7.67 (2H, d), 8.08 (1H, d), 9.22 (2H, brs), 9.27 (2H, brs).

Example 87

Synthesis of N-[(1R)-2-(3-amidinophenoxy)-1-(4-hydroxybenzyl)ethyl]-4-amidinobenzamide bistrifluoroacetate Step 1

Synthesis of (2R)-(t-butoxycarbonyl)amino-2-[4-(ethoxycarbonyloxy)benzyl]ethanol 3.5 g (19.3 mmol) of D-tyrosine was t-butoxycarbonylated with di-t-butyl dicarbonate to obtain (2R)-2-(t-butoxycarbonyl)amino-3-[4-hydroxyphenyl]propionic acid. A mixed acid anhydride was prepared from this compound, ethyl chloroformate and diisopropylethylamine. After the reduction with sodium borohydride, the title compound was obtained.

Yield: 5.72 g

H-NMR (CDCl3) δ 1.38 (3H, t), 1.42 (9H, s), 2.83 (2H, d), 3.58 (1H, dd), 3.65 (1H, dd), 3.78-3.88 (1H, m), 4.28 (2H, q), 4.73 (1H, d), 7.11 (2H, d), 7.22 (2H, d)

Step 2

Synthesis of N-[(1R)-2-(3-amidinophenoxy)-1-(4-hydroxybenzyl)ethyl]-4-amidinobenzamide bistrifluoroacetate t-Butyl (1R)-1-[4-(ethoxycarbonyloxy)benzyl]-2-(3-cyanophenoxy)ethylcarbamate was obtained from 5.72 g of crude (2R)-2-(t-butoxycarbonyl)amino-2-[4-(ethoxycarbonyloxy)benzyl]ethanol, obtained in step 1, in the same manner as that of steps 5 and 6 in Example 71. This product was treated in the same manner as that of step 2 in Example 51 and then step 6 in Example 1 to obtain the title compound.

Yield: 16.5 mg

MS (ESI, m/z) 432 (MH+)

H-NMR (DMSO-d6) δ 2.83 (1H, dd), 2.97 (1H, dd), 4.10-4.23 (2H, m), 4.43-4.57 (1H, m), 6.63 (2H, d), 7.10 (2H, d), 7.28 (1H, dd), 7.36-7.41 (2H, m), 7.58 (1H, dd), 7.90 (2H, d), 8.01 (2H, d), 8.75 (1H, d), 9.25 (2H, s), 9.31 (2H, s), 9.38 (2H, s), 9.41 (2H, s).

Example 88

Synthesis of N-[(1R)-1-(4-iodobenzyl)-2-(3-amidinophenoxy)ethyl]-4-amidinobenzamide bistrifluoroacetate and methyl 4-[(2R)-2-(4-amidinobenzoylamino)-3-(3-amidinophenoxy)propyl]benzoate bistrifluoroacetate Step 1

Synthesis of D-4-iodophenylalanine 12.3 g (48 mmol) of iodine and 5.1 g (24 mmol) of sodium iodate were added to 20 g (121 mmol) of D-phenylalanine, 14.5 ml of concentrated sulfuric acid and 110 ml of acetic acid, and they were stirred for 24 hours. After cooling, 0.5 g of sodium periodate was added thereto, and the solvent was evaporated at 35° C. under reduced pressure. Water was added to the reaction mixture and the resultant mixture was washed with dichloromethane trice. The aqueous phase was neutralized with 1 N aqueous sodium hydroxide solution. After cooling, the obtained precipitate was taken by the filtration and then washed with water and ethanol to obtain the crude product.

Yield: 30 g (103 mmol) (85%).

Step 2

Synthesis of methyl (2R)-2-t-butoxycarbonylamino-3-(4-iodophenyl)propionate 17 ml (230 mmol) of thionyl chloride was added to 3 ml of methanol under cooling with ice. 22.2 g (76.3 mmol) of D-4-iodophenylalanine was added to the resultant mixture, and they were heated under reflux for 2 hours. The solvent was evaporated. 15 ml (137 mmol) of N-methylmorpholine, 12 g (55 mmol) of di-t-butyl carbonate and 100 ml of dichloromethane were added to the residue, and they were stirred for 19 hours. The reaction liquid was diluted with water. After the extraction with dichloromethane, the organic layer was successively washed with saturated aqueous sodium hydrogencarbonate solution and saturated aqueous NaCl solution, and dried over anhydrous magnesium sulfate. The solvent was evaporated, and the residue was purified by the silica gel column chromatography to obtain the title compound.

Yield: 12.2 g (35.8 mmol) (47%)

H-NMR (CDCl3) δ 1.42 (9H, s), 2.83-3.18 (2H, m), 3.71 (3H, s), 4.43-4.60 (2H, m), 4.84-5.06 (1H, m), 6.85 (2H, d), 7.60 (2H, d).

Step 3

Synthesis of t-butyl [(1R)-2-chloro-1-(4-iodobenzyl)ethyl]carbamate 25 ml of methanol and 25 ml of tetrahydrofuran were added to 6.2 g (18 mmol) of methyl (2R)-t-butoxycarbonylamino-3-(4-iodophenyl)propionate. 3.44 g (91 mmol) of sodium borohydride was added to the resultant mixture under cooling with ice, and they were stirred for 17 hours. The reaction liquid was slowly poured into 1 N hydrochloric acid. After the extraction with ethyl acetate, the organic layer was successively washed with water, 1 N hydrochloric acid, 1 N sodium hydroxide and saturated aqueous NaCl solution, and then dried over anhydrous magnesium sulfate. The solvent was evaporated. 50 ml of dichloromethane was added to the residue. Then, 5.02 ml (36 mmol) of triethylamine and 3.09 g (27 mmol) of methanesulfonyl chloride were added to the resultant mixture under cooling with ice, and they were stirred for 30 minutes. The temperature was elevated to room temperature, and the mixture was stirred for 15 hours. The reaction liquid was diluted with water. After the extraction with dichloromethane, the organic layer was successively washed with 1 N hydrochloric acid, 1 N sodium hydroxide and saturated aqueous NaCl solution, and dried over anhydrous magnesium sulfate. The solvent was evaporated under reduced pressure. 40 ml of dimethylformamide and 3.85 g (91 mmol) of lithium chloride were added to the residue, and they were stirred at 50° C. for 19 hours. The reaction liquid was diluted with water. After the extraction with ethyl acetate, the organic layer was successively washed with water and saturated aqueous NaCl solution. The solvent was evaporated, and the residue was purified by the silica gel column chromatography to obtain the title compound.

Yield: 3.4 g (8.6 mmol) (47%)

H-NMR (CDCl3) δ 1.43 (9H, s), 2.80-2.93 (2H, m), 3.48 (1H, dd), 3.62 (1H, dd), 4.00-4.18 (1H, m), 7.00 (2H, d), 7.63 (2H, d)

Step 4

Synthesis of t-butyl [(1R)-2-(3-cyanophenoxy)-1-(4-iodobenzyl)ethyl]carbamate 724 mg (6.08 mmol) of 3-cyanophenol and 1.12 g (8.1 mmol) of potassium carbonate were added to 1.6 g (0.60 mmol) of t-butyl [(1R)-2-chloro-1-(4-iodobenzyl)ethyl]carbamate and 25 ml of dimethylformamide, and they were stirred at 70° C. for 55 hours. The reaction liquid was diluted with water. After extraction with ethyl acetate, the organic layer was successively washed with water and saturated aqueous NaCl solution. The solvent was evaporated, and the residue was purified by the silica gel column chromatography to obtain the title compound.

Yield: 1.44 g (3.01 mmol) (74%)

H-NMR (CDCl3) δ 1.43 (9H, s), 2.93 (2H, d), 3.84-3.94 (2H, m), 4.73-4.89 (1H, m), 6.94 (2H, d), 7.09 (2H, d), 7.13 (1H, d), 7.38 (1H, dd), 7.60 (2H, d)

Step 5

Synthesis of N-[(1R)-2-(3-cyanophenoxy)-1-(4-iodobenzyl)ethyl]-4-cyanobenzamide 1.44 g (3.01 mmol) of t-butyl [(1R)-2-(3-cyanophenoxy)-1-(4-iodobenzyl)ethyl]carbamate was dissolved in 5 ml of 4 N dioxane hydrochloride and 2.5 ml of dioxane, and the solution was stirred for 15 hours. The solvent was evaporated under reduced pressure, and the residue was dissolved in 10 ml of dichloromethane. 488 mg (3.3 mmol) of 4-cyanobenzoic acid 1.3 ml (9.3 mmol) of triethylamine, 633 mg (1.5 mmol) of 1-(3-dimethylaminopropyl)-3-ethylcarbodiimide hydrochloride and 445 mg (3.3 mmol) of 1-hydroxybenzotriazole were added to the solution, and they were stirred for 16 hours. The reaction liquid was diluted with water. After the extraction with ethyl acetate, the organic layer was successively washed with water, 1 N sodium hydroxide and saturated aqueous NaCl solution, and then dried over anhydrous magnesium sulfate. The solvent was evaporated. The residue was purified by the silica gel column chromatography to obtain the title compound.

Yield: 1.51 g (3.00 mmol) (99%).

H-NMR (CDCl3) δ 3.03-3.17 (2H, m), 3.97-4.18 (2H, m), 4.62-4.77 (1H, m), 7.00 (2H, d), 7.18 (2H, dd), 7.30 (1H, dd), 7.41 (1H, dd), 7.61 (2H, d), 7.77 (2H, d), 7.83 (2H, d)

Step 6

Synthesis of N-[(1R)-1-(4-iodobenzyl)-2-(3-amidinophenoxy)ethyl]-4-amidinobenzamide bistrifluoroacetate and methyl 4-[(2R)-2-(4-amidinobenzoylamino)-3-(3-amidinophenoxy)propyl]benzoate bistrifluoroacetate N-[(1R)-2-(3-cyanophenoxy)-1-(4-iodobenzyl)ethyl]-4-cyanobenzamide was carbonylated in the same manner as that of step 1 in Example 39, and the obtained product was treated in the same manner as that of step 6 in Example 1 to obtain the title compound.

4-Amidino-N-[(2R)-(3-amidinophenoxy)-1-(iodobenzyl)ethyl]benzamide bistrifluoroacetate Yield: 8 mg (0.015 mmol) (1%)

MS (ESI, m/z) 543 (MH+)

H-NMR (DMSO-d6) δ 2.86-3.12 (2H, m), 4.13-4.27 (2H, m), 4.48-4.62 (1H, m), 7.12 (2H, d), 7.30-7.45 (3H, m), 7.54

(1H, dd), 7.62 (2H, d), 7.88 (2H, d), 7.96 (2H, d), 8.78 (1H, d), 9.12 (2H, br), 9.22 (2H, br), 9.28 (2H, b), 9.39 (2H, br).

Methyl 4-[(2R)-(4-amidinobenzoylamino)-3-(3-amidinophenoxy)-2-propyl]benzoate bistrifluoroacetate Yield: 47 mg (0.067 mmol) (7%)
MS (ESI, m/z) 474 (MH+)
H-NMR (DMSO-d6) δ3.02-3.25 (2H, m), 3.81 (3H, s), 4.17-4.28 (2H, m), 4.55-4.71 (1H, m), 7.32-7.50 (2H, m), 7.55 (1H, dd), 7.87 (4H, dd), 7.95 (2H, d), 8.80 (1H, d) 9.10 (2H, br), 9.20 (2H, br), 9.28 (2H, br), 9.38 (2H, br).

Example 89

Synthesis of N-[(1R)-2-(3-amidinophenoxy)-1-(3-indolylmethyl)ethyl]-4-amidinobenzamide bistrifluoroacetate The title compound was obtained from 5.09 g (20.0 mmol) of hydrochloride of methyl ester of D-tryptophane in the same manner as that of Example 86 except that the intermediate was not purified. However, 4-(pyrrolidine-1-yl)benzoic acid was replaced with 4-cyanobenzoic acid.
Yield: 209 mg (0.306 mmol) (1.5%)
MS (ESI, m/z) 455 (MH+)
H-NMR (DMSO-d6) δ 3.02-3.12 (2H, m), 4.20-4.35 (2H, m), 4.60-4.88 (2H, m), 6.95-7.66 (13H, m), 7.85 (2H, d), 8.03 (2H, d), 8.81 (1H, d), 9.07-941 (8H, m), 10.81 (1H, s).

Example 90

Synthesis of 4-[(2R)-2-(4-amidinobenzoylamino)-3-(3-amidinophenoxy)propyl]benzoic acid bistrifluoroacetate 5 ml of concentrated hydrochloric acid was added to 8 mg (0.011 mmol) of methyl 4-[(2R)-2-(4-amidinobenzoylamino)-3-(3-amidinophenoxy)propyl]benzoate bistrifluoroacetate, and they were stirred at 60° C. for 19 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-died to obtain the title compound.
Yield: 6 mg (0.009 mmol) (80%)
MS (FAB, m/z) 460 (MH+)
H-NMR (DMSO-d6) δ 3.00-3.24 (2H, m), 4.46-4.26 (2H, m), 4.58-4.68 (1H, m), 7.33-7.48 (2H, m), 7.55 (1H, dd), 7.84 (2H, d), 7.87 (2H, d), 7.94 (2H, d), 8.79 (1H, d), 9.08 (2H, br), 9.18 (2H, br), 9.28 (2H, br), 9.37 (2H, br).

Example 91

Synthesis of (2S)-2-(4-amidinobenzoylamino)-4-(3-amidinophenoxy)butanoic acid bistrifluoroacetate Step 1

Synthesis of benzyl (2S)-2-t-butoxycarbonylamino-4-(3-cyanophenoxy)butanoate 3.23 g (10.0 mmol) of α-benzyl N-t-butoxycarbonyl-L-aspartate and 1.39 ml (10.0 mmol) of triethylamine were dissolved in 50 ml of tetrahydrofuran. 0.96 ml (10.0 mmol) of ethyl chloroformate was added to the solution under cooling with ice, and they were stirred for 20 minutes. A precipitate thus formed was removed by the filtration by suction. 3 g of ice and 380 mg (10.0 mmol) of sodium borohydride were added to the filtrate under cooling with ice, and they were stirred for 1.5 hours. 50 ml of 1 N aqueous hydrogen chloride solution was added thereto, and they were stirred at room temperature for additional 1 hour. After the treatment with ethyl acetate as the extractant in an ordinary manner, an oily residue was obtained, which was dissolved in 30 ml of tetrahydrofuran. 737 mg (6.18 mmol) of 3-cyanophenol, 1.77 g (6.74 mmol) of triphenylphosphine and 2.70 g (6.18 mmol) of diethyl azodicarboxylate (40% solution in toluene) were added to the solution, and they were stirred at room temperature overnight. The solvent was evaporated, and the residue was purified by the silica gel column chromatography to obtain the title compound.
Yield: 1.12 g (2.73 mmol) (27%).
H-NMR (CDCl3) δ 1.40 (9H, s), 2.30 (2H, br), 4.05 (2H, t), 4.58 (1H, br), 5.20 (2H, t), 5.70 (1H, br), 7.0-7.2 (4H, m), 7.3 (5H, s).

Step 2

Synthesis of benzyl (2S)-2-(4-cyanobenzoylamino)-4-(3-cyanophenoxy)butanoate 1.12 g (2.73 mmol) of benzyl (2S)-2-t-butoxycarbonylamino-4-(3-cyanophenoxy)butanoate was dissolved in 10 ml of 4 N solution of hydrogen chloride in dioxane, and they were stirred at room temperature for 2 hours. The solvent was evaporated, and the obtained oily residue was dissolved in 14 ml of dichloromethane. 390 mg (2.73 mmol) of 4-cyanobenzoic acid, 405 mg (3.00 mmol) of HOBt, 0.83 ml (6.00 mmol) of triethylamine and 575 mg (3.00 mmol) of WSC.HCl were successively added to the solution under cooling with ice, and they were stirred at room temperature overnight. After the treatment with methylene chloride as the extractant in an ordinary manner, the title compound was obtained.
Yield: 900 mg (2.05 mmol) (75%)
H-NMR (CDCl3) δ 2.50 (2H, br), 4.10 (2H, t), 5.05 (1H, q), 5.20 (1H, d), 5.28 (1H, d), 6.9-7.3 (4H, m), 7.36 (5H, s), 7.72 (2H, d), 7.89 (2H, d)

Step 3

Synthesis of (2S)-2-(4-amidinobenzoylamino)-4-(3-amidinophenoxy)butanoic acid bistrifluoroacetate 900 mg (2.05 mmol) of benzyl (2S)-2-(4-cyanobenzoylamino)-4-(3-cyanophenoxy)butanoate was added to 20 ml of ethanol containing 30% (w/v) of hydrogen chloride, and they were stirred overnight. Then, the solvent was evaporated under reduced pressure. The residue was dissolved in 20 ml of 10% (w/v) solution of ammonia in ethanol at room temperature, and they were stirred at that temperature overnight. The solvent was evaporated, and the residue was dissolved in 10 ml of concentrated hydrochloric acid. The solution was stirred at 40° C. for 4 hours. Hydrogen chloride was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 364 mg (0.596 mmol) (29%)
MS (ESI, m/z) 384 (MH+)
H-NMR (DMSO-d6) δ 2.20 (2H, br), 4.20 (2H, br), 4.70 (1H, br), 7.30 (1H, d), 7.38 (1H, br), 7.93 (2H, d), 8.08 (2H, d), 9.02 (1H, d), 9.20 (2H, s), 9.30 (2H, s), 9.34 (2H, s), 9.47 (2H, d).

Example 92

Synthesis of (2R)-2-(4-amidinobenzoylamino)-4-(3-amidinophenoxy)butanoic acid bistrifluoroacetate

Step 1

Synthesis of benzyl (2R)-2-t-butoxycarbonylamino-4-(3-cyanophenoxy)butanoate

The title compound was obtained from 5.0 g (15.0 mmol) of α-benzyl N-t-butoxycarbonyl-D-aspartate in the same manner as that of step 1 in Example 91.
Yield: 3.13 g (7.63 mmol) (51%).
H-NMR (CDCl3) δ 1.40 (9H, s), 2.30 (2H, br), 4.05 (2H, t), 4.58 (1H, br), 5.20 (2H, t), 5.70 (1H, br), 7.0-7.2 (4H, m), 7.3 (5H, s)

Step 2

Synthesis of benzyl (2R)-2-(4-cyanobenzoylamino)-4-(3-cyanophenoxy)butanoate

The title compound was obtained from 3.13 g (7.63 mmol) of benzyl (2R)-2-t-butoxycarbonylamino-4-(3-cyanophenoxy)butanoate in the same manner as that of step 2 in Example 91.
Yield: 2.19 g (6.62 mmol) (87%).
H-NMR (CDCl3) δ 2.50 (2H, br), 4.10 (2H, t), 5.05 (1H, q), 5.20 (1H, d), 5.28 (1H, d), 6.9-7.3 (4H, m), 7.36 (5H, s), 7.72 (2H, d), 7.89 (2H, d)

Step 3

Synthesis of (2R)-2-(4-amidinobenzoylamino)-4-(3-amidinophenoxy)butanoic acid bistrifluoroacetate The title compound was obtained from 2.91 g (6.62 mmol) of benzyl (2R)-2-(4-cyanobenzoylamino)-4-(3-cyanophenoxy)butanoate in the same manner as that of step 3 in Example 91.
Yield: 895 mg (1.46 mmol) (22%)
MS (ESI, m/z) 384 (MH+)
H-NMR (DMSO-d6) δ 2.20 (2H, br), 4.20 (2H, br), 4.70 (1H, br), 7.30 (1H, d), 7.38 (1H, br), 7.93 (2H, d), 8.08 (2H, d), 9.02 (1H, d), 9.20 (2H, s), 9.30 (2H, s), 9.34 (2H, s), 9.47 (2H, d).

Example 93

Determination of Activity of Inhibiting the Activated Blood Coagulation Factor X 130 μl of 100 mM Tris-HCl buffer adjusted to pH 8.4 was added to 10 μl of an aqueous solution of a compound to be tested. Then 10 μl of a 0.5 unit/ml solution of activated human blood coagulation factor X (a product of Enzyme Research Co.) in Tris-HCl buffer hydrochloride of pH 8.4 was added to the resultant mixture. After the incubation at room temperature for 10 minutes, 50 μl of a solution of N-benzoyl-L-isoleucyl-L-glutamyl-glycyl-L-arginyl-p-nitroanilide hydrochloride (a product of Peptide Institute, Inc.) adjusted to 0.8 mM with Tris-HCl buffer (pH 8.4) was added thereto. The absorbance was determined and then the initial reaction rate was determined. A control was prepared in the same manner as that described above except that the solution of the compound to be tested was replaced with 10 μl of Tris-HCl buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC50) of a concentration of the test compound which inhibits 50% of the activity (initial rate) of the activated blood coagulation factor X in the absence of the test compound was determined, and employed as the index of the activity of inhibiting activated blood coagulation factor X. The activities, of inhibiting activated blood coagulation factor X, of representative compounds are shown in Table 1 given below.

Example 94

Determination of Thrombin-Inhibiting Activity

130 μl of 100 mM Tris-HCl buffer adjusted to pH 8.4 was added to 10 μl of an aqueous solution of a test compound. Then 10 μl of a solution of human thrombin (a product of SIGMA Co.) adjusted to 2 units/ml with Tris-HCl buffer of pH 8.4 was added to the resultant mixture. After the incubation at room temperature for 10 minutes, 50 μl of a solution of D-phenylalanyl-L-pipecolyl-L-arginyl-p-nitroanilide dihydrochloride (S-2238; a product of Daiichi Kagaku Yakuhin Co.) adjusted to 0.4 mM with Tris-HCl of pH 8.4 was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC50) of a concentration of the test compound which inhibits 50% of the activity (initial rate) of the thrombin in the absence of the test compound was determined, and employed as the index of the activity of inhibiting thrombin. The activities, of inhibiting thrombin, of representative compounds are shown in Table 1 given below.

TABLE 1

| | Activity of inhibiting activated blood coagulation factor X (pIC$_{50}$) | Thrombin-inhibiting activity (pIC$_{50}$) |
|---|---|---|
| Compound of Ex. 1 | 6.4 | 3.4 |
| Compound of Ex. 3 | 7.6 | 3.6 |
| Compound of Ex. 7 | 7.1 | 3.6 |
| Compound of Ex. 9 | 7.7 | 4.3 |
| Compound of Ex. 10 | 7.0 | 3.9 |
| Compound of Ex. 14 | 7.3 | 4.7 |
| Compound of Ex. 18 | 7.3 | 4.4 |
| Compound of Ex. 24 | 6.5 | 3.2 |
| Compound of Ex. 43 | 6.6 | 4.3 |
| Compound of Ex. 54 | 7.3 | 4.6 |
| Compound of Ex. 56 | 7.8 | <3.0 |
| Compound of Ex. 57 | 7.9 | <3.0 |
| Compound of Ex. 58 | 7.6 | <3.0 |
| Compound of Ex. 59 | 7.4 | 4.8 |
| Compound of Ex. 62 | 7.4 | <3.3 |
| Compound of Ex. 64 | 7.2 | 3.6 |

TABLE 1-continued

| | Activity of inhibiting activated blood coagulation factor X (pIC$_{50}$) | Thrombin-inhibiting activity (pIC$_{50}$) |
|---|---|---|
| Compound of Ex. 67 | 6.5 | 3.5 |
| Compound of Ex. 69 | 6.6 | 4.5 |
| Compound of Ex. 73 | 8.1 | 3.9 |
| Compound of Ex. 74 | 7.6 | <3.7 |
| Compound of Ex. 79 | 7.7 | 4.6 |
| Compound of Ex. 80 | 7.9 | 4.4 |
| Compound of Ex. 81 | 7.1 | 4.5 |
| Compound of Ex. 82 | 7.6 | 5.2 |
| Compound of Ex. 83 | 6.8 | <3.0 |
| Compound of Ex. 90 | 7.4 | <3.6 |
| Compound of Ex. 92 | 7.3 | <3 |

In Table 1, the compound of Example 83 was (4S)-4-(4-amidinobenzoylamino)-5-(3-amidinophenoxy)pentanoic acid bistrifluoroacetate.

It is apparent from the results that the benzamidine derivatives of the present invention have a specifically high activity of inhibiting the activated blood coagulation factor X.

The structural formulae of the compounds of the present invention used in the above Examples are given below.

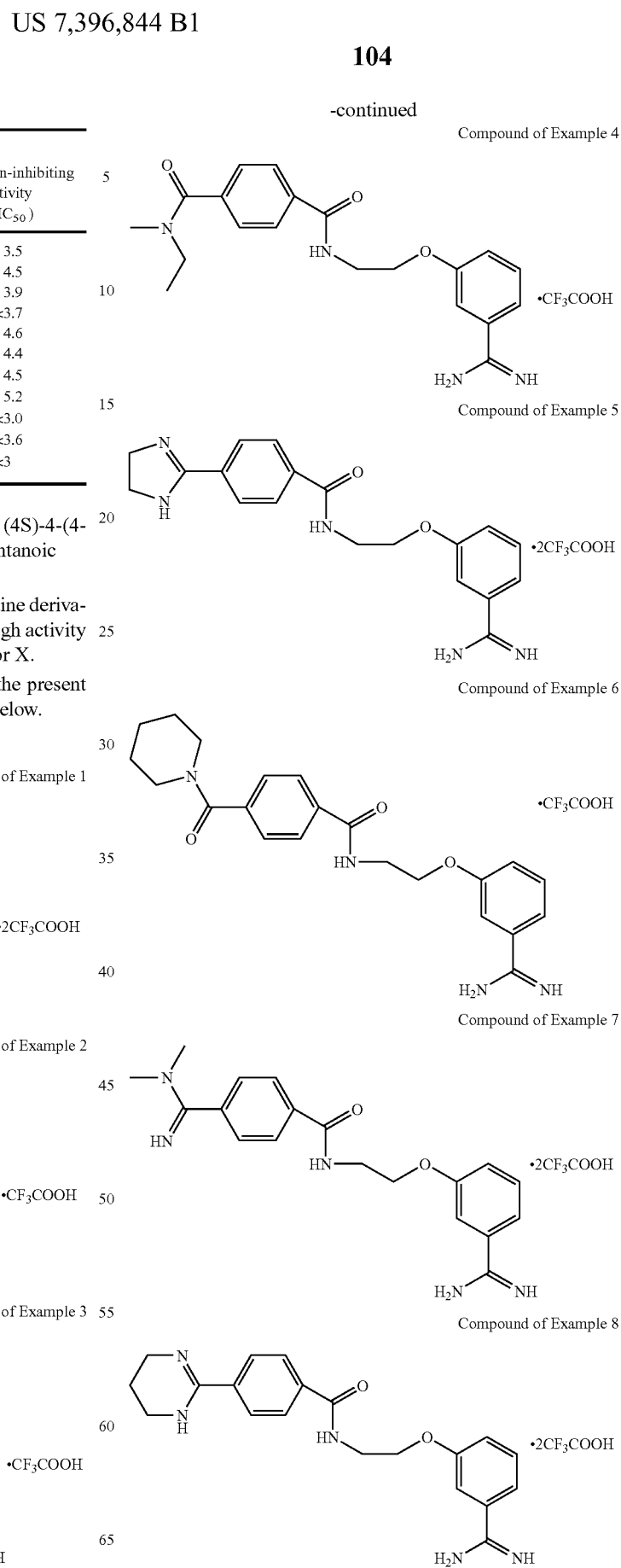

-continued
Compound of Example 9
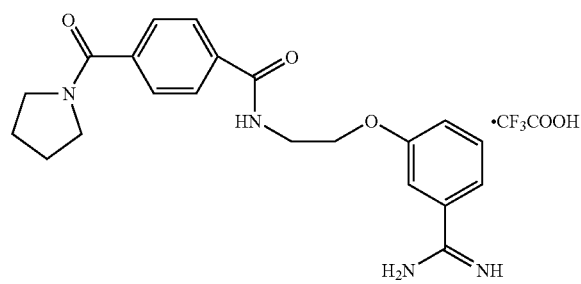
Compound of Example 10
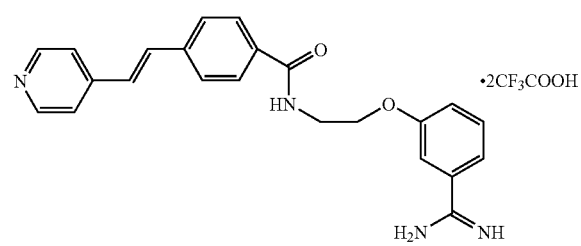
Compound of Example 11
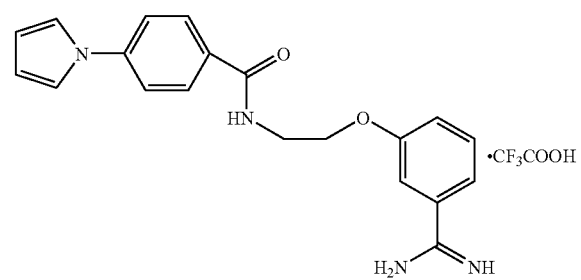
Compound of Example 12
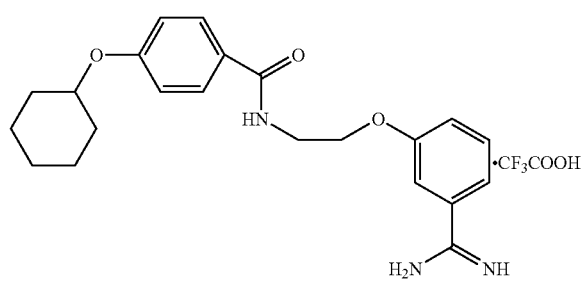
Compound of Example 13
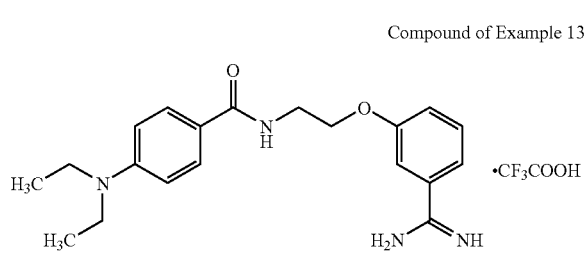
-continued
Compound of Example 14
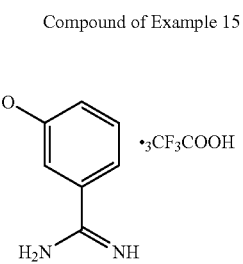
Compound of Example 15
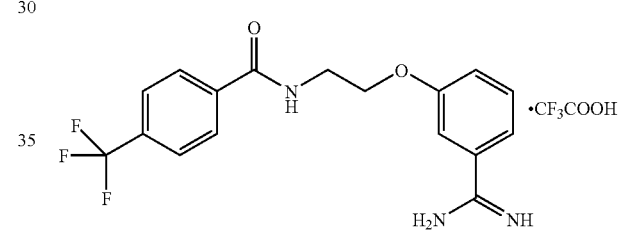
Compound of Example 16
Compound of Example 17
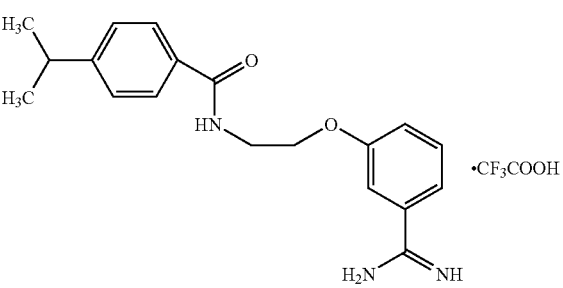
Compound of Example 18
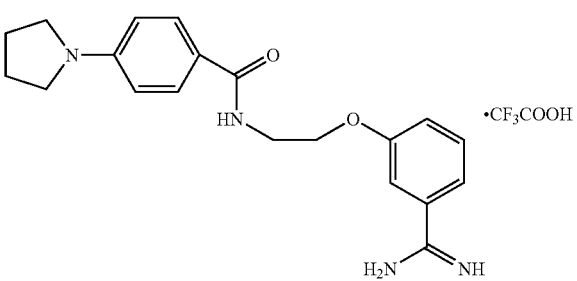

-continued
Compound of Example 19
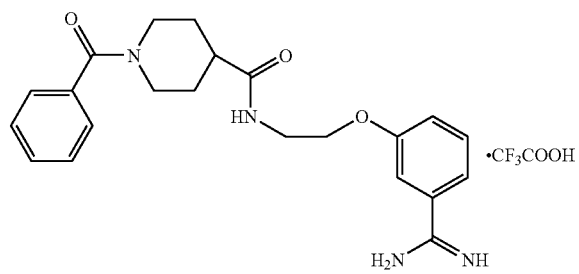
Compound of Example 20
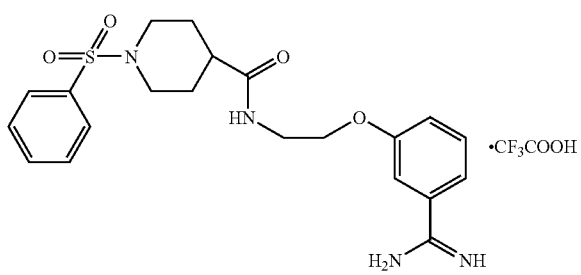
Compound of Example 21
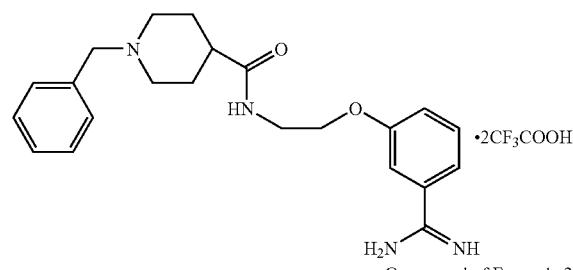
Compound of Example 22
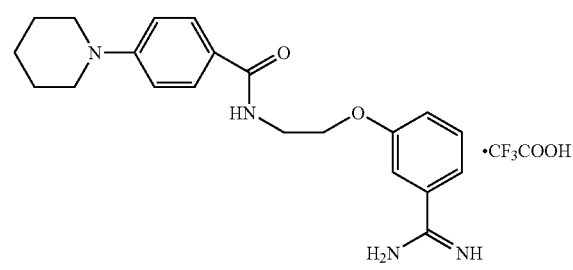
Compound of Example 23
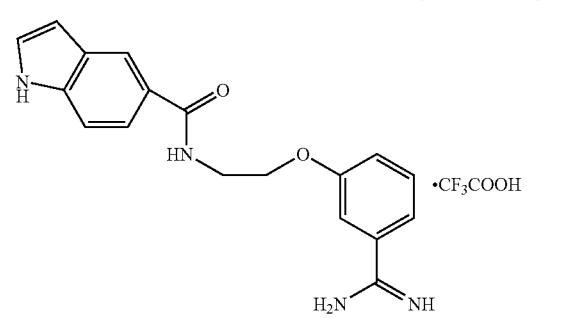
-continued
Compound Example 24
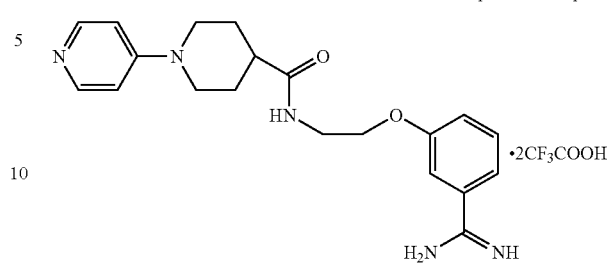
Compound Example 25
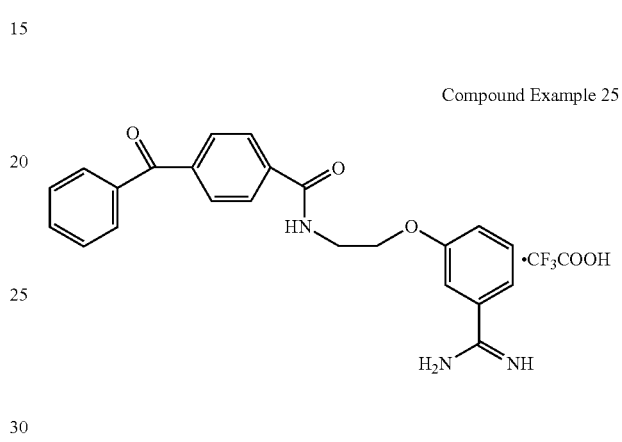
Compound Example 26
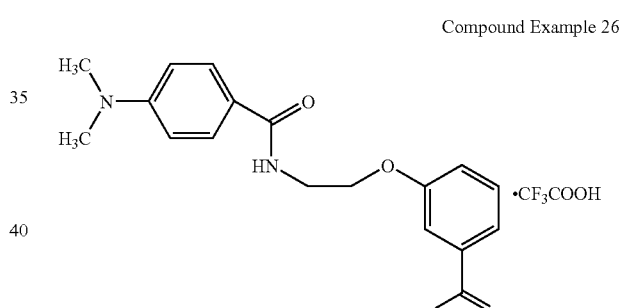
Compound Example 27
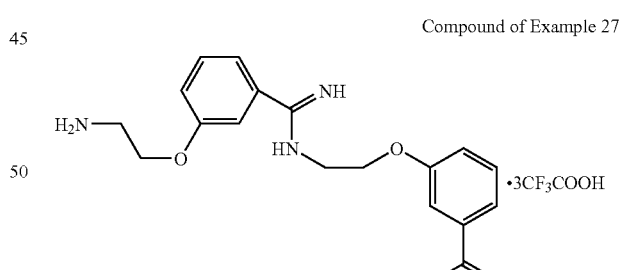
Compound Example 28
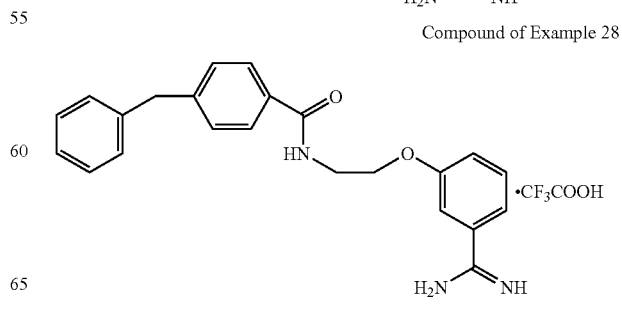

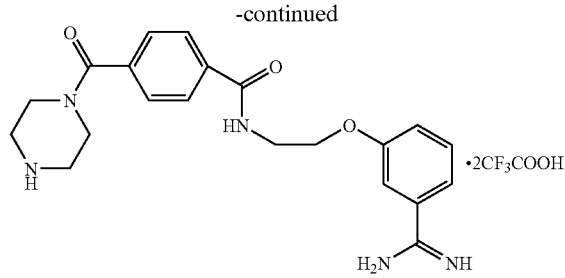
N-[2-(3-amidinophenoxy)ethyl]-4-(piperazine-1-carbonyl)benzamide bistrifluoroacetate of Example 29
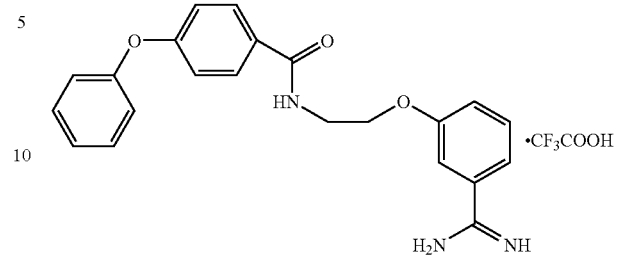
Compound of Example 33
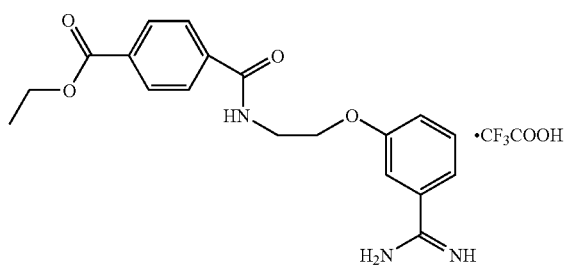
ethyl 4-[N-[2-(3-amidinophenoxy)ethyl]carbamoyl]benzoate trifluoroacetate of Example 29
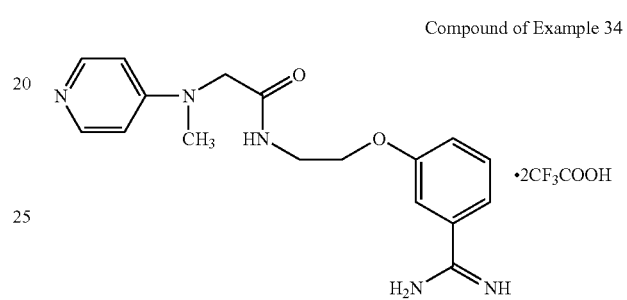
Compound of Example 34
Compound of Example 30
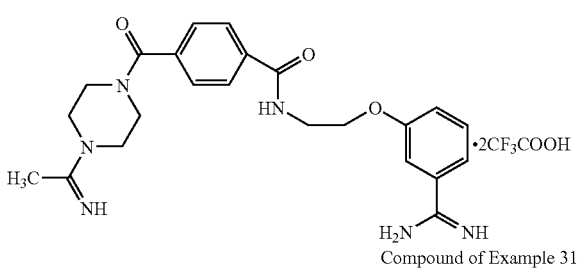
Compound of Example 35
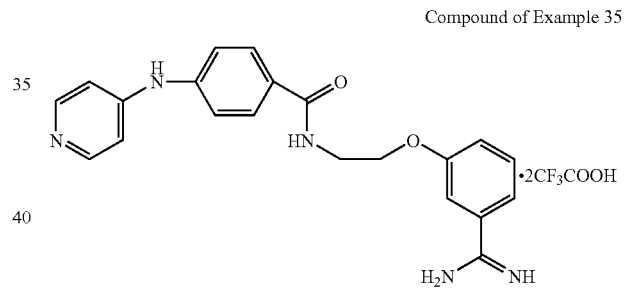
Compound of Example 31
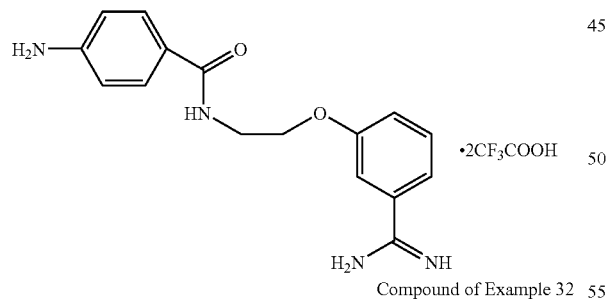
Compound of Example 36
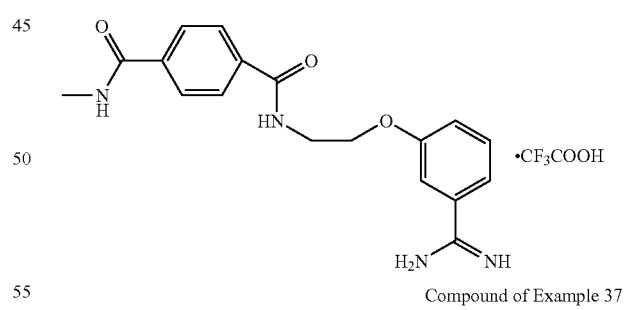
Compound of Example 32
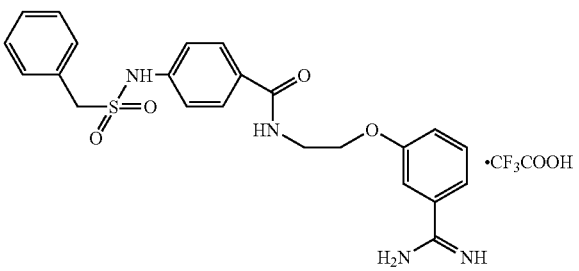
Compound of Example 37
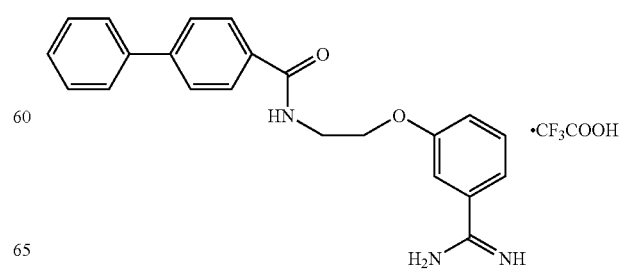

-continued
Compound of Example 38
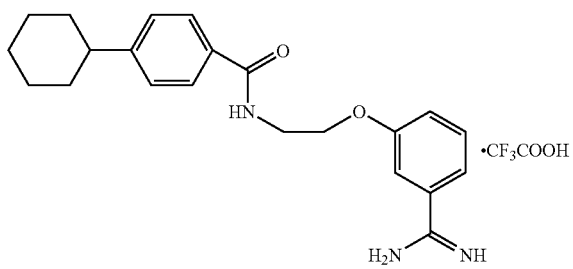
Compound of Example 43
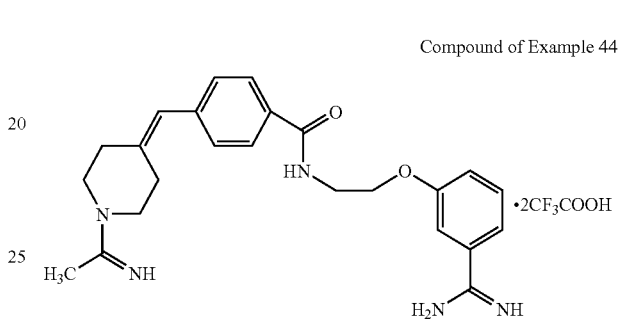
Compound of Example 39
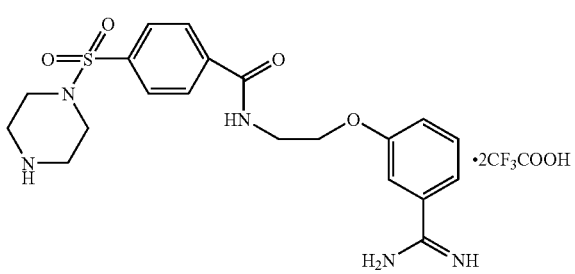
Compound of Example 44
Compound of Example 40
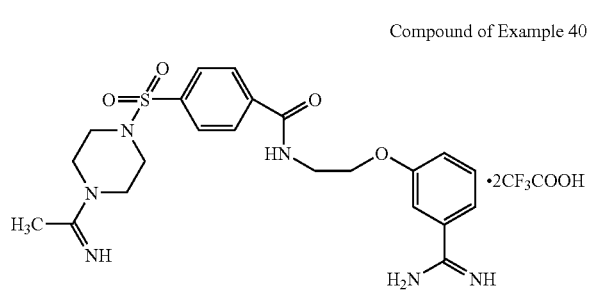
Compound of Example 45
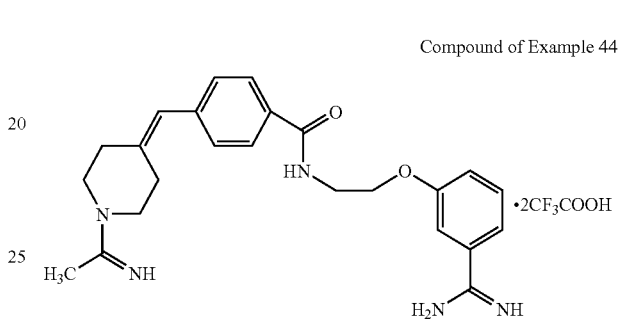
Compound of Example 41
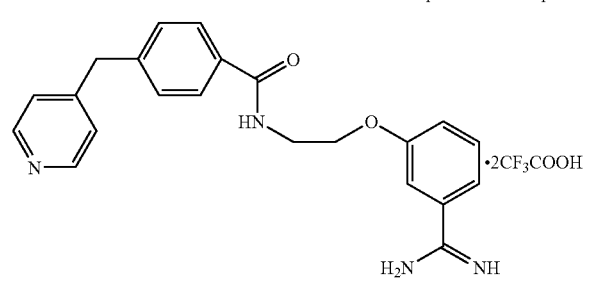
Compound of Example 46
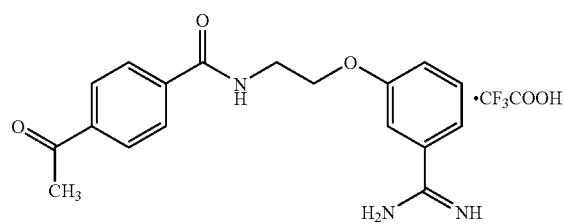
Compound of Example 42
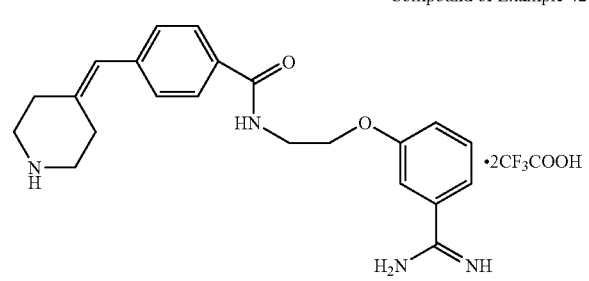
Compound of Example 47

-continued

Compound of Example 48

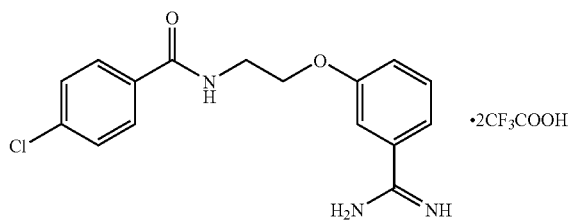

Compound of Example 49

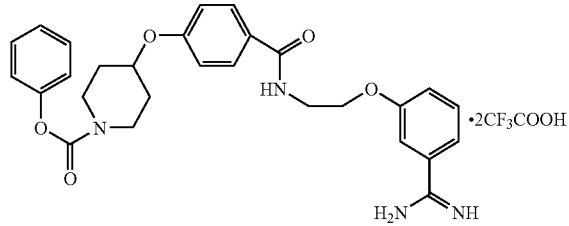

Compound of Example 50

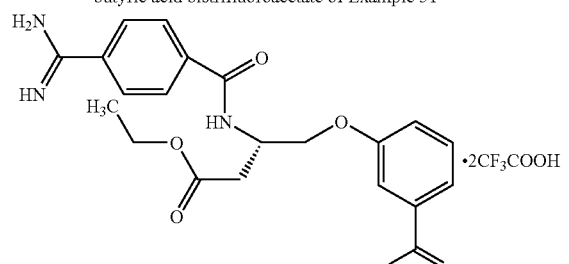

(3S)-3-(4-amidinobenzoylamino)-4-(3-amidinophenoxy)
butyric acid bistrifluoroacetate of Example 51 ethyl(3S)-3-(4-amidinobenzoylamino)-4-(3-
amidinophenoxy)butyrate bistrifluoroacetate of Example 51

-continued

Compound of Example 52

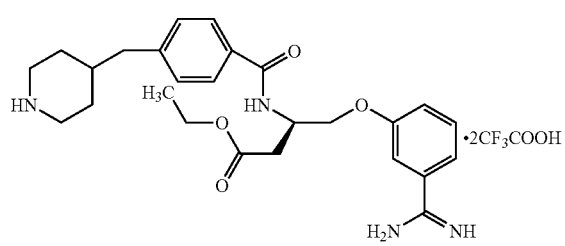

Compound of Example 53

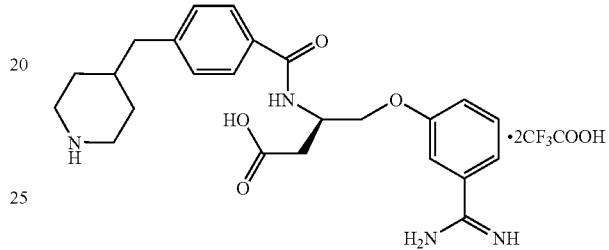

Compound of Example 54

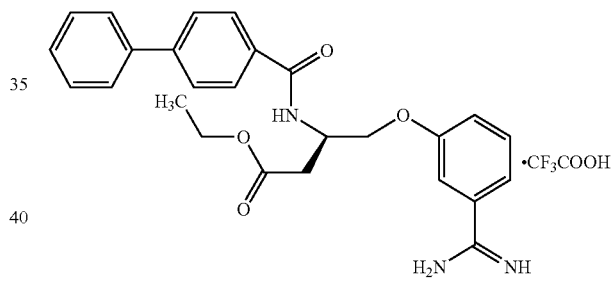

Compound of Example 55

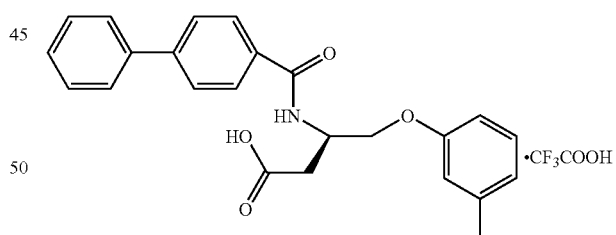

Compound of Example 56

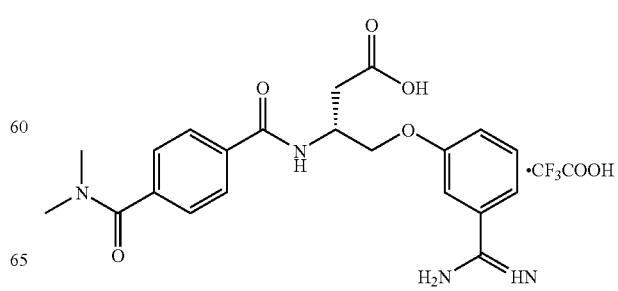

-continued
Compound of Example 57
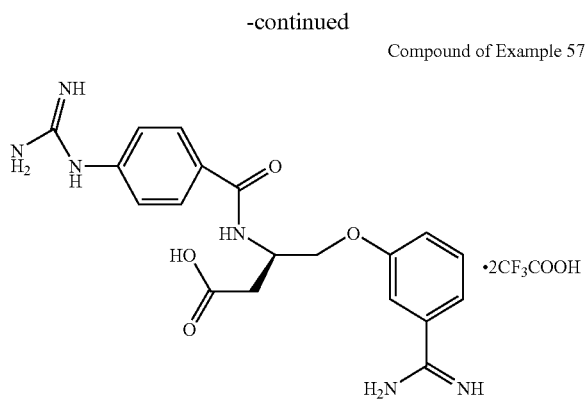
Compound of Example 58
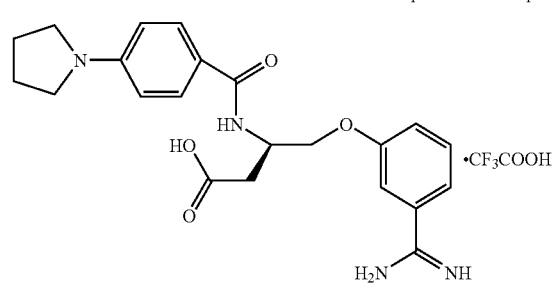
Compound of Example 59
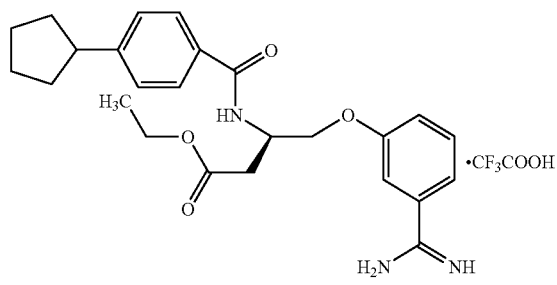
Compound of Example 60
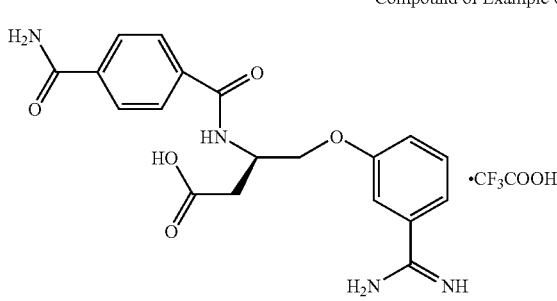
-continued
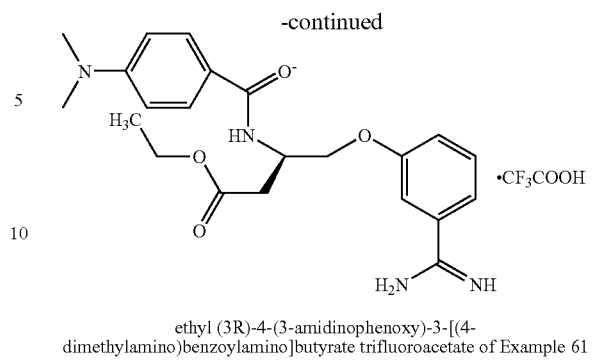
ethyl (3R)-4-(3-amidinophenoxy)-3-[(4-dimethylamino)benzoylamino]butyrate trifluoroacetate of Example 61
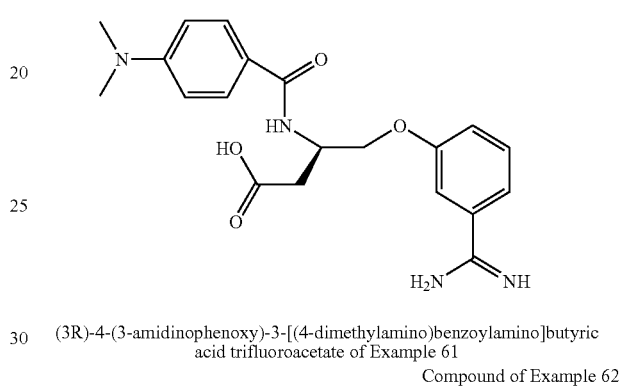
(3R)-4-(3-amidinophenoxy)-3-[(4-dimethylamino)benzoylamino]butyric acid trifluoroacetate of Example 61
Compound of Example 62
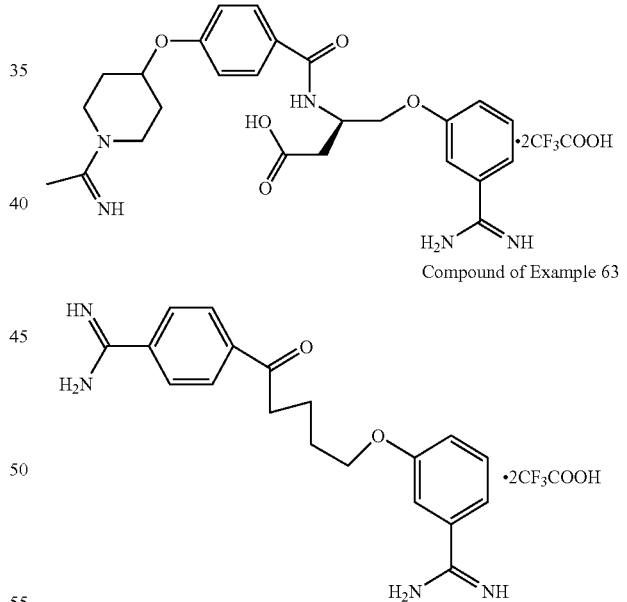
Compound of Example 63
Compound of Example 64
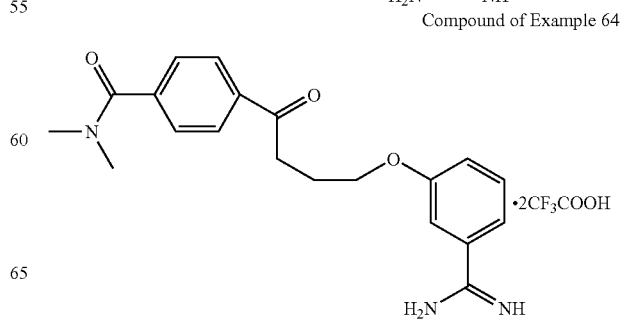

-continued

Compound of Example 65

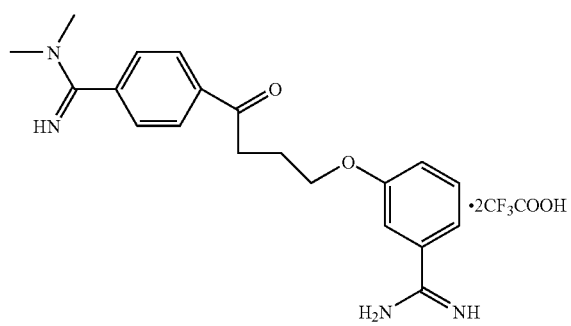

Compound of Example 66

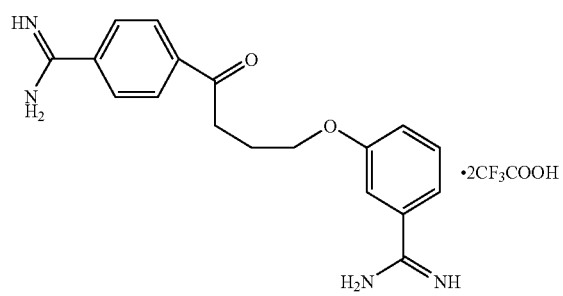

Compound of Example 67

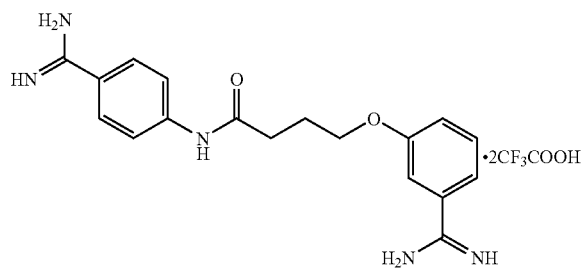

Compound of Example 68

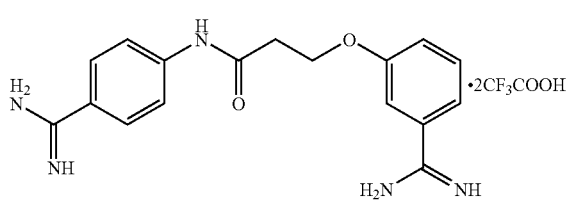

-continued

Compound of Example 69

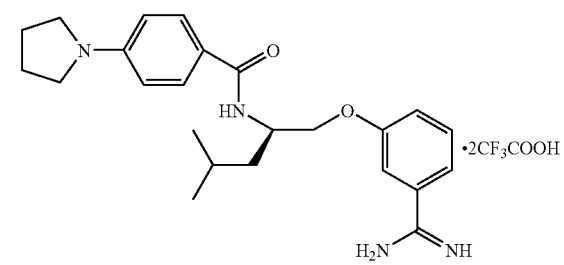

Compound of Example 70

Compound of Example 71 monoethyl 4-[(1S)-2-(3-amidinophenoxy)-1-[4-(4-piperidyloxy) phenylmethyl]ethyl]sulfamoyl]phenylphosphonate bistrifluoroacetate of Example 71 diethyl 4-[(1S)-2-(3-amidinophenoxy)-1-[4-(4-piperidyloxy) phenylmethyl]ethyl]sulfamoyl]phenylphosphonate bistrifluoroacetate of Example 71

Compound of Example 72

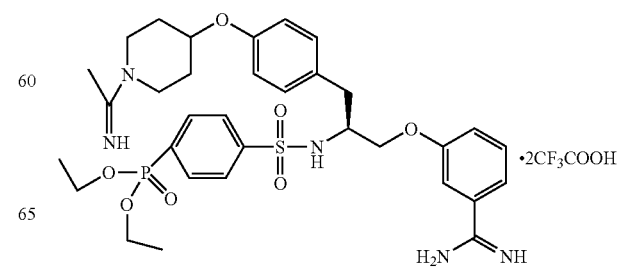

-continued
Compound of Example 73
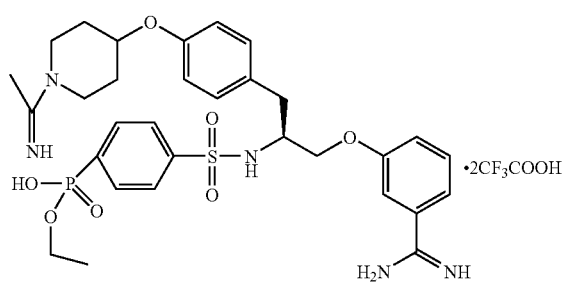
·2CF₃COOH
Compound of Example 74
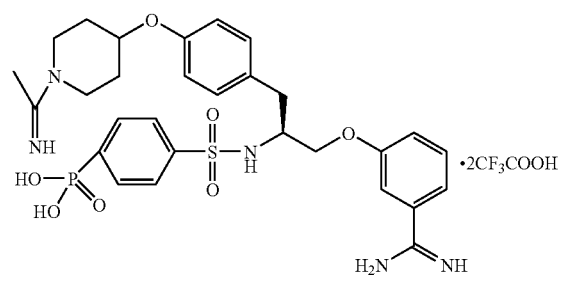
·2CF₃COOH
Compound of Example 75
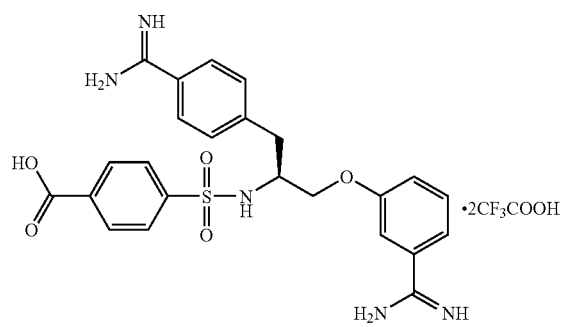
·2CF₃COOH
Compound of Example 76
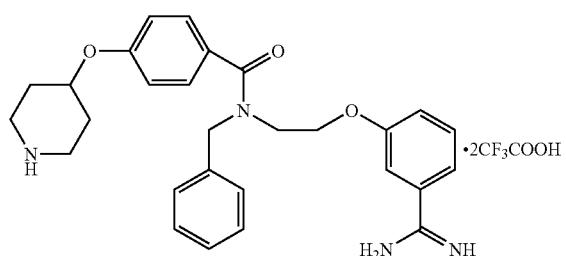
·2CF₃COOH
Compound of Example 77
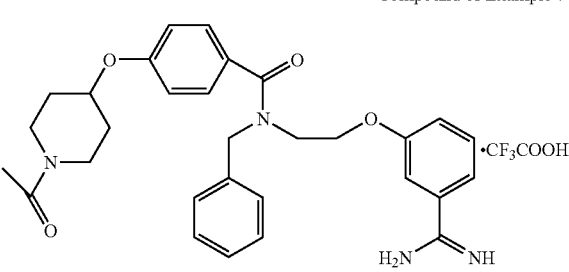
·CF₃COOH
-continued
Compound of Example 78
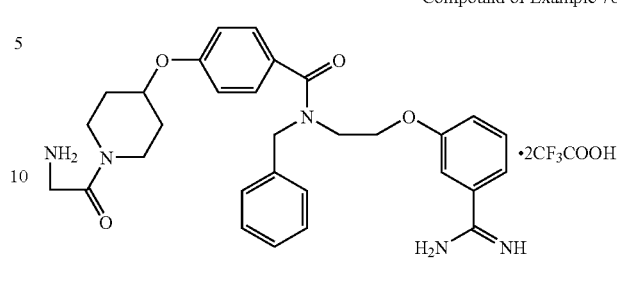
·2CF₃COOH
Compound of Example 79
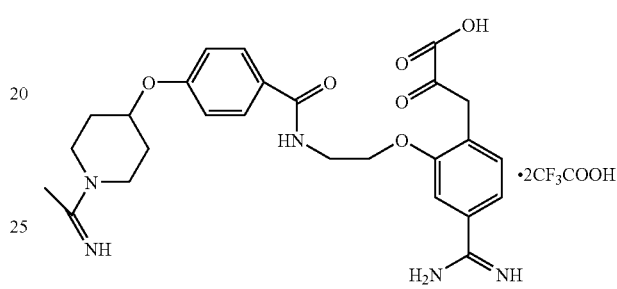
·2CF₃COOH
Compound of Example 80
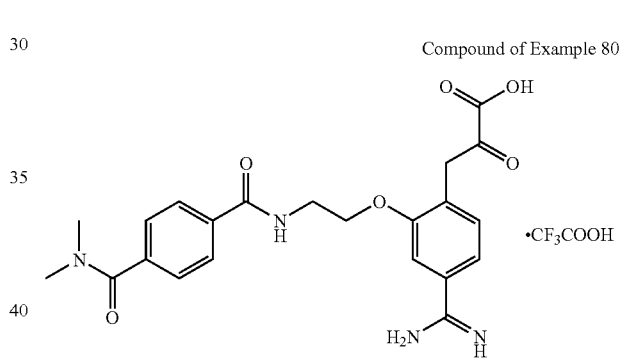
·CF₃COOH
Compound of Example 81
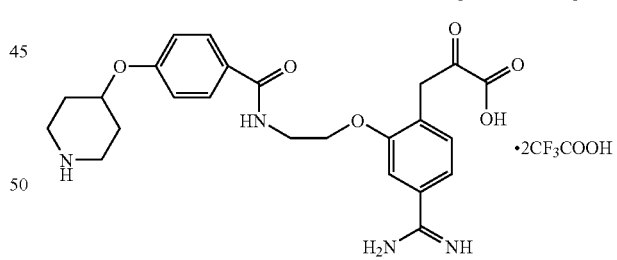
·2CF₃COOH
Compound of Example 82
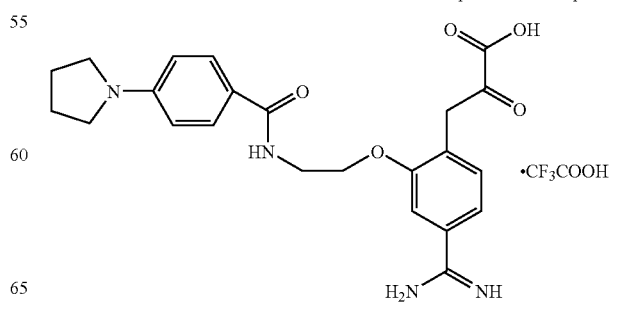
·CF₃COOH

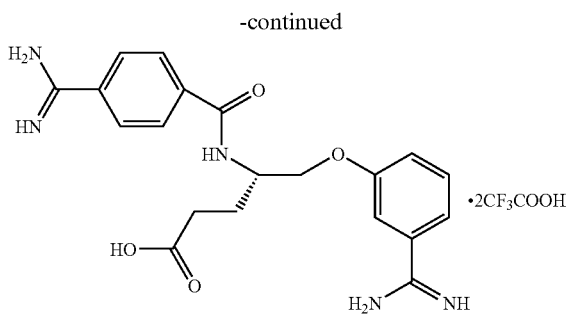

(4S)-4-(4_amidnobenzoylamino)-5-(3-amidinophenoxy)
pentanoic acid bistrifluoroacetate of Example 83

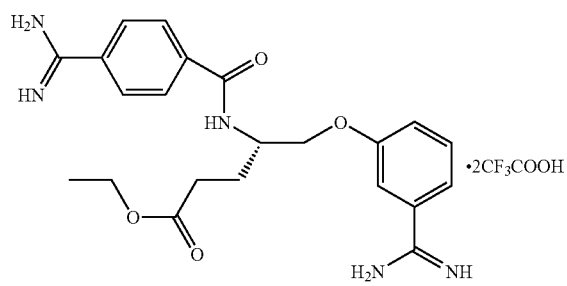

ethyl(4S)-(4-amdinobenzoylamino)-5-(3-amidinophenoxy)
pentanoate bistrifluoroacetate of Example 83

Compound of Example 84

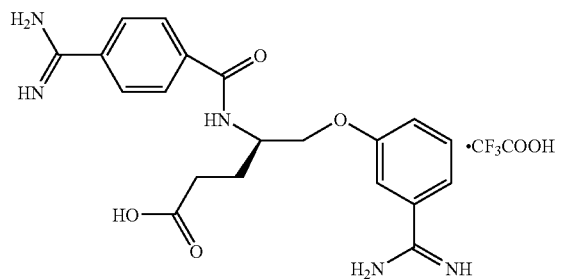

Compound of Example 85

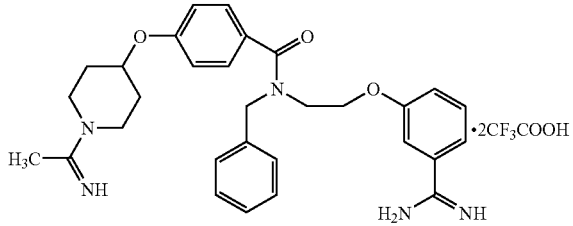

Compound of Example 86

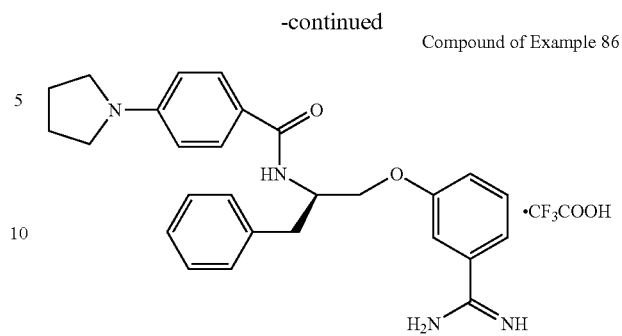

Compound of Example 87

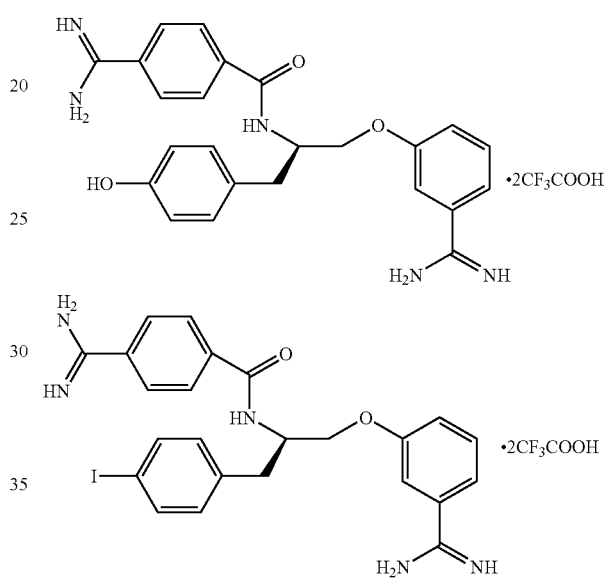

N-[(1R)-1-(4-iodobenzyl)-2-(3-amidinophenoxy)ethyl]-4-
amidinobenzamide bistrifluoroacetate of Example 88 methyl 4-[(2R)-2-(4-amidinobenzoylamino)-3-(3-
amidinophenoxy)propyl]benzoate bistrifluoroacetate of Example 88

Compound of Example 89

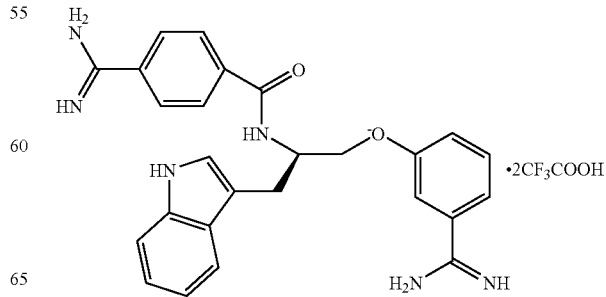

-continued

Compound of Example 90

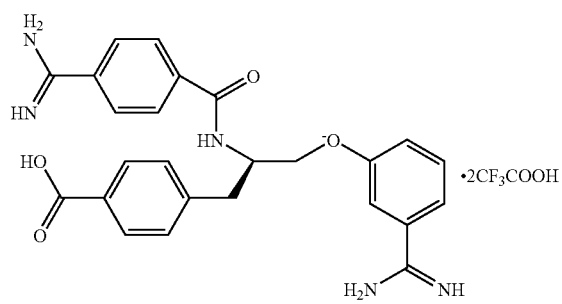

Compound of Example 91

Compound of Example 92

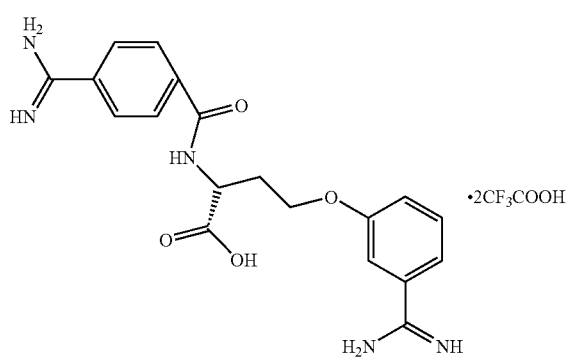

Example 95

Synthesis of
N-[2-(3-amidinophenoxy)ethyl]-4-amidinobenzamide
bistrifluoroacetate N-[2-(3-Cyanophenoxy)ethyl]-4-cyanobenzamide was synthesized in steps 1-4 of Example 1.

Step 5

Synthesis of
N-[2-(3-amidinophenoxy)ethyl)-4-amidinobenzamide
bistrifluoroacetate 2.43 g (8.35 mmol) of N-[2-(3-cyanophenoxy)ethyl]-4-cyanobenzamide was dissolved in 56 ml of 4 N solution of hydrogen chloride in dioxane. 24 ml of ethanol containing 30% (w/v) of hydrogen chloride was added to the solution. The obtained mixture was stirred at room temperature for 96 hours and then the solvent was evaporated under reduced pressure. The residue was dissolved in 30 ml of 10% (w/v) solution of ammonia in ethanol, and the obtained solution was stirred at room temperature for 24 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 1.19 g (2.15 mmol) (26%)

MS (FAB, m/z) 326 (MH+)

H-NMR (DMSO-d6) δ 3.69 (2H, dt), 4.24 (2H, t), 7.32 (1H, d), 7.39 (1H, d), 7.40 (1H, s), 7.53 (1H, t), 7.90 (2H, d), 8.05 (2H, d), 9.02 (1H, t), 9.18 (2H, br), 9.30 (4H, br), 9.43 (2H, br).

Example 96

Synthesis of
N-[2-(3-amidinophenoxy)ethyl]-3-amidinobenzamide
bistrifluoroacetate Step 1

Synthesis of
N-[2-(3-cyanophenoxy)ethyl]-3-cyanobenzamide

The title compound was obtained from 162 mg (1.1 mmol) of 3-cyanobenzoic acid and 163 mg (1.0 mmol) of 3-(2-aminoethoxy)benzonitrile in the same manner as that of step 4 in Example 1.

Yield: 251 mg (0.86 mmol) (86%)

H-NMR (CDCl3) δ 3.92 (2H, dt), 4.19 (2H, t), 6.67 (1H, br), 7.16 (1H, d), 7.18 (1H, s), 7.28 (1H, d), 7.40 (1H, t), 7.59 (1H, t), 7.80 (1H, t), 7.80 (1H, d), 8.03 (1H, d), 8.09 (1H, s)

Step 2

Synthesis of
N-[2-(3-amidinophenoxy)ethyl]-3-amidinobenzamide
bistrifluoroacetate The title compound was obtained from 240 mg (0.82 mmol) of N-[2-(3-cyanophenoxy)ethyl]-3-cyanobenzamide in the same manner as that of step 5 in Example 95.

Yield: 66.3 mg (0.12 mmol) (14%)

MS (FAB, m/z) 326 (MH+)

H-NMR (DMSO-d6) δ 3.70 (2H, dt), 4.25 (2H, t), 7.32 (1H, d), 7.41 (1H, d), 7.45 (1H, s), 7.51 (1H, t), 7.71 (1H, t), 7.97 (1H, d), 8.18 (1H, d), 8.45 (1H, s), 8.92 (4H, br), 9.14 (1H, t).

Example 97

Synthesis of N-[2-(3-amidinophenoxy)ethyl]-4-(4-piperidyloxy)benzamide bistrifluoroacetate

Step 1

Synthesis of ethyl 4-(1-t-butoxycarbonyl-4-piperidyloxy)benzoate 1.7 g (10.2 mmol) of ethyl 4-hydroxybenzoate, 1.76 g (9.3 mmol) of 1-t-butoxycarbonyl-4-hydroxypiperidine and 2.44 g (9.3 mmol) of triphenylphosphine were dissolved in 40 ml of tetrahydrofuran. 1.62 g (9.3 mmol) of diethyl azodicarboxylate was added to the solution at room temperature, and they were stirred overnight. The crude product was obtained by the same isolation process as that of step 1 in Example 1 with ethyl acetate as the extractant. After the purification by the silica gel column chromatography, the title compound was obtained.

Yield: 1.57 g (4.5 mmol) (44%)

H-NMR (CDCl3) δ 1.38 (3H, t), 1.50 (9H, s) 1.70-1.80 (2H, m), 1.90-2.00 (2H, m), 3.30-3.41 (2H, m), 3.63-3.75 (2H, m), 4.35 (2H, q), 4.55 (1H, m), 6.90 (2H, d), 8.00 (2H, d)

Step 2

Synthesis of 4-(1-t-butoxycarbonyl-4-piperidyloxy)benzoic acid 847 mg (2.43 mmol) of ethyl 4-(1-t-butoxycarbonyl-4-piperidyloxy)benzoate was dissolved in 50 ml of ethanol. 5 ml of 1 N sodium hydroxide solution was added to the solution, and they were stirred at room temperature for 3 days. The reaction liquid was concentrated, and the title compound was obtained by the same isolation process as that of step 1 in Example 1 with ethyl acetate as the extractant.

Yield: 697 mg (2.2 mmol) (92%)

H-NMR (CDCl3) δ 1.50 (9H, s), 1.70-2.00 (4H, m), 3.30-3.40 (2H, m), 3.65-3.75 (2H, m), 4.60 (1H, s), 6.95 (2H, d), 8.05 (2H, d)

Step 3

Synthesis of N-[2-(3-cyanophenoxy)ethyl]-4-(1-t-butoxycarbonyl-4-piperidyloxy)benzamide The title compound was obtained from 211.2 mg (0.65 mmol) of 4-(1-t-butoxycarbonyl-4-piperidyloxy)benzoic acid and 129.2 mg (0.65 mmol) of 3-(2-aminoethoxy)benzonitrile hydrochloride in the same manner as that of step 4 in Example 1.

Yield: 167 mg (0.36 mmol) (55%)

H-NMR (CDCl3) δ 1.50 (9H, s), 1.65-1.80 (2H, m), 1.85-2.00 (2H, m), 3.30-3.40 (2H, m), 3.60-3.75 (2H, m), 3.90 (2H, dt), 4.20 (2H, t), 4.55 (1H, m), 6.45 (1H, t), 6.94 (2H, d), 7.15 (1H, d), 7.17 (1H, s), 7.26 (1H, d), 7.38 (1H, t), 6.74 (2H, d)

Step 4

Synthesis of N-[2-(3-amidinophenoxy)ethyl]-4-(4-piperidyloxy)benzamide bistrifluoroacetate 165 mg (0.35 mmol) of N-[2-(3-cyanophenoxy)ethyl]-4-(1-t-butoxycarbonyl-4-piperidyloxy)benzamide was converted into N-[2-(3-cyanophenoxy)ethyl]-4-(4-piperidyloxy) benzamide in the same manner as that of step 3 in Example 1. After the same treatment as that of step 5 in Example 95, the title compound was obtained.

Yield: 124 mg (0.20 mmol) (57%)

MS (ESI, m/z) 383 (MH+)

H-NMR (DMSO-d6) δ 1.80-1.90 (2H, m), 2.08-2.18 (2H, d), 3.02-3.30 (4H, m), 3.62 (2H, q), 4.21 (2H, t), 4.75 (1H, m), 7.06 (2H, d), 7.30-7.42 (3H, m), 7.53 (1H, t), 7.85 (2H, d), 8.58 (2h, br), 8.61 (1H, br), 9.12 (2H, br), 9.28 (2H, br).

Example 98

Synthesis of N-[2-(3-amidinophenoxy)ethyl]-4-(aminomethyl)benzamide bistrifluoroacetate

Step 1

Synthesis of ethyl 4-(aminomethyl)benzoate 3 g (19.9 mmol) of 4-aminomethylbenzoic acid was suspended in 100 ml of ethanol. 10 ml of ethanol containing 25% of hydrogen chloride was added to the suspension, and they were heated under reflux for 8 hours. The solvent was evaporated, and the title compound was obtained by the same isolation process as that of step 1 in Example 1 with ethyl acetate as the extractant.

Yield: 1.19 g (6.77 mmol) (34%)

H-NMR (CDCl3) δ 1.35 (3H, t), 4.05 (2H, brs), 4.30 (2H, q), 6.60 (2H, d), 7.85 (2H, d)

Step 2

Synthesis of ethyl 4-[(t-butoxycarbonylamino)methyl]benzoate

The title compound was obtained from ethyl 4-(aminomethyl)benzoate and di-t-butyl dicarbonate in the same manner as that of step 1 in Example 1.

H-NMR (CDCl3) δ 1.45 (9H, s), 4.36 (2H, d), 4.36 (2H, q), 4.90 (1H, br), 7.35 (2H, d), 8.00 (2H, d)

Step 3

Synthesis of 4-[(t-butoxycarbonylamino)methyl]benzoic acid

The title compound was obtained from ethyl 4-[(t-butoxycarbonylamino)methyl]benzoate in the same manner as that of step 2 in Example 97.

H-NMR (CDCl3) δ 1.43 (9H, s), 4.40 (2H, br), 4.95 (1H, br), 7.40 (2H, d), 8.10 (2H, d)

Step 4

Synthesis of N-[2-(3-amidinophenoxy)ethyl]-4-(aminomethyl)benzamide bistrifluoroacetate N-[2-(3-cyanophenoxy)ethyl]-4-[(t-butoxycarbonylamino)methyl]benzamide was obtained from 439 mg (2 mmol) of 4-[(t-butoxycarbonylamino)methyl]benzoic acid and 400 mg (2 mmol) of 3-(2-aminoethoxy)benzonitrile hydrochloride in the same manner as that of step 4 in Example 1. This compound was converted into N-[2-(3-cyanophenoxy)ethyl]-4-(aminomethyl)benzamide hydrochloride in the same manner as that of step 3 in Example 1. After the same treatment as that of step 5 in Example 95, the title compound was obtained.

MS (ESI, m/z) 313 (MH+)

H-NMR (DMSO-d6) δ 3.70 (2H, q), 4.10 (2H, s), 4.25 (2H, t), 7.30-7.40 (3H, m), 7.51-7.56 (3H, m), 7.91 (2H, d), 8.24 (3H, r), 8.78 (1H, t), 9.10 (2H, br), 9.27 (2H, br).

Example 99

Synthesis of N-[2-(3-amidinophenoxy)ethyl]-4-(1-acetimidoyl-4-piperidyloxy)benzamide bistrifluoroacetate 124 mg (0.2 mmol) of N-[2-(3-amidinophenoxy)ethyl]-4-(4-piperidyloxy)benzamide bistrifluoroacetate was dissolved in 5 ml of ethanol. 183 mg (1.8 mmol) of triethylamine and 147 mg (1.2 mmol) of ethyl acetimidate hydrochloride were added to the solution, and they were stirred at room temperature for 6 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 120 mg (0.18 mmol) (92%)

MS (ESI, m/z) 424 (MH+)

H-NMR (DMSO-d6) δ 1.70-1.82 (2H, m), 2.02-2.14 (2H, m), 2.30 (3H, s), 3.50-3.60 (2H, m), 3.65 (2H, q), 3.70-3.80 (2H, m), 4.20 (2H, t), 4.80 (1H, m), 7.07 (2H, d), 7.30-7.40 (3H, m), 7.53 (1H, t), 7.85 (2H, d), 8.57-8.63 (2H, m), 9.11-9.18 (3H, m), 9.28 (2H, br).

Example 100

Synthesis of N-[2-(3-amidinophenoxy)ethyl]-(E)-3-(4-amidinophenyl)-2-propenamide bistrifluoroacetate Step 1

Synthesis of (E)-3-(4-cyanophenyl)acrylic acid 3.64 g (20 mmol) of 4-bromobenzonitrile and 2.88 g (40 mmol) of acrylic acid were dissolved in 40 ml of acetonitrile. 49 mg (0.2 mmol) of palladium (II) acetate, 365 mg (1.2 mmol) of tri-o-tolylphosphine and 7.41 g (40 mmol) of tributylamine were added to the solution, and they were heated under reflux overnight. The reaction liquid was poured into 4 N aqueous hydrogen chloride solution. The precipitates thus formed were taken by the filtration, washed with 4 N aqueous hydrogen chloride solution, water and ethyl acetate, and then dried in vacuo to obtain the title compound.

Yield: 2.36 g (13.6 mmol) (68%).

H-NMR (DMSO-d6) δ 6.70 (1H, d), 7.65 (1H, d), 7.90 (4H, m).

Step 2

Synthesis of N-[2-(3-cyanophenoxy)ethyl]-(E)-3-(4-cyanophenyl)-2-propenamide

The title compound was obtained from 173 mg (1 mmol) of (E)-3-(4-cyanophenyl)acrylic acid and 146 mg (0.9 mmol) of 3-(2-aminoethoxy)benzonitrile in the same manner as that of step 4 in Example 1.

Yield: 254 mg (0.8 mmol) (89%)

H-NMR (CDCl3) δ 3.82 (2H, q), 4.15 (2H, t), 6.10 (1H, br), 6.50 (1H, d), 7.15 (1H, d), 7.18 (1H, s), 7.25 (1H, d), 7.40 (1H, t), 7.60 (2H, d), 7.68 (1H, d), 7.70 (2H, d)

Step 3

Synthesis of N-[2-(3-amidinophenoxy)ethyl]-(E)-3-(4-amidinophenyl)-2-propenamide bistrifluoroacetate The title compound was obtained from 254 mg (0.8 mmol) of N-[2-(3-cyanophenoxy)ethyl]-(E)-3-(4-cyanophenyl)-2-propenamide in the same manner as that of step 5 in Example 95.

Yield: 23 mg (0.04 mmol) (5%)

MS (ESI, m/z) 326 (MH+)

H-NMR (DMSO-d6) δ 3.60 (2H, q), 4.20 (2H, t), 6.85 (1H, d), 7.34 (1H, d), 7.38 (1H, s), 7.40 (1H, d), 7.54 (1H, d), 7.55 (1H, t), 7.79 (2H, d), 7.85 (2H, d), 8.54 (1H, br), 9.18 (4H, br), 9.28 (2H, br), 9.33 (2H, br).

Example 101

Synthesis of N-[3-(3-amidinophenoxy)ethyl]-4-[(N-t-butoxycarbonyl-N-methylamino)methyl]benzamide trifluoroacetate Step 1

Synthesis of methyl 4-(N-t-butoxycarbonyl-N-methylamino)methylbenzoate 365 mg (1.45 mmol) of methyl 4-(t-butoxycarbonylamino)methylbenzoic acid and 160 mg (4 mmol) of sodium hydride were dissolved in dimethylformamide, and the solution was stirred at room temperature for 5 minutes. 1 ml of methyl iodide was added to the solution, and they were stirred for 2 hours. The crude product was obtained by the same isolation process as that of step 1 in Example 1 with ethyl acetate as the extractant. After the purification by the silica gel column chromatography, the title compound was obtained.

Yield: 380 mg (1.36 mmol) (94%)

Step 2

Synthesis of 4-(N-t-butoxycarbonyl-N-methylamino)methylbenzoic acid

The title compound was obtained from 370 mg (1.3 mmol) of methyl 4-(N-t-butoxycarbonyl-N-methylamino)methylbenzoate in the same manner as that of step 2 in Example 97.

Yield: 330 mg (1.24 mmol) (95%)

Step 3

Synthesis of N-[3-(3-amidinophenoxy)ethyl]-4-[N-t-butoxycarbonyl-N-methylamino]methyl]benzamide trifluoroacetate The title compound was obtained from 330 mg (1.24 mmol) of 4-(N-t-butoxycarbonyl-N-methylamino)methylbenzoic acid and 313 mg (1.24 mmol) of 3-(2-aminoethoxy)benzamidine dihydrochloride by the condensation and reversed-phase high-performance liquid chromatography in the same manner as that of step 5 in Example 124.

Yield: 155 mg (0.237 mmol) (20%)

MS (ESI, m/z) 427 (MH+).

Example 102

Synthesis of N-[3-(3-aminophenoxy)ethyl)-4-[(methylamino)methyl]benzamide bistrifluoroacetate 140 mg (0.26 mmol) of N-[3-(3-amidinophenoxy)ethyl]-4-[N-t-butoxycarbonyl-N-methylamino]methyl]benzamide trifluoroacetate was dissolved in trifluoroacetic acid, and the solution was stirred at room temperature for 30 minutes. Then, trifluoroacetic acid was evaporated to obtain the title compound.

Yield: 133 mg (0.24 mmol) (92%)

MS (ESI, m/z) 411 (MH++DMSO-d6).

Example 103

Synthesis of N-[2-(3-amidinophenoxy)ethyl]-4-[1-t-butoxycarbonyl-(3S)-3-pyrrolidyloxy]phenylacetamide trifluoroacetate

Step 1

Synthesis of (3R)-1-(t-butoxycarbonyl)-3-hydroxypyrrolidine 25.0 g (191 mmol) of trans-4-hydroxy-L-proline and 1.5 ml of cyclohexanone were dissolved in 150 ml of cyclohexanol, and the solution was stirred at 160° C. for 16 hours. The solution was diluted with methyl isobutyl ketone, and the same isolation procedure as that of step 1 in Example 1 was at repeated by using 1 N aqueous hydrochloric acid solution as the extractant to obtain the crude product. The oily residue thus obtained was dissolved in 300 ml of tetrahydrofuran and 300 ml of water. 34 ml (244 mmol) of triethylamine and 31.4 g (143 mmol) of di-t-butyl dicarbonate were added to the solution at 0° C., and they were stirred for 4 hours. The reaction mixture was treated by the same isolation procedure as that of step 1 in Example 1 with ethyl acetate as the extractant to obtain the crude product, which was then purified by the silica gel column chromatography to obtain the title compound.

Yield: 27.4 g (14.6 mmol) (76%).

MS (FAB, m/z) 188 (MH+)

H-NMR (CDCl3) δ 1.46 (9H, s), 2.25-2.31 (2H, m), 3.20-3.57 (4H, m), 4.42 (1H, s), 4.74 (1H, s).

Step 2

Synthesis of ethyl 2-[4-[(3S)-1-(t-butoxycarbonyl)-3-pyrrolidyloxy]phenyl]acetate 6.0 g (33.3 mmol) of ethyl 4-hydroxyphenylacetate, 6.25 g (33.3 mmol) of (3R)-1-(t-butoxycarbonyl)-3-hydroxypyrrolidine and 10.5 g (40 mmol) of triphenylphosphine were dissolved in 125 ml of tetrahydrofuran. 6.3 ml (40 mmol) of diethyl azodicarboxylate was added to the solution at room temperature, and they were stirred for 42 hours. After the same isolation process as that of step 1 in Example 1 with ethyl acetate as the extractant, the crude product was obtained. The crude product was purified by the silica gel column chromatography to obtain the title compound.

Yield: 5.7 g (16.3 mmol) (49%)

H-NMR (CDCl3) δ 1.24 (3H, t), 1.46 (9H, s), 2.05-2.20 (2H, m), 3.50 (2H, s), 3.40-3.62 (4H, m), 4.15 (2H, q), 4.85 (1H, s), 6.81 (1H, d), 6.83 (1H, d), 7.19 (1H, d), 7.23 (1H, d)

Step 3

Synthesis of 2-[4-[(3S)-1-t-butoxycarbonyl-3-pyrrolidyloxy]phenyl]acetic acid 750 mg of ethyl 2-[4-[(3S)-1-(t-butoxycarbonyl)-3-pyrrolidyloxy]phenyl]acetate was dissolved in 10 ml of ethanol. 4 ml of 1 N aqueous sodium hydroxide solution was added to the obtained solution. After stirring at room temperature overnight, the solvent was evaporated. 1 N hydrochloric acid was added to the residue. After the same isolation process as that of step 1 in Example 1 with ethyl acetate as the extractant, the title compound was obtained.

Yield: 830 mg

H-NMR (CDCl3) δ 1.45 (9H, s), 2.00-2.20 (2H, m), 3.42-3.62 (6H, m), 3.85 (1H, brs), 6.80 (2H, d), 7.20 (2H, d)

Step 4

Synthesis of 4-[1-t-butoxycarbonyl-(3S)-3-pyrrolidyloxy]phenylacetic acid

The title compound was obtained from ethyl 4-[1-t-butoxycarbonyl-(3S)-3-pyrrolidyloxy]phenylacetate in the same manner as that of step 2 in Example 97.

Step 5

Synthesis of N-[2-(3-amidinophenoxy)ethyl]-4-[1-t-butoxycarbonyl-(3S)-3-pyrrolidyloxy]phenylacetamide trifluoroacetate The title compound was obtained from 4-[1-t-butoxycarbonyl-(3S)-3-pyrrolidyloxy]phenylacetic acid and 3-(2-aminoethoxy)benzamidine dihydrochloride by the condensation reaction and reversed-phase high-performance liquid chromatography in the same manner as that of step 5 in Example 124.

MS (ESI, m/z) 483 (MH+)

H-NMR (DMSO-d6) δ 1.40 (9H, s), 1.95-2.15 (2H, m), 3.25-3.55 (8H, m), 4.10 (2H, t), 4.90 (1H, brs), 6.84 (2H, d), 7.17 (2H, d), 7.30 (1H, d), 7.36 (1H, s), 7.38 (1H, d), 7.53 (1H, t), 8.26 (1H, brt), 9.04 (2H, brs), 9.28 (2H, brs).

Example 104

Synthesis of N-[2-(3-amidinophenoxy)ethyl]-4-[(3S)-3-pyrrolidyloxy]phenylacetamide bistrifluoroacetate N-[2-(3-amidinophenoxy)ethyl]-4-[1-t-butoxycarbonyl-(3S)-3-pyrrolidyloxy]phenylacetamide trifluoroacetate was dissolved in 4 N solution of hydrogen chloride in dioxane, and the solution was stirred at room temperature for 1 hour. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

MS (ESI, m/z) 383 (MH+)

H-NMR (DMSO-d6) δ 2.05-2.25 (2H, m), 3.20-3.60 (8H, m), 4.10 (2H, t), 7.08 (2H, d), 7.20 (2H, d), 7.30 (1H, d), 7.40 (1H, d), 7.38 (1H, s), 7.54 (1H, t), 8.36 (1H, brt), 9.19 (2H, brs), 9.31 (2H, brs), 9.33 (2H, brs).

Example 105

Synthesis of N-[2-(3-amidinophenoxy)ethyl]-(1-acetyl-4-piperidine)carboxamide trifluoroacetate Step 1

Synthesis of N-[2-(3-cyanophenoxy)ethyl]-(1-acetyl-4-piperidine)carbamide

The title compound was obtained from 175 mg (1.02 mmol)) of 1-acetyl-4-piperidinecarboxylic acid and 150 mg (0.92 mmol) of 3-(2-aminoethoxy)benzonitrile in the same manner as that of step 4 in Example 1.

Yield: 84.4 mg (0.27 mmol) (29%)

H-NMR (CDCl3) δ 1.60-1.77 (2H, m), 1.82-1.93 (2H, m), 2.10 (3H, s), 2.35 (1H, m), 2.65 (1H, m), 3.09 (1H, m), 3.69 (2H, dt), 3.87 (1H, m), 4.06 (2H, t), 4.60 (1H, m), 5.97 (1H, br), 7.12 (1H, d), 7.14 (1H, s), 7.27 (1H, d), 7.40 (1H, t)

Step 2

Synthesis of N-[2-(3-amidinophenoxy)ethyl]-(1-acetyl-4-piperidine)carbamide trifluoroacetate The title compound was obtained from 75 mg (0.24 mmol) of N-[2-(3-cyanophenoxy)ethyl]-(1-acetyl-4-piperidine)carbamide in the same manner as that of step 5 in Example 95.

Yield: 12.3 mg (0.028 mmol) (12%)

MS (ESI, m/z) 333 (MH+)

H-NMR (CD3OD) δ 1.43-1.82 (4H, m), 2.15 (3H, s), 2.50 (1H, m), 2.65 (1H, m), 3.15 (1H, m), 3.60 (2H), 3.95 (1H, m), 4.15 (2H, t), 4.50 (1H, m), 7.31 (1H, d), 7.35 (1H, s), 7.37 (1H, d), 7.52 (1H, t).

Example 106

Synthesis of N-[2-(3-amidinophenoxy)ethyl]-(1S)-10-camphorsulfonamide trifluoroacetate Step 1

Synthesis of N-[2-(3-cyanophenoxy)ethyl]-(1S)-10-camphorsulfonamide 700 mg (4.32 mmol) of 3-(2-aminoethoxy)benzonitrile was dissolved in 20 ml of DMF. 0.75 ml (4.32 mmol) of diisopropylethylamine and a solution of 1.08 g (4.32 mmol) of (1S)-(+)-10-camphorsulfonyl chloride in 5 ml of DMF were added to the solution at 0° C., and they were stirred for 4 hours. The crude product was obtained by the same isolation process as that of step 1 in Example 11 with ethyl acetate as the extractant. After the purification by the silica gel column chromatography, the title compound was obtained.

Yield: 1.41 g (3.75 mmol) (87%)

MS (ESI, m/z) 377 (MH+)

H-NMR (CDCl3) δ 0.88 (3H, s), 1.04 (3H, s), 1.47 (1H, ddd), 1.89-2.15 (5H, m), 2.33 (1H, td), 2.98 (1H, d), 3.46 (1H, d), 3.59 (2H, dt), 4.14 (2H, t), 6.00 (1H, t), 7.15 (1H, d), 7.18 (1H, s), 7.26 (1H, d), 7.39 (1H, t)

Step 2

Synthesis of N-[2-(3-amidinophenoxy)ethyl]-(1S)-10-camphorsulfonamide trifluoroacetate The title compound was obtained from 1.41 g (3.75 mmol) of N-[2-(3-cyanophenoxy)ethyl]-(1S)-10-camphorsulfonamide in the same manner as that of step 5 in Example 95.

Yield: 342 mg (0.67 mmol) (18%).

MS (ESI, m/z) 394 (MH+)

H-NMR (DMSO-d6) δ 0.86 (3H, s), 0.93 (3H, s), 1.38 (1H, ddd), 1.78-1.91 (2H, m), 2.17-2.21 (2H, m), 2.52 (1H, d), 2.56 (1H, d), 3.05-3.30 (2H, m), 4.00-4.05 (2H, m), 4.37 (2H, t), 7.34 (1H, d), 7.40 (1H, s), 7.45 (1H, d), 7.55 (1H, q), 9.13 (2H, s), 9.31 (2H, s).

Example 107

Synthesis of N-[2-(3-amidinophenoxy)ethyl]-(1R)-10-camphorsulfonamide trifluoroacetate Step 1

Synthesis of N-[2-(3-cyanophenoxy)ethyl]-(1R)-10-camphorsulfonamide

The title compound was obtained from 700 mg (4.32 mmol) of 3-(2-aminoethoxy)benzonitrile and 1.08 g (4.32 mmol) of (1R)-(−)-10-camphorsulfonyl chloride in the same manner as that of step 1 in Example 106.

Yield: 1.33 g (3.54 mmol) (82%)

MS (ESI, m/z) 377 (MH+)

Step 2

Synthesis of N-[2-(3-amidinophenoxy)ethyl]-(1R)-10-camphorsulfonamide trifluoroacetate The title compound was obtained from 1.33 g (3.54 mmol) of N-[2-(3-cyanophenoxy)ethyl]-(1R)-10-camphorsulfonamide in the same manner as that of step 5 in Example 95.

Yield: 320 mg (0.63 mmol) (18%)

MS (ESI, m/z) 394 (MH+)

H-NMR (DMSO-d6) δ 0.86 (3H, s), 0.93 (3H, s), 1.35 (1H, ddd), 1.78-1.91 (2H, m), 2.12-2.21 (2H, m), 2.59 (1H, d), 2.76 (1H, d), 3.11 (1H, d), 3.14 (1H, d), 4.08 (2H, br), 4.37 (2H, br), 7.33 (1H, dd), 7.40 (1H, s), 7.42 (1H, d), 7.56 (1H, t), 7.55 (1H, q), 9.11 (2H, s), 9.31 (2H, s).

Example 108

Synthesis of 1-[2-(3-amidinophenoxy)ethylcarbamoyl]methyl]quinuclidinium bistrifluoroacetate Step 1

Synthesis of N-[2-(3-cyanophenoxy)ethyl]bromoacetamide 1.50 g (9.26 mmol) of 3-(2-aminoethoxy)benzonitrile and 1.77 ml (10.2 mmol) of diisopropylethylamine were dissolved in 15 ml of tetrahydrofuran. A solution of 0.92 ml (11.1 mmol) of bromoacetyl chloride in 5 ml of tetrahydrofuran was added to the obtained solution at 0° C., and they were stirred for 8 hours. The solvent was evaporated, and the residue was purified by the silica gel column chromatography to obtain the title compound.

Yield: 2.18 g (7.73 mmol) (83%)
MS (ESI, m/z) 305 (M+Na+)
H-NMR (CDCl3) δ 3.76 (2H, dt), 3.98 (2H, d), 4.08 (2H, t), 7.14 (1H, dd), 7.16 (1H, s), 7.28 (1H, dd), 7.39 (1H, td)

Step 2

Synthesis of [1-[2-(3-amidinophenoxy)ethylcarbamoyl]methyl]quinuclidinium bistrifluoroacetate 500 mg (1.77 mmol) of N-[2-(3-cyanophenoxy)ethyl]bromoacetamide and 196 mg (1.77 mmol) of quinuclidine were dissolved in 5 ml of chloroform. The solution was stirred at 100° C. for 2 hours and then at room temperature for 15 hours. The solvent was evaporated to obtain an oily residue, which was treated in the same manner as that of step 5 in Example 95 to obtain the title compound.
Yield: 258 mg (0.46 mmol) (26%).
MS (ESI, m/z) 331 (MH+)
H-NMR (DMSO-d6) δ 1.88 (6H, m), 2.07 (1H, br), 3.58 (8H, m), 3.95 (2H, s), 4.14 (2H, t), 7.29 (1H, dd), 7.39 (1H, s), 7.43 (1H, d), 7.53 (1H, t), 9.02 (1H, t), 9.34 (2H, s), 9.55 (2h, s).

Example 109

Synthesis of N-[2-(3-amidinophenoxy)ethyl]-(3-quinuclidinyl)aminoacetamide tristrifluoroacetate 500 mg (1.77 mmol) of N-[2-(3-cyanophenoxy)ethyl]-bromoacetamide, 423 mg (2.13 mmol) of 3-aminoquinuclidine hydrochloride, 586 mg (4.25 mmol) of potassium carbonate and 323 mg (1.95 mmol) of potassium iodide were dissolved in 5 ml of DMF, and the solution was stirred at 0° C. for 105 minutes and then at room temperature for 6 hours. The solvent was evaporated under reduced pressure, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain a crystalline substance, which was treated in the same manner as that in step 5 of Example 95 to obtain the title compound.
Yield: 80 mg (0.12 mmol) (6.8%)
MS (FAB, m/z) 346 (MH+)
H-NMR (DMSO-d6) δ 1.91-2.03 (4H, m), 2.28-2.38 (1H, m), 3.10-3.40 (5H, m), 3.55 (2H, dd), 3.70-3.83 (2H, m), 4.08 (2H, t), 4.15 (2H, m), 7.27 (1H, s), 7.32 (1H, d), 7.46 (1H, d), 7.54 (1H, t), 9.23 (2H, br), 9.46 (2H, br).

Example 110

Synthesis of 3-[2-(2-naphthalenesulfonylamino)ethoxy]benzamidine trifluoroacetate Step 1

Synthesis of 3-[2-(2-naphthalenesulfonylamino)ethoxy]benzonitrile 163 mg of 3-(2-aminoethoxy)benzonitrile and 0.5 ml of diisopropylethylamine were dissolved in 10 ml of dimethylformamide. A solution of 250 mg (1.1 mmol) of 2-naphthalenesulfonyl chloride in dimethylformamide was added to the obtained solution under cooling with ice, and they were stirred under cooling with ice for 2 hours. The title compound was obtained by the same isolation process as that of step 1 in Example 1 with ethyl acetate as the extractant.
Yield: 320 mg (0.91 mmol) (91%)
H-NMR (CDCl3) δ 3.45 (2H, dt), 4.00 (2H, t), 5.05 (1H, br), 6.96 (1H, s), 6.97 (1H, d), 7.20 (1H, d), 7.30 (1H, t), 7.59-7.70 (2H, m), 7.82-7.98 (4H, m), 8.46 (1H, s)

Step 2

Synthesis of 3-[2-(2-naphthalenesulfonylamino)ethoxy]benzamidine trifluoroacetate The title compound was obtained from 300 mg (0.85 mol) of 3-[2-(2-naphthalenesulfonylamino)ethoxy]benzonitrile in the same manner as that of step 5 in Example 95.
Yield: 168 mg (0.35 mmol) (41%)
MS (FAB, m/z) 384 (MH+)
H-NMR (DMSO-d6) δ 3.20 (2H, br), 4.10 (2H, br), 7.14 (1H, d), 7.22 (1H, s), 7.33 (1H, d), 7.44 (1H, t), 7.60-8.20 (7H, m), 8.41 (1H, s), 9.10 (4H, br).

Example 111

Synthesis of 3-[2-(4-amidinobenzenesulfonylamino)ethoxy]benzamidine bistrifluoroacetate Step 1

Synthesis of 3-[2-(4-bromobenzenesulfonylamino)ethoxy]benzonitrile

The title compound was obtained from 460 mg (1.8 mmol) of 4-bromobenzenesulfonyl chloride and 294 mg (1.8 mmol) of 3-(2-aminoethoxy)benzonitrile in the same manner as that of step 1 in Example 110.
Yield: 604 mg (1.7 mmol) (94%)
H-NMR (CDCl3) δ 3.40 (2H, dt), 4.02 (2H, t), 5.00 (1H, br), 7.03 (1H, d), 7.50 (1H, s), 7.27 (1H, d), 7.37 (1H, t), 7.65 (2H, d), 7.75 (2H, d)

Step 2

Synthesis of 3-[2-(4-cyanobenzenesulfonylamino)ethoxy]benzonitrile 300 mg (0.84 mmol) of 3-[2-(4-bromobenzenesulfonylamino)ethoxy]benzonitrile was dissolved in 1 ml of N-methylpyrrolidone. 76 mg (0.84 mmol) of copper (I) cyanide was added to the solution, and they were stirred at 140° C. overnight. The crude product was obtained by the treatment with ethyl acetate as the extractant in an ordinary manner. After the silica gel column chromatography, the title compound was obtained.
Yield: 45 mg (0.14 mmol) (16%)
MS (ESI, m/z) 350 (MNa+)
H-NMR (CDCl3) δ 3.25 (2H, dt), 4.05 (2H, t), 5.15 (1H, br), 7.40 (1H, d), 7.50 (1H, s), 7.28 (1H, d), 7.38 (1H, t), 7.82 (2H, d), 8.01 (2H, d)
4-[2-(3-cyanophenoxy)ethylsulfamoyl]benzamide was also obtained.
Yield: 21 mg (0.06 mmol) (7%)
H-NMR (CD3OD) δ 3.35 (2H, t), 4.00 (2H, t), 7.10 (1H, d), 7.15 (1H, s), 7.39 (1H, t), 7.92-8.01 (4H, m)

Step 3

Synthesis of 3-[2-(4-amidinobenzenesulfonylamino) ethoxy]benzamidine bistrifluoroacetate The title compound was obtained from 40 mg (0.14 mmol) of 3-[2-(4-cyanobenzenesulfonylamino)ethoxy]benzonitrile in the same manner as that of step 5 in Example 95.
Yield: 9.0 mg (0.015 mmol) (11%)
MS (ESI, m/z) 362 (MH+)
H-NMR (DMSO-d6) δ 3.20 (2H, dt), 4.10 (2H, t), 7.21 (1H, d), 7.33 (1H, s), 7.40 (1H, d), 7.51 (1H, t), 7.98-8.05 (4H, m), 8.41 (1H, br), 9.25 (2H, br), 9.30 (2H, br), 9.48 (4H, br)

Example 112

Synthesis of 4-[2-(3-amidinophenoxy)ethylsulfamoyl]benzamide trifluoroacetate

The title compound was obtained from 20 mg (0.058 mmol) of 4-[2-(3-cyanophenoxy)ethylsulfamoyl]benzamide in the same manner as that of step 5 in Example 95.
Yield: 5 mg (0.010 mmol) (17%)
MS (ESI, m/z) 363 (MH+)
H-NMR (DMSO-d6) δ 3.20 (2H, dt), 4.05 (2H, q), 7.20 (1H, d), 7.31 (1H, s), 7.37 (1H, d), 7.50 (1H, t), 7.59 (1H, br), 7.89 (2H, d), 8.02 (2H, d), 8.10 (1H, br), 8.14 (1H, br), 9.05 (2H, br), 9.30 (2H, br).

Example 113

Synthesis of 3-[2-(4-bromobenzenesulfonylamino) ethoxy]benzamidine trifluoroacetate The title compound was obtained from 40 mg (0.11 mmol) of 3-[2-(4-bromobenzenesulfonylamino)ethoxy]benzonitrile in the same manner as that of step 5 in Example 95.
Yield: 26 mg (0.04 mmol) (36%)
MS (ESI, m/z) 398 (MH+), 400 ((M+2)H+)
H-NMR (DMSO-d6) δ 3.20 (2H, dt), 4.05 (2H, t), 7.20 (1H, d), 7.28 (1H, s), 7.38 (1H, d), 7.51 (1H, t), 7.73-7.82 (4H, m), 8.10 (1H, br), 9.10 (2H, br), 9.28 (2H, br).

Example 114

Synthesis of N-[2-(3-amidinophenoxy)ethyl]-N-phenylmethyl-4-amidinobenzamide bistrifluoroacetate

Step 1

Synthesis of N-[2-(3-cyanophenoxy)ethyl]-N-phenylmethyl-4-cyanobenzamide 28 mg (0.7 mmol) of sodium hydride (oily, 60%) was stirred in dimethylformamide under cooling with ice. A solution of 200 mg (0.69 mmol) of N-[2-(3-cyanophenoxy)ethyl]-4-cyanobenzamide in a small amount of dimethylformamide was added thereto. After the completion of the generation of hydrogen, 257 mg (1.5 mmol) of benzyl bromide was added to the mixture, and they were stirred at room temperature for 2 hours. The solvent was evaporated under reduced pressure. 1N aqueous hydrogen chloride solution was added to the residue. The same procedure for the isolation as that of step 1 in Example 1 was repeated with ethyl acetate as the extractant to obtain the title compound.
Yield: 315 mg (0.83 mmol) (>100%).

H-NMR (CDCl3) mixture of rotational isomers A and B (1:3) of amide δ 3.30 (2H, brs, A), 3.85 (2H, brs, B), 3.85 (2H, brs, A), 4.25 (2H, brs, B), 4.61 (2H, brs, B), 4.85 (2H, brs, A), 6.90-7.75 (13H, m).

Step 2

Synthesis of N-[2-(3-amidinophenoxy)ethyl]-N-phenylmethyl-4-amidinobenzamide bistrifluoroacetate The title compound was obtained from 300 mg (0.79 mmol) of N-[2-(3-cyanophenoxy)ethyl]-N-phenylmethyl-4-cyanobenzamide in the same manner as that of step 5 in Example 95.
Yield: 152 mg (0.24 mmol) (30%)
MS (ESI, m/z) 416 (MH+)
H-NMR (DMSO-d6) mixture of rotational isomers A and B (1:3) of amide δ 3.55 (2H, brs, A or B), 3.75 (2H, brs, A or B), 4.10 (2H, brs, A or B), 4.30 (2H, brs, A or B), 4.60 (2H, brs, A or B), 4.80 (2H, brs, A or B), 7.20-7.95 (13H, m), 9.20-9.50 (8H, m).

Example 115

Synthesis of N-[2-(3-amidinophenoxy)ethyl]-N-methyl-4-amidinobenzamide bistrifluoroacetate

Step 1

Synthesis of N-[2-(3-cyanophenoxy)ethyl]-N-methyl-4-cyanobenzamide

The title compound was obtained from 200 mg (0.69 mmol) of N-[2-(3-cyanophenoxy)ethyl]-4-cyanobenzamide and 500 mg (excess) of methyl iodide in the same manner as that of step 1 in Example 114.
Yield: 221 mg (0.73 mmol) (>100%)
H-NMR (CDCl3) mixture of rotational isomers A and B (1:3) of amide δ 3.15 (3H, brs, B), 3.20 (3H, brs, A), 3.70 (2H, brs, A), 3.95 (2H, brs, B), 4.05 (2H, brs, A), 4.30 (2H, brs, B), 7.04-7.20 (2H, m), 7.28 (1H, d), 7.40 (1H, t), 7.49-7.59 (2H, m), 7.72 (2H, d)

Step 2

Synthesis of N-[2-(3-amidinophenoxy)ethyl]-N-methyl-4-amidinobenzamide bistrifluoroacetate The title compound was obtained from 200 mg (0.66 mmol) of N-[2-(3-cyanophenoxy)ethyl]-N-methyl-4-cyanobenzamide in the same manner as that of step 5 in Example 95.
Yield: 130 mg (0.23 mmol) (35%)
MS (ESI, m/z) 340 (MH+)
H-NMR (DMSO-d6) mixture of rotational isomers A and B (1:1) of amide δ 3.00 (3H, S, A or B), 3.05 (3H, s, A or B), 3.62 (2H, s, A or B), 3.90 (2H, s, A or B), 4.15 (2H, s, A or B), 4.35 (2H, s, A or B), 7.22-7.70 (6H, m), 7.90 (2H, d), 9.18-9.42 (8H, m).

Example 116

Synthesis of N-[(1S)-2-(3-amidinophenoxy)-1-benzylethyl]-4-amidinobenzamide bistrifluoroacetate Step 1

Synthesis of N-[(1S)-1-benzyl-2-(3-cyanophenoxy)ethyl]-4-cyanobenzamide

The crude product was obtained from 4.5 g (20.9 mmol) of hydrochloride of methyl ester of L-phenylalanine in the same manner as that of step 1 in Example 117 without the purification of the intermediate. The crude product was purified by the silica gel column chromatography to obtain the title compound.

Yield: 1.03 g (2.70 mmol) (12.9%)
MS (ESI, m/z) 489 (MH+)
H-NMR (CDCl3) δ 3.15 (2H, d), 4.01-4.18 (2H, m), 4.63-4.80 (1H, m), 6.67 (1H, d), 7.15-7.42 (9H, m), 7.67 (2H, d), 7.81 (2H, d)

Step 2

Synthesis of N-[(1S)-2-(3-amidinophenoxy)-1-benzylethyl]-4-amidinobenzamide bistrifluoroacetate The title compound was obtained from 1.03 g (2.70 mmol) of N-[(1S)-1-benzyl-2-(3-cyanophenoxy)ethyl]-4-cyanobenzamide in the same manner as that of step 2 in Example 117.

Yield: 305 mg (0.474 mmol) (17.6%)
MS (ESI, m/z) 416 (MH+)
H-NMR (DMSO-d6) δ 2.95-3.17 (2H, m), 4.12-4.27 (2H, m), 4.55-4.62 (1H, m), 7.17-7.85 (2H, d), 7.97 (2H, d), 8.80 (1H, d), 9.24 (2H, br), 9.30 (2H, br), 9.42 (4H, br).

Example 117

Synthesis of N-[(1R)-2-(3-amidinophenoxy)-1-benzylethyl]-4-amidinobenzamide bistrifluoroacetate Step 1

Synthesis of N-[(1R)-1-benzyl-2-(3-cyanophenoxy)ethyl]-4-cyanobenzamide

The crude product was obtained from 4.5 g (20.9 mmol) of hydrochloride of methyl ester of D-phenylalanine in the same manner as that of steps 2, 4, 5 and 6 in Example 150 and steps 3 and 4 in Example 1 without the purification of the intermediate. The crude product was purified by the silica gel column chromatography to obtain the title compound.

Yield: 0.95 g (2.49 mmol) (11.9%)
MS (ESI, m/z) 489 (MH+)
H-NMR (CDCl3) δ 3.17 (2H, d), 4.01-4.17 (2H, m), 4.67-4.80 (1H, m), 6.38 (1H, d), 7.08-7.42 (9H, m), 7.75 (2H, d), 7.82 (2H, d)

Step 2

Synthesis of N-[(1S)-2-(3-amidinophenoxy)-1-benzylethyl]-4-amidinobenzamide bistrifluoroacetate The title compound was obtained from 0.95 g (2.49 mmol) of N-[(1R)-1-benzyl-2-(3-cyanophenoxy)ethyl]-4-cyanobenzamide in the same manner as that of step 7 in Example 150.

Yield: 188 mg (0.474 mmol) (17.6%)
MS (ESI, m/z) 416 (MH+)
H-NMR (DMSO-d6) δ 2.95-3.18 (2H, m), 4.17-4.27 (2H, m), 4.52-4.62 (1H, m), 7.19-7.57 (9H, m), 7.85 (2H, d), 7.98 (2H, d), 8.79 (1H, d), 9.24 (2H, br), 9.32 (2H, br), 9.42 (4H, br).

Example 118

Synthesis of ethyl (3R)-3-(4-amidinobenzoylamino)-4-(3-amidinophenoxy)butanoate bistrifluoroacetate Step 1

Synthesis of benzyl (3R)-3-t-butoxycarbonylamino-4-(3-cyanophenoxy)butanoate 3.23 g (10.0 mmol) of β-benzyl N-t-butoxycarbonyl-D-aspartate and 1.39 ml (10.0 mmol) of triethylamine were dissolved in 50 ml of tetrahydrofuran. 096 ml (10.0 mmol) of ethyl chloroformate was added to the solution under cooling with ice, and the resultant mixture was stirred for 20 minutes. A precipitate thus formed was removed by the suction filtration. 5 g of ice and 0.76 g (20.0 mmol) of sodium borohydride were added to the filtrate under cooling, and they were stirred at room temperature for additional 1.5 hours. After the addition of 1 N aqueous hydrogen chloride solution, they were stirred at room temperature for one hour. The reaction mixture was treated with ethyl acetate as the extractant in an ordinary manner to obtain an oily residue, which was dissolved in 36 ml of tetrahydrofuran. 0.96 g (8.04 mmol) of 3-cyanophenol, 2.30 g (8.77 mmol) of triphenylphosphine and 3.50 g (8.04 mmol) of diethyl azodicarboxylate (40% solution in toluene) were added to the solution, and the obtained mixture was stirred at room temperature overnight. The solvent was evaporated, and the residue was purified by the silica gel column chromatography to obtain the title compound.

Yield: 1.80 g (4.38 mmol) (44%)
H-NMR (CDCl3) δ 1.46 (9H, s), 2.79 (2H, d), 4.00 (1H, dd), 4.06 (1H, dd), 4.41 (1H, br), 5.13 (2H, s), 5.56 (1H, br), 7.05-7.18 (4H, m), 7.21-7.38 (5H, m).

Step 2

Synthesis of benzyl (3R)-3-(4-cyanobenzoylamino)-4-(3-cyanophenoxy)butanoate 1.8 g (4.38 mmol) of benzyl (3R)-3-t-butoxycarbonylamino-4-(3-cyanophenoxy)butanoate was dissolved in 20 ml of 4 N solution of hydrogen chloride in dioxane, and the solution was stirred at 0° C. for 6 hours. The solvent was evaporated, and the obtained oily residue was dissolved in 5 ml of dichloromethane. 1.09 g (6.58 mmol) of 4-cyanobenzoyl chloride and 1.22 ml (8.76 mmol) of triethylamine were added to the solution under cooling with ice, and they were stirred at room temperature overnight. The reaction mixture was treated with ethyl acetate as the extractant in an ordinary manner to obtain the crude product. After the silica gel column chromatography, the title compound was obtained.

Yield: 1.21 g (2.75 mmol) (63%)
H-NMR (CDCl3) δ 2.86 (1H, dd), 2.95 (1H, dd), 4.12 (1H, dd), 4.20 (1H, dd), 4.85 (1H, br), 5.16 (2H, s), 7.09 (1H, d), 7.11 (1H, dd), 7.24-7.40 (7H, m), 7.72 (2H, d), 7.83 (2H, d).

Step 3

Synthesis of ethyl (3R)-3-(4-amidinobenzoylamino)-4-(3-amidinophenoxy)butanoate bistrifluoroacetate 1.21 g (2.75 mmol) of benzyl (3R)-(4-cyanobenzoylamino)-4-(3-cyanophenoxy)butanoate was added to 20 ml of ethanol containing 30% (w/v) of hydrogen chloride, and they were stirred at room temperature overnight. Then the reaction mixture was dissolved in 30 ml of 10% (w/v) solution of ammonia in ethanol at room temperature, and the solution was stirred at room temperature for two days. The solvent was evaporated, and the residue was purified by the reversed phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 0.456 g (0.713 mmol) (25.9%)
MS (ESI, m/z) 412 (MH+)
H-NMR (DMSO-d6) δ 1.15 (3H, t), 2.82 (2H, d), 4.07 (2H, q), 4.12 (1H, dd), 4.24 (1H, dd), 4.72 (1H, br), 7.33 (1H, d), 7.39 (1H, s), 7.40 (1H, d), 7.54 (1H, dd), 7.91 (2H, d), 8.02 (2H, d), 8.84 (1H, d), 9.16 (2H, s), 9.28 (4H, s), 9.42 (2H, s).

Example 119

Synthesis of (3R)-3-(4-amidinobenzoylamino)-4-(3-amidinophenoxy)butanoic acid bistrifluoroacetate 0.466 g (0.729 mmol) of ethyl (3R)-3-(4-amidinobenzoylamino)-4-(3-amidinophenoxy)butanoate bistrifluoroacetate was dissolved in 10 ml of concentrated hydrochloric acid, and the solution was stirred at 40° C. for 6 hours. Hydrogen chloride was evaporated, the residue was treated by the reversed phase high-performance liquid chromatography with silica gel, containing octadodecyl group chemically bonded thereto, as the filler After the elution with a mixed solvent of water and acetonitrile containing 0.1% (v/v) of trifluoroacetic acid, the fraction of the intended product was freeze-dried to obtain the title compound.

Yield: 0.151 g (0.247 mmol) (46%)
MS (ESI, m/z) 384 (MH+)
H-NMR (DMSO-d6) δ 2.74 (2H, d), 4.13 (1H, dd), 4.24 (1H, dd), 4.69 (1H, ddt), 7.35 (1H, d), 7.40 (1H, d), 7.41 (1H, s), 7.55 (1H, dd), 7.91 (2H, d), 8.03 (2H, d), 8.81 (1H, d), 9.20 (2H, s), 9.28 (2H, s), 9.33 (2H, s), 9.43 (2H, s).

Example 120

Synthesis of ethyl (4R)-4-(4-amidinobenzoylamino)-5-(3-amidinophenoxy)pentanoate bistrifluoroacetate Step 1

Synthesis of benzyl (4R)-4-t-butoxycarbonylamino-5-(3-cyanophenoxy)pentanoate

The title compound was obtained from 3.37 g (10.0 mmol) of γ-benzyl N-t-butoxycarbonyl-D-glutamate in the same manner as that in the synthesis of benzyl (3R)-3-t-butoxycarbonylamino-4-(3-cyanophenoxy)butanoate.

Yield: 3.20 g (7.54 mmol) (75.4%)
H-NMR (CDCl3) δ 1.44 (9H, s), 1.69 (2H, br), 2.02 (2H, br), 3.98 (2H, br), 4.83 (1H, br), 5.11 (2H, s), 7.04-7.16 (4H, m), 7.24-7.40 (5H, m).

Step 2

Synthesis of benzyl (4R)-4-(4-cyanobenzoylamino)-5-(3-cyanophenoxy)pentanoate

The title compound was obtained from 3.20 g (7.54 mmol) of benzyl (4R)-4-t-butoxycarbonylamino-5-(3-cyanophenoxy)pentanoate in the same manner as that in the synthesis of benzyl (3R)-3-(4-cyanobenzoylamino)-4-(3-cyanophenoxy)butanoate Yield: 2.16 g (4.76 mmol) (63.2%).
H-NMR (CDCl3) δ 2.10-2.28 (2H, m), 2.54 (1H, ddd), 2.69 (1H, ddd), 4.10 (1H, dd), 4.18 (1H, dd), 4.48 (1H, br), 5.12 (2H, s), 7.00 (1H, br), 7.14-7.19 (2H, m), 7.24-7.41 (7H, m), 7.72 (2H, d), 7.87 (2H, d).

Step 3

Synthesis of ethyl (4R)-4-(4-amidinobenzoylamino)-5-(3-amidinophenoxy)pentanoate bistrifluoroacetate The title compound was obtained from 2.16 g (4.76 mmol) of benzyl (4R)-4-(4-cyanobenzoylamino)-5-(3-cyanophenoxy)pentanoate in the same manner as that of the synthesis of ethyl (3R)-3-(4-amidinobenzoylamino)-4-(3-amidinophenoxy)butanoate.

Yield: 1.78 g (2.72 mmol) (57.2%)
MS (ESI, m/z) 426 (MH+)
H-NMR (DMSO-d6) δ 1.15 (3H, t), 1.88-1.98 (1H, m), 2.01-2.11 (1H, m), 2.45 (2H, ddd), 4.03 (2H, q), 4.11 (1H, dd), 4.19 (1H, dd), 4.38 (1H, br), 7.34 (1H, d), 7.39 (1H, d), 7.40 (1H, s), 7.54 (1H, dd), 7.91 (2H, d), 8.05 (2H, d), 8.66 (1H, d), 9.17 (2H, s), 9.29 (4H, s), 9.42 (2H, s).

Example 121

Synthesis of (4R)-4-(4-amidinobenzoylamino)-5-(3-amidinophenoxy)pentanoic acid bistrifluoroacetate The title compound was obtained from 1.02 g (1.56 mmol) of ethyl (4R)-4-(4-aminobenzoylamino)-5-(3-amidinophenoxy)pentanoate bistrifluoroacetate in the same manner as that of the synthesis of (3R)-3-(4-amidinobenzoylamino)-4-(3-amidinophenoxy)butanoic acid bistrifluoroacetate.

Yield: 261 mg (0.417 mmol) (26.7%)
MS (ESI, m/z) 398 (MH+)
H-NMR (DMSO-d6) δ 1.84-1.96 (1H, m), 1.98-2.10 (1H, m), 2.37 (2H, ddd), 4.11 (1H, dd), 4.20 (1H, dd), 4.38 (1H, br), 7.33 (1H, d), 7.39 (1H, d), 7.40 (1H, s), 7.91 (2H, d), 8.05 (2H, d), 8.65 (1H, d), 9.18 (2H, s), 9.26 (2H, s), 9.29 (2H, s), 9.41 (2H, s).

Example 122

Synthesis of N-[3-(3-amidinophenoxy)propyl]-4-amidinobenzamide bistrifluoroacetate Synthesis of ethyl 4-[3-(3-amidinophenoxy)propylcarbamoylbenzoate trifluoroacetate Step 1

Synthesis of N-(3-bromopropyl)-t-butyl carbamate

The title compound was obtained from 18.4 g (84.2 mmol) of 3-bromopropylamine hydrobromide and 13.1 g (60.0 mmol) of di-t-butyl dicarbonate in the same manner as that of step 1 in Example 1.

Yield: 11.8 g (50.0 mmol) (83%)
H-NMR (CDCl3) δ 1.42 (9H, s), 2.05 (2H, tt), 3.25 (2H, dt), 3.45 (2H, t) 4.70 (1H, br)

Step 2

Synthesis of 3-[3-(t-butoxycarbonylamino)propoxy]benzonitrile

The title compound was obtained from 2 g (16.8 mmol) of N-(3-bromopropyl)-t-butyl carbamate and 2 g (16.8 mmol) of 3-hydroxybenznitrile in the same manner as that of step 2 in Example 1.

Yield: 4.51 g (16.3 mmol) (96%)
H-NMR (CDCl3) δ 1.42 (9H, s), 2.00 (2H, tt), 3.35 (2H, dt), 4.05 (2H, t), 4.70 (1H, br), 7.12 (1H, d), 7.14 (1H, s), 7.24 (1H, d), 7.37 (1H, t).

Step 3

Synthesis of 3-(3-aminopropoxy)benzonitrile hydrochloride

The title compound was obtained from 1 g (3.6 mmol) of 3-[3-(t-butoxycarbonylamino)propoxy]benzonitrile in the same manner as that of step 3 in Example 1.

Yield: 758 mg (3.6 mmol) (100%)

Step 4

Synthesis of N-[3-(3-cyanophenoxy)propyl]-4-cyanobenzamide

The title compound was obtained from 100 mg (0.47 mmol) of 3-(3-aminopropoxy)benzonitrile hydrochloride and 77 mg (0.52 mmol) of 4-cyanobenzoic acid in the same manner as that of step 4 in Example 1.

Yield: 124 mg (0.41 mmol) (87%)
H-NMR (CDCl3) δ 2.18 (2H, tt), 3.70 (2H, dt), 4.15 (2H, t), 6.50 (1H, br), 7.15 (1H, d), 7.18 (1H, s), 7.25 (1H, d), 7.38 (1H, t), 7.75 (2H, d), 7.85 (2H, d)

Step 5

Synthesis of N-[3-(3-amidinophenoxy)propyl]-4-amidinobenzamide bistrifluoroacetate Synthesis of ethyl 4-[3-(3-amidinophenoxy)propylcarbamoyl]benzoate trifluoroacetate The title compound was obtained from 125 mg (0.41 mmol) of N-[3-(3-cyanophenoxy)propyl]-4-cyanobenzamide in the same manner as that of step 5 in Example 95.

N-[3-(3-amidinophenoxy)propyl]-4-amidinobenzamide bistrifluoroacetate

Yield: 3 mg (0.01 mmol) (2%)
MS (ESI, m/z) 340 (MH+)
H-NMR (DMSO-d6) δ 2.05 (2H, tt), 3.50 (2H, dt), 4.18 (2H, t), 7.31 (1H, d), 7.38 (1H, s), 7.39 (1H, d), 7.54 (1H, s), 7.89 (2H, d), 8.04 (2H, d), 8.80 (1H, br), 9.10 (2H, br), 9.20 (2H, br), 9.30 (2H, br), 9.40 (2H, br).

Ethyl 4-[3-(3-amidinophenoxy)propylcarbamoyl]benzoate trifluoroacetate

MS (ESI, m/z) 370 (MH+)
H-NMR (DMSO-d6) δ 1.35 (3H, t), 2.05 (2H, tt), 3.45 (2H, dt), 4.15 (2H, t), 4.35 (2H, q), 7.32 (1H, d), 7.38 (1H, d), 7.37 (2H, s), 7.55 (1H, t), 7.97 (2H, d), 8.04 (2H, d), 8.75 (1H, br), 9.05 (2H, br), 9.27 (2H, br).

Example 123

Synthesis of N-[3-(3-amidinophenoxy)propyl]-(1-acetyl-4-piperidine)carboxamide trifluoroacetate Synthesis of N-[3-(3-cyanophenoxy)propyl]-(1-acetyl-4-piperidine)carbamide The title compound was obtained from 89 mg (0.52 mmol) of (1-acetyl-4-piperidine)carboxylic acid and 100 mg (0.47 mmol) of 3-(3-aminopropoxy)benzonitrile hydrochloride in the same manner as that of step 4 in Example 1.

Yield: 98 mg (0.30 mmol) (64%)
H-NMR (CDCl3) δ 1.50-1.90 (4H, m), 2.05 (2H, tt), 2.30 (1H, m), 2.65 (1H, m), 3.10 (1H, m), 3.45 (2H, dt), 3.85 (1H, m), 4.05 (2H, t), 4.60 (1H, m), 5.75 (1H, br), 7.15 (1H, d), 7.15 (1H, s), 7.25 (1H, d), 7.40 (1H, t)

Step 2

Synthesis of N-[3-(3-amidinophenoxy)propyl]-(1-acetyl-4-piperidinecarbamide trifluoroacetate The title compound was obtained from 98 mg (0.30 mmol) of N-[3-(3-cyanophenoxy)propyl]-(1-acetyl-4-piperidinecarbamide in the same manner as that of step 5 in Example 95.

Yield: 72 mg (0.16 mmol) (yield: 53%).
MS (ESI, m/z) 347 (MH+)
H-NMR (DMSO-d6) δ 1.30-1.50 (2H, m), 1.70 (2H, m), 1.85 (2H, tt), 2.35 (1H, m), 2.55 (1H, m), 3.00 (1H, m), 3.20 (2H, dt), 3.80 (1H, m), 4.05 (2H, t), 4.35 (1H, m), 7.28 (1H, d), 7.35 (1H, s), 7.37 (1H, s), 7.55 (1H, t), 7.90 (1H, br), 9.20 (2H, br), 9.30 (2H, br).

Example 124

Synthesis of N-[3-(3-amidinophenoxy)propyl]-4-piperidinecarboxamide bistrifluoroacetate Step 1

Synthesis of 3-hydroxybenzamidine hydrochloride 5 g (42 mmol) of 3-hydroxybenzonitrile was dissolved in 50 ml of ethanol containing 30% (w/v) of hydrogen chloride, and the solution was stirred at room temperature overnight. The solvent was evaporated, and the residue was dissolved in 50 ml of 30% (w/v) solution of ammonia in ethanol. After the stirring at room temperature overnight, the solvent was evaporated to obtain the title compound.

Yield: 4.4 g (25.5 mmol) (61%)

Step 2

Synthesis of N-t-butoxycarbonyl-3-hydroxybenzamidine 1 g (5.8 mmol) of 3-hydroxybenzamidine hydrochloride, 1.27 g (5.8 mmol) of di-t-butyl dicarbonate, 24 mg (0.2 mmol) of 4-(dimethylamino)pyridine and 1.30 g (12.8 mmol) of triethylamine were dissolved in 20 ml of dimethylformamide, and the solution was stirred at room temperature overnight. After the treatment with ethyl acetate as the extractant in an ordinary manner, the title compound was obtained.

Yield: 458 mg (1.94 mmol) (33%)

H-NMR (DMSO-d6) δ 1.45 (9H, s), 6.95 (1H, d), 7.25 (1H, t), 7.35 (1H, d), 7.38 (1H, s), 8.90 (2H, br), 9.65 (1H, br)

Step 3

Synthesis of N-t-butoxycarbonyl-3-[3-(t-butoxycarbonylamino)propoxy]benzamidine The title compound was obtained from N-t-butoxycarbonyl-3-hydroxybenzamidine and N-(3-bromopropyl)-t-butyl carbamate in the same manner as that of step 2 in Example 1.

H-NMR (CDCl3) δ 1.42 (9H, s), 1.55 (9H, s), 3.52 (2H, dt), 4.05 (2H, t), 4.95 (1H, br), 7.03 (1H, d), 7.33 (1H, t), 7.41 (1H, br), 7.47 (1H, br)

Step 4

Synthesis of 3-(3-aminopropoxy)benzamidine dihydrochloride

The title compound was obtained from 3-[3-(t-butoxycarbonylamino)propoxy]-N-t-butoxycarbonylbenzamidine in the same manner as that of step 3 in Example 1.

H-NMR (DMSO-d6) δ 3.20 (2H, br), 4.30 (2H, br), 7.34 (1H, d), 7.49 (1H, d), 7.51 (1H, s), 7.56 (1H, t), 8.38 (3H, br), 9.29 (2H, br); 9.50 (2H, br).

Step 5

Synthesis of N-[3-(3-amidinophenoxy)propyl]-4-piperidinecarboxamide bistrifluoroacetate 30 mg (0.13 mmol) of (1-t-butoxycarbonyl-4-piperidine) carboxylic acid and 12 mg (0.12 mmol) of N-methylmorpholine were dissolved in 5 ml of dimethylformamide. 13 mg (0.12 mmol) of ethyl chloroformate was added to the solution under cooling with ice. Five minutes after, a solution of 50 mg (0.12 mmol) of 3-[(3-aminopropyl)oxy]benzamidine bistrifluoroacetate and 24 mg (0.24 mmol) of N-methylmorpholine in 5 ml of dimethylformamide was added to the resultant mixture, and they were stirred at room temperature for 4 hours. After the treatment with ethyl acetate as the extractant in an ordinary manner, the crude product was obtained. This product was dissolved in 10 ml of 4 N solution of hydrogen chloride in dioxane, and the solution was stirred at room temperature for 2 hours. The solvent was evaporated, and the residue was treated by the reversed phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 32 mg (0.06 mmol) (50%)

MS (ESI, m/z) 305 (MH+)

H-NMR (DMSO-d6), 1.62-1.95 (6H, m), 2.40 (1H, m), 2.90 (2H, m), 3.20-3.38 (4H, m), 4.10 (2H, t), 7.28 (1H, d), 7.38 (1H, s), 7.39 (1H, d), 7.53 (1H, t), 8.04 (1H, br), 8.46 (1H, br), 8.78 (1H, br), 9.30 (2H, br), 9.42 (2H, br).

Example 125

Synthesis of N-[3-(3-amidinophenoxy)propyl]-4-aminobenzamide bistrifluoroacetate

Step 1

Synthesis of ethyl 4-(t-butoxycarbonylamino)benzoate

The title compound was obtained from ethyl 4-aminobenzoate and di-t-butyl dicarbonate in the same manner as that of step 1 in Example 1.

H-NMR (CDCl3) δ 1.38 (3H, t), 1.55 (9H, s), 4.35 (2H, q), 6.65 (1H, br), 7.42 (2H, d), 7.95 (2H, d)

Step 2

Synthesis of 4-(t-butoxycarbonylamino)benzoic acid

The title compound was obtained from ethyl 4-(t-butoxycarbonylamino)benzoate in the same manner as that of step 2 in Example 97.

Step 3

Synthesis of N-[3-(3-amidinophenoxy)propyl]-4-aminobenzamide bistrifluoroacetate The title compound was obtained from 50 mg (0.126 mmol) of 3-(aminopropoxy)benzamidine bistrifluoroacetate and 30 mg (0.126 mmol) of 4-(t-butoxycarbonylamino)benzoic acid in the same manner as that of step 5 in Example 124.

Yield: 9.5 mg (0.018 mmol) (15%)

MS (ESI, m/z) 313 (MH+)

H-NMR (DMSO-d6) δ 1.95 (2H, tt), 3.35 (2H, dt), 4.10 (2H, t), 6.57 (2H, d), 7.30 (1H, d), 7.36 (1H, s), 7.37 (1H, d), 7.53 (1H, t), 7.58 (2H, d), 8.08 (1H, br), 9.10 (2H, br), 9.30 (2H, br).

Example 126

Synthesis of N-[3-(3-amidinophenoxy)propyl]—4-(aminomethyl)benzamide bistrifluoroacetate The title compound was obtained from 80 mg (0.19 mmol) of 3-(aminopropoxy)benzamidine bistrifluoroacetate and 48 mg (0.19 mmol) of 4-(t-butoxycarbonylamino)methylbenzoic acid in the same manner as that of step 5 in Example 124.

Yield: 25 mg (0.045 mmol) (24%)

MS (ESI, m/z) 327 (MH+)

H-NMR (DMSO-d6) δ 2.00 (2H, tt), 3.40 (2H), 4.02-4.18 (4H, m), 7.29 (1H, d), 7.36-7.40 (2H, m), 7.48-7.54 (3H, m), 7.88 (2H, d), 8.38 (3H, br), 8.60 (1H, br), 9.30 (2H, br), 9.42 (2H, br).

Example 127

Synthesis of N-[3-(3-amidinophenoxy)propyl]-3-amidinobenzamide bistrifluoroacetate Synthesis of ethyl 3-[3-(3-amidinophenoxy)propylcarbamoyl]benzoate trifluoroacetate Step 1

Synthesis of N-[3-(3-cyanophenoxy)propyl]-3-cyanobenzamide

The title compound was obtained from 3-cyanobenzoic acid and 3-(3-aminopropoxy)benzonitrile hydrochloride in the same manner as that of step 4 in Example 1.

Step 2

Synthesis of N-[3-(3-amidinophenoxy)propyl]-3-amidinobenzamide bistrifluoroacetate Synthesis of ethyl 3-[3-(3-amidinophenoxy)propylcarbamoyl]benzoate trifluoroacetate The title compound was obtained from 125 mg (0.41 mmol) of N-[3-(3-cyanophenoxy)propyl]-3-cyanobenzamide in the same manner as that of step 5 in Example 95.

N-[3-(3-Amidinophenoxy)propyl]-3-amidinobenzamide bistrifluoroacetate

Yield: 3 mg (0.005 mmol) (1%)
MS (ESI, m/z) 340 (MH+)
H-NMR (DMSO-d6) δ 2.05 (2H, tt), 3.50 (2H, dt), 4.20 (2H, t), 7.31 (1H, d), 7.38 (1H, s), 7.39 (1H, d), 7.54 (1H, t), 7.72 (1H, t), 7.94 (1H, d), 8.18 (1H, d), 8.26 (1H, s), 8.75 (1H, br), 9.11 (2H, br), 9.21 (2H, br), 9.27 (2H, br), 9.38 (2H, br).

Ethyl 3-[3-(3-amidinophenoxy)propylcarbamoyl]benzoate trifluoroacetate

MS (ESI, m/z) 370 (MH+)
H-NMR (DMSO-d6) δ 1.35 (3H, t), 2.05 (2H, tt), 3.50 (2H, dt), 4.15 (2H, t), 4.35 (2H, q), 7.32 (1H, d), 7.38 (1H, s), 7.39 (1H, d), 7.54 (1H, t), 7.63 (1H, t), 8.09 (1H, d), 8.13 (1H, d), 8.44 (1H, s), 8.78 (1H, br), 9.15 (2H, br), 9.28 (2H, br).

Example 128

Synthesis of 3-[3-(2-naphthalenesulfonylamino)propoxy]benzamidine trifluoroacetate Step 1

Synthesis of 3-[3-(2-naphthalenesulfonylamino)propoxy]benzonitrile

The title compound was obtained from 2-naphthalenesulfonyl chloride and 3-(3-aminopropoxy)benzonitrile in the same manner as that of step 1 in Example 110.

H-NMR (CDCl3) δ 2.00 (2H, tt), 3.25 (2H, dt), 3.95 (2H, t), 4.80 (1H, br), 6.95 (1H, s), 7.00 (1H, d), 7.20 (1H, d), 7.30 (1H, t), 7.55-7.70 (2H, m), 7.80-8.00 (4H, m), 8.42 (1H, s)

Step 2

Synthesis of 3-[3-(2-naphthalenesulfonylamino)propoxy]benzamidine trifluoroacetate The title compound was obtained from 300 mg (0.82 mmol) of 3-[3-(2-naphthalenesulfonylamino)propoxy]benzonitrile in the same manner as that of step 5 in Example 95.

Yield: 169 mg (0.34 mmol) (41%)
MS (FAB, m/z) 384 (MH+)
H-NMR (DMSO-d6) δ 1.85 (2H, tt), 3.00 (2H, dt), 4.00 (2H, t), 7.17 (1H, d), 7.25 (1H, s), 7.35 (1H, d), 7.45 (1H, t), 7.62-8.16 (7H, m), 8.43 (1H, s), 9.18 (2H, br), 9.24 (2H, br).

Example 129

Synthesis of N-[3-(3-amidinophenoxy)propyl]-(2R)-2-(benzyloxycarbonylamino)propionamide trifluoroacetate 30 mg (0.11 mmol) of 3-(aminopropoxy)benzamidine dihydrochloride, 25.8 mg (0.135 mmol) of N-benzyloxycarbonyl-D-alanine, 23.0 mg (0.17 mmol) of 1-hydroxybenzotriazole, 25.9 mg (0.135 mmol) of 1-ethyl-3-(3-dimethylaminopropyl)carbodiimide hydrochloride and 23 mg (0.23 mmol) of N-methylmorpholine were dissolved in 2 ml of dimethylformamide, and the solution was stirred overnight. After the treatment with ethyl acetate as the extractant in an ordinary manner, the crude product was obtained. The residue was treated by the reversed phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 5 mg (0.01 mmol) (7%)
MS (ESI, m/z) 399 (MH+)
H-NMR (DMSO-d6) δ 1.20 (3H d), 1.90 (2H, tt), 3.25 (2H, dt), 3.92-4.10 (3H, m), 5.00 (2H, m), 7.26-7.44 (8H, m), 7.53 (1H, t), 7.97 (1H, br), 9.10 (2H, br), 9.30 (2H, br).

Example 130

Synthesis of N-[3-(3-amidinophenoxy)propyl]-(2S)-2-(benzyloxycarbonylamino)propionamide trifluoroacetate The title compound was obtained from 30 mg (0.11 mmol) of 3-(aminopropoxy)benzamidine dihydrochloride and 26 mg (0.135 mmol) of N-benzyloxycarbonyl-L-alanine in the same manner as that of step 5 in Example 124.

Yield: 17 mg (0.03 mmol) (22%)
MS (ESI, m/z) 399 (MH+)
H-NMR (DMSO-d6) δ 1.20 (3H, d), 1.90 (2H, tt), 3.25 (2H, dt), 3.92-4.10 (3H, m), 5.00 (2H, m), 7.26-7.44 (8H, m), 7.53 (1H, t), 7.97 (1H, br), 9.10 (2H, br), 9.30 (2H, br).

Example 131

Synthesis of (4S)-4-[3-(3-amidinophenoxy)propyl]
carbamoyl-4-(benzyloxycarbonylamino)butanoic
acid trifluoroacetate t-Butyl ester of the title compound was obtained from 30 mg (0.11 mmol) of 3-(aminopropoxy)benzamidine dihydrochloride and 46 mg (0.135 mmol) of γ-t-butyl N-benzyloxycarbonyl-L-glutamate in the same manner as that of step 1 in Example 129. This compound was dissolved in 4 N solution of hydrogen chloride in dioxane, and the solution was stirred for 5 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 12 mg (0.02 mmol) (15%)
MS (ESI, m/z) 457 (MH+)
H-NMR (DMSO-d6) δ 1.70-1.95 (4H, m), 2.25 (2H, t), 3.23 (2H, dt), 3.85-4.05 (3H, m), 4.95-5.05 (2H, m), 7.27-7.38 (7H, m), 7.44 (1H, d), 7.52 (1H, t), 8.02 (1H, t), 9.00 (2H, br), 9.30 (2H, br).

Example 132

Synthesis of N-[3-(3-amidinophenoxy)propyl]-(2S)-
2-(t-butoxycarbonylamino)-3-(4-imidazolyl)pro-
panamide bistrifluoroacetate

Step 1

Synthesis of N-[3-(3-amidinophenoxy)propyl]-(2S)-
2-(t-butoxycarbonylamino)-3-[1-(4-toluenesulfonyl)-
4-imidazolyl]propanamide bistrifluoroacetate The title compound was obtained from 3-(aminopropoxy)benzamidine dihydrochloride and (2S)-2-(t-butoxycarbonylamino)-3-[1-(4-toluenesulfonyl)-4-imidazolyl]propionic acid in the same manner as that of step 5 in Example 124.

Step 2

Synthesis of N-[3-(3-amidinophenoxy)propyl]-(2S)-
2-(t-butoxycarbonylamino)-3-(4-imidazolyl)pro-
panamide bistrifluoroacetate 40 mg (0.05 mmol) of N-[3-(3-amidinophenoxy)propyl]-(2S)-2-(t-butoxycarbonylamino)-3-[1-(4-toluenesulfonyl)-4-imidazolyl]propanamide bistrifluoroacetate and 13.5 mg (0.1 mmol) of 1-hydroxybenztriazole were dissolved in 2 ml of tetrahydrofuran, and the solution was stirred at room temperature overnight. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 23 mg (0.035 mmol) (70%)
MS (ESI, m/z) 431 (MH+)
H-NMR (DMSO-d6) δ 1.35 (9H, s), 1.85 (2H, tt), 2.80-3.10 (2H, m), 3.25 (2H, dt), 4.05 (2H, t), 4.20 (1H, m), 7.11 (1H, d), 7.26-7.40 (4H, m), 7.53 (1H, t), 8.03 (1H, br), 8.95 (1H, s), 9.15 (2H, br), 9.25 (2H, br).

Example 133

Synthesis of N-[3-(3-amidinophenoxy)propyl]-(2S)-
2-(benzyloxycarbonylamino)-3-(4-imidazolyl)pro-
panamide bistrifluoroacetate

Step 1

Synthesis of (2S)-2-amino-3-[1-(4-toluenesulfonyl)-
4-imidazolyl]propionic acid bistrifluoroacetate 5 g of (2S)-2-(t-butoxycarbonylamino)-3-[1-(4-toluenesulfonyl)-4-imidazolyl]propionic acid was stirred in trifluoroacetic acid at room temperature for 2 hours. The solvent was evaporated, and the residue was suspended in dichloromethane. After the filtration followed by the vacuum-drying, the title compound was obtained.

Yield: 6.00 g
H-NMR (DMSO-d6) δ 2.40 (3H, s), 3.00 (2H, m), 4.18 (1H, brs), 7.48-7.56 (3H, m), 7.96 (2H, d), 8.20 (3H, brs), 8.36 (1H, d)

Step 2

Synthesis of (2S)-2-(benzyloxycarbonylamino)-3-[1-
(4-toluenesulfonyl)-4-imidazolyl]propionic acid 1 g (2.4 mmol) of (2S)-2-amino-3-[1-(4-toluenesulfonyl)-4-imidazolyl]propionic acid bistrifluoroacetate and 840 mg (10 mmol) of sodium hydrogencarbonate were dissolved in 30 ml of water. A solution of 2.4 ml (15 mmol) of benzyl chloroformate in 30 ml of ether was added to the obtained solution, and they were stirred at room temperature for 4 hours. A saturated aqueous sodium hydrogencarbonate solution was added to the resultant mixture, and the aqueous layer was washed with ether. Then, the aqueous layer was acidified with hydrochloric acid. After the same isolation process as that of step 1 in Example 1 with ethyl acetate as the extractant, the title compound was obtained.

Yield: 628 mg
H-NMR (DMSO-d6) δ 2.30 (3H, s), 2.90-3.20 (2H, m), 4.35 (1H, brs), 5.00-5.10 (3H, m), 7.12 (2H, d), 7.27-7.40 (7H, m), 7.49 (2H, d)

Step 3

Synthesis of N-[3-(3-amidinophenoxy)propyl]-(2S)-
2-(benzyloxycarbonylamino)-3-(4-imidazolyl)pro-
panamide bistrifluoroacetate The title compound was obtained from (2S)-2-(benzyloxycarbonylamino)-3-[1-(4-toluenesulfonyl)-4-imidazolyl]propionic acid and 3-(aminopropoxy)benzamidine dihydrochloride in the same manner as that of step 5 in Example 124.

MS (ESI, m/z) 465 (MH+)
H-NMR (DMSO-d6) δ1.90 (2H, tt), 2.85-3.15 (2H, m), 3.25 (2H, dt), 4.05 (2H, t), 4.30 (1H, m), 4.95-5.05 (2H, m), 7.24-7.40 (9H, m), 7.53 (1H, t), 8.50 (1H, br), 8.96: (1H, s), 9.17 (2H, brs), 9.28 (2H, brs).

Example 134

Synthesis of N-[3-(3-amidinophenoxy)propyl]-(2S, 3S)-2-(benzyloxycarbonylamino)-3-methylpentanamide trifluoroacetate The title compound was obtained from 70 mg (0.28 mmol) of 3-(aminopropoxy)benzamidine dihydrochloride and 70 mg (0.26 mmol) of N-benzyloxycarbonyl-L-isoleucine in the same manner as that of step 5 in Example 124.
Yield: 33 mg (0.06 mmol) (23%)
MS (ESI, m/z) 441 (MH+)
H-NMR (DMSO-d6) δ 0.78-0.83 (6H, m), 1.10 (1H, m), 1.40 (1H, m), 1.70 (1H, m), 1.90 (2H, m), 3.22 (2H, m), 3.80 (1H, t), 4.05 (2H, t), 5.00 (2H, m), 7.22-7.40 (8H, m), 7.55 (1H, t), 8.05 (1H, br), 9.03 (2H, br), 9.30 (2H, br).

Example 135

Synthesis of N-[3-(3-amidinophenoxy)propyl]-(2S)-2-(benzyloxycarbonylamino)-6-aminohexanamide bistrifluoroacetate t-Butyl carbamate of the title compound was obtained from 70 mg (0.28 mmol) of 3-(aminopropoxy)benzamidine dihydrochloride and 99 mg (0.26 mmol) of N-α-benzyloxycarbonyl-N-ε-t-butoxycarbonyl-L-lysine in the same manner as that of step 5 in Example 124. This compound was then dissolved in 4 N solution of hydrogen chloride in dioxane, and the obtained solution was stirred for 5 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 70 mg (0.1 mmol) (38%)
MS (ESI, m/z) 456 (MH+)
H-NMR (DMSO-d6) δ 1.30 (2H, m), 1.43-1.61 (4H, m), 1.90 (2H, m), 2.75 (2H, m), 3.23 (2H, m), 3.90 (1H, m), 4.05 (2H, t), 5.01 (2H), 7.26-7.41 (8H, m), 7.53 (1H, t), 7.69 (3H, br), 8.23 (1H, br), 9.15 (2H, br), 9.30 (2H, br).

Example 136

Synthesis of N-[3-(3-amidinophenoxy)propyl]-(2S)-2-(benzyloxycarbonylamino)-3-phenylpropanamide trifluoroacetate The title compound was obtained from 30 mg (0.11 mmol) of 3-(aminopropoxy)benzamidine dihydrochloride and 40 mg (0.135 mmol) of N-benzyloxycarbonyl-L-phenylalanine in the same manner as that of step 5 in Example 124.
Yield: 7 mg (0.012 mmol) (9%)
MS (ESI, m/z) 475 (MH+)
H-NMR (DMSO-d6) δ 1.82 (2H), 2.70-3.00 (2H, m), 3.23 (2H, m), 4.00 (2H, t), 4.20 (1H, m), 4.90-5.00 (4H, m), 7.17-7.40 (2H, m), 7.50-7.60 (2H), 8.10 (1H, br), 9.10 (2H, br), 9.30 (2H, br).

Example 137

Synthesis of N-[3-(3-amidinophenoxy)propyl]-(2R)-2-(benzyloxycarbonylamino)-3-phenylpropanamide trifluoroacetate The title compound was obtained from 70 mg (0.28 mmol) of 3-(aminopropoxy)benzamidine dihydrochloride and 78 mg (0.26 mmol) of N-benzyloxycarbonyl-D-phenylalanine in the same manner as that of step 5 in Example 124.
Yield: 14.1 mg (0.024 mmol) (9%)
MS (ESI, m/z) 475 (MH+)
H-NMR (DMSO-d6) δ 1.82 (2H), 2.70-3.00 (2H, m), 3.23 (2H, m), 4.00 (2H, t), 4.20 (1H, m), 4.90-5.00 (4H, m), 7.17-7.40 (2H, m), 7.50-7.60 (2H), 8.10 (1H, br), 9.05 (2H, br), 9.30 (2H, br).

Example 138

Synthesis of N-[3-(3-amidinophenoxy)propyl]-(2S)-2-aminopropanamide bistrifluoroacetate 11 mg (0.02 mmol) of N-[3-(3-amidinophenoxy)propyl]-(2S)-2-(benzyloxycarbonylamino)propanamide trifluoroacetate was dissolved in 1 ml of ethanol. 1 mg of 10% palladium/carbon was added to the solution, and they were stirred at room temperature in 1 atm. hydrogen atmosphere for 5 hours. Palladium/carbon was removed by the suction filtration. Water containing 0.1% (v/v) of trifluoroacetic acid was added to the filtrate, and the resultant mixture was concentrated to obtain the title compound.
Yield: 7 mg (0.014 mmol) (70%)
MS (ESI, m/z) 349 (MH++DMSO-d6)
H-NMR (DMSO-d6) δ 1.35 (3H, d), 1.90 (2H, tt), 3.30 (2H, dt), 3.80 (1H, br), 4.10 (2H, t), 7.30 (1H, d), 7.37 (1H, s), 7.39 (1H, d), 7.54 (1H, t), 8.12 (3H, br), 8.52 (1H, br), 9.31 (2H, br), 9.37 (2H, br).

Example 139

Synthesis of N-[3-(3-amidinophenoxy)]propyl]-(2S)-amino-3-(4-imidazolyl)propanamide tristrifluoroacetate 10 mg of N-[3-(3-amidinophenoxy)propyl]-(2S)-2-(t-butoxycarbonylamino)-3-(4-imidazolyl)propanamide bistrifluoroacetate was dissolved in 4 N solution of hydrogen chloride in dioxane, and they were stirred for 2 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 7 mg (0.010 mmol) (67%)
MS (ESI, m/z) 331 (MH+)
H-NMR (DMSO-d6) δ 1.85 (2H, m), 3.15 (2H, m), 3.30 (2H, dt), 4.02-4.12 (3H, m), 7.28 (1H, d), 7.34-7.42 (3H, m), 7.54 (1H, t), 8.40 (3H, br), 8.60 (1H, br), 8.85 (1H, s), 9.30 (4H, br).

Example 140

Synthesis of N-[3-(3-amidinophenoxy)propyl]-(2S, 3S)-2-amino-3-methylpentanamide bistrifluoroacetate The title compound was obtained from 28 mg (0.050 mmol) of N-[3-(3-amidinophenoxy)propyl]-(2S,3S)-2-(benzyloxycarbonylamino)-3-methylpentaneamide trifluoroacetate in the same manner as that of Example 138.
Yield: 25 mg (0.047 mmol) (94%)
MS (ESI, m/z) 307 (MH+)

H-NMR (DMSO-d6) δ 0.80-0.90 (6H, m), 1.05 (1H, m), 1.43 (1H, m), 1.80 (1H, m), 1.95 (2H, m), 3.20-3.40 (2H, m), 3.55 (1H, br), 4.10 (2H, t), 7.29 (2H, d), 7.37 (1H, s), 7.39 (1H, d), 7.55 (1H, t), 8.13 (3H, br), 8.55 (1H, br), 9.28 (2H, br), 9.32 (2H, br).

Example 141

Synthesis of N-[3-(3-amidinophenoxy)propyl]-(2S)-2,6-diaminohexanamide tristrifluoroacetate The title compound was obtained from 20 mg (0.03 mmol) of N-[3-(amidinophenoxy)propyl]-(2S)-(benzyloxycarbonylamino)-6-aminohexanamide in the same manner as that of Example 138.

Yield: 17 mg (0.026 mmol) (87%)
MS (ESI, m/z) 322 (MH+)
H-NMR (DMSO-d6) δ 1.35 (2H, m), 1.55 (2H, m), 1.70 (2H, m), 1.90 (2H, tt), 2.75 (2H, br), 3.30 (2H, dt), 3.60-3.90 (1H), 4.10 (2H, t), 7.28 (2H, d), 7.38 (2H, s), 7.40 (2H, d), 7.54 (1H, t), 7.90 (3H, br), 8.24 (3H, br), 8.66 (1H, br), 9.34 (2H, br), 9.53 (2H, br).

Example 142

Synthesis of N-[3-(3-amidinophenoxy)propyl]-(2R)-2-amino-3-phenylpropanamide bistrifluoroacetate The title compound was obtained from 10 mg (0.017 mmol) of N-[3-(amidinophenoxy)propyl]-(2R)-2-(benzyloxycarbonylamino)-3-phenylpropanamide in the same manner as that of Example 138.

Yield: 8 mg (0.014 mmol) (82%)
MS (ESI, m/z) 349 (MH+)
H-NMR (DMSO-d6) δ 1.75 (2H, m), 3.00 (2H, d), 3.05-3.35 (2H, m), 3.85-4.00 (3H, m), 7.20-7.34 (7H, m), 7.40 (1H, d), 7.54 (1H, t), 8.28 (3H, br), 8.50 (1H, br), 9.31 (2H, br), 9.38 (2H, br).

Example 143

Synthesis of N-[2-(3-amidinophenylthio)ethyl]-4-amidinobenzamide bistrifluoroacetate Step 1

Synthesis of benzyl-N-(2-bromoethyl)carbamate 10 g (49 mmol) of 2-bromoethylamine bromate and 15 ml of triethylamine were dissolved in dichloromethane. 7.8 ml (49 mmol) of benzyl chloroformate was added to the solution under cooling with ice, and they were stirred at room temperature. After the treatment with dichloromethane as the extractant in an ordinary manner, the crude product was obtained. The crude product was purified by the silica gel column chromatography to obtain the title compound.

Yield: 10.6 g (41 mmol) (84%)
H-NMR (CDCl3) δ 3.45 (2H, t), 3.60 (2H, dt), 5.10 (2H, s), 5.20 (1H, brs), 7.30-7.38 (5H, m)

Step 2

Synthesis of 3-mercaptobenzonitrile 2 g (17 mmol) of 3-aminobenzonitrile was suspended in 6 N aqueous hydrogen chloride solution. A solution obtained by dissolving 1.17 g (17 mmol) of sodium nitrite in cold water and kept at 4° C. or below was added to the obtained suspension. The resultant reaction liquid was poured into an aqueous solution of 3.04 g (19 mmol) of potassium O-ethyldithiocarbonate; which was heated at 45° C., and they were stirred at 45° C. for 2 hours. After the treatment with ethyl acetate as the extractant in an ordinary manner, the crude product was obtained. This product was purified by the silica gel column chromatography to obtain O-ethyl-S-(3-cyanohenyl) dithiocarbonate.

This product was dissolved in ethanol in argon atmosphere, and the solution was heated under reflux. 500 mg of potassium hydroxide was added to the solution, and they were heated again under reflux for 4 hours. The solvent was evaporated, and the residue was treated with ethyl acetate as the extractant in an ordinary manner to obtain the title compound.

Yield: 446 mg (3.30 mmol) (19%).
H-NMR (DMSO-d6) δ 3.60 (1H, s), 7.33 (1H, t), 7.44 (1H, d), 7.49 (1H, d), 7.54 (1H, s).

Step 3

Synthesis of 3-[2-(benzyloxycarbonylamino)ethylthio]benzonitrile 440 mg (3.3 mmol) of 3-mercaptobenzonitrile, 460 mg (3.3 mmol) of potassium carbonate, 1.0 g (4 mmol) of N-benzyl-(2-bromoethyl) carbamate and 160 mg (0.5 mmol) of tetrabutylammonium bromide were dissolved in dimethylformamide, and the solution was stirred at room temperature in argon atmosphere for 4 hours. The solvent was evaporated, and the residue was treated with ethyl acetate as the extractant in an ordinary manner to obtain the crude product, which was then purified by the silica gel column chromatography to obtain the title compound.

Yield: 414 mg (1.3 mmol) (39%)
H-NMR (CDCl3) δ 3.10 (2H, t), 3.40 (2H, dt), 5.10 (3H, brs), 7.31-7.40 (6H, m), 7.45 (1H, d), 7.57 (1H, brd), 7.59 (1H, brs)

Step 4

Synthesis of (2-aminoethylthio)benzonitrile hydrochloride 400 mg (1.26 mmol) of 3-[2-(benzyloxycarbonylamino)ethylthio]benzonitrile was dissolved in acetic acid containing 20% of hydrogen bromide. The solution was stirred at room temperature for 2 hours. The solvent was evaporated and the residue was dissolved in 1 N hydrogen chloride. The solution was washed with ethyl acetate, and then made alkaline with 1 N aqueous sodium hydroxide solution. After the treatment with ethyl acetate as the extractant in an ordinary manner, the title compound was obtained.

Yield: 190 mg (1.1 mmol) (84%)
H-NMR (CDCl3) δ 2.95 (2H, t), 3.05 (2H, t), 7.38 (1H, t), 7.45 (1H, d), 7.55 (1H, d), 7.59 (1H, s).

Step 5

Synthesis of N-[2-(3-cyanophenylthio)ethyl]-4-cyanobenzamide

The title compound was obtained from 190 mg (1.1 mmol) of (2-aminoethylthio)benzonitrile and 177 mg (1.2 mmol) of 4-cyanobenzoic acid in the same manner as that of step 4 in Example 1.

Yield: 223 mg (0.73 mmol) (66%)

H-NMR (CDCl3) δ 3.25 (2H, t), 3.70 (2H, dt), 6.50 (1H, brt), 7.40 (1H, t), 7.43 (1H, d), 7.61 (1H, d), 7.64 (1H, s), 7.75 (2H, d), 7.83 (2H, d)

Step 6

Synthesis of
N-[2-(3-cyanophenylthio)ethyl]-4-amidinobenzamide

The title compound was obtained from 210 mg (0.68 mmol) of N-[2-(3-cyanophenylthio)ethyl]-4-cyanobenzamide in the same manner as that of step 5 in Example 95.
Yield: 137 mg (0.24 mmol) (35%)
MS (ESI, m/z) 342 (MH+)
H-NMR (DMSO-d6) δ 3.30 (2H, t), 3.55 (2H, m), 7.57 (1H, t), 7.60 (1H, d), 7.75 (1H, d), 7.80 (1H, s), 7.91 (2H, d), 8.02 (2H, d), 9.03 (1H, brt), 9.26 (2H, brs), 9.31 (4H, brs), 9.41 (2H, brs).

Example 144

Synthesis of
N-[3-(3-amidinophenyl)propyl]-4-amidinobenzamide
bistrifluoroacetate Step 1

Synthesis of 3-(3-bromopropyl)benzonitrile 1.5 g (8.56 mmol) of 3-(3-cyanophenyl)propionic acid and 1.19 ml (8.56 mmol) of triethylamine were dissolved in 42 ml of tetrahydrofuran. 0.819 ml (8.56 mmol) of ethyl chloroformate was added to the solution under cooling with ice, and they were stirred for 20 minutes. Precipitates thus formed were removed by the suction filtration. 3 g of ice and 0.648 g (17.12 mmol) of sodium borohydride were added to the filtrate under cooling with ice, and they were stirred for 1 hour. 20 ml of 1 N aqueous hydrogen chloride solution was added to the reaction mixture, and they were stirred at room temperature for one hour. After the treatment with ethyl acetate as the extractant in an ordinary manner, an oily residue was obtained, which was dissolved in 86 ml of dichloromethane. 5.68 g (17.12 mmol) of carbon tetrabromide and 2.69 g (10.27 mmol) of triphenylphosphine were added to the solution, and they were stirred at room temperature for one hour. The reaction mixture was treated with ethyl acetate as the extractant in an ordinary manner to obtain the crude compound, which was purified by the silica gel column chromatography to obtain the title compound.
Yield: 1.48 g (6.59 mmol) (77%).

Step 2

Synthesis of
N-[3-(3-cyanophenyl)propyl]-4-cyanobenzamide 267 mg (7.23 mmol) of sodium hydride (65%) was dissolved in 8 ml of DMF in argon atmosphere. 1.43 g (6.57 mmol) of di-t-butyl iminodicarboxylate was added to the solution, and they were stirred at room temperature for 30 minutes. 1.47 g (6.57 mmol) of 3-(3-bromopropyl)benzonitrile was added to the resultant mixture. They were stirred at 45° C. for 3 hours. After the treatment with ethyl acetate as the extractant in an ordinary manner, an oily residue was obtained. This residue was dissolved in 4 N solution of hydrogen chloride in dioxane, and the solution was stirred at room temperature for 4 hours. The solvent was evaporated, and the oily residue was dissolved in 10 ml of dichloromethane. 1.63 g (9.86 mmol) of 4-cyanobenzoyl-chloride and 1.83 ml (13.4 mmol) of triethylamine were added to the solution, and they were stirred at room temperature for 5 hours. After the treatment with ethyl acetate as the extractant in an ordinary manner, the crude product was obtained, which was purified by the silica gel column chromatography to obtain the title compound.
Yield: 1.35 g (4.66 mmol) (71%).
H-NMR (CDCl3) δ 1.98 (2H, quint), 2.76 (2H, t), 3.50 (2H, dt), 6.94 (1H, br), 7.36-7.50 (4H, m), 7.69 (2H, d), 7.89 (2H, d)

Step 3

Synthesis of
N-[3-(3-amidinophenyl)propyl]-4-amidinobenzamide
bistrifluoroacetate 800 mg (2.76 mmol) of N-[3-(3-cyanophenyl)propyl]-4-cyanobenzamide was added to 8 ml of ethanol containing 30% (w/v) of hydrogen chloride, and they were stirred at room temperature overnight. The reaction mixture was dissolved in 30 ml of 10% (w/v) solution of ammonia in ethanol at room temperature, and the solution was stirred at room temperature overnight. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 130 mg (0.236 mmol) (8.5%)
MS (ESI, m/z) 324 (MH+)
H-NMR (DMSO-d6) δ 1.91 (2H, quint), 2.75 (2H, t), 3.34 (2H, dt), 7.50-7.70 (4H, m), 7.89 (2H, d), 8.03 (2H, d), 8.79 (1H, t), 9.14 (2H, s), 9.27 (4H, s), 9.40 (2H, s).

Example 145

Synthesis of N-[(2E)-3-(3-amidinophenyl)-2-propenyl]-4-amidinobenzamide bistrifluoroacetate Step 1

Synthesis of
3-[(1E)-3-bromo-1-propenyl]benzonitrile

The title compound was obtained from 2.5 g (14.4 mmol) of (3E)-3-(3-cyanophenyl)acrylic acid in the same manner as that of the synthesis of 3-(3-bromopropyl)benzonitrile.
Yield 95%

Step 2

Synthesis of N-[(2E)-3-(3-cyanophenyl)-2-propenyl]-4-cyanobenzamide

The title compound was obtained from 3.65 g (16.44 mmol) of 3-[(1E)-3-bromo-1-propenyl]benzonitrile in the same manner as that of the synthesis of N-[3-(3-cyanophenyl)propyl]-4-cyanobenzamide.
Yield: 3.02 g (10.52 mmol) (64%)
H-NMR (CDCl3) δ 4.27 (1H, dd), 6.35 (1H, dt), 6.56 (1H, d), 7.16 (1H, br), 7.37-7.59 (4H, m), 7.72 (2H, d), 7.96 (2H, d)

Step 3

Synthesis of N-[(2E)-3-(3-amidinophenyl)-2-propenyl]-4-amidinobenzamide bistrifluoroacetate The title compound was obtained from 780 mg (2.71 mmol) of N-[(2E)-3-(3-cyanophenyl)-2-propenyl]-4-cyanobenzamide in the same manner as that of the synthesis of N-[3-(3-amidinophenyl)propyl]-4-amidinobenzamide.
Yield: 33 mg (0.06 mmol) (2.2%)
MS (ESI, m/z) 322 (MH+)
H-NMR (DMSO-d6) δ 4.15 (2H, t), 6.55 (1H, dt), 6.65 (1H, d), 7.58 (1H, dd), 7.68 (1H, d), 7.79 (1H, d), 7.89 (1H, s), 7.92 (2H, d), 8.10 (2H, d), 9.10 (1H, t), 9.21 (2H, s), 9.32 (4H, s), 9.41 (2H, s).

Example 146

Synthesis of N-[2-(5-amidino-2-iodophenoxy)ethyl]-4-amidinobenzamide bistrifluoroacetate

Step 1

Synthesis of 3-hydroxy-4-iodobenzoic acid 30.0 g (217 mmol) of 3-hydroxybenzoic acid was dissolved in 200 ml of acetic acid. 53.0 g (326 mmol) of iodine monochloride was added to the solution at room temperature. After stirring at 45° C. for 15 hours, the solvent was evaporated under reduced pressure. The residue was washed with 500 ml of 1% aqueous sodium thiosulfate solution twice and then with 500 ml of water twice, and dried to solid at 80° C. under reduced pressure to obtain the title compound.
Yield: 17.2 g (65.2 mmol) (30%)
MS (FAB, m/z) 265 (MH+)
H-NMR (DMSO-d6) δ 7.13 (1H, dd), 7.43 (1H, d), 7.80 (1H, d)

Step 2

Synthesis of 3-hydroxy-4-iodobenzonitrile 19.7 ml (206 mmol) of ethyl chloroformate and 28.7 ml (206 mmol) of triethylamine were added to a solution of 22.3 g (89.7 mmol) of 3-hydroxy-4-iodobenzoic acid in 300 ml of tetrahydrofuran at 0° C. After stirring for 15 minutes, triethylamine hydrochloride thus formed was removed by the filtration. The filtrate was added to 300 ml of a solution, obtained by bubbling ammonia in tetrahydrofuran, at 0° C. After stirring at room temperature for 10 hours, the solvent was evaporated under reduced pressure. The residue was dissolved in 450 ml of dioxane, and then 17.4 ml (117 mmol) of anhydrous trifluoromethanesulfonic acid and 21.8 ml (269 mmol) of pyridine were added to the solution at 0° C. After stirring at room temperature for 18 hours, the solvent was evaporated under reduced pressure. The residue was treated with chloroform as the extractant in an ordinary manner to obtain the oily residue, which was dissolved in 180 ml of tetrahydrofuran/methanol (1/1). 90 ml (90.0 mmol) of 1 N aqueous sodium hydroxide solution was added to the solution at room temperature. After stirring for 4 hours, the solvent was evaporated under reduced pressure. The residue was washed with dichloromethane and then acidified with 1 N hydrogen chloride. After the treatment with ethyl acetate as the extractant in an ordinary manner, the crude product was obtained. The crude product was purified by the silica gel column chromatography to obtain the title compound.

Yield: 9.29 g (37.9 mmol) (42%)
H-NMR (CDCl3) δ 5.63 (1H, br), 6.96 (1H, dd), 7.23 (1H, d), 7.79 (1H, d)

Step 3

Synthesis of 3-(2-aminoethoxy)-4-iodobenzonitrile

The title compound was obtained from 7.44 g (30.4 mmol) of 3-hydroxy-4-iodobenzonitrile and 6.52 g (36.4 mmol) of N-t-butyl-2-chloroethyl carbamate in the same manner as that of steps 2 and 3 in Example 1.
Yield: 4.90 g (17.0 mmol) (56%)
MS (ESI, m/z) 289 (MH+)
H-NMR (DMSO-d6) δ 2.90 (2H, t), 4.06 (2H, t), 7.18 (1H, dd), 7.45 (1H, d), 7.99 (1H, d)

Step 4

Synthesis of N-[2-(5-cyano-2-iodophenoxy)ethyl]-4-cyanobenzamide

The title compound was obtained from 800 mg (2.47 mmol) of 3-(2-aminoethoxy)-4-iodobenzonitrile and 436 mg (2.96 mmol) of 4-cyanobenzoic acid in the same manner as that of step 4 in Example 1.
Yield: 940 mg (2.25 mmol) (91%).
MS (ESI, m/z) 418 (MH+)
H-NMR (CDCl3) δ 2.90 (2H, t), 4.06 (2H, t), 7.18 (1H, dd), 7.45 (1H, d), 7.99 (1H, d).

Step 5

Synthesis of N-[2-(5-amidino-2-iodophenoxy)ethyl]-4-amidinobenzamide bistrifluoroacetate The title compound was obtained from 200 mg (0.48 mmol) of N-[2-(5-cyano-2-iodophenoxy)ethyl]-4-cyanobenzamide in the same manner as that of step 5 in Example 95.
Yield: 93 mg (0.14 mmol) (29%)
MS (ESI, m/z) 452 (MH+)
H-NMR (DMSO-d6) δ 3.74 (2H, dt), 4.33 (2H, t), 7.18 (1H, d), 7.41 (1H, s), 7.90 (2H, d), 8.03 (1H, d), 8.06 (2H, d), 8.96 (1H, t), 9.10 (2H, br), 9.16 (2H, br), 9.33 (2H, br), 9.40 (2H, br).

Example 147

Synthesis of 3-[4-amidino-2-[2-(4-amidinophenylcarbamoyl)ethoxy]phenyl]-2-oxopropionic acid bistrifluoroacetate 50 mg (0.074 mmol) of N-[2-(5-amidino-2-iodophenoxy)ethyl]-4-amidinobenzamide bistrifluoroacetate was dissolved in 0.5 ml of DMF. 35 mg (0.16 mmol) of di-t-butyl dicarbonate and 0.05 mol (0.37 mmol) of triethylamine were added to the solution at 0° C., and they were stirred for 4 hours. After the treatment with ethyl acetate as the extractant in an ordinary manner, the crude product was obtained. This product was purified by the silica gel column chromatography. This purified product was dissolved in 0.8 ml of acetonitrile. 27 mg (0.19 mmol) of methyl 2-acetamide acrylate, 2 mg (0.0095 mmol) of palladium acetate, 5.8 mg (0.019 mmol) of tris(2-methylphenyl)phosphine and 0.06 ml (0.22 mmol) of tributylamine were added to the solution at room temperature. They were stirred at 90° C. in argon atmosphere for 21 hours. After the filtration by suction, the filtrate was evaporated under reduced pressure. 5 ml of 3 N aqueous hydrogen chloride solution was added to the residue at room temperature, and they were stirred at 60° C. for 30 minutes and then at 110° C. for 30 minutes. The solvent was evaporated, and the residue was treated by the reversed phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 4.6 mg (0.0072 mmol) (9.7%)
MS (FAB, m/z) 412 (MH+)
H-NMR (DMSO-d6) δ 3.72 (2H, dt), 4.15 (2H, s, keto form), 4.31 (2H, t), 6.81 (1H, s, enol form), 7.36-7.48 (2H, m), 7.88 (2H, d), 8.04 (2H, d), 8.33 (1H, d), 9.02 (1H, t), 9.07 (2H, m), 9.25 (4H, br), 9.40 (2H, br).

Example 148

Synthesis of: N-[2-(5-amidino-2-methylphenoxy)ethyl]-4-amidinobenzamide bistrifluoroacetate Step 1

Synthesis of 3-hydroxy-4-methylbenzonitrile 29.8 g (196 mmol) of 3-hydroxy-4-methylbenzoic acid was dissolved in 450 ml of tetrahydrofuran. 43.1 ml (450 mmol) of ethyl chloroformate and 62.7 ml (450 mmol) of triethylamine were added to the solution at 0° C. After stirring for 20 minutes, triethylamine hydrochloride thus formed was removed by the filtration. The filtrate was added to 300 ml of a solution obtained by bubbling ammonia in tetrahydrofuran at 0° C. After stirring at room temperature for 2 hours, the solvent was evaporated under reduced pressure. The residue was dissolved in 500 ml of dioxane. 38.8 ml (274 mmol) of trifluoromethanesulfonic anhydride and 75 ml (931 mmol) of pyridine were added to the solution at 0° C. After stirring at room temperature for 18 hours, the solvent was evaporated under reduced pressure. The residue was isolated with chloroform as the extractant in the same manner as that of step 1 in Example 1 to obtain an oily residue, which was dissolved in 330 ml of tetrahydrofuran/methanol (1/1). 165 ml (167 mmol) of 1 N aqueous sodium hydroxide solution was added to the solution at room temperature. They were stirred for 4 hours. The solvent was evaporated under reduced pressure. The residue was washed with dichloromethane and then made acidic with 1 N aqueous hydrogen chloride solution. Then the crude product was separated with ethyl acetate as the extractant in the same manner as that of step 1 in Example 1 to obtain the crude product, which was purified by the silica gel column chromatography to obtain the title compound.

Yield: 20.1 g (151 mmol) (77%)
MS (FAB, m/z) 134 (MH+)
H-NMR (CDCl3) δ 2.30 (3H, s), 5.93 (1H, s), 7.08 (1H, s), 7.14 (1H, d), 7.21 (1H, d).

Step 2

Synthesis of 3-(2-aminoethoxy)-4-methylbenzonitrile

The title compound was obtained from 13.7 g (103 mmol) of 3-hydroxy-4-methylbenzonitrile and 22.2 g (124 mmol) of N-t-butyl-2-chloroethyl carbamate in the same manner as that of steps 2 and 3 in Example 1.

Yield: 6.13 g (34.8 mmol) (34%)
MS (ESI, m/z) 261 (M+DMSO+H+)
MS (ESI, m/z) 261 (M+DMSO+H+)
H-NMR (CDCl3) δ 2.29 (3H, s), 3.14 (2H, t), 4.01 (2H, t), 7.03 (1H, d), 7.17 (1H, dd), 7.22 (1H, d)

Step 3

Synthesis of N-[2-(5-cyano-2-methylphenoxy)ethyl]-4-cyanobenzamide

The title compound was obtained from 6.13 g (34.8 mmol) of 3-(2-aminoethoxy)-4-methylbenzonitrile, 6.14 g (41.8 mmol) of 4-cyanobenzoic acid and 3.7 ml (38.3 mmol) of ethyl chloroformate in the same manner as that of step 4 in Example 1.

Yield: 13.9 g (45.6 mmol) (>100%)
MS (FAB, m/z) 306 (MH+)
H-NMR (CDCl3) δ 2.28 (3H, s), 3.95 (2H, dd), 4.19 (2H, t), 7.05 (1H, s), 7.22 (2H, s), 7.76 (2H, d), 7.88 (2H, d)

Step 4

Synthesis of N-[2-(5-amidino-2-methylphenoxy)ethyl]-4-amidinobenzamide bistrifluoroacetate The title compound was obtained from 2.00 g (6.55 mmol) of N-[2-(5-cyano-2-methylphenoxy)ethyl]-4-cyanobenzamide in the same manner as that of step 5 in Example 95.

Yield: 914 mg (1.61 mmol) (25%)
MS (EIS, m/z) 340 (MH+)
H-NMR (DMSO-d6) δ 2.23 (3H, s), 3.73 (2H, d), 4.26 (2H, t), 7.36 (1H, d), 7.37 (1H, s), 7.41 (1H, d), 7.90 (2H, d), 8.05 (2H, d), 8.93 (2H, br), 9.02 (1H, br), 9.11 (2H, br), 9.24 (2H, br), 9.41 (2H, br).

Example 149

Synthesis of N-[5-amidino-2-[2-(2-furyl)-2-oxoethyl]phenoxy]ethyl-4-amidinobenzamide bistrifluoroacetate Step 1

Synthesis of N-[2-(5-cyano-2-bromomethylphenoxy)ethyl]-4-cyanobenzamide 12.0 g (39.3 mmol) of N-[2-(5-cyano-2-methylphenoxy)ethyl]-4-cyanobenzamide was dissolved in 200 ml of carbon tetrachloride. 7.00 g (39.3 mmol) of N-bromosuccinimide and 700 mg (4.26 mmol) of azoisobutyronitrile were added to the solution. After stirring at 100° C. for 3 days, 16.8 g (94.4 mmol) of N-bromosuccinimide and 2.1 g (12.8 mmol) of azoisobutyronitrile were added to the resultant mixture, and they were stirred for additional 2 days. After the treatment with ethyl acetate as the extractant in an ordinary manner, the crude product was obtained, which was purified by the silica gel column chromatography to obtain the title compound.

Yield: 11.96 g (31.2 mmol) (79%)
MS (FAB, m/z) 384 (MH+)
H-NMR (CDCl3) δ 4.00 (2H, dd), 4.30 (2H, t), 4.55 (2H, s), 7.14 (1H, d), 7.26 (1H, dd), 7.42 (1H, d), 7.72 (2H, d), 7.82 (2H, d).

Step 2

Synthesis of N-[5-amidino-2-[2-(2-furyl)-2-oxoethyl]phenoxy]ethyl-4-amidinobenzamide bistrifluoroacetate 5 ml of acetonitrile and 0.2 ml (2.0 mmol) of 2-furoyl chloride were added to 230 mg (0.20 mmol) of palladium tetrakis triphenylphosphine and 85 mg (1.30 mmol) of zinc powder in argon atmosphere. A solution of 383 mg (1.0 mmol) of N-[2-(5-cyano-2-bromomethylphenoxy)ethyl]-4-cyanobenzamide in 5 ml of acetonitrile was added to the resultant mixture at room temperature, and they were stirred for 24 hours. The solvent was evaporated, and the residue was purified by the silica gel column chromatography. The obtained compound was treated in the same manner as that of step 5 in Example 95 to obtain the title compound.

Yield: 6.6 g (0.010 mmol) (1.0%)
MS (ESI, m/z) 434 (MH+)
H-NMR (DMSO-d6) δ 3.58 (2H, dd), 4.19 (2H, t), 4.28 (2H, s), 6.68 (1H, dd), 7.38-7.41 (1H, m), 7.42 (1H, d), 7.43 (1H, s), 7.48 (1H, dd), 7.88 (2H, d), 7.96 (2H, d), 7.99-8.05 (1H, m), 8.80 (1H, t), 9.13 (2H, br), 9.28 (4H, br), 9.41 (2H, br). keto form 100%

Example 150

Synthesis of 3-[(2S)-2-amino-3-[4-(4-piperidyloxy)phenyl]propoxy]benzamidine tristrifluoroacetate Synthesis of 3-[(2S)-2-amino-3-[4-[1-(benzyloxycarbonyl)-4-piperidyloxy]phenyl]propoxy]benzamidine bistrifluoroacetate

Step 1

Synthesis of benzyl 4-hydroxypiperidine-1-carboxylate 25.0 g (247 mmol) of 4-hydroxypiperidine was dissolved in 800 ml of dichloromethane. 38 ml (266 mmol) of benzyl chloroformate and 75 ml (538 mmol) of triethylamine were added to the solution at 0° C., and they were stirred at room temperature for 15 hours. After the treatment with dichloromethane as the extractant in an ordinary manner, an oily residue was obtained. This residue was subjected to the subsequent reaction without further purification.

Yield: 44.6 g (203 mmol) (82%).

Step 2

Synthesis of methyl (2S)-2-(t-butoxycarbonylamino)-3-(4-hydroxyphenyl)propionate 15.2 g (65.6 mmol) of L-tyrosine methyl ester hydrochloride was dissolved in 200 ml of dichloromethane. A solution of 20 ml (143 mmol) of triethylamine and 13.1 g (60.0 mmol) of di-t-butyl dicarbonate in 50 ml of dichloromethane was added to the solution at room temperature and they were stirred for 15 hours. After the same isolation process as that of step 1 in Example 1 with dichloromethane as the extractant, an oily residue was obtained. This residue was subjected to the subsequent reaction without further purification.

Yield: 19.2 g (65.2 mmol) (99%)

Step 3

Synthesis of methyl (2S)-3-[4-[1-(benzyloxycarbonyl)-4-piperidyloxy]phenyl]-2-(t-butoxycarbonylamino)propionate 18.9 g (86.2 mmol) of benzyl 4-hydroxypiperidine-1-carboxylate, 25.4 g (86.2 mmol) of methyl (2S)-2-(t-butoxycarbonylamino)-3-(4-hydroxyphenyl)propionate and 27.1 g (103.4 mmol) of triphenylphosphine were dissolved in 500 ml of tetrahydrofuran. 37.5 g (86.2 mmol) of diethyl azodicarboxylate was added to the solution at room temperature, and they were stirred for 15 hours. After the isolation treatment with ethyl acetate as the extractant in the same manner as that of step 1 in Example 1, the crude product was obtained, which was purified by the silica gel column chromatography to obtain the title compound.

Yield: 32.1 g (62.6 mmol) (73%)
H-NMR (CDCl3) δ 1.42 (9H, s), 1.70-1.84 (2H, m), 1.86-2.00 (2H, m), 2.91-3.10 (2H, m), 3.38-3.53 (2H, m), 3.70 (3H, s), 3.71-3.82 (2H, m), 4.40-4.44 (1H, m), 4.45-4.60 (1H, m), 4.93-5.00 (1H, m), 5.18 (2H, s), 6.92 (2H, d), 7.02 (2H, d), 7.13-7.21 (5H, m).

Step 4

Synthesis of benzyl 4-[4-(2S)-2-(t-butoxycarbonylamino)-3-hydroxypropyl]phenoxy]piperidine-1-carboxylate 10.4 g (20.3 mmol) of methyl (2S)-3-[4-[1-(benzyloxycarbonyl)-4-piperidyloxy]phenyl]-2-(t-butoxycarbonylamino)propionate was dissolved in 30 ml of tetrahydrofuran and 30 ml of methanol. 2.44 g (64.5 mmol) of sodium borohydride was added to the solution at 0° C. The temperature was elevated to room temperature. After stirring at that temperature for 15 hours, 0.82 g (21.7 mmol) of sodium borohydride was again added to the reaction mixture at 0° C. The temperature was elevated to room temperature. After stirring at that temperature for 2 hours followed by the isolation treatment with ethyl acetate as the extractant in the same manner as that of step 1 in Example 1, the crude product was obtained, which was purified by the silica gel column chromatography to obtain the title compound.

Yield: 9.45 g (19.5 mmol) (96%)
H-NMR (CDCl3) δ 1.44 (9H, s), 1.68-1.82 (2H, m), 1.84-1.98 (2H, m), 2.78 (2H, d), 3.29-3.95 (7H, m), 4.40-4.44 (1H, m), 5.14 (2H, s), 6.92 (2H, d), 7.12 (2H, d), 7.28-7.40 (5H, m).

Step 5

Synthesis of benzyl 4-[4-[(2S)-3-chloro-2-(t-butoxycarbonylamino)propyl]phenoxy]piperidine-1-carboxylate 5.5 g (11.3 mmol) of benzyl 4-[4-[(2S)-2-(t-butoxycarbonylamino)-3-hydroxypropyl]phenoxy]piperidine-1-carboxylate was dissolved in 60 ml of dichloromethane. 3.2 ml (22.6 mmol) of triethylamine and 1.95 g (17.0 mmol) of methanesulfonyl chloride were added to the solution. After stirring for 4 hours, the reaction mixture was treated by the isolation process with dichloromethane as the extractant in the same manner as that of step 1 in Example 1 to obtain an oily residue, which was dissolved in 120 ml of dimethylformamide. 2.57 g (60.6 mmol) of lithium chloride was added to the solution, and they were stirred at 50° C. for 15 hours. After the isolation process with ethyl acetate as the extractant in the same manner as that of step 1 in Example 1, the crude product was obtained, which was purified by the silica gel column chromatography to obtain the title compound.

Yield: 2.60 g (5.16 mm) (45%)

H-NMR (CDCl3) δ 1.44 (9H, s), 1.63-1.82 (2H, m), 1.83-2.00 (2H, m), 2.91-3.10 (2H, m), 2.83 (2H, d), 3.40-3.54 (3H, m), 3.57-3.63 (1H, m), 3.66-3.80 (3H, m), 4.40-4.52 (1H, m), 5.14 (2H, s), 6.92 (2H, d), 7.16 (2H, d), 7.13-7.21 (5H, m).

Step 6

Synthesis of 3-[(2S)-3-[4-[1-(benzyloxycarbonyl)-4-pipelidyloxy]phenyl]-2-(t-butoxycarbonylamino)propoxy]benzonitrile 6.4 g (12.7 mmol) of benzyl 4-[4-[(2S)-3-chloro-2-(t-butoxycarbonylamino)propyl]phenoxy]]piperidine-1-carboxylate was dissolved in 70 ml of dimethylformamide. 2.27 g (19.1 mmol) of 3-cyanophenol and 3.51 g (25.4 mmol) of potassium carbonate were added to the solution, and they were stirred at 70° C. for 15 hours. After the isolation process with ethyl acetate as the extractant in the same manner as that of step 1 in Example 1, the crude product was obtained, which was purified by the silica gel column chromatography to obtain the title compound.

Yield: 5.0 g (8.54 mm) (67%)

H-NMR (CDCl3) δ 1.44 (9H, s), 1.66-1.83 (2H, m), 1.84-2.00 (2H, m), 2.50-2.60 (1H, m), 2.82-2.93 (1H, d), 3.40-3.53 (3H, m), 3.58-3.63 (1H, m), 3.65-3.80 (3H, m), 4.40-4.53 (1H, m), 5.14 (2H, s), 6.92 (2H, d), 7.16 (2H, d), 7.13-7.21 (5H, m).

Step 7

Synthesis of 3-[(2S)-2-amino-3-[4-(4-piperidyloxy)phenyl]propoxy]benzamidine tristrifluoroacetate Synthesis of 3-[(2S)-2-amino-3-[4-[1-(benzyloxycarbonyl)-4-pipelidyloxy]phenyl]propoxy]benzamidine bistrifluoroacetate 10 mg (0.0171 mmol) of 3-[(2S)-3-[4-[1-(benzyloxycarbonyl)-4-piperidyloxy]phenyl]-2-(t-butoxycarbonylamino)propoxy]benzonitrile hydrochloride was added to 5 ml of ethanol containing 30% (w/v) of hydrogen chloride, and they were stirred at room temperature for 24 hours. The mixture thus obtained was dissolved in 10 ml of 30% (w/v) solution of ammonia in ethanol at room temperature, and the solution was stirred at room temperature for 24 hours. The solvent was evaporated, and the residue was treated by the reversed-phase high-performance liquid chromatography with silica gel, containing octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

3-[(2S)-2-amino-3-[4-(4-piperidyloxy)phenyl]propoxy]benzamidine tristrifluoroacetate Yield: 2.2 mg (0.0031 mmol) (18.1%)

MS (FAB, m/z) 369 (MH+)

H-NMR (DMSO-d6) δ 1.65-1.85 (2H, m), 2.00-2.10 (2H, m), 2.82-3.60 (6H, m), 3.60-3.90 (1H, m), 3.93-4.01 (1H, m), 4.10-4.20 (1H, m), 4.58-4.62 (1H, m), 6.75 (2H d), 6.98 (2H, d), 7.20-7.60 (4H, m), 8.10 (3H, br), 8.55 (2H, br) 9.08 (2H, br), 9.30 (2H, br)

3-[(2S)-2-Amino-3-[4-[1-(benzyloxycarbonyl)-4-piperidyloxy]phenyl]propoxy]benzamidine bistrifluoroacetate Yield: 3.2 mg (0.00438 mmol) (25.6%)

MS (FAB, m/z) 503 (MH+)

H-NMR (DMSO-d6) δ 1.42-1.61 (2H, m), 1.83-1.97 (2H, m), 2.89-2.99 (2H, m), 3.20-3.62 (3H, m), 3.65-3.89 (2H, m), 3.95-4.05 (1H, m), 4.11-4.20 (1H, m), 4.50-4.60 (1H, m), 5.08 (2H, s), 6.98 (2H, d), 7.20 (2H, d), 7.30-7.60 (9H, m), 8.10 (3H, br), 9.05 (2H, br), 9.35 (2H, br).

Example 151

Synthesis of 3-[(2R)-2-amino-3-[4-(4-piperidyloxy)phenyl]propoxy]benzamidine tristrifluoroacetate Synthesis of 3-[(2R)-2-amino-3-[4-[1-(benzyloxycarbonyl)-4-pipelidyloxy]phenyl]propoxy]benzamidine bistrifluoroacetate 39.4 mg (0.0657 mmol) of 3-[(2R)-3-[4-[1-(benzyloxycarbonyl)-4-piperidyloxy]phenyl]-2-(t-butoxycarbonylamino)propoxy]benzonitrile hydrochloride was added to 10 ml of ethanol containing 30% (W/V) hydrogen chloride, and they were stirred at room temperature for 24 hours. Then, the mixture was dissolved at room temperature in 10 ml of an ethanol solution containing 10% (W/V) ammonia and stirred at room temperature for 24 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

3-[(2R)-2-amino-3-[4-(4-piperidyloxy)phenyl]propoxy]benzamidine tristrifluoroacetate Yield: 2.4 mg (0.00338 mmol) (5.05%)

MS (ESI, m/z) 369 (MH+)

H-NMR (DMSO-d6) δ 1.65-1.82 (2H, m), 1.95-2.11 (2H, m), 2.61-2.85 (2H, m), 3.02-4.10 (7H, m), 4.52-4.64 (1H, m), 6.70 (2H, d), 7.02 (2H, d), 7.20-7.35 (5H, m), 7.28-7.48 (3H, m), 7.55 (1H, t), 8.37 (3H, br), 9.22 (2H, d), 9.32 (2H, br), 9.47 (2H, br).

3-[(2R)-2-amino-3-[4-[1-(benzyloxycarbonyl)-4-piperidyloxy]phenyl]propoxy]benzamidine bistrifluoroacetate Yield: 3.2 mg (0.00438 mmol) (5.53%)

MS (ESI, m/z) 503 (MH+)

H-NMR (DMSO-d6) δ 1.47-1.61 (2H, m), 1.85-1.96 (2H, m), 2.90-3.01 (2H, m), 3.20-3.35 (2H, m), 3.67-3.87 (2H, m), 3.95-4.05 (1H, m), 4.12-4.18 (1H, m), 5.08 (2H, s), 6.95 (2H, d), 7.20 (2H, d), 7.30-7.45 (8H, m), 7.57 (1H, t), 8.21 (3H, br), 9.18 (2H, br), 9.31 (2H, br).

Example 152

Synthesis of 3-[(2S)-2-(ethanesulfonylamino)-3-[4-(4-piperidyloxy)phenyl]propoxy]benzamidine bistrifluoroacetate Synthesis of 3-[(2S)-2-(ethanesulfonylamino)-3-[4-(ethanesulfonyloxy)phenyl]propoxy]benzamidine, trifluoroacetate Synthesis of 3-[(2S)-3-[4-[1-(benzyloxycarbonyl)-4-piperidyloxy]phenyl]-2-(ethanesulfonylamino)propoxy]benzamidine trifluoroacetate 25 mg (0.0479 mmol) of 3-[(2S)-3-[4-[1-(benzyloxycarbonyl)-4-piperidyloxy]phenyl]-2-(t-butoxycarbonylamino)propoxy]benzonitrile hydrochloride and 72.6 mg (0.735 mmol) of triethylamine were dissolved in 5 ml of DMF, and 21.3 mg (0.166 mmol) of ethane sulfonyl chloride was added thereto at room temperature, and the mixture was stirred at room temperature overnight. The oily residue was obtained by use of ethyl acetate as the extractant in the same isolation process as in step 1 in Example 1. Then, the title compound was obtained in the same operation as in Example 150.

3-[(2S)-2-(ethanesulfonylamino)-3-[4-(4-piperidyloxy)phenyl]propoxy]benzamidine bistrifluoroacetate Yield: 4.8 mg (0.00697 mmol) (14.6%)
MS (ESI, m/z) 461 (MH+)
H-NMR (DMSO-d6) δ 0.93 (3H, t), 1.68-1.82 (2H, m), 1.98-2.18 (2H, m), 2.58 (2H, q), 2.62-3.02 (2H, m), 3.02-3.50 (5H, m), 4.00 (2H, d), 4.55-4.62 (1H, m), 6.97 (2H, d), 7.22 (2H, d), 7.27-7.60 (4H, m), 8.21 (1H, br), 8.35 (2H, br), 9.10 (2H, br), 9.38 (2H, br)

3-[(2S)-2-(ethanesulfonylamino)-3-[4-(ethanesulfonyloxy)phenyl]propoxy]benzamidine trifluoroacetate Yield: 1.6 mg (0.00274 mmol) (5.9%)
MS (ESI, m/z) 470 (MH+)
H-NMR (DMSO-d6) δ 0.88 (3H, t), 1.38 (3H, t), 2.52-3.10 (4H, m), 3.46 (2H, q), 3.78-3.86 (1H, m), 4.15 (2H, t), 7.27 (2H, d), 7.30-7.40 (2H, m), 7.43 (2H, d), 7.46-7.58 (2H, m), 7.43 (2H, d), 7.46-7.58 (2H, m), 8.95 (2H, br), 9.32 (2H, br)

3-[(2S)-3-[4-[1-(benzyloxycarbonyl)-4-piperidyloxy]phenyl]-2-(ethanesulfonylamino)propoxy]benzamidine trifluoroacetate Yield: 2.8 mg (0.00395 mmol) (8.14%)
MS (ESI, m/z) 595 (MH+)
H-NMR (DMSO-d6) δ 0.93 (3H, t), 1.47-1.61 (2H, m), 1.85-1.96 (2H, m), 2.90-3.01 (2H, m), 3.20-3.35 (2H, m), 3.67-3.87 (2H, m), 3.95-4.05 (1H, m), 4.12-4.18 (1H, m), 5.08 (2H, s), 6.95 (2H, d), 7.20 (2H, d), 7.30-7.45 (8H, m), 7.57 (1H, t), 8.21 (3H, br), 9.18 (2H, br), 9.31 (2H, br)

Example 153

Synthesis of 3-[(2S)-2-(butanesulfonylamino)-3-[4-(4-piperidyloxy)phenyl]propoxy]benzamidine bistrifluoroacetate Synthesis of 3-[(2S)-2-(butanesulfonylamino)-3-[4-(butanesulfonyloxy)phenyl]propoxy]benzamidine trifluoroacetate Synthesis of 3-[(2S)-3-[4-[1-(benzyloxycarbonyl)-4-piperidyloxy]phenyl]-2-(butanesulfonylamino)propoxy]benzamidine trifluoroacetate 25 mg (0.0479 mmol) of 3-[(2S)-3-[4-[1-(benzyloxycarbonyl)-4-piperidyloxy]phenyl]-2-(t-butoxycarbonylamino)propoxy]benzonitrile hydrochloride and 72.6 mg (0.735 mmol) of triethylamine were dissolved in 5 ml of DMF, and 20.0 mg (0.128 mmol) of butane sulfonyl chloride was added thereto at room temperature, and the mixture was stirred at room temperature overnight. The mixture was treated in an ordinary manner with ethyl acetate as the extractant to obtain an oily residue. Then, the title compound was obtained in the same operation as in Example 150.

3-[(2S)-2-(butanesulfonylamino)-3-[4-(4-piperidyloxy)phenyl]propoxy]benzamidine bistrifluoroacetate Yield: 2.0 mg (0.00279 mmol) (5.80%)
MS (ESI, m/z) 489 (MH+)
H-NMR (DMSO-d6) δ 0.82 (3H, t), 1.08-1.42 (4H, m), 1.70-1.84 (2H, m), 1.95-2.13 (2H, m), 2.58 (2H, t), 2.60-3.10 (2H, m), 3.20-3.58 (4H, m), 3.62-3.82 (1H, m), 3.92-4.10 (2H, m), 4.56-4.65 (1H, m), 5.08 (2H, s), 6.92 (2H, d), 7.24 (2H, d), 7.30-7.58 (4H, m), 8.10 (1H, m), 8.26 (2H, br), 9.05 (2H, br), 9.26 (2H, br)

3-[(2S)-2-(butanesulfonylamino)-3-[4-(butanesulfonyloxy)phenyl]propoxy]benzamidine trifluoroacetate Yield: 2.9 mg (0.00453 mmol) (9.54%)
MS (ESI, m/z) 526 (MH+)
H-NMR (DMSO-d6) δ 0.76 (3H, t), 0.92 (3H, t), 1.10-1.82 (10H, m), 2.52-2.70 (4H, m), 2.71-3.10 (2H, m), 3.42-3.58 (2H, m), 3.76-3.88 (1H, m), 4.00-4.18 (2H, m), 7.20-7.60 (8H, m), 8.92 (2H, br), 9.28 (2H, br)

3-[(2S)-3-[4-(1-(benzyloxycarbonyl)-4-piperidyloxy)phenyl]-2-(butanesulfonylamino)propoxy]benzamidine trifluoroacetate Yield: 2.8 mg (0.00380 mmol) (8.00%)
MS (ESI, m/z) 623 (MH+)
H-NMR (DMSO-d6) δ 0.93 (3H, t), 1.25-1.98 (4H, m), 2.58 (2H, t), 2.62-3.00 (2H, m), 3.62-3.80 (3H, m), 3.95-4.12 (2H, m), 4.28-4.32 (2H, m), 4.48-4.60 (1H, m), 5.08 (2H, s), 6.92 (2H, d), 7.22 (2H, d), 7.30-7.46 (8H, m), 7.52-7.58 (1H, m), 8.97 (2H, br), 9.29 (2H, br)

Example 154

Synthesis of 3-[(2S)-2-(benzenesulfonylamino)-3-[4-(4-piperidyloxy)phenyl]propoxy]benzamidine bistrifluoroacetate Synthesis of 3-[(2S)-3-[4-[1-(benzyloxycarbonyl)-4-piperidyloxy]phenyl]-2-(benzenesulfonylamino)propoxy]benzamidine trifluoroacetate 25 mg (0.0479 mmol) of 3-[(2S)-3-[4-[1-(benzyloxycarbonyl)-4-piperidyloxy]phenyl]-2-(t-butoxycarbonylamino)propoxy]benzonitrile hydrochloride and 72.6 mg (0.735 mmol) of triethylamine were dissolved in 5 ml of DMF, and 20.0 mg (0.113 mmol) of butane sulfonyl chloride was added thereto at room temperature, and the mixture was stirred at room temperature overnight. The oily residue was obtained by use of ethyl acetate as the extractant in the same isolation process as in step 1 in Example 1. Then, the title compound was obtained in the same operation as in Example 150.

3-[(2S)-2-(benzenesulfonylamino)-3-[4-(4-piperidyloxy)phenyl]propoxy]benzamidine bistrifluoroacetate Yield: 3.7 mg (0.00502 mmol) (10.5%)
MS (ESI, m/z) 509 (MH+)
H-NMR (DMSO-d6) δ 1.76-1.90 (2H, m), 2.03-2.17 (2H, m), 2.62 (1H, dd), 2.83 (1H, dd), 3.00-3.39 (4H, m), 3.58-3.64 (1H, m), 3.94 (2H, d), 4.52-4.64 (1H, m), 6.79 (2H, d), 7.01 (2H, d), 7.08-7.56 (7H, m), 7.64-7.70 (2H, m), 8.12 (1H, d), 9.14 (2H, br), 9.33 (2H, br), 9.38 (2H, br).

3-[(2S)-3-[4-[1-(benzyloxycarbonyl)-4-piperidyloxy]phenyl]-2-(benzenesulfonylamino)propoxy]benzamidine trifluoroacetate Yield: 2.8 mg (0.00370 mmol) (7.79%)
MS (ESI, m/z) 643 (MH+)
H-NMR (DMSO-d6) δ 1.42-1.60 (2H, m), 1.86-1.97 (2H, m), 2.68 (1H, dd), 2.80 (1H, dd), 3.20-3.58 (2H, m), 3.58-3.64 (1H, m), 3.64-3.80 (2H, m), 3.94 (2H, d), 4.40-4.53 (1H, m), 5.06 (2H, s), 6.76 (2H, d), 6.96 (2H, d), 7.10-7.24 (2H, m), 7.32-7.54 (10H, m), 7.62-7.70 (2H, m), 8.08 (1H, d), 8.94 (2H, br), 9.26 (2H, br)

Example 155

Synthesis of 3-[(2S)-2-(2-naphthalenesulfonylamino)-3-[4-(4-piperidyloxy)phenyl]propoxy]benzamidine bistrifluoroacetate Synthesis of 3-[(2S)-2-(butanesulfonylamino)-3-(4-hydroxyphenyl)propoxy]benzamidine trifluoroacetate Synthesis of 3-[(2S)-3-[4-[1-(benzyloxycarbonyl)-4-piperidyloxy]phenyl]-2-(2-naphthalenesulfonylamino)propoxy]benzamidine trifluoroacetate 25 mg (0.0479 mmol) of 3-[(2S)-3-[4-[1-(benzyloxycarbonyl)-4-pipelidyloxy]phenyl]-2-(t-butoxycarbonylamino)propoxy]benzonitrile hydrochloride and 72.6 mg (0.735 mmol) of triethylamine were dissolved in 5 ml of DMF, and 20.0 mg (0.0882 mmol) of 2-naphthalene sulfonyl chloride was added thereto at room temperature, and the mixture was stirred at room temperature overnight. The oily residue was obtained by use of ethyl acetate as the extractant in the same isolation process as in step 1 in Example 1. Then, the title compound was obtained in the same operation as in Example 150.

3-[(2S)-2-(2-naphthalenesulfonylamino)-3-[4-(4-piperidyloxy)phenyl]propoxy]benzamidine bistrifluoroacetate Yield: 5.5 mg (0.00699 mmol) (14.7%)
MS (ESI, m/z) 559 (MH+)
H-NMR (DMSO-d6) δ 1.70-1.91 (2H, m), 2.00-2.12 (2H, m), 2.62 (1H, dd), 2.82 (1H, dd), 2.94-3.24 (4H, m), 3.64-3.76 (1H, m), 3.95 (2H, d), 4.38-4.48 (1H, m), 6.65 (2H, d), 6.97 (2H, d), 6.92-7.04 (1H, m), 7.10-7.55 (5H, m), 7.60-7.70 (3H, m), 7.82 (1H, d), 7.92 (1H, d), 8.08 (1H, d), 8.22 (1H, d), 8.31 (1H, s), 9.17 (2H, br), 9.29 (2H, br), 9.34 (2H, br).

3-[(2S)-2-(butanesulfonylamino)-3-(4-hydroxyphenyl)propoxy]benzamidine trifluoroacetate Yield: 2.1 mg (0.00356 mmol) (7.52%)
MS (ESI, m/z) 476 (MH+)
H-NMR (DMSO-d6) δ 2.58 (1H, dd), 2.76 (1H, dd), 3.60-3.70 (1H, m), 3.86 (2H, d), 6.49 (2H, d), 6.84 (2H, d), 6.94-7.02 (1H, m), 7.08 (1H, s), 7.29 (1H, d), 7.37 (1H, dd), 7.60-8.00 (8H, m), 8.08 (1H, d), 8.14 (1H, d), 8.94 (2H, br), 9.13 (1H, s), 9.20 (2H, br)

3-[(2S)-3-[4-[1-(benzyloxycarbonyl)-4-pipelidyloxy]phenyl]-2-(2-naphthalenesulfonylamino)propoxy]benzamidine trifluoroacetate Yield: 2.7 mg (0.00335 mmol) (14.7%)
MS (ESI, m/z) 693 (MH+)
H-NMR (DMSO-d6) δ 1.40-1.58 (2H, m), 1.78-1.92 (2H, m), 2.60 (1H, dd), 2.80 (1H, dd), 3.20-3.40 (2H, m), 3.62-3.86 (3H, m), 3.95 (2H, d), 4.25-4.38 (1H, m), 5.07 (2H, s), 6.60 (2H, d), 6.93 (2H, d), 7.04-7.08 (1H, m), 7.14-7.18 (1H, m), 7.28-7.40 (9H, m), 7.58-7.64 (3H, m), 7.91 (1H, d), 7.94 (1H, d), 8.05 (1H, d), 8.16 (1H, d), 8.30 (1H, s), 8.90 (2H, br), 9.21 (2H, br).

Example 156

Synthesis of 3-[(2R)-2-(ethanesulfonylamino)-3-[4-(4-piperidyloxy)phenyl]propoxy]benzamidine bistrifluoroacetate 11 mg (0.0183 mmol) of 3-[(2S)-3-[4-[1-(benzyloxycarbonyl)-4-piperidyloxy]phenyl]-2-(t-butoxycarbonylamino)propoxy]benzonitrile trifluoroacetate and 72.6 mg (0.735 mmol) of triethylamine were dissolved in 5 ml of DMF, and 10.0 mg (0.166 mmol) of ethane sulfonyl chloride was added thereto at room temperature, and the mixture was stirred at room temperature overnight. The mixture was treated in an ordinary manner with ethyl acetate as the extractant to obtain an oily residue. Then, the title compound was obtained in the same operation as in Example 150.

Yield: 1.76 mg (0.00256 mmol) (14.0%)
MS (ESI, m/z) 461 (MH+)
H-NMR (DMSO-d6) δ 0.94 (3H, t), 1.68-1.83 (2H, m), 2.00-2.16 (2H, m), 2.58 (2H, q), 2.70 (1H, dd), 2.95 (1H, dd), 2.98-3.38 (4H, m), 3.68-3.81 (1H, m), 4.01-4.04 (2H, m), 4.58-4.61 (1H, m), 6.95 (2H, m), 7.25 (2H, m), 7.40-7.60 (4H, m), 8.42 (2H, br), 8.90 (2H, br), 9.11 (2H, br)

Example 157

Synthesis of 3-[(2R)-2-(benzenesulfonylamino)-3-[4-(4-piperidyloxy)phenyl]propoxy]benzamidine bistrifluoroacetate 11 mg (0.0183 mmol) of 3-[(2S)-3-[4-[1-(benzyloxycarbonyl)-4-pipelidyloxy]phenyl]-2-(t-butoxycarbonylamino)propoxy]benzonitrile trifluoroacetate and 4.3 mg (0.10 mmol) of pyridine were dissolved in 2.5 ml of DMF, and 4.3 mg (0.0245 mmol) of benzene sulfonyl chloride was added thereto at room temperature, and the mixture was stirred at room temperature overnight. The oily residue was obtained by use of ethyl acetate as the extractant in the same isolation process as in step 1 in Example 1. Then, the title compound was obtained in the same operation as in Example 150.

Yield: 1.58 mg (0.00214 mmol) (11.7%)
MS (ESI, m/z) 509 (MH+)
H-NMR (DMSO-d6) δ 1.56-1.71 (2H, m), 1.84-2.01 (2H, m), 2.69-2.96 (3H, m), 3.19-3.28 (2H, m), 3.42-3.57 (1H, m), 3.71-3.81 (1H, m), 3.94-4.02 (1H, m), 4.04-4.18 (1H, m), 4.26-4.41 (1H, m), 6.86 (2H, d), 7.13 (2H, d), 7.28-7.81 (9H, m), 8.12 (1H, d), 8.14 (2H, br), 9.01 (2H, br), 9.29 (2H, br).

Example 158

Synthesis of 3-[(2S)-2-(benzenesulfonylamino)-3-[4-(1-acetimidoyl-4-piperidyloxy)phenyl]propoxy]benzamidine bistrifluoroacetate 20 mg (0.0271 mmol) of 3-[(2S)-2-(benzenesulfonylamino)-3-[4-(4-piperidyloxy)phenyl]propoxy]benzamidine ditrifluoroacetate and 218 mg (2.15 mmol) triethylamine were dissolved in 5 ml of ethanol, and 10.0 mg (0.0809 mmol) of ethylacetoimidate hydrochloride was added thereto at room temperature, and they were stirred at room temperature overnight. Then, the solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 13.2 mg (0.00169 mmol) (62.6%)
MS (ESI, m/z) 550 (MH+)
H-NMR (DMSO-d6) δ 1.63-1.82 (2H, m), 1.97-2.17 (2H, m), 2.29 (3H, s), 2.60 (1H, dd), 2.81 (1H, dd), 3.42-3.81 (5H, m), 3.86 (2H, d), 4.58-4.64 (1H, m), 6.78 (2H, d), 7.01 (2H, d), 7.11-7.68 (9H, m), 8.09 (1H, d), 8.58 (1H, s), 9.04 (2H, br), 9.11 (1H, br), 9.27 (2H, br)

Example 159

Synthesis of 3-[(2S)-2-(benzenesulfonylamino)-3-[4-(1-amidino-4-piperidyloxy)phenyl]propoxy]benzamidine bistrifluoroacetate 20 mg (0.0271 mmol) of 3-[(2S)-2-(benzenesulfonylamino)-3-[4-(4-piperidyloxy)phenyl]propoxy]benzamidine ditrifluoroacetate and 72 mg (2.15 mmol) of triethylamine were dissolved in 2 ml of DMF, and 20.0 mg (0.185 mmol) of amidinesulfinic acid was added thereto at room temperature, and they were stirred at room temperature overnight. The reaction solution was purified in the same manner as in Example 150 to obtain the title compound.

Yield: 8.4 mg (0.0108 mmol) (39.8%)
MS (ESI, m/z) 551 (MH+)
H-NMR (DMSO-d6) δ 1.58-1.68 (2H, m), 1.89-1.96 (2H, m), 2.54-2.62 (1H, m), 2.68-2.97 (3H, m), 3.21-3.42 (2H, m), 3.54-3.68 (1H, m), 3.92 (2H, d) 4.30-4.41 (1H, m), 6.73 (2H, d), 6.92 (2H, d), 7.05-7.72 (9H, m), 8.08 (1H, d), 8.90 (4H, br), 9.21 (4H, br)

Example 160

Synthesis of 3-[(2S)-2-(ethanesulfonylamino)-3-[4-(1-acetimidoyl-4-piperidyloxy)phenyl]propoxy]benzamidine bistrifluoroacetate 1.19 g (1.99 mmol) of 3-[(2S)-3-[4-[1-benzyloxycarbonyl)-4-piperidyloxy]phenyl]-2-(t-butoxycarbonylamino)propoxy]benzonitrile hydrochloride was subjected as the starting material to the same operation as in Example 152, and the resulting intermediate was subjected without purification to the same operation as in Example 158 to obtain the crude product. Thereafter, it was purified in the same manner as in Example 150 to obtain the title compound.

Yield: 63 mg (0.086 mmol) (4.3%)
MS (ESI, m/z) 502 (MH+)
H-NMR (D20) δ 1.05 (3H, t), 1.82-1.97 (2H, m), 2.07-2.17 (2H, m), 2.37 (3H, s), 2.62-3.21 (4H, m), 3.47-3.96 (5H, m), 4.06-4.20 (2H, m), 4.67-4.73 (1H, m), 7.18 (2H, d), 7.29 (2H, d), 7.30-7.61 (4H, m)

Example 161

Synthesis of 3-[(2S)-2-(butanesulfonylamino)-3-[4-(1-acetimidoyl-4-piperidyloxy)phenyl]propoxy]benzamidine bistrifluoroacetate 1.19 g (1.99 mmol) of 3-[(2S)-3-[4-[1-benzyloxycarbonyl)-4-piperidyloxy]phenyl]-2-(t-butoxycarbonylamino)propoxy]benzonitrile hydrochloride was subjected as the starting material to the same operation as in Example 153, and the resulting intermediate was subjected without purification to the same operation as in Example 158 to obtain the crude product. Thereafter, it was purified in the same manner as in Example 150 to obtain the title compound.

Yield: 11.8 mg (0.234 mmol) (11.8%)
MS (ESI, m/z) 530 (MH+)
H-NMR (DMSO-d6) δ 0.89 (3H, t), 1.10-1.50 (4H, m), 1.71-1.90 (2H, m), 1.98-2.12 (2H, m), 2.28-2.56 (2H, q), 2.60-2.98 (2H, m), 3.52-3.60 (2H, m), 3.62-3.92 (3H, m), 3.98-4.07 (2H, m), 4.58-4.69 (1H, m), 6.92 (2H, d), 7.21 (2H, d), 7.24-7.61 (4H, m), 8.57 (1H, br), 9.05 (1H, br), 9.22 (2H, br), 9.28 (2H, br)

Example 162

Synthesis of 3-[(2S)-2-(2-naphthalenesulfonylamino)-3-[4-(1-acetimidoyl-4-piperidyloxy)phenyl]propoxy]benzamidine bistrifluoroacetate 1.19 g (1.99 mmol) of 3-[(2S)-3-[4-[1-benzyloxycarbonyl)-4-piperidyloxy]phenyl]-2-(t-butoxycarbonylamino)propoxy]benzonitrile hydrochloride was subjected as the starting material to the same operation as in Example 155, and the resulting intermediate was subjected without purification to the same operation as in Example 158 to obtain the crude product. Thereafter, it was purified in the same manner as in Example 150 to obtain the title compound.

Yield: 36 mg (0.0435 mmol) (2.2%)
MS (ESI, m/z) 600 (MH+)

H-NMR (DMSO-d6) δ 1.60-1.79 (2H, m), 1.90-2.08 (2H, m), 2.25 (3H, s), 2.58-2.92 (2H, s), 3.41-3.58 (2H, m), 3.60-3.91 (3H, m), 3.96 (2H, d), 4.41-4.57 (1H, m), 6.67 (2H, d), 6.98 (2H, d), 7.04 (1H, d), 7.15 (1H, s), 7.34 (1H, d), 7.41 (1H, dd), 7.60-7.78 (5H, m), 7.92 (1H, d), 7.97 (1H, d), 8.01 (1H, d), 8.17 (1H, d), 8.30 (1H, s)

Example 163

Synthesis of 3-[3-[4-[(3S)-1-acetimidoyl-3-pyrrolidyloxy]phenyl]-2-(benzenesulfonylamino)propoxy]benzamidine bistrifluoroacetate Benzyl (3S)-3-hydroxypyrrolidine-1-carboxylate and methyl 2S)-2-(t-butoxycarbonylamino)-3-(4-hydroxyphenyl)propionate were subjected as the starting materials to the same operations as in Example 154 and 158 successively, whereby the title compound was obtained.

MS (ESI, m/z) 536 (MH+)

H-NMR (DMSO-d6) mixture of geometrical isomers A and B (1:1) in acetimidoyl part δ 1.90-2.05 (2H, m), 1.99 (3H, s, for A), 2.03 (3H, s, for B), 2.35 (1H, dd), 2.58 (1H, dd), 3.15-3.60 (6H, m), 3.67 (2H, m), 4.87 (1H, d), 6.50 (2H, dd), 6.76 (2H, d), 6.86 (1H, dd), 6.96 (1H, br), 7.10-7.28 (4H, m), 7.40 (2H, d), 7.82 (1H, d), 8.10 (1H, s, for A), 8.18 (1H, s, for A), 8.80 (1H, s, for B), 8.87 (1H, s, for B), 8.88 (2H, s), 9.01 (2H, s)

Example 164

Synthesis of 3-[(2S)-2-(benzenesulfonylamino)-3-[4-(4-piperidylmethyl)phenyl]propoxy]benzamidine bistrifluoroacetate Step 1

Synthesis of (2S)-3-[4-[(1-acetyl-4-piperidyl)hydroxymethyl]phenyl]-2-(benzenesulfonylamino)propanol 6.32 g (19.8 mmol) of methyl (2S)-2-(benzenesulfonylamino)-3-phenyl propionate and 3.88 g (20.4 mmol) of N-acetyl-iso-nipectinoate chloride were suspended in 60 ml of dichloromethane, and 13.6 g (102.0 mmol) of aluminum chloride was added thereto, and they were stirred at room temperature overnight. The oily residue was obtained by use of dichloroethane as the extractant in the same isolation process as in step 1 in Example 1. Subsequently, this residue was dissolved in a mixed solvent of 30 ml ethanol and 50 ml methanol, and 1.68 g (44.4 mmol) of sodium borohydride was added thereto, and the mixture was stirred overnight. The title compound was obtained by use of ethyl acetate as the extractant in the same isolation process as in step 1 in Example 1.

Yield: 2.11 g (4.73 mmol) (23.9%)

MS (ESI, m/z) 469 (MNa+)

Step 2

Synthesis of 4-[4-[(2S)-3-acetoxy-2-(benzenesulfonylamino)propyl]phenyl]methyl]piperidine 2.11 g (4.73 mmol) of (2S)-3-[4-[(1-acetyl-4-piperidyl)hydroxymethyl]phenyl]-2-(benzenesulfonylamino)propanol was dissolved in 20 ml of 4 N hydrogen chloride and 40 ml of ethanol, and stirred at 95° C. overnight. The solvent was distilled off, and 100 mg of 10% palladium carbon, 0.5 ml of conc. sulfuric acid and 20 ml of acetic acid were added to the resulting residue and reduced at 50° C. in a hydrogen atmosphere at 4 atmospheric pressure. The solvent was distilled off to obtain the title crude product.

Yield: 291 mg (0.675 mmol) (14.3%)

Step 3

Synthesis of t-butyl 4-[4-[(2S)-3-acetoxy-2-(benzenesulfonylamino)propyl]phenyl]methyl]piperidine-1-carboxylate 291 mg (0.675 mmol) of 4-[4-[(2S)-3-acetoxy-2-(benzenesulfonylamino)propyl]phenyl]methyl]piperidine, 151 mg (0.693 mmol) of di-t-butyl dicarbonate, and 726 mg (7.17 mmol) of triethylamine were dissolved in 20 ml of dichloromethane and stirred overnight. The solvent was distilled off, and 0.5 ml of 1 N aqueous sodium hydroxide and 40 ml of methanol were added to the residue, followed by overnight reaction at 40° C. The solvent was distilled off, and the resulting residue was applied to reverse phase high performance liquid chromatography with silica gel having octadodecyl group chemically bonded thereto as the filler, and eluted with a mixed solvent of water and acetonitrile, and the fraction of the intended product was distilled off under reduced pressure to obtain the title compound.

Yield: 168 mg (0.344 mmol) (51.0%)

MS (ESI, m/z) 489 (MH+)

Step 4

Synthesis of t-butyl 4-[4-[(2S)-2-(benzenesulfonylamino)-3-methanesulfonyloxypropyl]phenyl]methyl]piperidine-1-carboxylate 168 mg (0.344 mmol) of t-butyl 4-[4-[(2S)-3-acetoxy-2-(benzenesulfonylamino)propyl]phenyl]methyl]piperidine-1-carboxylate and 500 mg (4.94 mmol) of triethylamine were dissolved in 15 ml of dichloromethane, and 100 mg (0.873 mmol) of methane sulfonyl chloride was added thereto, and the mixture was stirred for 3 hours under cooling with ice. The title crude compound was obtained by use of ethyl acetate as the extractant by the same isolation process as in step 1 in Example 1.

Yield: 139 mg (0.245 mmol) (71.2%)

MS (ESI, m/z) 567 (MH+)

H-NMR (CDCl3) δ 1.03-1.90 (5H, m), 1.42 (9H, s), 2.43 (2H, d), 2.60-2.84 (2H, m), 3.15 (3H, s), 3.60-3.71 (1H, m), 3.98-4.21 (6H, m), 6.92 (2H, d), 6.97 (2H, d), 7.41-7.77 (5H, m)

Step 5

Synthesis of t-butyl 4-[[4-[(2S)-2-(benzenesulfonylamino)-3-chloropropyl]phenyl]methyl]piperidine-1-carboxylate 139 mg (0.245 mmol) of t-butyl 4-[4-[(2S)-2-(benzenesulfonylamino)-3-methanesulfonyloxypropyl]phenyl]methyl]piperidine-1-carboxylate and 500 mg (11.7 mmol) of lithium chloride were dissolved in 15 ml of DMF, and the mixture was stirred at 50° C. for 6 hours. The title crude compound was obtained by use of ethyl acetate as the extractant by the same isolation process as in step 1 in Example 1.

Yield: 94.8 mg (0.187 mmol) (76.3%)

MS (ESI, m/z) 508 (MH+)

H-NMR (CDCl3) δ 1.03-1.80 (5H, m), 1.42 (9H, s), 2.45 (2H, d), 2.60-2.84 (2H, m), 3.10 (3H, s), 3.47 (2H, d), 3.64-3.80 (1H, m), 4.01-4.18 (4H, m), 6.94-7.00 (4H, m), 7.40-7.82 (5H, m)

Step 6

Synthesis of 3-[2-(benzenesulfonamino)-3-[4-[[1-(t-butoxycarbonylamino)piperidyl]methyl]phenyl]propoxy]benzamidine 94.8 mg (0.187 mmol) of t-butyl 4-[[4-[(2S)-2-(benzenesulfonylamino)-3-chloropropyl]phenyl]methyl]piperidine-1-carboxylate, 275 mg (2.31 mmol) of 3-cyanophenol, and 385 mg (2.79 mmol) of potassium carbonate were dissolved in 15 ml of DMF and stirred at 75° C. for 60 hours. The oily residue was obtained by use of ethyl acetate as the extractant in the same isolation process as in step 1 in Example 1 and then subjected to the same operation as in Example 150 whereby the title compound was obtained.

Yield: 87.5 mg (0.0148 mmol) (79.1%)
MS (ESI, m/z) 590 (MH+)
H-NMR (CDCl3) δ 1.03-1.79 (5H, m), 1.42 (9H, s), 2.24 (2H, d), 2.48-2.92 (2H, m), 3.68-3.91 (2H, m), 3.92 (2H, d), 3.98-4.10 (2H, m), 4.27-4.38 (1H, m), 6.91 (2H, d), 6.98 (2H, d), 7.28-7.91 (9H, m)

Step 7

Synthesis of 3-[(2S)-2-(benzenesulfonylamino)-3-[4-(4-piperidylmethyl)phenyl]propoxy]benzamidine ditrifluoroacetate 43.8 mg (0.0743 mmol) of 3-[2-(benzenesulfonamino)-3-[4-[[1-(t-butoxycarbonylamino)piperidyl]methyl]phenyl] propoxy]benzamidine was used and subjected to the same operation as in Example 150 whereby the title compound was obtained.

Yield: 3.6 mg (0.00490 mmol) (6.6%)
MS (ESI m/z) 507 (MH+)
H-NMR (DMSO-d6) δ 1.18-1.31 (2H, m), 1.59-1.81 (3H, m), 2.41 (2H, d), 2.55-2.87 (4H, m), 3.10-3.22 (2H, m), 3.51-3.68 (1H, m), 3.86 (2H, d), 6.87-6.96 (4H, m), 7.03 (1H, dd), 7.17 (1H, d), 7.28-7.51 (4H, m), 7.58-7.65 (2H, m), 8.04 (1H, d), 8.18 (1H, br), 8.47 (1H, br), 9.05 (2H, br), 9.21 (2H, br)

Example 165

Synthesis of 3-[(2S)-2-(benzenesulfonylamino)-3-[4-[(1-acetimidoyl-4-piperidyl)methyl]phenyl]propoxy]benzamidine bistrifluoroacetate 6.8 mmol (0.0094 mmol) of 3-[(2S)-2-(benzenesulfonylamino)-3-[4-(-4-piperidylmethyl)phenyl]propoxy]benzamidine ditrifluoroacetate was used and subjected to the same operation as in Example 158 whereby the title compound was obtained.

Yield: 1.7 mg (0.00219 mmol) (23.4%)
MS (ESI m/z) 548 (MH+)
H-NMR (DMSO-d6) δ 1.10-1.28 (2H, m), 1.60-1.73 (2H, m), 1.77-1.91 (1H, m), 2.22 (3H, s), 1.44 (2H, d), 2.63 (1H, dd), 2.84 (1H, dd), 3.01-3.28 (2H, m), 3.58-3.67 (1H, m), 3.82-4.01 (2H, m), 3.92 (2H, d), 6.98 (2H, d), 6.99 (2H, d), 7.11 (1H, dd), 7.21 (1H, d), 7.35-7.56 (4H, m), 7.61-7.71 (2H, m), 8.09 (1H, d), 8.45 (1H, br), 9.00 (2H, br), 9.27 (2H, br)

Example 166

Synthesis of (2E)-3-[4-[(2S)-1-[4-(4-piperidyloxy) phenyl]-3-(3-amidinophenoxy)-2-propylsulfamoyl] phenyl]acrylic acid bistrifluoroacetate Synthesis of ethyl (2E)-3-[4-[(2S)-1-[4-(4-piperidyloxy)phenyl]-3-(3-amidinophenoxy)-2-propylsulfamoyl]phenyl]acrylate bistrifluoroacetate Step 1

Synthesis of 3-[(2S)-3-[4-[1-(benzyloxycarbonyl)-4-piperidyloxy]phenyl]-2-(4-iodobenzenesulfonylamino)propoxy]benzonitrile 25 ml of 4 N solution of hydrogen chloride in dioxane and 12.5 ml of dioxane were added to 2.54 g (4.34 mmol) of 3-[(2S)-3-[4-[1-(benzyloxycarbonyl)-4-piperidyloxy]phenyl]-2-(t-butoxycarbonylamino)propoxy]benzonitrile. After stirring at room temperature for 24 hours, the solvent was distilled off under reduced pressure. The residue was dissolved in 40 ml of DMF. 1.77 ml (13.0 mmol) of diisopropylethylamine and 1.97 g (6.51 mmol)) of 4-iodobenzenesulfonyl chloride were added to the solution at 0° C. 30 minutes after, the temperature was elevated to room temperature, and the reaction mixture was stirred for 19 hours. Ater the same isolation process as that of step 1 in Example 1 with ethyl acetate as the extractant, the crude product was obtained, which was purified by the silica gel column chromatography to obtain the title compound.

Yield: 2.50 g (3.39 mmol) (78%)
H-NMR (CDCl3) δ 1.62-1.83 (2H, m), 1.63-2.00 (2H, m), 2.62-2.80 (1H, m), 2.83-3.00 (1H, m), 3.40-3.53 (2H, m), 3.62-3.80 (3H, m), 3.81-4.00 (2H, m), 4.40-4.45 (1H, m), 5.14 (2H, s), 5.20-5.36 (1H, m), 6.73 (2H, d), 6.90 (2H, d), 7.01 (2H, d), 7.24-7.44 (9H, m), 7.70 (2H, d)

Step 2

Synthesis of ethyl (2E)-3-[4-[(2S)-1-[4-[1-(benzyloxycarbonyl)-4-piperidyloxy]phenyl]-3-(3-cyanophenoxy)-2-propylsulfamoyl]phenyl]acrylate 738 mg (1.00 mmol)) of 3-[(2S)-3-[4-[1-(benzyloxycarbonyl)-4-piperidyloxy]phenyl]-2-(4-iodobenzenesulfonylamino)propoxy]benzonitrile was dissolved in 5 ml of acetonitrile. 0.22 ml (2.0 mmol) of ethyl acrylate, 11 mg (0.05 mmol) of palladium acetate, 91 mg (0.3 mmol) of tris-o-tolylphosphine and 0.48 ml (2.0 mmol) of tributylamine were added to the solution, and they were heated under reflux for 15 hours. After the same isolation process as that of step 1 in Example 1 with dichloromethane as the extractant, the crude product was obtained, which was purified by the silica gel column chromatography to obtain the title compound.

Yield: 544 mg (0.75 mmol) (75%)
H-NMR (CDCl3) δ 0.93 (3H, s), 1.64-1.83 (2H, m), 1.85-2.00 (2H, m), 2.70-3.00 (2H, m), 3.40-3.52 (1H, m), 3.66-3.80 (3H, m), 3.82-4.28 (2H, q), 4.36-4.44 (1H, m), 5.14 (2H, s), 6.50 (1H, d), 6.72 (2H, d), 6.92 (2H, d), 7.28-7.40 (7H, m), 7.52 (2H, d), 6.99-7.04 (2H, m), 7.73 (2H, d)

Step 3

Synthesis of (2E)-3-[4-[(2S)-1-[4-(4-piperidyloxy)phenyl]-3-(3-amidinophenoxy)-2-propylsulfamoyl]phenyl]acrylic acid bistrifluoroacetate Synthesis of ethyl (2E)-3-[4-[(2S)-1-[4-(4-piperidyloxy)phenyl]-3-(3-amidinophenoxy)-2-propylsulfamoyl]phenyl]acrylate bistrifluoroacetate (2E)-3-[4-[(2S)-1-[4-(4-piperidyloxy)phenyl]-3-(3-amidinophenoxy)-2-propylsulfamoyl]phenyl]acrylic acid bistrifluoroacetate MS (ESI m/z) 579 (MH+)

H-NMR (DMSO-d6) δ 1.70-1.85 (2H, m), 1.98-2.12 (2H, m), 2.55-2.65 (1H, m), 2.78-2.88 (1H, m), 3.00-3.16 (2H, m), 3.18-3.30 (2H, m), 3.57-3.70 (1H, m), 3.95-4.00 (2H, m), 4.53 (1H, m), 6.60 (1H, d), 6.72 (2H, d), 6.99 (2H, d), 7.15 (1H, dd), 7.29 (1H, d), 7.39 (1H, d), 7.54 (1H, t), 7.57 (2H, d), 7.59 (1H, d), 7.67 (2H, d), 8.18 (1H, d), 8.60 (2H, br), 9.20 (2H, br), 9.38 (2H, br)

Ethyl (2E)-3-[4-[(2S)-1-[4-[1-(benzyloxycarbonyl)-4-piperidyloxy]phenyl]-3-(3-cyanophenoxy)-2-propylsulfamoyl]phenyl]acrylate was dissolved in 4.5 ml of 4 N hydrogen chloride in dioxane and then added to 0.5 ml of ethanol containing 30% (W/V) hydrogen chloride. After the mixture was stirred at room temperature for 96 hours, the solvent was distilled off under reduced pressure, and the resulting residue was dissolved in 24 ml of an ethanol solution containing 10% (w/v) ammonia and stirred at room temperature for 24 hours. The solvent was distilled off, and the resulting residue was added to 18 ml of acetic acid containing 20% hydrogen bromide at 0° C., then stirred for 1 hour, allowed to reach room temperature, and stirred for 7 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 88 mg (0.11 mmol) (14%)

MS (ESI, m/z) 579 (MH+)

H-NMR (DMSO-d6)) δ 1.70-1.85 (2H, m), 1.98-2.12 (2H, m), 2.55-2.65 (1H, m), 2.78-2.88 (1H, m), 3.00-3.16 (2H, m), 3.18-3.30 (2H, m). 3.57-3.70 (1H, m), 3.95-4.00 (2H, m), 4.5:3 (1H, m), 6.60 (1H, d), 6.72 (2H, d), 6.99 (2H, d), 7.15 (1H, dd), 7.29 (1H, d.), 7.39 (1H, d), 7.54 (1H, t), 7.57 (2H, d), 7.59 (1H, d), 7.6.7 (2H, d), 8.18 (1H, d), 8.60 (2H, br), 9.20 (2H, br), 9.38 (2H, br)

Ethyl (2E)-3-[4-[(2S)-1-[4-(4-piperidyloxy)phenyl]-3-(3-amidinophenoxy)-2-propylsulfamoyl]phenyl]acrylate bistrifluoroacetate Yield: 149 mg (0.18 mmol) (23%)

MS (ESI m/z) 607 (MH+)

H-NMR (DMSO-d6) δ 1.70-1.85 (2H, m), 1.98-2.12 (2H, m), 2.55-2.65 (1H, m), 2.78-2.88 (1H, m), 3.00-3.16 (2H, m), 3.18-3.30 (2H, m), 3.57-3.70 (1H, m), 3.95-4.00 (2H, m), 4.53 (1H, m), 6.60 (1H, d), 6.72 (2H, d), 6.99 (2H, d), 7.15 (1H, dd), 7.29 (1H, d), 7.39 (1H, d), 7.54 (1H, t), 7.57 (2H, d), 7.59 (1H, d), 7.67 (2H, d), 8.18 (1H, d), 8.60 (2H, br), 9.20 (2H, br), 9.38 (2H, br)

Example 167

Synthesis of 4-[(2S)-1-[4-(4-piperidyloxy)phenyl]-3-(3-amidinophenoxy)-2-propylsulfamoyl]benzoic acid bistrifluoroacetate Synthesis of methyl 4-[(2S)-1-[4-(4-piperidyloxy)phenyl]-3-(3-amidinophenoxy)-2-propylsulfamoyl]benzoate bistrifluoroacetate Synthesis of ethyl 4-[(2S)-1-[4-(4-piperidyloxy)phenyl]-3-(3-amidinophenoxy)-2-propylsulfamoyl]benzoate bistrifluoroacetate

Step 1

Synthesis of methyl [4-[(2S)-1-[4-[1-(benzyloxycarbonyl)-4-piperidyloxy]phenyl]-3-(3-cyanophenoxy)-2-propylsulfamoyl]benzoate 738 mg (1.00 mmol) of 3-[(2S)-3-[4-[1-(benzyloxycarbonyl)-4-piperidyloxy]phenyl]-2-(4-iodobenzenesulfonylamino)propoxy]benzonitrile was dissolved in 5 ml of dimethylformamide, and 11 mg (0.05 mmol) of palladium acetate, 0.81 ml (2.0 mmol) of methanol and 0.28 ml (2.0 mmol) of triethylamine were added thereto and heated at 70° C. for 3.5 hours in the presence of carbon monoxide. The reaction mixture was treated in an ordinary manner with dichloromethane as the extractant to obtain the crude product. Then, it was purified by silica gel column chromatography to obtain the title compound.

Yield: 518 mg (0.76 mmol) (76%)

Step 2

Synthesis of 4-[(2S)-1-[4-(4-piperidyloxy)phenyl]-3-(3-amidinophenoxy)-2-propylsulfamoyl]benzoate ditrifluoroacetate Synthesis of methyl 4-[(2S)-1-[4-(4-piperidyloxy)phenyl]-3-(3-amidinophenoxy)-2-propylsulfamoyl]benzoate ditrifluoroacetate Synthesis of ethyl 4-[(2S)-1-[4-(4-piperidyloxy)phenyl]-3-(3-amidinophenoxy)-2-propylsulfamoyl]benzoate ditrifluoroacetate 518 mg (0.76 mmol) of methyl 4-[(2S)-1-[4-[1-(benzyloxycarbonyl)-4-piperidyloxy]phenyl]-3-(3-cyanophenoxy)-2-propylsulfamoyl]benzoate was used as the starting material and converted according to the same operation as in step 5 in Example 95, and de-protected to obtain the title compound.

4-[(2S)-1-[4-(4-piperidyloxy)phenyl]-3-(3-amidinophenoxy)-2-propylsulfamoyl]benzoic acid bistrifluoroacetate Yield: 17 mg (0.02 mmol) (3%)

MS (FAB, m/z) 553 (MH+)

H-NMR (DMSO-d6) δ 1.70-1.85 (2H, m), 2.00-2.15 (2H, m), 2.53-2.66 (1H, m), 2.80-2.90 (1H, m), 3.00-3.16 (2H, m), 3.20-3.30 (2H, m), 3.60-3.72 (1H, m), 3.98-4.03 (2H, m), 4.53 (1H, m), 6.72 (2H, d), 6.99 (2H, d), 7.18 (1H, dd), 7.29 (1H, d), 7.39 (1H, d), 7.50 (1H, t), 7.65 (2H, d), 7.89 (2H, d), 8.28 (1H, d), 8.50 (2H, br), 9.05 (2H, br), 9.28 (2H, br)

Methyl 4-[(2S)-1-[4-(4-piperidyloxy)phenyl]-3-(3-amidinophenoxy)-2-propylsulfamoyl]benzoate bistrifluoroacetate Yield: 80 mg (0.10 mmol) (13%)
MS (FAB, m/z) 567 (MH+)
H-NMR (DMSO-d6) δ 1.35 (3H, t), 1.70-1.85 (2H, m), 2.00-2.15 (2H, m), 2.55-2.68 (1H, m), 2.80-2.90 (1H, m), 3.00-3.16 (2H, m), 3.20-3.28 (2H, m), 3.60-3.72 (1H, m), 3.96-4.00 (2H, m), 4.34 (2H, q), 4.53 (1H, m), 6.75 (2H, d), 7.02 (2H, d), 7.15 (1H, dd), 7.20 (1H, d), 7.37 (1H, d), 7.48 (1H, t), 7.69 (2H, d), 7.91 (2H, d), 8.30 (1H, d), 8.53 (2H, br), 9.15 (2H, br), 9.26 (2H, br)

Ethyl 4-[(2S)-1-[4-(4-piperidyloxy)phenyl]-3-(3-amidinophenoxy)-2-propylsulfamoyl]benzoate bistrifluoroacetate Yield: 51 mg (0.06 mmol) (8%)
MS (FAB, m/z) 581 (MH+)
H-NMR (DMSO-d6) δ 1.70-1.85 (2H, m), 2.00-2.15 (2H, m), 2.53-2.66 (1H, m), 2.80-2.90 (1H, m), 3.00-3.16 (2H, m), 3.20-3.30 (2H, m), 3.60-3.72 (1H, m), 3.98-4.03 (2H, m), 4.53 (1H, m), 6.72 (2H, d), 6.99 (2H, d), 7.18 (1H, dd), 7.29 (1H, d), 7.39 (1H, d), 7.50 (1H t), 7.65 (2H, d), 7.89 (2H, d), 8.28 (1H, d), 8.50 (2H, br), 9.05 (2H, br), 9.28 (2H, br).

Example 168

Synthesis of 4-[(2S)-1-[4-(1-acetimidoyl-4-piperidyloxy)phenyl]-3-(3-amidinophenoxy)-2-propylsulfamoyl]benzoic acid bistrifluoroacetate 8 mg (0.01 mmol) of 4-[(2S)-1-[4-(4-piperidyloxy)phenyl]-3-(3-amidinophenoxy)-2-propylsulfamoyl]benzoate ditrifluoroacetate was dissolved in 2 ml of ethanol, and 9 mg (0.07 mmol) of ethylacetoimidate hydrochloride and 0.5 ml of triethylamine were added thereto and stirred for 24 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.
Yield: 3 mg (0.0037 mmol) (36%)
MS (ESI, m/z) 594 (MH+)
H-NMR (DMSO-d6) δ 1.60-1.80 (2H, m), 1.97-2.10 (2H, m), 2.29 (3H, s), 2.54-2.65 (1H, m), 2.69-2.90 (1H, m), 3.43-3.60 (2H, m), 3.62-3.84 (3H, m), 3.93-4.10 (2H, m), 4.55 (1H, m), 6.72 (2H, d), 6.99 (2H, d), 7.17 (1H, dd), 7.29 (1H, d), 7.39 (1H, d), 7.50 (1H, t), 7.65 (2H, d), 7.90 (2H, d), 8.27 (1H, d), 8.54-8.60 (1H, m), 9.03 (2H, br), 9.12 (1H, br), 9.28 (2H, br)

Example 169

Synthesis of methyl 4-[(2S)-1-[4-(1-acetimidoyl-4-piperidyloxy)phenyl]-3-(3-amidinophenoxy)-2-propylsulfamoyl]benzoate bistrifluoroacetate 40 mg (0.05 mmol) of methyl 4-[(2S)-1-[4-(4-piperidyloxy)phenyl]-3-(3-amidinophenoxy)-2-propylsulfamoyl]benzoate ditrifluoroacetate was used as the starting material, and the title compound was obtained according to the same operation as in Example 168.
Yield: 20 mg (0.024 mmol) (48%)
MS (ESI, m/z) 608 (MH+)
H-NMR (DMSO-d6) δ 1.62-1.82 (2H, m), 1.98-2.12 (2H, m), 2.30 (3H, s), 2.58-2.65 (1H, m), 2.80-2.87 (1H, m), 3.20-3.40 (2H, m), 3.42-3.80 (3H, m), 3.89 (3H, s), 3.96-4.05 (2H, m), 4.53 (1H, m), 6.78 (2H, d), 7.02 (2H, d), 7.18 (1H, dd), 7.20 (1H, d), 7.39 (1H, d), 7.45 (1H, t), 7.70 (2H, d), 7.92 (2H, d), 8.32 (1H, d), 8.60-8.70 (1H, m), 9.16 (1H, br), 9.26 (2H, br), 9.32 (2H, br)

Example 170

Synthesis of ethyl 4-[(2S)-1-[4-(1-acetimidoyl-4-piperidyloxy)phenyl]-3-(3-amidinophenoxy)-2-propylsulfamoyl]benzoate bistrifluoroacetate 26 mg (0.032 mmol) of ethyl 4-[(2S)-1-[4-(4-piperidyloxy)phenyl]-3-(3-amidinophenoxy)-2-propylsulfamoyl] benzoate ditrifluoroacetate was used as the starting material, and the title compound was obtained according to the same operation as in Example 168.
Yield: 10 mg (0.012 mmol) (37%)
MS (ESI, m/z) 622 (MH+)
H-NMR (DMSO-d6) δ 1.34 (3H, s), 1.55-1.70 (2H, m), 2.00-2.10 (2H, m), 2.29 (3H, s), 2.55-2.68 (1H, m), 2.77-2.88 (1H, m), 3.45-3.60 (2H, m), 3.66-3.80 (3H, m), 3.95-4.00 (2H, m), 4.34 (2H, q), 4.53 (1H, m), 6.74 (2H, d), 7.01 (2H, d), 7.14 (1H, dd), 7.21 (1H, d), 7.38 (1H, d), 7.48 (1H, t), 7.69 (2H, d), 7.92 (2H, d), 8.29 (1H, d), 8.54-8.58 (1H, m), 8.99 (2H, br), 9.10 (1H, br), 9.26 (2H, br)

Example 171

Synthesis of (2E)-3-[4-[(2S)-1-[4-(1-acetimidoyl-4-piperidyloxy)phenyl]-3-(3-amidinophenoxy)-2-propylsulfamoyl]phenyl]acrylic acid bistrifluoroacetate 39 mg (0.047 mmol) of (2E)-3-[4-[(2S)-1-[4-(4-piperidyloxy)phenyl]-3-(3-amidinophenoxy)-2-propylsulfamoyl] phenyl]acrylate ditrifluoroacetate was used as the starting material, and the title compound was obtained according to the same operation as in Example 168.
Yield: 20 mg (0.012 mmol) (49%)
MS (FAB, m/z) 620 (MH+)
H-NMR (DMSO-d6) δ 1.60-1.80 (2H, m), 1.95-2.10 (2H, m), 2.28 (3H, s), 2.54-2.65 (1H, m), 2.77-2.88 (1H, m), 3.45-3.60 (2H, m), 3.60-3.80 (3H, m), 3.91-4.03 (2H, m), 4.53 (1H, m), 6.60 (1H, d), 6.72 (2H, d), 6.98 (2H, d), 7.15 (1H, dd), 7.29 (1H, d), 7.39 (1H, d), 7.50 (1H, t), 7.56 (2H, d), 7.63 (1H, d), 7.67 (2H, d), 8.18 (1H, d), 8.55-8.60 (1H, m), 9.07 (2H, br), 9.13 (1H, br), 9.28 (2H, br).

Example 172

Synthesis of ethyl (2E)-3-[4-[(2S)-1-[4-(1-acetimidoyl-4-piperidyloxy)phenyl]-3-(3-amidinophenoxy)-2-propylsulfamoyl]phenyl]acrylate bistrifluoroacetate 72 mg (0.086 mmol) of ethyl (2E)-3-[4-[(2S)-1-[4-(4-piperidyloxy)phenyl]-3-(3-amidinophenoxy)-2-propylsulfamoyl]phenyl]acrylate ditrifluoroacetate was used as the starting material, and the title compound was obtained according to the same operation as in Example 168.
Yield: 40 mg (0.046 mmol) (53%)
MS (FAB, m/z) 648 (MH+)

H-NMR (DMSO-d6) δ 1.29 (3H, t), 1.60-1.80 (2H, m), 1.96-2.10 (2H, m), 2.28 (3H, s), 2.54-2.65 (1H, m), 2.78-2.88 (1H, m), 3.45-3.56 (2H, m), 3.60-3.80 (3H, m), 3.95-4.02 (2H, m), 4.22 (2H, q), 4.53 (1H, m), 6.68 (1H, d), 6.72 (2H, d), 6.98 (2H, d), 7.17 (1H, dd), 7.27 (1H, d), 7.38 (1H, d), 7.50 (1H, t), 7.56 (2H, d), 7.64 (1H, d), 7.67 (2H, d), 8.18 (1H, d), 8.50-8.60 (1H, m), 9.03 (2H, br), 9.10 (1H, br), 9.27 (2H, br)

Example 173

Synthesis of 2-[(2S)-1-[4-(1-acetimidoyl-4-piperidyloxy)phenyl]-3-(3-amidinophenoxy)-2-propylsulfamoyl]benzoic acid bistrifluoroacetate Step 1

Synthesis of benzyl 2-[(2S)-1-[4-[1-(benzyloxycarbonyl)-4-piperidyloxy]phenyl]-3-(3-cyanophenoxy)-2-propylsulfamoyl]benzoate 5 ml of 4 N hydrogen chloride in dioxane and 2.5 ml of dioxane were added to 500 mg (0.854 mmol) of 3-[(2S)-3-[4-[1-(benzyloxycarbonyl)-4-piperidyloxy]phenyl]-2-(4-iodobenzenesulfonylamino)propoxy]benzonitrile. The mixture was stirred at room temperature for 24 hours, and the solvent was distilled off under reduced pressure, and the resulting residue was dissolved in 8 ml of DMF, and 0.49 ml (2.56 mmol) of di-isopropylethylamine and 398 mg (1.28 mmol) of 2-(benzyloxycarbonyl)benzene sulfonyl chloride were added thereto at 0° C. The mixture was stirred for 1 hour, then allowed to reach room temperature, and stirred for additional 24 hours. The reaction solution was extracted with ethyl acetate, washed with water, 1 N hydrogen chloride and saturated saline, and dried over powdery magnesium sulfate. The solvent was distilled off, and the resulting residue was purified by silica gel column chromatography to obtain the title compound.

Yield: 490 mg (0.646 mmol) (77%)

H-NMR (CDCl3) δ 1.63-1.80 (2H, m), 1.82-2.00 (2H, m), 2.70-3.00 (2H, m), 3.38-3.49 (2H, m), 3.61-3.93 (4H, m), 4.22-4.45 (2H, m), 5.15 (2H, s), 5.37 (2H, m), 6.38 (1H, d), 6.55 (1H, d), 6.78 (1H, d), 6.83 (1H, t), 6.93 (1H, d), 7.00 (1H, d), 7.20-7.60 (1H, m), 7.71 (1H, d), 7.82 (1H, d)

Step 2

Synthesis of 2-[(2S)-1-[4-(4-piperidyloxy)phenyl]-3-(3-amidinophenoxy)-2-propylsulfamoyl]benzoate ditrifluoroacetate 490 mg (0.646 mmol) of benzyl 2-[(2S)-1-[4-[1-(benzyloxycarbonyl)-4-piperidyloxy]phenyl]-3-(3-cyanophenoxy)-2-propylsulfamoyl]benzoate was used as the starting material and converted according to the same operation as in step 5 in Example 95, and de-protected to obtain the title compound.

Yield: 50 mg (0.046 mmol) (10%)

MS (FAB, m/z) 552 (M+)

H-NMR (DMSO-d6) δ 1.70-1.85 (2H, m), 2.00-2.12 (2H, m), 2.60-2.62 (1H, m), 2.77-2.88 (1H, m), 3.01-3.16 (2H, m), 3.19-3.27 (2H, m), 3.78-3.94 (2H, m), 4.46-4.59 (2H, m), 6.77 (2H, d), 7.02 (2H, d), 7.09 (2H, d), 7.22 (1H, d), 7.31 (1H, d), 7.38 (1H, t), 7.49 (1H, dd), 7.58 (1H, d), 7.73 (1H, br), 7.80 (1H, d), 8.15 (1H, d), 8.42-8.58 (1H, m), 9.07 (1H, br), 9.27 (1H, br)

Step 3

Synthesis of 2-[(2S)-1-[4-(1-acetoimidoyl-4-piperidyloxy)phenyl]-3-(3-amidinophenoxy)-2-propylsulfamoyl]benzoate ditrifluoroacetate 50 mg (0.046 mmol) of 2-[N-[(1S)-1-[(3-amidino-1-phenyl)oxy]methyl-2-[4-(4-piperidyl)oxy]phenyl]ethyl]sulfamoyl benzoate ditrifluoroacetate was subjected as the starting material to the same operation as in Example 168 to obtain the title compound.

Yield: 25 mg (0.030 mmol) (66%)

MS (FAB, m/z) 593 (MH+)

H-NMR (DMSO-d6) δ 1.65-1.80 (2H, m), 1.95-2.10 (2H, m), 2.28 (3H, s), 2.59-2.70 (1H, m), 2.73-2.88 (1H, m), 3.44-3.58 (2H, m), 3.67-3.80 (2H, m), 3.82-3.94 (3H, m), 4.62 (1H, m), 6.77 (2H, d), 7.00 (2H, d), 7.10 (1H, dd), 7.21 (1H, d), 7.37 (1H, t), 7.42 (1H, d), 7.49 (1H, d), 7.58 (1H, d), 7.73 (1H, br), 7.75 (1H, d), 8.15 (1H, d), 8.57 (1H, br), 9.03 (2H, r), 9.12 (1H, br), 9.26 (2H, br)

Example 174

Synthesis of 3-[(3R)-3-(benzenesulfonylamino)-4-[4-(4-piperidyloxy)phenyl]butyl]benzamidine bistrifluoroacetate Step 1

Synthesis of 3-[(3S)-4-[4-[1-(benzyloxycarbonyl)-4-piperidyloxy]phenyl]-3-(t-butoxycarbonylamino)-1-butenyl]benzonitrile 3.87 g (7.70 mmol) of methyl (2S)-3-[4-[1-(benzyloxycarbonyl)-4-piperidyloxy]phenyl]-2-(t-butoxycarbonylamino) propionate was dissolved in 77 ml of toluene. 19.3 ml (19.3 mmol) of 1.0 M solution of diisobutylaluminum hydride in hexane was added to the obtained solution at −78° C., and they were stirred for 10 minutes. 10 ml of methanol and 20 ml of saturated aqueous solution of potassium sodium tartrate were added to the resultant mixture, and they were stirred at room temperature for additional one hour. After the treatment with ethyl acetate as the extractant in an ordinary manner, the obtained oily residue was dissolved in a mixed solvent of 30 ml of ethanol and 30 ml of tetrahydrofuran. After the addition of 3.53 g (7.70 mmol) of (3-cyanobenzyl)triphenylphosphonium bromide and 1.15 ml (7.70 mmol) of DBU at room temperature, the resultant mixture was stirred for one hour. The solvent was distilled off under reduced pressure, and the residue was purified by the silica gel column chromatography to obtain the title compound in the form of a mixture of geometrical isomers (E:Z=2:3).

Yield: 2.33 g (4.00 mmol) (52%)

MS (ESI, m/z) 604 (MNa+)

H-NMR (CDCl3) δ 1.43 (9H, s), 1.69-1.83 (2H, m), 1.85-1.98 (2H, m), 2.68 (1H, dd), 2.89 (1H, dd), 3.46 (2H, ddd), 3.76 (2H, ddd), 4.42-4.50 (1H, m), 4.52-4.67 (1H, m), 5.14 (2H, s), 5.59 (1H, dd, for Z isomer) 6.20 (1H, dd, for E isomer), 6.41 (1H, d, for E isomer), 6.42 (1H, d, for Z isomer), 6.81 (1H, d, for Z isomer), 6.85 (1H, d, for E isomer), 7.03 (1H, d, for Z isomer), 7.11 (1H, d, for E isomer), 7.28-7.50 (9H, m)

Step 2

Synthesis of 3-[(3S)-4-[4-[1-(benzyloxycarbonyl)-4-pipelidyloxy]phenyl]-3-(benzenesulfonylamino)-1-butenyl]benzonitrile 2.33 g (4.00 mmol) of 3-[(3S)-4-[4-[1-(benzyloxycarbonyl)-4-piperidyloxy]phenyl]-3-(t-butoxycarbonylamino)-1-butenyl]benzonitrile was dissolved in 20 ml of 4 N hydrogen chloride in dioxane and 10 ml dioxane, and then stirred at room temperature for 24 hours. The solvent was distilled off under reduced pressure whereby an oily residue was obtained. The oily residue thus obtained was dissolved in 20 ml of DMF, and 2.09 ml (12.00 mmol) of di-isopropylethylamine and 1.06 g (6.00 mmol) of benzene sulfonyl chloride were added thereto at 0° C. and stirred for 2.5 hours. The crude product was obtained by use of ethyl acetate as the extractant in the same isolation process as in step 1 in Example 1. Subsequently, it was purified by silica gel column chromatography to obtain the title compound as a mixture of geometrical isomers (E: Z=2:3).

Yield: 2.11 g (3.39 mmol) (85%)

H-NMR (CDCl3) δ 1.70-1.83 (2H, m), 1.86-2.01 (2H, m), 2.73 (1H, dd, for Z isomer), 2.81 (1H, d, for E isomer), 2.86 (1H, dd, for Z isomer), 2.98 (1H, d, for E isomer), 3.45 (2H, ddd), 3.76 (2H, ddd), 4.11-4.22 (1H, m), 4.43-4.49 (1H, m), 5.14 (2H, s), 5.52 (1H, dd, for Z isomer), 5.94 (1H, dd, for E isomer), 6.27 (1H, d, for E isomer), 6.34 (1H, d, for Z isomer), 6.77 (2H, d), 6.90 (2H, d), 7.08 (1H, d), 7.26-7.38 (9H, m), 7.49 (1H, t), 7.56 (1H, d).

Step 3

Synthesis of 3-[(3R)-3-(benzenesulfonylamino)-4-[4-(4-piperidyloxy)phenyl]butyl]benzamidine bistrifluoroacetate 669 mg (1.08 mmol) of 3-[(3S)-4-[4-[1-(benzyloxycarbonyl)-4-piperidyloxy]phenyl]-3-(benzenesulfonylamino)-1-butenyl]benzonitrile and 20 mg of 10% palladium/carbon were dissolved in a mixed solvent of 2 ml of methanol and 3 ml of dichloromethane, and they were stirred at room temperature in 1 atm. hydrogen atmosphere for 2 hours. Palladium/carbon was removed by the suction filtration, and the filtrate was concentrated to obtain an oily residue. The residue was added to 10 ml of ethanol containing 30% (w/v) of hydrogen chloride, and they were stirred at room temperature overnight. The solvent was distilled off, and the residue was dissolved in 30 ml of 10% (w/v) solution of ammonia in ethanol at room temperature. The solution was stirred at room temperature overnight. The solvent was distilled to obtain a residue, which was dissolved in 20 ml of a solution of hydrogen bromide in acetic acid, and they were stirred at room temperature for 2 hours. The solvent was distilled off, and the residue was treated by the reversed phase high-performance liquid chromatography with silica gel having octadodecyl group chemically bonded thereto. After the elution with a mixed solvent of water and acetonitrile containing 0.1% (v/v) of trifluoroacetic acid, the fraction of the intended product was freeze-dried to obtain the title compound.

Yield: 0.302 g (0.41 mmol) (38%)

H-NMR (DMSO-d6) δ 1.50-1.70 (2H, m), 1.70-1.86 (2H, m), 2.00-2.11 (2H, m), 2.33-2.74 (4H, m), 3.01-3.16 (2H, m), 3.18-3.30 (2H, m), 3.31-3.44 (1H, m), 4.51-4.60 (1H, m), 6.81 (2H, d), 6.96 (2H, d), 7.33 (1H, d), 7.43-7.62 (5H, m), 7.74 (2H, d), 7.80 (1H, d), 8.53 (2H, br), 9.08 (2H, s), 9.22 (2H, s)

Example 175

Synthesis of 3-[(3R)-3-(benzenesulfonylamino)-4-[4-(1-acetimidoyl-4-piperidyloxy)phenyl]butyl]benzamidine bistrifluoroacetate 0.7 mg (0.015 mmol) of 3-[(3R)-3-(benzenesulfonylamino)-4-[4-(4-piperidyloxy)phenyl]butyl]benzamidine ditrifluoroacetate was used as the starting material, and the title compound was obtained according to the same operation as in Example 158.

Yield: 11.1 mg (0.014 mmol) (95%)

MS (ESI, m/z) 548 (MH+)

H-NMR (DMSO-d6) δ 1.50-1.82 (4H, m), 1.97-2.10 (2H, m), 2.29 (3H, s), 2.34-2.72 (4H, m), 3.22-3.59 (4H, m), 3.68-3.82 (1H, m), 4.57-4.66 (1H, m), 6.82 (2H, d), 6.97 (2H, d), 7.33 (1H, d), 7.43-7.62 (5H, m), 7.74 (2H, d), 7.81 (1H, d), 8.60 (1H, s), 9.15 (1H, s), 9.20 (2H, s), 9.23 (2H, s)

Example 176

Synthesis of 3-[(3S, 1Z)-3-(benzenesulfonylamino)-4-[4-(1-acetimidoyl-4-piperidyloxy)phenyl]-1-butenyl]benzamidine bistrifluoroacetate 120 mg (0.19 mmol) of 3-[(3S)-4-[4-[1-(benzyloxycarbonyl)-4-piperidyloxy]phenyl]-3-(benzenesulfonylamino)-1-butenyl]benzonitrile was added to 2 ml of ethanol containing 30% (V/V) hydrogen chloride and stirred at room temperature overnight. Subsequently, it was dissolved in 5 ml of an ethanol solution containing 10% (w/v) ammonia at room temperature and stirred at room temperature overnight. The solvent was distilled off, and the resulting residue was dissolved in 5 ml solution of hydrogen bromide in acetic acid under cooling with ice and stirred for 2 hours. The solvent was distilled off, and the resulting residue was converted according to the same operation as in Example 158 whereby the title compound was obtained.

Yield: 12 mg (0.016 mmol) (8.4%)

MS (ESI, m/z) 546 (MH+)

H-NMR (DMSO-d6) δ 1.64-1.81 (2H, m), 1.96-2.10 (2H, m), 2.28 (3H, s), 2.46-2.52 (1H, m), 2.67-2.73 (1H, m), 3.47-3.52 (2H, m), 3.70-3.77 (2H, m), 4.11-4.23 (1H, m), 4.56-4.67 (1H, m), 5.47 (1H, dd), 6.27 (1H, d), 6.82 (2H, d), 6.96 (2H, d), 7.06 (1H, d), 7.28 (1H, s), 7.42-7.49 (3H, m), 7.54-7.58 (3H, m), 7.65 (1H, d), 8.02 (1H, d), 8.58 (1H, s), 9.12 (1H, s), 9.18 (2H, s), 9.29 (2H, s)

Example 177

Synthesis of (2S)—N-(3-amidinophenyl)-2-(benzenesulfonylamino)-3-[4-(4-piperidyloxy)phenyl]propionamide bistrifluoroacetate

Step 1

Synthesis of methyl (2S)-2-(benzenesulfonylamino)-3-[4-[1-(benzyloxycarbonyl)-4-piperidyloxy]phenyl]propionate 3.96 g (7.94 mmol) of methyl (2S)-3-[4-[1-(benzyloxycarbonyl)-4-piperidyloxy]phenyl]-2-(t-butoxycarbonylamino)propionate was dissolved in 30 ml of a dioxane solution containing 4 N hydrogen chloride and stirred at room temperature for 4 hours. The solvent was distilled off, and the resulting oily residue was dissolved in 40 ml of DMF, and 5.14 ml (23.83 mmol) of di-isopropylethylamine and 2.10 g (11.91 mmol) of benzene sulfonium chloride were added thereto at 0° C., and the mixture was stirred at room temperature for 2.5 hours. The crude product was obtained in an ordinary manner by treatment with ethyl acetate as the extractant. Then, it was purified by silica gel column chromatography to obtain the title compound.

Yield: 3.5 g (6.52 mmol) (82%)

H-NMR (CDCl3) δ 1.60-2.00 (4H, m), 2.95 (1H, d), 3.45 (2H, ddd), 3.47 (3H, s), 3.76 (2H, ddd), 4.19 (1H, dt), 4.41-4.49 (1H, m), 5.16 (2H, s), 6.78 (2H, d), 6.98 (2H, d), 7.30-7.58 (8H, m), 7.76 (2H, d)

Step 2

Synthesis of (2S)—N-(3-amidinophenyl)-2-(benzenesulfonylamino)-3-[4-[1-(benzyloxycarbonyl)-4-piperidyloxy]phenyl]propionamide 1.75 g (3.26 mmol) of methyl (2S)-2-(benzenesulfonylamino)-3-[4-[1-(benzyloxycarbonyl)-4-piperidyloxy]phenyl]propionate was dissolved in a mixed solvent of 10 ml of methanol and 10 ml of tetrahydrofuran. 6.52 ml (6.52 mmol) of 1 N aqueous sodium hydroxide solution was added to the solution, and they were stirred at 50° C. overnight. The reaction mixture was washed with ether and then made acidic with concentrated hydrochloric acid. After the isolation process with dichloromethane as the extractant in the same manner as that of step 1 in Example 1, an oily residue was obtained, which was dissolved in 60 ml of pyridine. 747 mg (3.61 mmol) of 3-aminobenzamidine dihydrochloride and 750 mg (3.92 mmol) of WSC were added to the solution, and they were stirred at room temperature overnight. The solvent was distilled off, and the residue was purified by the silica gel column chromatography to obtain the title compound.

Yield: 1.89 g (2.90 mmol) (89%)

H-NMR (CDCl3) δ 1.72-1.83 (2H, m), 1.85-2.00 (2H, m), 3.32 (1H, dd), 3.44 (2H, ddd), 3.61 (1H, dd), 3.78 (2H, ddd), 4.04-4.14 (1H, m), 4.42-4.51 (1H, m), 5.32 (2H, s), 6.84 (2H, d), 7.18 (2H, d), 7.28-7.38 (9H, m), 7.43-7.50 (2H, m), 7.64-7.69 (2H, m), 7.77-7.83 (1H, m), 8.02 (4H, s)

Step 3

Synthesis of (2S)—N-(3-amidinophenyl)-2-(benzenesulfonylamino)-3-[4-(4-piperidyloxy)phenyl]propionamide bistrifluoroacetate 90 mg (0.13 mmol) of (2S)—N-(3-amidinophenyl)-2-(benzenesulfonylamino)-3-[4-[1-(benzyloxycarbonyl)-4-piperidyloxy]phenyl]propionamide was dissolved in 20 ml solution of hydrogen bromide in acetic acid and stirred at room temperature for 2 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 34 mg (0.065 mmol) (49%)

MS (ESI, m/z) 522 (MH+)

H-NMR (DMSO-d6) δ 1.71-1.88 (2H, m), 2.02-2.16 (2H, m), 2.68 (1H, dd), 2.88 (1H, dd), 3.03-3.17 (2H, m), 3.20-3.30 (2H, m), 4.05-4.15 (1H, m), 4.54-4.62 (1H, m), 6.83 (2H, d), 7.10 (2H, d), 7.34 (2H, dt), 7.42-7.50 (2H, m), 7.57 (2H, d), 7.70 (1H, d), 7.92 (1H, d), 8.38 (1H, d), 8.58 (2H, br), 9.13 (2H, s), 9.31 (2H, s), 10.42 (1H, s)

Example 178

Synthesis of (2S)—N-(3-amidinophenyl)-2-(benzenesulfonylamino)-3-[4-(1-acetimidoyl-4-piperidyloxy)phenyl]propionamide bistrifluoroacetate 80 mg (0.153 mmol) of (2S)—N-(3-amidinophenyl)-2-(benzenesulfonylamino)-3-[4-(4-piperidyloxy)phenyl]propionamide ditrifluoroacetate was used as the starting material, and the title compound was obtained according to the same operation as in Example 158.

Yield: 30 mg (0.038 mmol) (25%)

MS (ESI, m/z) 563 (MH+)

H-NMR (DMSO-d6) δ 1.65-1.72 (2H, m), 1.98-2.12 (2H, m), 2.30 (3H, s), 2.67 (1H, dd), 2.88 (1H, dd), 3.46-3.60 (2H, m), 3.69-3.82 (2H, m), 4.04-4.16 (1H, m), 4.58-4.68 (1H, m), 6.82 (2H, d), 7.11 (2H, d), 7.33 (2H, t), 7.42-7.48 (2H, m), 7.53 (2H, t), 7.70 (1H, d), 7.92 (1H, s), 8.38 (1H, d), 8.60 (1H, s), 9.11 (2H, s), 9.12 (1H, s), 9.32 (2H, s), 10.41 (1H, s)

Example 179

Synthesis of 3-[(2S)-2-(benzenesulfonylamino)-3-[4-(4-piperidyloxy)phenyl]propoxy]-4-iodobenzamidine bistrifluoroacetate Step 1

Synthesis of 3-[(2S)-3-[4-(1-benzyloxycarbonyl-4-piperidyloxy)phenyl]-2-(t-butoxycarbonylamino)propoxy]-4-iodobenzonitrile 1.3 g (2.6 mmol) of benzyl 4-[4-[(2S)-3-chloro-2-(t-butoxycarbonylamino)propyl]phenoxy]piperidine-1-carboxylate, 686 mg (2.8 mmol) of 3-hydroxy-4-iodobenzonitrile and 390 mg (2.8 mmol) of potassium carbonate were dissolved in dimethylformamide. The solution was stirred at 65° C. for 4 days, and then treated with ethyl acetate as the extractant in an ordinary manner to obtain the title compound, which was then subjected to the subsequent reaction without further purification.

Step 2

Synthesis of 3-[(2S)-2-(benzenesulfonylamino)-3-[4-(1-benzyloxycarbonyl-4-piperidyloxy)phenyl]propoxy]-4-iodobenzonitrile 1.6 g (2.7 mmol) of 3-[(2S)-3-[4-(1-benzyloxycarbonyl-4-piperidyloxy)phenyl]-2-(t-butoxycarbonylamino)propoxy]-4-iodobenzonitrile was dissolved in 4 N solution of hydrogen chloride in dioxane, and the solution was stirred at room temperature overnight. The solvent was distilled off, and the residue was dissolved in dimethylformamide. 1 ml (6 mmol) of N,N-diisobutylethylamine and 0.34 ml (2.7 mmol) of benzenesulfonyl chloride were added to the solution under cooling with ice, and they were stirred for 2 hours. After the isolation process with ethyl acetate as the extractant in the same manner as that of step 1 in Example 1, the crude product was obtained, which was purified by the silica gel column chromatography to obtain the title compound.

Yield: 1.17 g (1.56 mmol) (71%).

H-NMR (CDCl3) δ 1.70-1.80 (2H, m), 1.85-1.95 (2H, m), 2.85-3.05 (2H, m), 3.40-3.50 (2H, m), 3.70-3.90 (5H, m), 4.40 (1H, m), 4.90 (1H, d), 5.15 (2H, s), 6.71 (1H, s), 6.75 (2H, d), 6.95 (2H, d), 7.01 (1H, d), 7.30-7.55 (8H, m), 7.76-7.81 (2H, m), 7.89 (1H, d)

Step 3

Synthesis of 3-[(2S)-2-(benzenesulfonylamino)-3-[4-(4-piperidyloxy)phenyl]propoxy]-4-iodobenzamidine bistrifluoroacetate 97 mg (0.13 mmol) of 3-[(2S)-2-(benzenesulfonylamino)-3-[4-(1-benzyloxycarbonyl-4-piperidyloxy)phenyl]propoxy]-4-iodobenzonitrile was dissolved in 3 ml of 4 N hydrogen chloride in dioxane, 0.5 ml of ethanol was added thereto, and the mixture was stirred at room temperature for 4 days. The solvent was distilled off under reduced pressure, and the resulting residue was dissolved in 30 ml of an ethanol solution containing 10% (w/v) ammonia and stirred at room temperature overnight. The solvent was distilled off, and the resulting residue was dissolved in acetic acid containing 20% hydrogen bromide and stirred for 2 hours under cooling with ice. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 35 mg (0.04 mmol) (31%)

MS (ESI, m/z) 635 (MH+)

H-NMR (DMSO-d6) δ 1.70-1.85 (2H, m), 2.00-2.12 (2H, m), 2.50-3.60 (7H, m), 4.05 (2H, m), 4.50 (1H, m), 6.74 (2H, d), 6.98 (2H, d), 7.21 (1H, d), 7.26 (1H, s), 7.37-7.67 (5H, m), 8.30 (1H, d), 8.16 (1H, d), 8.56 (2H, brs), 9.18 (2H, brs), 9.32 (2H, brs)

Example 180

Synthesis of 3-[4-amidino-2-[(2S)-2-(benzenesulfonylamino)-3-[4-(4-piperidyloxy)phenyl]propoxy]phenyl]-2-oxopropionic acid bistrifluoroacetate

Step 1

Synthesis of methyl 2-acetylamino-3-[2-[(2S)-2-(benzenesulfonylamino)-3-[4-(4-piperidyloxy)phenyl]propoxy]-4-cyanophenyl]acrylate 197 mg (0.26 mmol)) of 3-[(2S)-2-(benzenesulfonylamino)-3-[4-(1-benzyloxycarbonyl-4-piperidyloxy)phenyl]propoxy]-4-iodobenzonitrile and 74.4 mg (0.52 mmol) of methyl 2-acetaminoacrylate were dissolved in 6 ml of acetonitrile. 7.3 mg (0.03 mmol) of palladium (II) acetate, 55 mg (0.18 mmol) of tri-o-tolylphosphine and 96 mg (0.52 mmol) of tributylamine were added to the solution, and they were heated under reflux overnight. The solvent was distilled off and the residue was treated with ethyl acetate as the extractant in an ordinary manner to obtain the crude product, which was purified by the silica gel column chromatography to obtain the title compound.

Yield: 111 mg (0.15 mmol) (58%).

H-NMR (CDCl3) δ 1.68-1.80 (2H, m), 1.84-1.96 (2H, m), 2.07 (3H, s), 2.75-2.90 (2H, m), 3.40-3.50 (2H, m), 3.70-3.95 (8H, m), 4.40 (1H, m), 5.15 (2H, s), 5.35 (1H, d), 6.73 (2H, d), 6.89 (1H, s), 6.91 (2H, d), 7.22 (1H, d), 7.28-7.47 (9H, m), 7.53 (1H, m), 7.74-7.76 (2H, m)

Step 2

Synthesis of 3-[4-amidino-2-[(2S)-2-(benzenesulfonylamino)-3-[4-(4-piperidyloxy)phenyl]propoxy]phenyl]-2-oxopropionic acid bistrifluoroacetate 500 mg of methyl 2-acetylamino-3-[2-[(2S)-2-(benzenesulfonylamino)-3-[4-(4-piperidyloxy)phenyl]propoxy]-4-cyanophenyl]acrylate was dissolved in 10 ml of 4 N hydrogen chloride in dioxane, 2 ml of ethanol was added thereto, and the mixture was stirred at room temperature for 2 days. The solvent was distilled off, and the resulting residue was dissolved in an ethanol solution containing 10% (w/v) ammonia and stirred at room temperature for 3 days. The solvent was distilled off, and the resulting residue was dissolved in 10 ml acetic acid containing 20% hydrogen bromide and stirred for 3 hours under cooling with ice. The solvent was distilled off, and 25 ml of 3 N hydrogen chloride and 8 ml of acetic acid were added to the resulting residue which was then heated under reflux for 5 hours. The solvent was distilled off under reduced pressure, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 152 mg (0.19 mmol) (30%)

MS (ESI, m/z) 595 (MH+)

H-NMR (DMSO-d6) δ

1.70-1.82 (2H, m), 2.00-2.12 (2H, m), 2.55 (1H, m), 2.90 (1H, m), 3.02-4.05 (7H, m), 4.15 (1H, d, keto form), 4.30 (1H, d, keto form), 4.50 (1H, m), 6.70-7.02 (4H, m), 6.91 (1H, s, enol form), 7.15-7.70 (7H, m), 8.23 (1H, d), 8.34 (1H, d), 8.6 (2H, brs), 9.05-9.30 (4H, m)

Example 181

Synthesis of 3-[4-amidino-2-[(2S)-3-[4-(1-acetimidoyl-4-piperidyloxy)phenyl]-2-(benzenesulfonylamino)propoxy]phenyl]-2-oxopropionic acid bistrifluoroacetate 162 mg (0:2 mmol) of 3-[4-amidino-2-[(2S)-2-(benzenesulfonylamino)-3-[4-(4-piperidyloxy)phenyl]propoxy]phenyl]-2-oxopropionic acid bistrifluoroacetate was dissolved in 5 ml of ethanol. 1.5 g (15 mmol) of triethylamine and 435 mg (3.5 mmol) of ethyl acetimidate hydrochloride were added to the solution, and they were stirred at room temperature for 14 days. The solvent was distilled off, and the residue was treated by the reversed phase high-performance liquid chromatography with silica gel having octadodecyl group chemically bonded thereto. After the elution with a mixed solvent of water and acetonitrile containing 0.1% (v/v) of trifluoroacetic acid, the fraction of the intended product was freeze-dried to obtain the title compound.

Yield: 117 mg (0.135 mmol) (67%)

MS (ESI, m/z) 636 (MH+)

H-NMR (DMSO-d6) δ 1.60-1.80 (2H, m), 1.95-2.10 (2H, m), 2.25 (3H, s), 2.60 (1H, m), 2.90 (1H, m), 3.30-4.10 (7H, m), 4.22 (1H, d, keto form), 4.45 (1H, d, keto form), 4.59 (1H, m), 6.70-7.00 (4H, m), 6.90 (1H, s, enol form), 7.15-7.67 (7H, m), 8.23 (1H, d), 8.33 (1H, d), 8.58 (1H, brs), 9.00-9.30 (5H, m), 9.80 (1H, br, enol form)

Example 182

The activity of inhibiting the activated blood coagulation factor X was determined in the same manner as that of Example 93. The representative compounds (Example No.) and the results are shown in Table 2 given below.

Example 183

The activity of inhibiting thrombin was determined in the same manner as that of Example 94. The representative compounds (Example No.) and the results are shown in Table 2 given below.

Example 184

Determination of Blood Anticoagulating Activity

The blood anticoagulating activity was determined by a prothrombin time (PT) determination method. The PT was determined as follows: The blood was taken from healthy people. 3.8% aqueous trisodium citrate solution was added to the blood in a volume ratio of 1:10. The blood plasma was separated by the centrifugation. 5 μl of DMSO solution containing a test compound was added to 45 μl of the blood plasma. After the incubation at room temperature for 2 minutes, a test tube containing the blood plasma solution was placed in Sysmex CA-3000 fully automatic blood coagulation determination device (a product of Toa Medical Electronics Co., Ltd), and incubated at 37° C. for 3 minutes. 100 μl of Sysmex PT II (rabbit brain tissue thromboplastin, 13.2 mM calcium chloride; a product of Toa Medical Electronics Co., Ltd) was fed into the test tube. PT was automatically determined with the device. A sample containing 5 μl of DMSO in place of the solution of the test compound was used as the control. The negative logarithm (PT2) of the concentration of the test compound which elongated PT of the control to the twice as long was determined, and employed as the index of the blood anticoagulating activity. The blood anticoagulating activities of representative compounds are shown in Table 2 given below.

TABLE 2

| | Activity of inhibiting activated blood coagulation factor X (pIC$_{50}$) | Thrombin-inhibiting activity (pIC$_{50}$) | Blood anticoagulating activity (PT2) |
|---|---|---|---|
| Compound of Ex. 95 | 6.5 | 3.4 | 5.9 |
| Compound of Ex. 96 | 5.8 | <3 | — |
| Compound of Ex. 98 | 5.5 | 3.2 | <4.5 |
| Compound of Ex. 99 | 6.6 | 3.5 | 6.2 |
| Compound of Ex. 114 | 7.3 | 4.1 | — |
| Compound of Ex. 117 | 7.4 | 3.6 | 6.7 |
| Compound of Ex. 119 | 7.6 | <3 | — |
| Compound of Ex. 121 | 7.3 | <3 | — |
| Compound of Ex. 122 | 6.3 | <3 | 4.5 |
| Compound of Ex. 143 | 6.3 | 3.4 | 5.3 |
| Compound of Ex. 144 | 5.8 | 3.4 | 5 |
| Compound of Ex. 147 | 7.4 | 4.7 | 6.5 |
| Compound of Ex. 154 | 5.8 | 4.1 | 5.1 |
| Compound of Ex. 158 | 6.8 | 4.3 | 6.2 |
| Compound of Ex. 160 | 6.5 | 3.8 | — |
| Compound of Ex. 162 | 6.6 | 4.4 | — |
| Compound of Ex. 165 | 6.7 | 4 | 6 |
| Compound of Ex. 167 | 6.3 | 3.9 | 5 |
| Compound of Ex. 168 | 7.5 | 4.1 | 6.2 |
| Compound of Ex. 171 | 7 | 4.4 | 6 |
| Compound of Ex. 175 | 6.6 | 4.2 | 5.9 |
| Compound of Ex. 178 | 6.3 | <3.4 | 5.7 |

TABLE 2-continued

| | Activity of inhibiting activated blood coagulation factor X (pIC$_{50}$) | Thrombin-inhibiting activity (pIC$_{50}$) | Blood anticoagulating activity (PT2) |
|---|---|---|---|
| Compound of Ex. 180 | 6.8 | 5.5 | 5.7 |
| Compound of Ex. 181 | 7.7 | 5.8 | 6.7 |

In Table 2, the compound of Example 122 was N-[3-(3-amidinophenoxy)propyl]-4-amidinobenzamide bistrifluoroacetate, that of Example 154 was 3-[(2S)-2-(benzenesulfonylamino)-3-[4-(4-piperidyloxy)phenyl]propoxy]benzamidine bistrifluoroacetate, and that of Example 167 was 4-[(2S)-1-[4-(4-piperidyloxy)phenyl]-3-(3-amidinophenoxy)-2-propylsulfamoyl]benzoic acid bistrifluoroacetate.

It is apparent from the results that the benzamidine derivatives of the present invention have a high activity of specifically inhibiting the activated blood coagulation factor X and, therefore, also a high blood anticoagulating activity.

The structural formulae of the compounds of the present invention used in Examples 95 to 181 are given below.

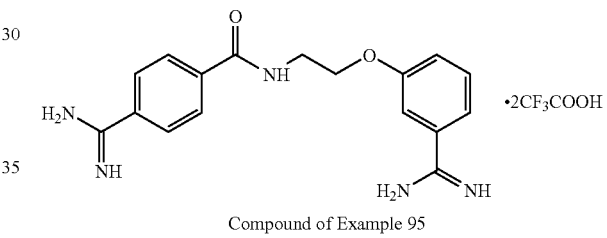

Compound of Example 95

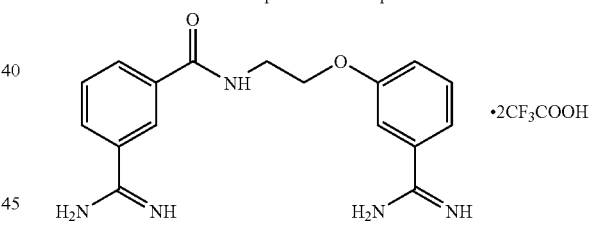

Compound of Example 96

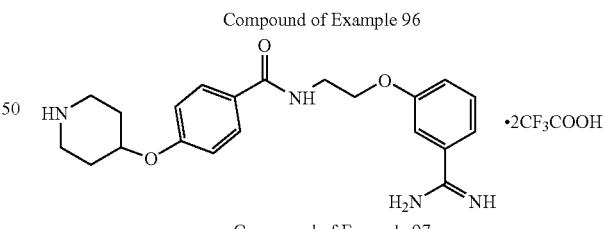

Compound of Example 97

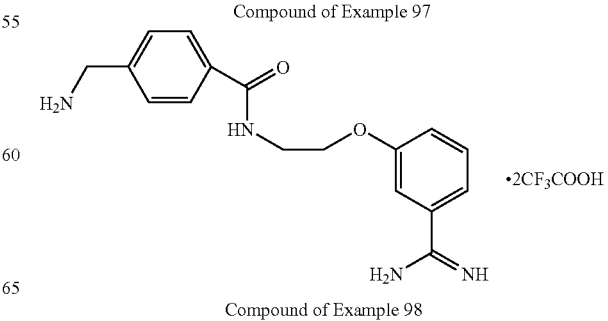

Compound of Example 98

-continued
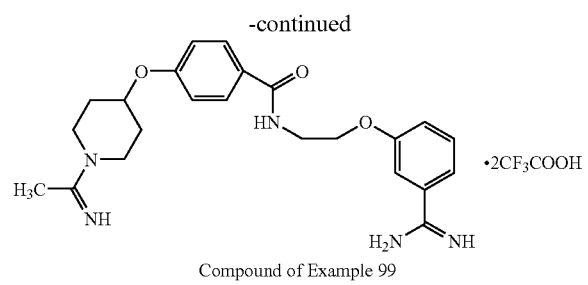
Compound of Example 99
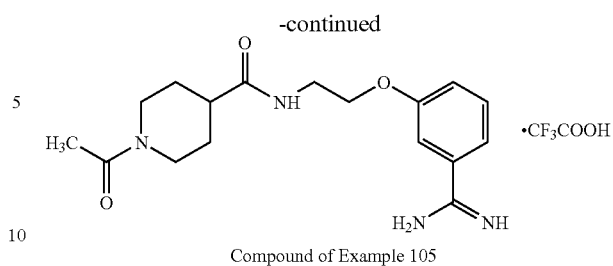
Compound of Example 105
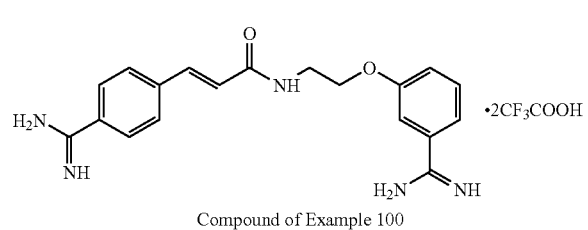
Compound of Example 100
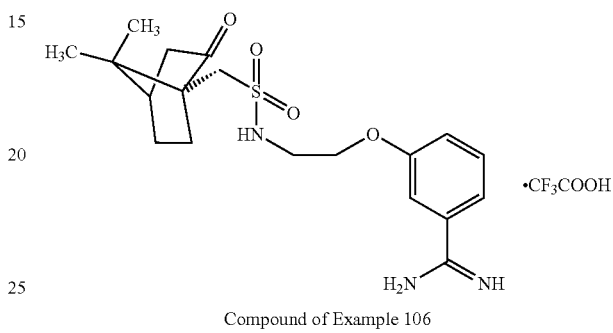
Compound of Example 106
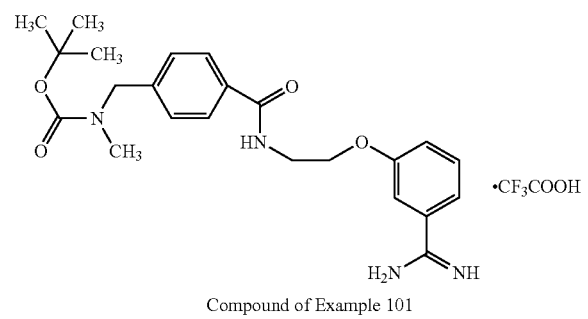
Compound of Example 101
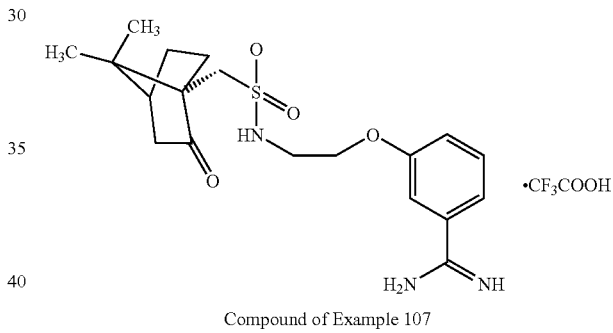
Compound of Example 107
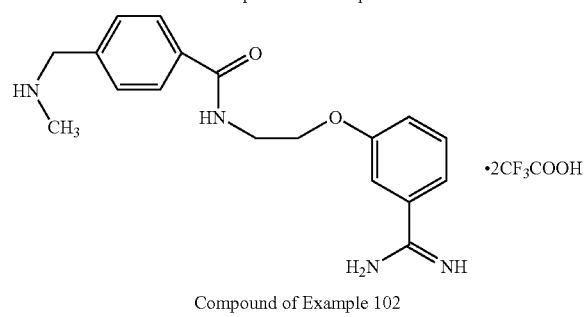
Compound of Example 102
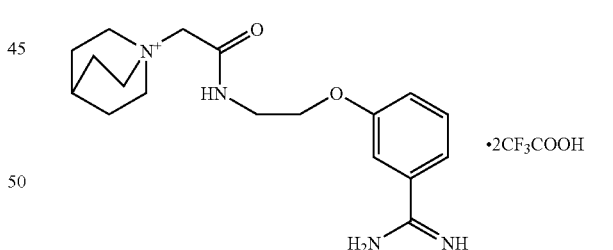
Compound of Example 108
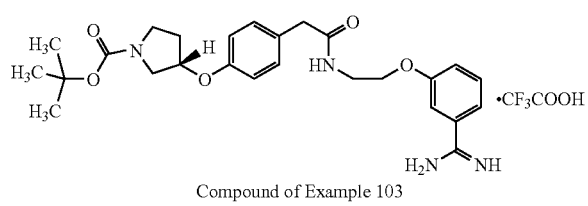
Compound of Example 103
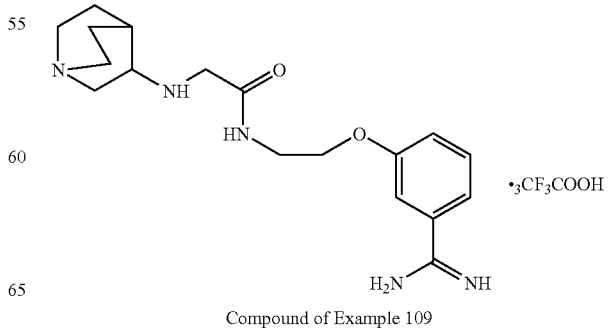
Compound of Example 109
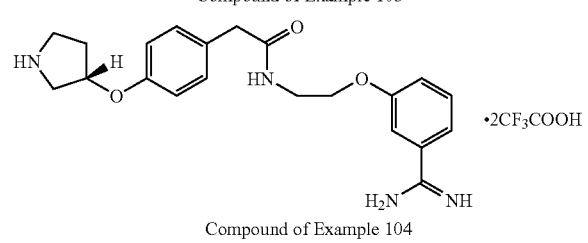
Compound of Example 104

-continued
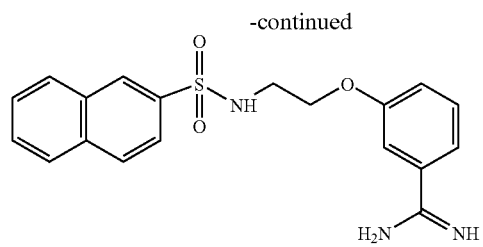
Compound of Example 100 ·CF₃COOH
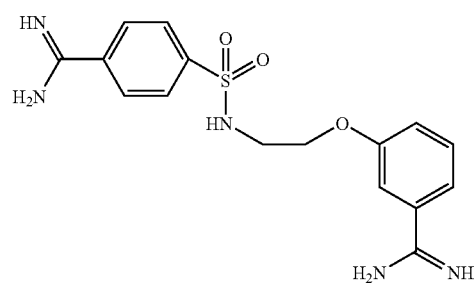
Compound of Example 111 ·2CF₃COOH
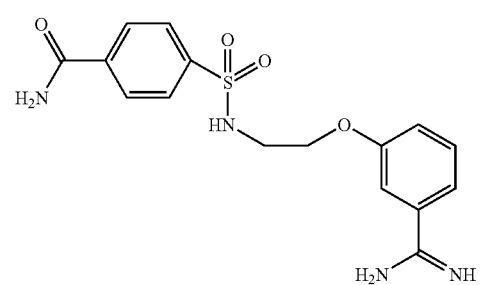
Compound of Example 112 ·CF₃COOH
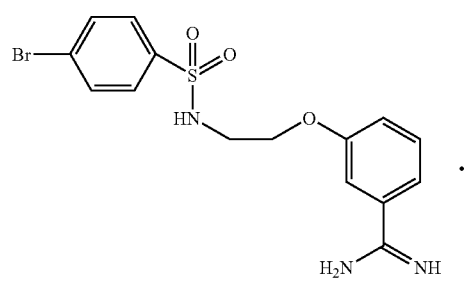
Compound of Example 113 ·CF₃COOH
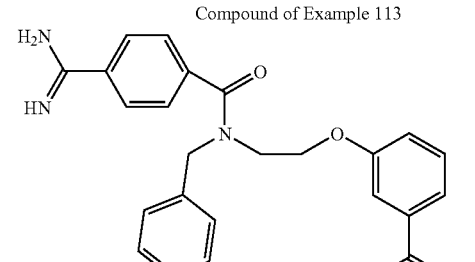
Compound of Example 114 ·2CF₃COOH
-continued
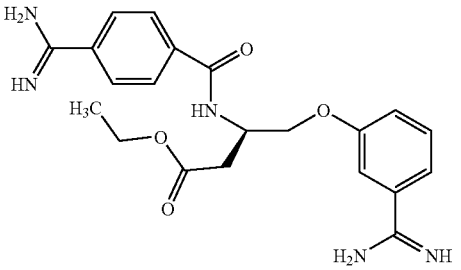
Compound of Example 115 ·2CF₃COOH
Compound of Example 116 ·2CF₃COOH
Compound of Example 117 ·2CF₃COOH
Compound of Example 118 ·2CF₃COOH

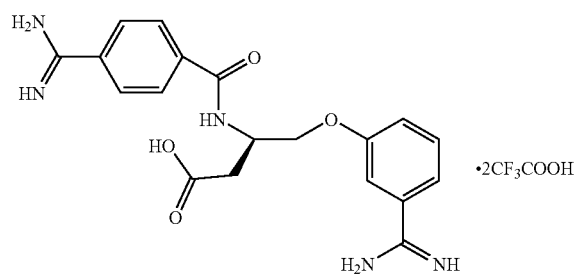

Compound of Example 119

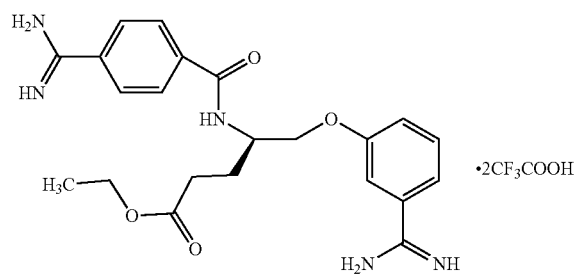

Compound of Example 120

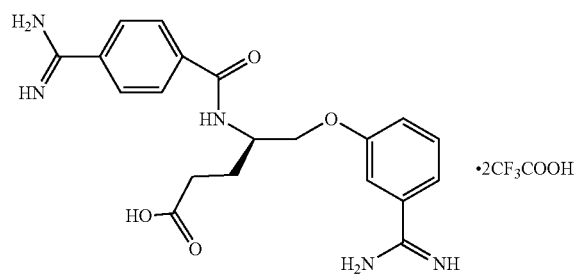

Compound of Example 121

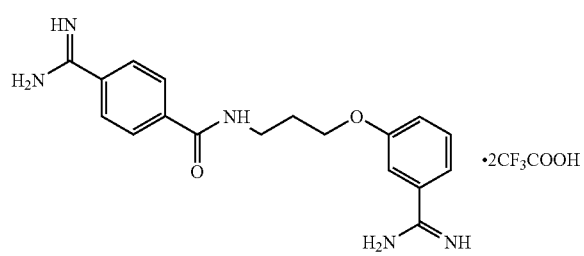

N-[3-(3-amidinophenoxy)propyl]-4-amidinobenzamide bistrifluoroacetate of Example 122

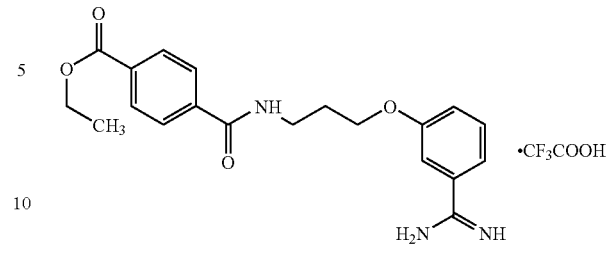

ethyl 4-[3-(3-amidinophenoxy)propylcarbamoylbenzoate trifluoroacetate of Example 122

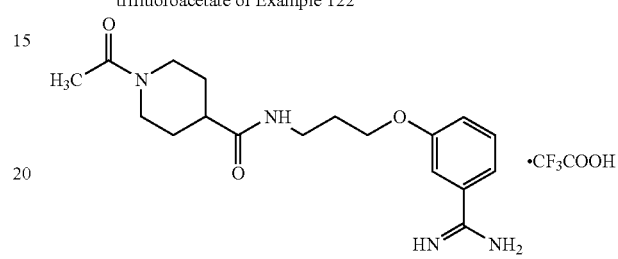

Compound of Example 123

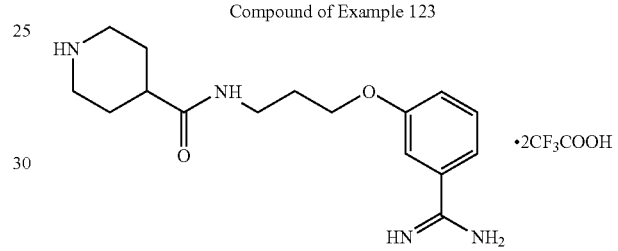

Compound of Example 124

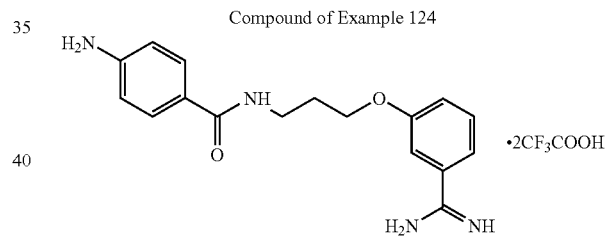

Compound of Example 125

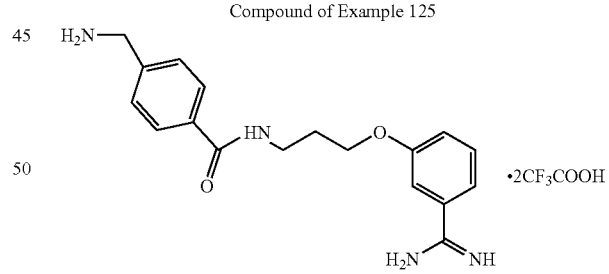

Compound of Example 126

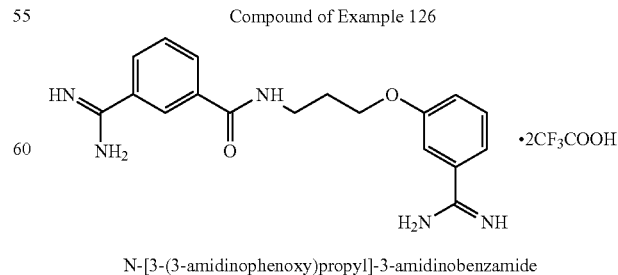

N-[3-(3-amidinophenoxy)propyl]-3-amidinobenzamide bistrifluoroacetate of Example 127

-continued
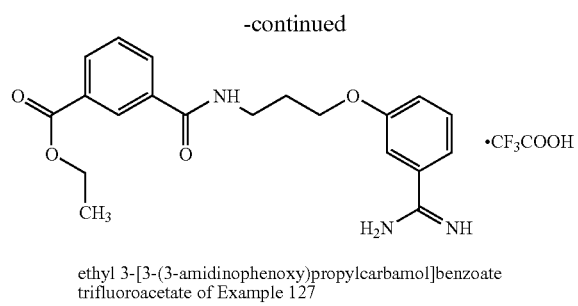
ethyl 3-[3-(3-amidinophenoxy)propylcarbamol]benzoate trifluoroacetate of Example 127
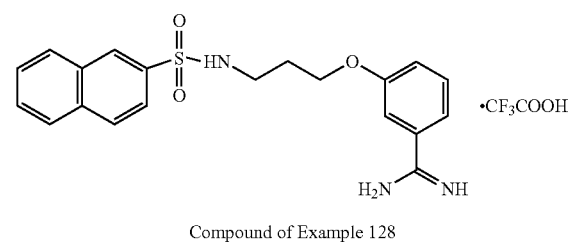
Compound of Example 128
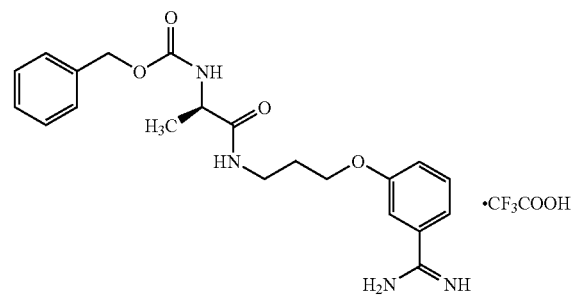
Compound of Example 129
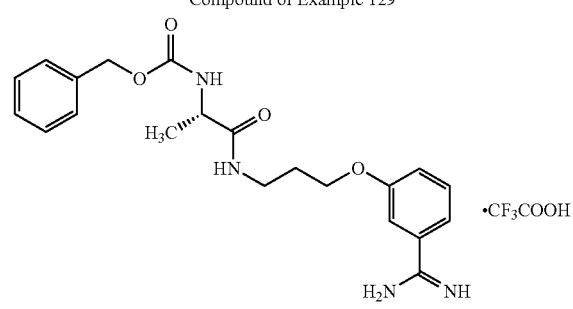
Compound of Example 130
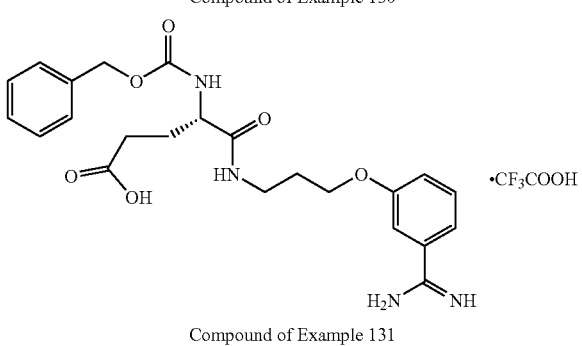
Compound of Example 131
-continued
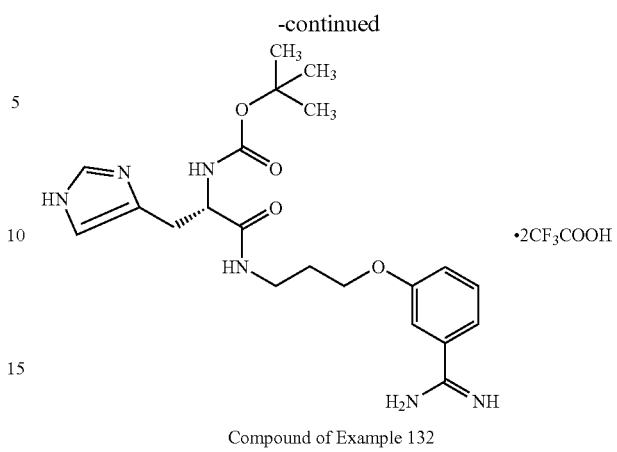
Compound of Example 132
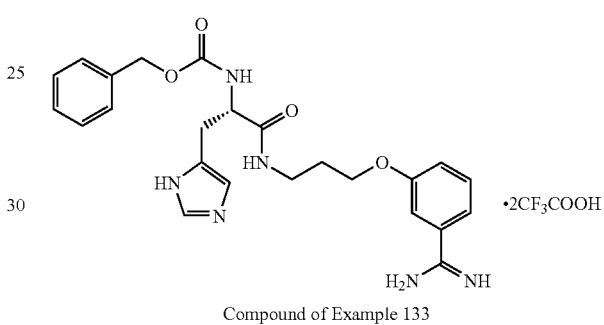
Compound of Example 133
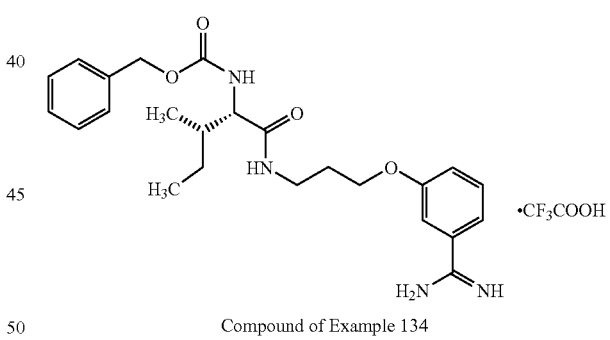
Compound of Example 134
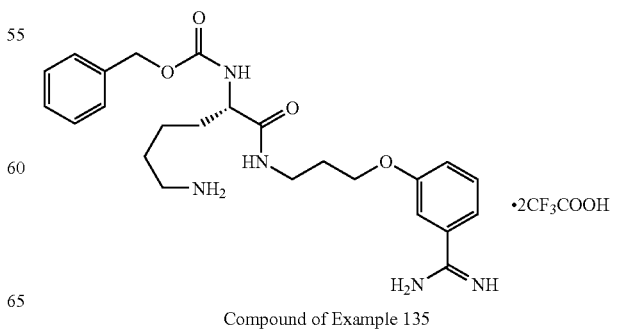
Compound of Example 135

-continued
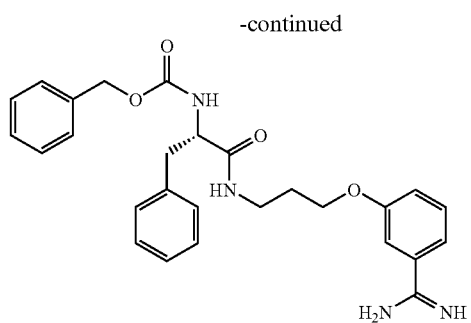
Compound of Example 136
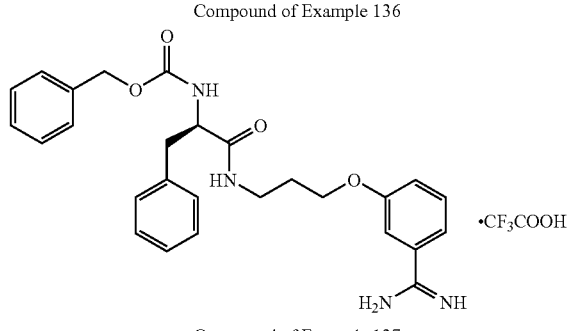
Compound of Example 137
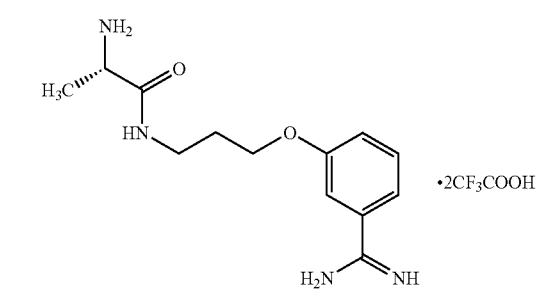
Compound of Example 138
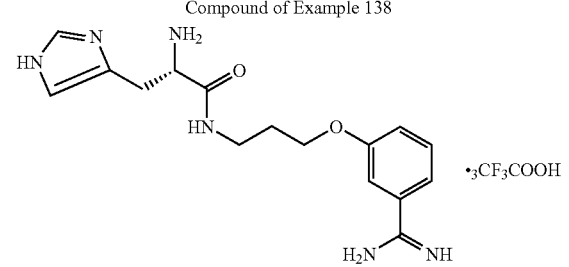
Compound of Example 139
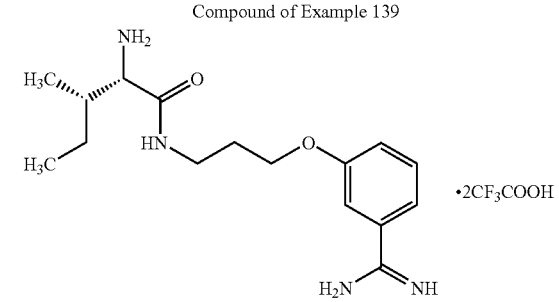
Compound of Example 140
-continued
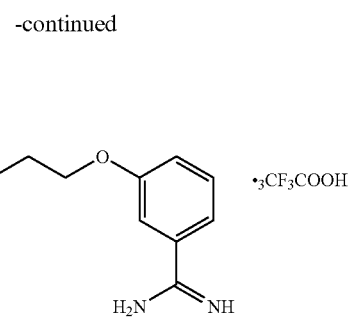
Compound of Example 141
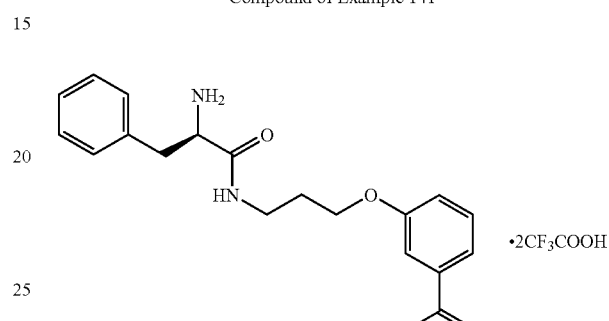
Compound of Example 142
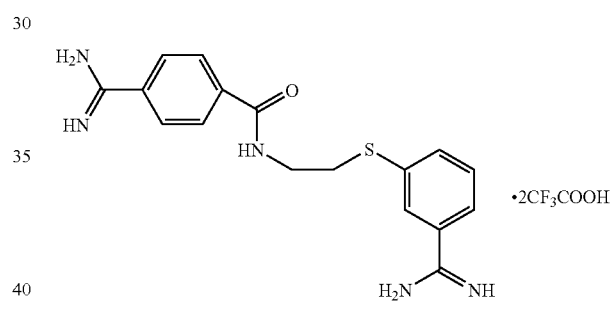
Compound of Example 143
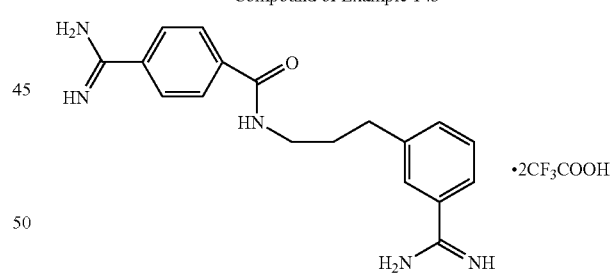
Compound of Example 144
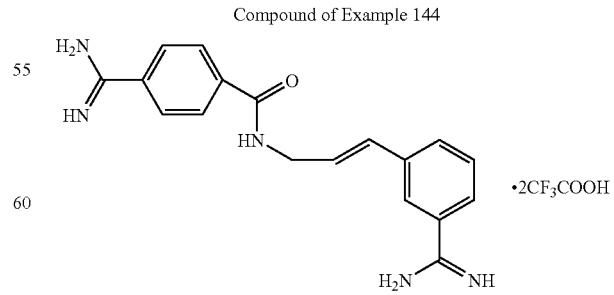
Compound of Example 145

-continued

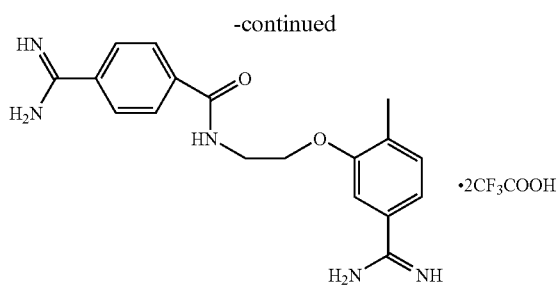

Compound of Example 146

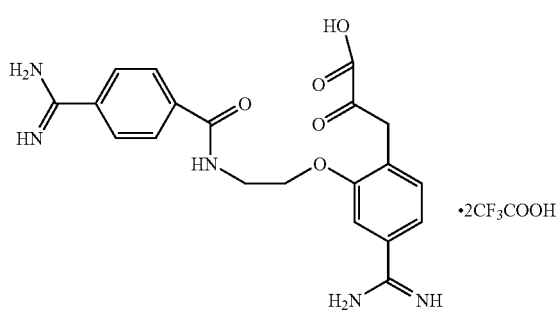

Compound of Example 147

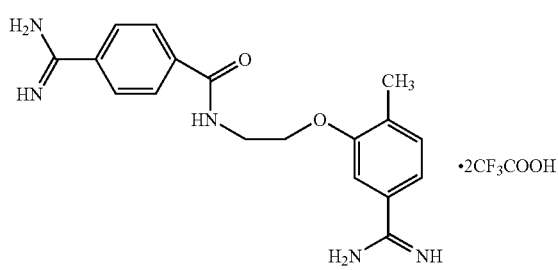

Compound of Example 148

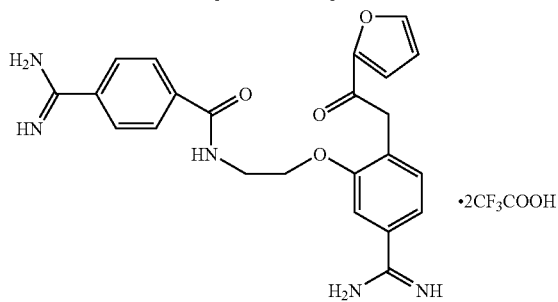

Compound of Example 149

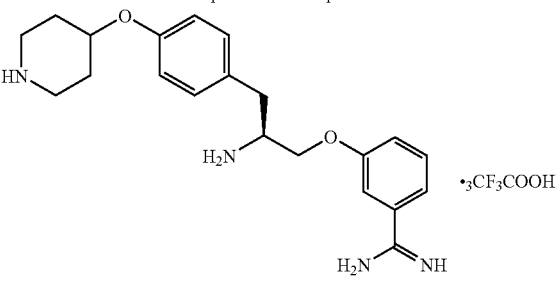

3-[(2S)-2-amino-3-[4-(4-piperidyloxy)phenyl]propoxy]benzamide tristrifluoroacetate of Example 150

-continued

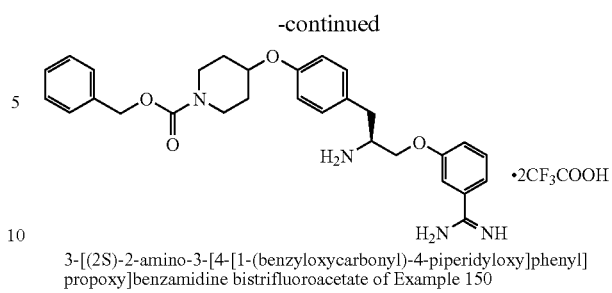

3-[(2S)-2-amino-3-[4-[1-(benzyloxycarbonyl)-4-piperidyloxy]phenyl]propoxy]benzamidine bistrifluoroacetate of Example 150

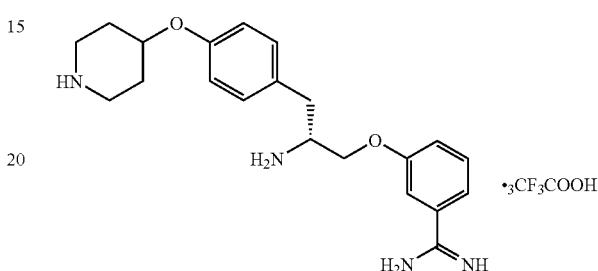

3-[(2R)-2-amino-3-[4-(4-piperidyloxy)phenyl]propoxy]benzamidine tristrifluoroacetate of Example 151

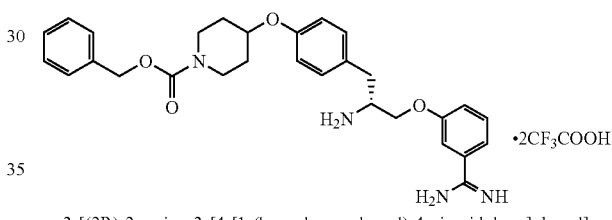

3-[(2R)-2-amino-3-[4-[1-(benzyloxycarbonyl)-4-piperidyloxy]phenyl]propoxy]benzamidine bistrifluoroacetate of Example 151

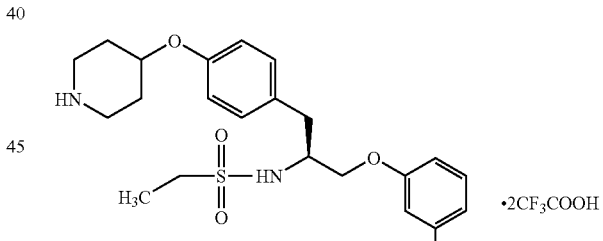

3-[(2S)-2-(ethanesulfonylamino)-3-[4-(4-piperidyloxy)phenyl]propoxy]benzamidine bistrifluoroacetate of Example 152

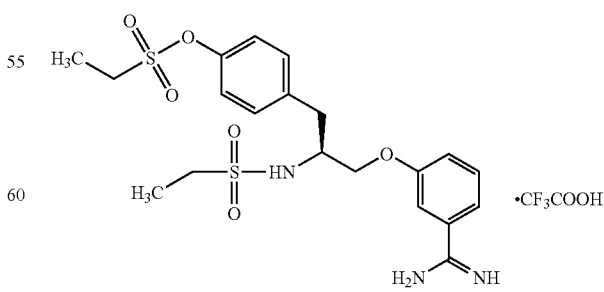

3-[(2S)-2-(ethanesulfonylamino)-3-[4-(4-piperidyloxy)phenyl]propoxy]benzamidine trifluoroacetate of Example 152

-continued

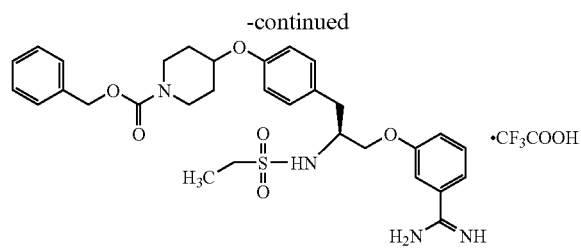

3-[(2S)-3-[4-[1-(benzyloxycarbonyl)-4-piperidyloxy]phenyl]-2-(ethanesulfonylamino)propoxy]benzamidine trifluoroacetate of Example 152

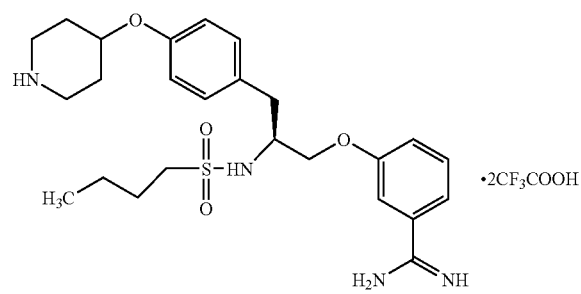

3-[(2S)-2-(butanesulfonylamino)-3-[4-(4-piperdyloxy)phenyl)propoxy]benzamidine bistrifluoroacetate of Example 153

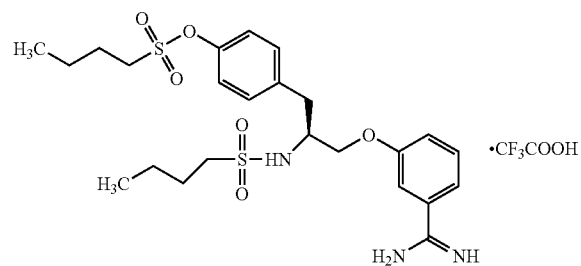

3-[(2S)-2-(butanesulfonylamino)-3-[4-(butanesulfonyloxy)phenyl]benzamidine trifluoroacetate of Example 153

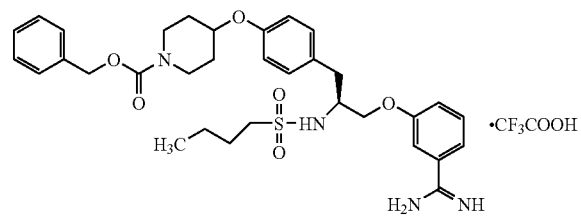

3-[(2S)-3-[4-[1-benzyloxycarbonyl)-4-piperdyloxy]phenyl]-2-(butanesulfonylamino)propxy]benzamidine trifluoroacetate of Example 153

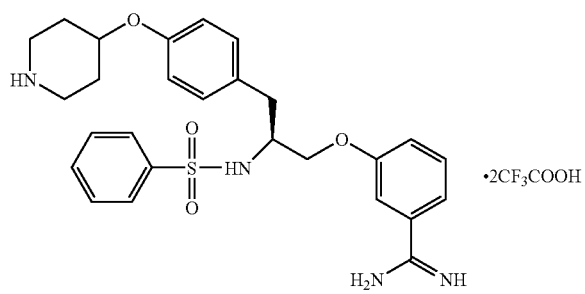

3-[(2S)-2-(benzenesulfonylamino)-3-[4-(4-piperidyloxy)phenyl]propoxy]benzamidine bistrifluoroacetate of Example 154

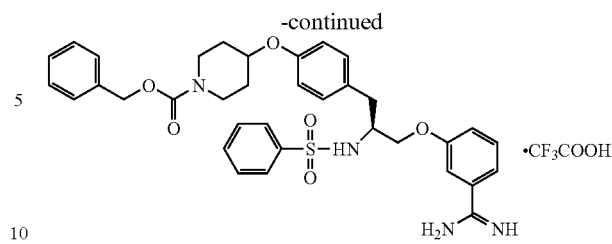

3-[(2S)-3-[4-[1-benzyloxycarbonyl)-4-piperdyloxy]phenyl]-2-(benzenesulfonylamino)propoxy]benzamidine trifluoroacetate of Example 154

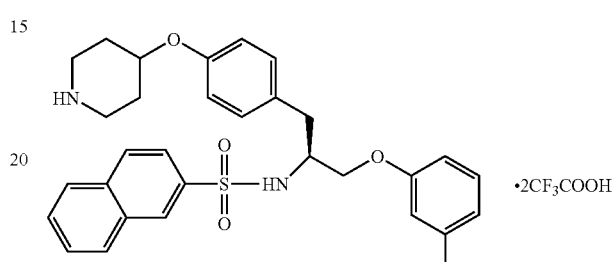

3-[(2S)-2(2-naphthalenesulfonylamino)-3-[4-(4-piperidyloxy)phenyl]propoxy]benzamidine bistrifluouoacetate of Example 155

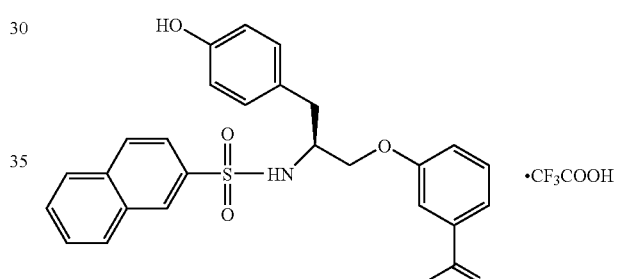

3-[(2S)-2-(butanesulfonylamino)-3-(4-hydroxyphenyl)propoxy]benzamidine trifluoroacetate of Example 155

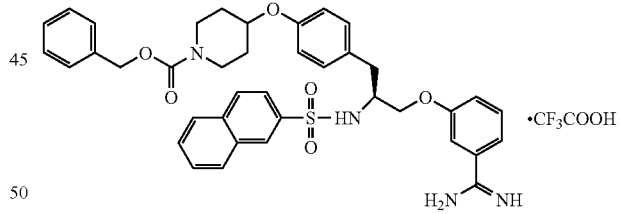

3-[(2S)-3-[4-[1-(benzyloxycarbonyl)-4-piperidyloxy]phenyl]-2-(2-naphthalenesulfonylamino)propoxy]benzamidine trifluoroacetate of Example 155

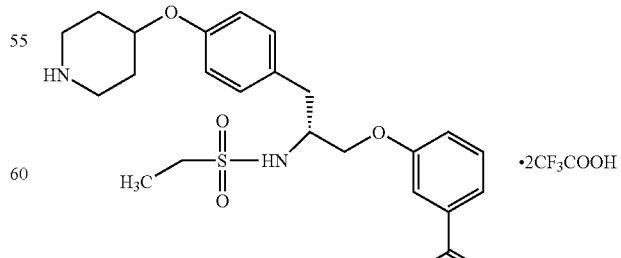

Compound of Example 156

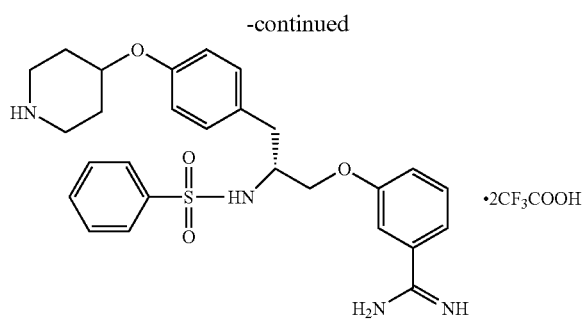
Compound of Example 157
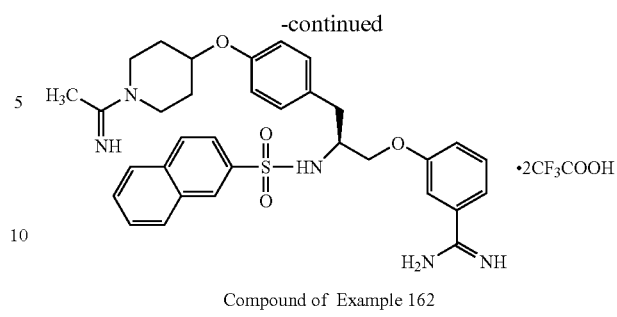
Compound of Example 162
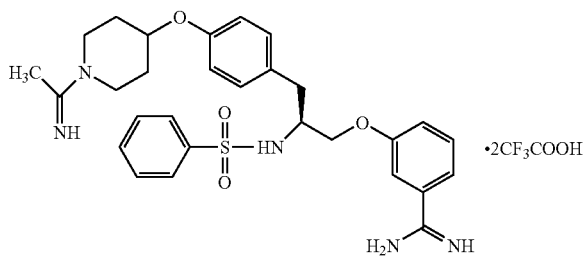
Compound of Example 158
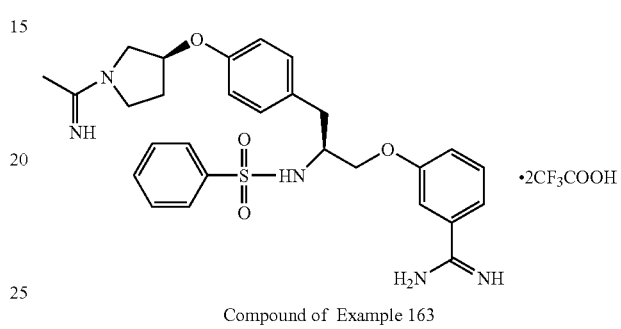
Compound of Example 163
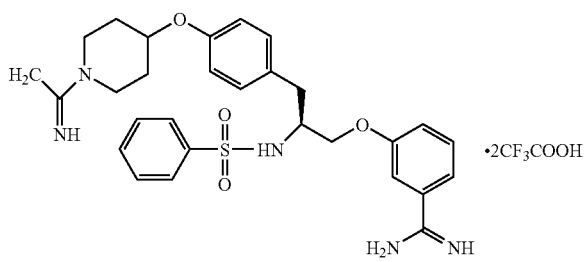
Compound of Example 159
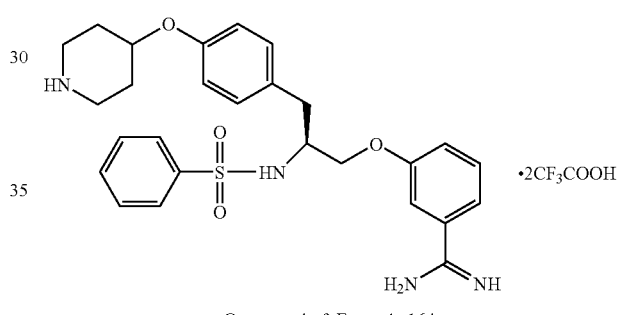
Compound of Example 164
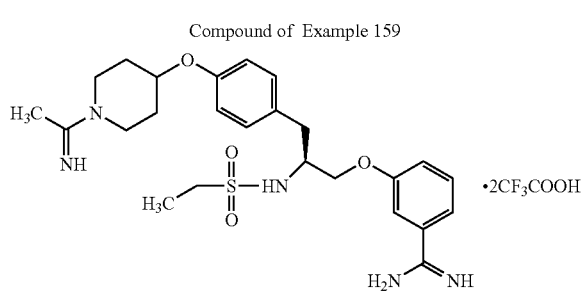
Compound of Example 160
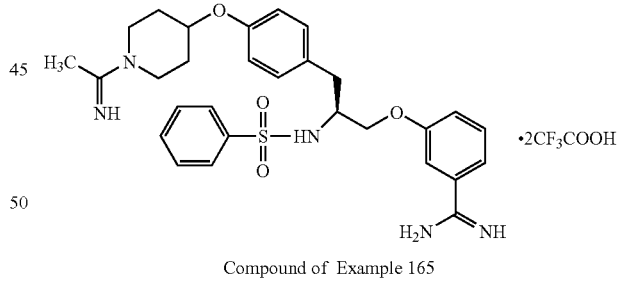
Compound of Example 165
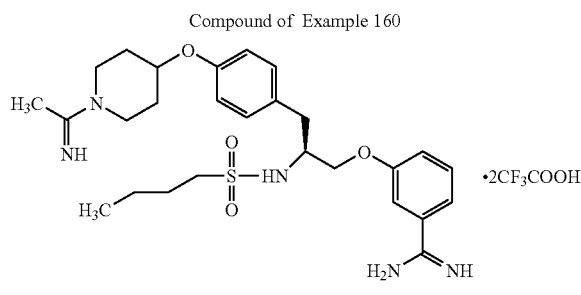
Compound of Example 161
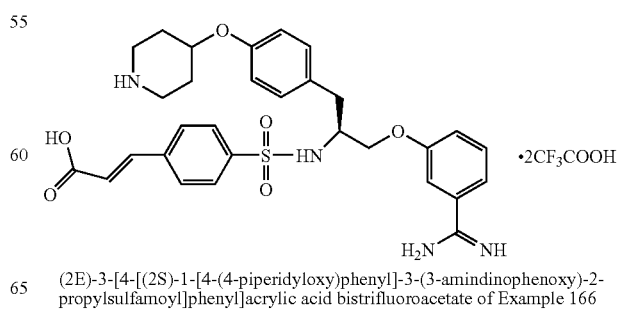
(2E)-3-[4-[(2S)-1-[4-(4-piperidyloxy)phenyl]-3-(3-amindinophenoxy)-2-propylsulfamoyl]phenyl]acrylic acid bistrifluoroacetate of Example 166

-continued

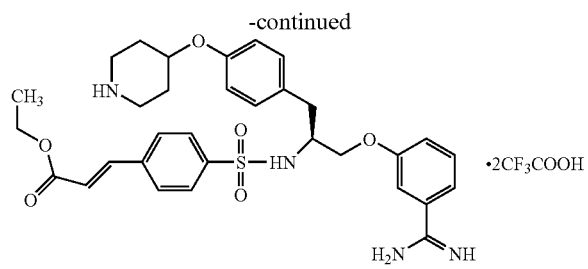

ethyl (2E)-3-[4-[(2S)-1-[4-(4-piperidyloxy)phenyl]-3-(3-amindinophenoxy)
-2-propylsulfamoyl]phenyl]acrylate bistrifluoroacetate of Example 166

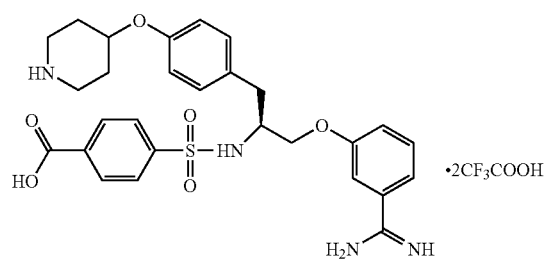

4-[(2S)-1-[4-(4-piperidyloxy)pheny]-3-(3-amidinophenoxy)-2-
propylsulfamoyl]benzoic acid bistrifluoroacetate of Example 167

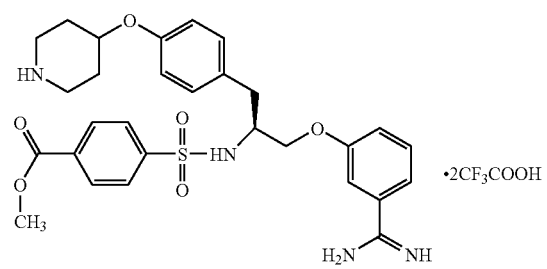

methyl 4-[(2S)-1-[4-(4-piperidyloxy)pheny]-3-(3-amidinophenoxy)-2-
propylsulfamoyl]benzoate bistrifluoroacetate of Example 167

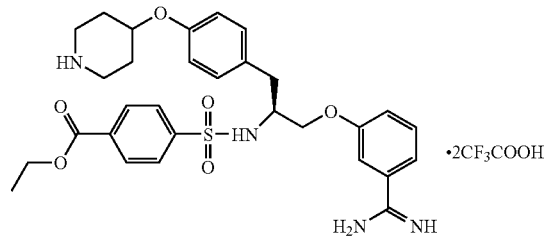

ethyl 4-[(2S)-1-[4-(4-piperidyloxy)pheny]-3-(3-amidinophenoxy)-2-
propylsulfamoyl]benzoate bistrifluoroacetate of Example 167

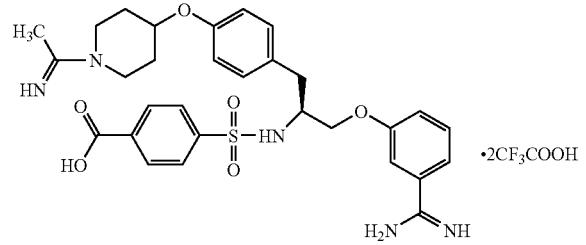

Compound of Example 168

-continued

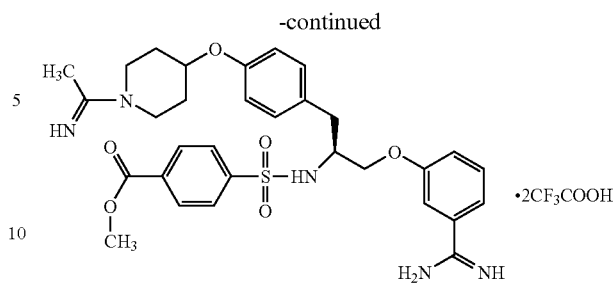

Compound of Example 169

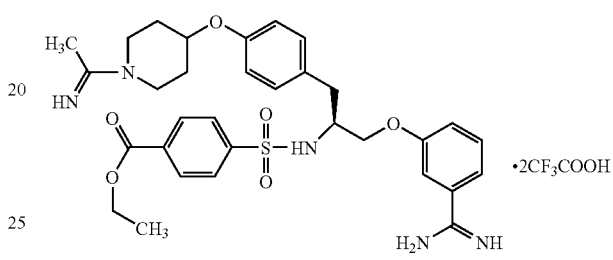

Compound of Example 170

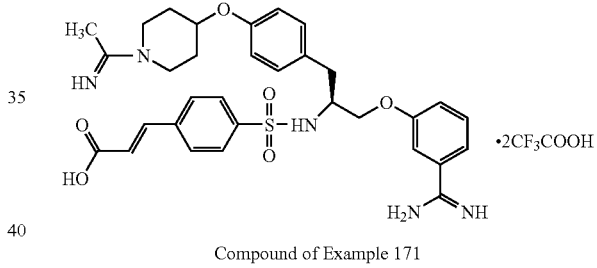

Compound of Example 171

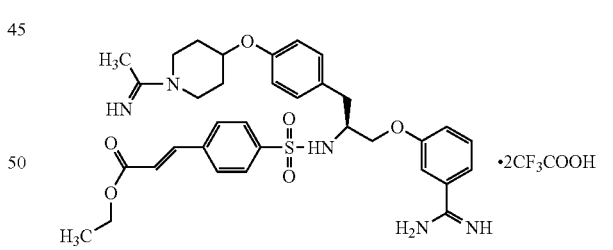

Compound of Example 172

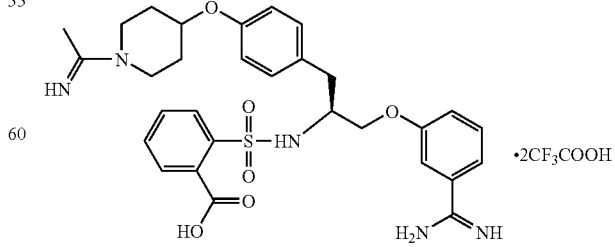

Compound of Example 173

Example 185

Synthesis of methyl 2-acetamido-3-[4-amidino-2-[(2R)-2-(4-amidinobenzoylamino)-3-ethoxycarbonylpropoxy]phenyl]acrylate bistrifluoroacetate

Step 1

Synthesis of benzyl (3R)-3-t-butoxycarbonylamino-4-hydroxybutanoate 15.0 g (46.4 mmol) of β-benzyl N-t-butoxycarbonyl-D-aspartate and 6.47 ml (46.4 mmol) of triethylamine were dissolved in 230 ml of tetrahydrofuran. 4.4 ml (46.4 mmol) of ethyl chloroformate was added to the solution under cooling with ice, and they were stirred for 15 minutes. The precipitate thus formed was removed by the suction filtration. 5 g of ice and 1.8 g (46.4 mmol) of sodium borohydride were added to the filtrate under cooling with ice, and they were stirred for 1.5 hours. Then 200 ml of 1 N aqueous hydrogen chloride solution was added to the resultant mixture, and they were stirred at room temperature for additional one hour. After the treatment with ethyl acetate as the extractant in an ordinary manner, the crude product was obtained. This product was purified by the silica gel column chromatography (volume ratio of hexane:ethyl acetate=2:1) to obtain the title compound.

Yield: 10.2 g (32.8 mmol) (71%).

1H-NMR (CDCl3) δ: 1.42 (9H, s), 2.66 (2H, d), 3.65 (2H, dd), 4.00 (1H, ddt), 5.14 (2H, s), 7.35-7.40 (5H, m)

Step 2

Synthesis of 3-hydroxy-4-iodobenzonitrile 22.3 g (89.7 mmol) of 3-hydroxy-4-iodobenzoic acid was dissolved in 300 ml of tetrahydrofuran. 19.7 ml (206 mmol) of ethyl chloroformate and 28.7 ml (206 mmol) of triethylamine were added to the solution at 0° C. After stirring for 15 minutes, triethylamine hydrochloride thus formed was filtered out. The filtrate was added to 300 ml of tetrahydrofuran solution, obtained by bubbling ammonia, at 0° C. After stirring at room temperature for 10 hours, the solvent was distilled off under reduced pressure, and the residue was dissolved in 450 ml of dioxane. 17.4 ml (117 mmol) of trifluoromethanesulfonic anhydride and 21.8 ml (269 mmol) of pyridine were added to the solution at 0° C. After stirring at room temperature for 18 hours, the solvent was distilled off under reduced pressure. The residue was treated with chloroform as the extractant in an ordinary manner to obtain an oily residue. The residue was dissolved in 180 ml of tetrahydrofuran:methanol (1:1). 90 ml (90.0 mmol) of 1 N aqueous sodium hydroxide solution was added to the solution at room temperature. The obtained mixture was stirred for 4 hours and then the solvent was distilled off under reduced pressure. The residue was washed with dichloromethane, acidified with 1 N aqueous hydrogen chloride solution and then treated with ethyl acetate as the extractant in an ordinary manner to obtain the crude product, which was purified by the silica gel column chromatography to obtain the title compound.

Yield: 9.29 g (37.9 mmol) (42%)

MS (FAB, m/z) 246 (MH+)

1H-NMR (CDCl3) δ: 5.63 (1H, br), 6.96 (1H, dd), 7.23 (1H, d), 7.79 (1H, d)

Step 3

Synthesis of benzyl (3R)-3-t-butoxycarbonylamino-4-(5-cyano-2-iodophenoxy)butanoate 10.16 g (32.8 mmol) of benzyl (3R)-3-t-butoxycarbonylamino-4-hydroxybutanoate was dissolved in 100 ml of toluene. 10.5 g (42.7 mmol) of 3-hydroxy-4-iodobenzonitrile, 11.2 g (42.7 mmol) of triphenylphosphine and 7.4 g (42.7 mmol) of N,N,N',N'-tetramethylazodicarboxyamide were added to the solution under cooling with ice, and they were stirred at room temperature overnight. The solvent was distilled off, and the residue was purified by the silica gel column chromatography (volume ratio of hexane:ethyl acetate=2:1) to obtain the title compound.

Yield: 11.9 g (22.1 mmol) (67%)

1H-NMR (CDCl3) δ: 1.47 (9H, s), 2.90 (2H, t), 4.03 (1H, dd), 4.15 (1H, dd), 4.40-4.50 (1H, m), 5.19 (2H, s), 7.01 (1H, d), 7.30 (1H, s), 7.35-7.40 (5H, m), 7.92 (1H, d)

Step 4

Synthesis of (1R)-1-benzyloxycarbonylmethyl-2-(5-cyano-2-iodophenoxy)ethylammonium chloride 11.9 g (22.1 mmol) of benzyl (3R)-3-t-butoxycarbonylamino-4-(5-cyano-2-iodophenoxy)butanoate was dissolved in 120 ml of 4 N solution of hydrogen chloride in dioxane. The solution was stirred at 0° C. for one hour and then at room temperature for 2 hours. The solvent was distilled off. 50 ml of a mixed solvent of hexane/ethyl acetate in a volume ratio of 1:1 was added to the oily residue thus obtained. The precipitate formed was taken by the filtration to obtain the title compound.

Yield: 6.1 g (12.9 mmol) (58%).

MS (ESI, M/Z) 437 (MH+)

1H-NMR (DMSO-d6) δ: 3.02 (2H, d), 3.94 (1H, ddt), 4.30 (1H, dd), 4.34 (1H, dd), 5.16 (2H, s), 7.26 (1H, dd), 7.32-7.40 (5H, m), 7.54 (1H, s), 8.03 (1H, d), 8.52 (2H, brs)

Step 5

Synthesis of benzyl (3R)-4-(5-cyano-2-iodophenoxy)-3-(4-cyanobenzoylamino)butanoate 4.73 g (10 mmol) of (1R)-1-benzyloxycarbonylmethyl-2-(5-cyano-2-iodophenoxy)ethylammonium chloride, 2.9 g (20 mmol) of 4-cyanobenzoic acid, 3.0 g (22 mmol) of 1-hydroxybenzotriazole and 6.1 ml (44 mmol) of triethylamine were dissolved in 50 ml of dichloromethane. 4.2 g (22 mmol) of 1-(3-dimethylaminopropyl)-3-ethylcarbodiimide hydrochloride was added to the solution under cooling with ice, and they were stirred for 10 minutes and then at room temperature for one hour. Water is added to the reaction mixture to terminate the reaction. The mixture was treated with dichloromethane as the extractant in an ordinary manner to obtain the crude product, which was purified by the silica gel column chromatography (volume ratio of hexane:ethyl acetate=3:1) to obtain the title compound.

Yield: 2.8 g (5.0 mmol) (50%)

1H-NMR (CDCl3) δ: 2.93 (1H, dd), 3.08 (1H, dd), 4.13 (1H, dd), 4.30 (1H, dd), 4.94 (1H, dddd), 5.14 (1H, d), 5.19 (1H, d), 6.96 (1H, d), 7.03 (1H, dd), 7.28-7.33 (5H, m), 7.72 (2H, d), 7.86 (2H, d), 7.88 (1H, d)

Step 6

Synthesis of methyl 2-acetamido-3-[2-[(2R)-3-ethoxycarbonyl-2-(4-cyanobenzoylamino)propoxy]-4-cyanophenyl]acrylate 1.28 g (2.27 mmol) of benzyl (3R)-4-(5-cyano-2-iodophenoxy)-3-(4-cyanobenzoylamino)butanoate, 975 mg (6.81 mmol) of methyl 2-acetamidoacrylate, 415 mg (1.36 mmol) of tris(2-methylphenyl)phosphine, 0.95 ml (6.81 mmol) of triethylamine and 0.5 ml of dimethylformamide were dissolved in 8.0 ml of acetonitrile. 56 mg (0.23 mmol) of palladium acetate was added to the solution at room temperature, and they were stirred at 90° C. for 12 hours. The solvent was distilled off, and the residue was purified by the silica gel column chromatography (volume ratio of chloroform:methanol=30:1) to obtain the title compound.

Yield: 991 mg (1.71 mmol) (75%)

Step 7

Synthesis of methyl 2-acetamido-3-[4-amidino-2-[(2R)-2-(4-amidinobenzoylamino)-3-ethoxycarbonylpropoxy]phenyl]acrylate bistrifluoroacetate 398 mg (0.69 mmol) of methyl 2-acetamido-3-[2-[(2R)-3-ethoxycarbonyl-2-(4-cyanobenzoylamino)propoxy]-4-cyanophenyl]acrylate was dissolved in 1.0 ml of ethanol. 10.0 ml of 4 N solution of hydrogen chloride in dioxane was added to the solution, and they were stirred at room temperature for 21 hours. The solvent was distilled off, and the residue was dissolved in 10.0 ml of ethanol. 1.0 g (10.4 mmol) of ammonium carbonate was added to the solution, and they were stirred at room temperature for 12 hours. The solvent was distilled off, and the residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 118.6 mg (0.15 mmol) (22%)
MS (ESI, M/Z) 553 (MH+)
1H-NMR (DMSO-d6) δ: 1.17 (3H, t), 1.96 (3H, s), 2.81 (1H, d), 3.66 (3H, s), 4.08 (2H, q), 4.23 (1H, dd), 4.31 (1H, dd), 4.76 (1H, brs), 7.28 (1H, s), 7.44 (1H, dd), 7.53 (1H, d), 7.73 (1H, d), 7.90 (2H, d), 8.01 (2H, d), 8.87 (1H, d), 9.28 (2H, s), 9.32 (2H, s), 9.35 (2H, s), 9.42 (2H, s), 9.68 (2H, s)

Example 186

Synthesis of (3R)-3-(4-amidinobenzoylamino)-4-[5-amidino-2-(2-carboxy-2-oxoethyl)phenoxy]butanoic acid bistrifluoroacetate 118.6 mg (0.15 mmol) of methyl 2-acetamido-3-[4-amidino-2-[(2R)-2-(4-amidinobenzoylamino)-3-ethoxycarbonylpropoxy]phenyl]acrylate bistrifluoroacetate was dissolved in 10.0 ml of 6 N hydrochloric acid, and they were stirred at 60° C. for 4 hours. The solvent was distilled off, and the residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 56.8 mg (0.081 mmol) (54%)
MS (ESI, M/Z) 470 (MH+)
1H-NMR (DMSO-d6) δ: 2.27 (2H, t), 4.02 (1H, dd), 4.19 (1H, dd), 4.72 (1H, brs). 6.78 (1H, s), 7.35 (1H, s), 7.43 (1H, d), 7.90 (2H, d), 8.02 (2H, d), 9.10 (1H, d), 9.31 (4H, s), 9.42 (4H, s)

Example 187

Synthesis of methyl 2-acetamido-3-[4-amidino-2-[(2R)-3-ethoxycarbonyl-2-(4-dimethylcarbamoylbenzoylamino)propoxy]phenyl]acrylate trifluoroacetate

Step 1

Synthesis of benzyl (3R)-4-(5-cyano-2-iodophenoxy)-3-(4-dimethylcarbamoylbenzoylamino)butyrate 2.05 g (4.33 mmol) of (1R)-1-benzyloxycarbonylmethyl-2-(5-cyano-2-iodophenoxy)ethyl ammonium chloride, 1.25 g (6.49 mmol) of 4-dimethylcarbamoylbenzoic acid, 994 mg (7.35 mmol) of 1-hydroxybenzotriazole, and 2.71 ml (19.46 mmol) of triethylamine were dissolved in 25 ml of dichloromethane, and 1.41 g (7.35 mmol) of 1-(3-dimethylaminopropyl)-3-ethyl carbodiimide hydrochloride was added thereto and stirred under cooling with ice for 10 minutes and then at room temperature for 18 hours. The reaction was stopped by adding water, and the title compound was obtained in an ordinary manner by treatment with dichloromethane as the extractant to obtain the crude product. It was purified by silica gel column chromatography (hexane:ethyl acetate=3:1, v/v) to obtain the title compound.

Yield: 2.30 g (3.76 mmol) (87%)
1H-NMR (DMSO-d6) δ: 2.96 (3H, s), 2.97 (1H, dd), 3.07 (1H, dd), 3.12 (3H, s), 4.16 (1H, dd), 4.30 (1H, dd), 4.89-4.99 (1H, m), 5.14 (1H, d), 5.20 (1H, d), 6.97 (1H, d), 7.02 (1H, dd), 7.29-7.33 (5H, m), 7.44 (2H, d), 7.80 (2H, d), 7.88 (1H, d)

Step 2

Synthesis of methyl 2-acetamide-3-[4-amidino-2-[(2R)-3-ethoxycarbonyl-2-[4-dimethylcarbamoylbenzoylamino)propoxy]phenyl]acrylate trifluoroacetate 1.76 g (2.88 mmol) of benzyl (3R)-4-(5-cyano-2-iodophenoxy)-3-(4-dimethylcarbamoylbenzoylamino)butyrate, 1.24 g (8.63 mmol) of methyl 2-acetamide acrylate, 536 mg (1.73 mmol) of tris(2-methylphenyl)phosphine, 1.2 ml (8.63 mmol) of triethylamine, and 0.5 ml of dimethylformamide were dissolved in 10 ml of acetonitrile, and 70 mg (0.29 mmol) of palladium acetate was added thereto at room temperature and stirred at 100° C. for 5.5 hours. The solvent was distilled off, and the resulting residue was purified by silica gel column chromatography (chloroform:methanol=30:1, v/v) and then dissolved in 1.5 ml of ethanol, and 15 ml of a dioxane solution containing 4 N hydrogen chloride, and the mixture was stirred at room temperature for 15 hours. Then, the solvent was dissolved off, and the resulting residue was dissolved in 20.0 ml of ethanol, and 974 mg (10.13 mmol) of ammonium carbonate was added thereto, and the mixture was stirred at room temperature for 14 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 536 mg (0.77 mmol) (27%)
MS (ESI, M/Z) 582 (MH+)
1H-NMR (DMSO-d6) δ: 1.08 (3H, t), 1.96 (3H, s), 2.81 (2H, d), 2.90 (3H, s), 2.99 (3H, s), 3.64 (3H, s), 4.07 (2H, q), 4.24 (2H, t), 4.70-4.79 (1H, m), 7.30 (1H, s), 7.42 (1H, d), 7.48 (2H, d), 7.70 (1H, d), 7.84 (2H, d), 8.69 (1H, d), 9.10 (2H, s), 9.32 (2H, s), 9.67 (1H, s)

Example 188

Synthesis of (3R)-4-[5-amidino-2-(2-carboxy-2-oxoethyl)phenoxy]-3-(4-dimethylcarbamoylbenzoylamino)butanoic acid trifluoroacetate 151 mg (0.22 mmol) of methyl 2-acetamide-3-[4-amidino-2-[(2R)-3-ethoxycarbonyl-2-(4-dimethylcarbamoylbenzoylamino)propoxy]phenyl]acrylate trifluoroacetate was dissolved in 6 ml of 6 N hydrochloric acid and stirred at 60° C. for 3 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 49.2 mg (0.08 mmol) (37%)

MS (ESI, M/Z) 499 (MH+)

1H-NMR (DMSO-d6) δ: 2.69 (1H, d), 2.74 (1H, d), 2.87 (3H, s), 2.98 (2H, s), 4.22 (1H, d), 4.26 (1H, d), 4.60-4.76 (1H, m), 7.30 (1H, s), 7.40 (1H, d), 7.48 (2H, d), 7.50 (1H, s), 7.88 (2H, d), 8.32 (1H, d), 9.02 (2H, s), 9.26 (2H, s)

Example 189

Synthesis of (3R)-4-[5-amidino-2-(2-carboxy-2-oxo-ethyl)phenoxy]-3-(4-carboxylbenzoylamino)butanoic acid trifluoroacetate 54 mg (0.086 mmol) of methyl 2-acetamide-3-[4-amidino-2-[(2R)-3-ethoxycarbonyl-2-(4-dimethylcarbamoylbenzoylamino)propoxy]phenyl]acrylate trifluoroacetate was dissolved in 4 ml of 6 N hydrochloric acid and stirred at 80° C. for 2 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 10.5 mg (0.02 mmol) (21%)

MS (ESI, M/Z) 472 (MH+)

1H-NMR (DMSO-d6) δ: 2.75 (2H, d), 4.24 (2H, d), 4.60-4.76 (1H, m), 6.79 (1H, s), 7.36 (1H, d), 7.45 (1H, d), 7.48 (1H, s), 7.90 (2H, d), 8.02 (2H, d), 8.32 (1H, d), 9.04 (2H, s), 9.25 (2H, s)

Example 190

Synthesis of methyl 2-acetamido-3-[4-amidino-2-[(2R)-3-ethoxycarbonyl-2-[4-(pyrrolidine-1-carbonyl)benzoylamino]propoxy]phenyl]acrylate trifluoroacetate Step 1

Synthesis of benzyl (3R)-4-(5-cyano-2-iodophenoxy)-3-[4-(pyrrolidine-1-carbonyl)benzoylamino]butyrate 2.0 g (4.23 mmol) of (1R)-1-benzyloxycarbonylmethyl-2-(5-cyano-2-iodophenoxy)ethyl ammonium chloride, 1.02 g (4.65 mmol) of 4-pyrrolidine-1-carbonyl)benzoic acid, 630 mg (4.65 mmol) of 1-hydroxybenzotriazole, and 1.30 ml (9.31 mmol) of triethylamine were dissolved in 40 ml of dichloromethane, and 890 mg (4.65 mmol) of 1-(3-dimethylaminopropyl)-3-ethyl carbodiimide hydrochloride was added thereto and stirred under cooling with ice for 10 minutes and then at room temperature for 18 hours. The reaction was stopped by adding water, and the title compound was obtained in an ordinary manner by treatment with dichloromethane as the extractant.

Yield: 2.61 g (4.09 mmol) (97%)

1H-NMR (CDCl3) δ: 1.83-2.02 (4H, m), 2.95 (1H, dd), 3.08 (1H, dd), 3.37 (2H, t), 3.64 (2H, t), 4.15 (1H, dd), 4.31 (1H, dd), 4.89-5.00 (1H, m), 5.13 (1H, d), 5.20 (1H, d), 6.97 (1H, d), 7.02 (1H, dd), 7.29-7.33 (5H, m), 7.54 (2H, d), 7.79 (2H, d), 7.88 (1H, d)

Step 2

Synthesis of methyl 2-acetamide-3-[4-amidino-2-[(2R)-3-ethoxycarbonyl-2-[4-(pyrrolidine-1-carbonyl)benzoylamino]propoxy]phenyl]acrylate trifluoroacetate 2.61 g (4.09 mmol) of benzyl (3R)-4-(5-cyano-2-iodophenoxy)-3-[4-(pyrrolidine-1-carbonyl)benzoylamino]butyrate, 1.82 g (12.69 mmol) of methyl 2-acetamide acrylate, 773 mg (2.54 mmol) of tris(2-methylphenyl)phosphine, 1.77 ml (12.69 mmol) of triethylamine, and 0.5 ml of dimethylformamide were dissolved in 14 ml of acetonitrile, and 103 mg (0.42 mmol) of palladium acetate was added thereto and stirred at 100° C. for 4 hours. The solvent was distilled off, and the resulting residue was purified by silica gel column chromatography (chloroform:methanol=30:1, v/v) and then dissolved in 4 ml of ethanol, and 20 ml of a dioxane solution containing 4 N hydrogen chloride was added thereto, and the mixture was stirred at room temperature for 18 hours. Then, the solvent was dissolved off, and the resulting residue was dissolved in 20 ml of ethanol, and 1.18 g (12.26 mmol) of ammonium carbonate was added thereto, and the mixture was stirred at room temperature for 14 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 680 mg (0.94 mmol) (23%)

1H-NMR (DMSO-d6) δ: 1.16 (3H, t), 1.78-1.91 (4H, m), 1.95 (3H, s), 2.79 (2H, d), 3.34 (2H, t), 3.47 (2H, t), 3.64 (3H, s), 4.07 (2H, q), 4.25 (2H, t), 4.73 (1H, ddt), 7.31 (1H, s), 7.43 (1H, dd), 7.52 (1H, d), 7.58 (2H, d), 7.80 (1H, d), 7.84 (2H, d), 8.69 (1H, d), 9.09 (2H, s), 9.33 (2H, s), 9.65 (1H, brs)

Example 191

Synthesis of (3R)-4-[5-amidino-2-(2-carboxy-2-oxo-ethyl)phenoxy]-3-[4-(pyrrolidine-1-carbonyl)benzoylamino]butanoic acid trifluoroacetate Synthesis of methyl 2-acetamido-3-[4-amidino-2-[(2R)-3-carboxyl-2-[4-(pyrrolidine-1-carbonyl)benzoylamino]propoxy]phenyl]acrylate trifluoroacetate Synthesis of 2-acetamido-3-[4-amidino-2-[(2R)-3-carboxyl-2-[4-(pyrrolidine-1-carbonyl)benzoylamino]propoxy]phenyl]acrylic acid trifluoroacetate 105 mg (0.15 mmol) of methyl 2-acetamido-3-[4-amidino-2-[(2R)-3-ethoxycarbonyl-2-[4-(pyrrolidine-1-carbonyl)benzoylamino]propoxy]phenyl]acrylate trifluoroacetate was dissolved in 6 ml of 6 N hydrochloric acid and stirred at 40° C. for 2 hours and further stirred at 60° C. for 1 hour. The solvent was distilled off, and the resulting crude product was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compounds respectively.

(3R)-4-[5-amidino-2-(2-carboxy-2-oxoethyl)phenoxy]-3-[4-(pyrrolidine-1-carbonyl)benzoylamino]butanoic acid trifluoroacetate Yield: 18.2 mg (0.03 mmol) (20%)
MS (ESI, M/Z) 525 (MH+)
1H-NMR (DMSO-d6) δ: 1.75-1.92 (4H, m), 2.70 (1H, d), 2.76 (1H, d), 3.35 (2H, d), 3.47 (2H, t), 4.24 (2H, d), 4.70 (1H, ddt), 6.81 (1H, s), 7.46 (1H, d), 7.49 (1H, s), 7.57 (2H, d), 7.88 (2H, d), 8.33 (1H, d), 9.15 (2H, m), 9.27 (2H, s)

Synthesis of methyl 2-acetamido-3-[4-amidino-2-[(2R)-3-carboxyl-2-[4-(pyrrolidine-1-carbonyl)benzoylamino]propoxy]phenyl acrylate trifluoroacetate Yield: 32.8 mg (0.05 mmol) (33%)
MS (ESI, M/Z) 580 (MH+)
1H-NMR (DMSO-d6) δ: 1.76-1.91 (4H, m), 1.95 (3H, s), 2.73 (1H, d), 3.34 (2H, t), 3.48 (2H, t), 3.65 (3H, s), 4.26 (2H, t), 4.64-4.77 (1H, m), 7.32 (1H, s), 7.44 (1H, d), 7.55 (1H, s), 7.59 (2H, d), 7.73 (1H, d), 7.88 (2H, d), 8.67 (1H, d), 9.13 (2H, s), 9.33 (2H, s), 9.63 (1H, s)

Synthesis of 2-acetamido-3-[4-amidino-2-[(2R)-3-carboxyl-2-[4-(pyrrolidine-1-carbonyl)benzoylamino]propoxy]phenyl]acrylic acid trifluoroacetate Yield: 13.2 mg (0.02 mmol) (13%)
MS (ESI, M/Z) 566 (MH+)
1H-NMR (DMSO-d6) δ: 1.77-1.91 (4H, m), 1.94 (3H, s), 2.76 (2H, d), 3.35 (2H, t), 3.47 (2H, t), 4.27 (2H, d), 4.63-4.76 (1H, m), 7.36 (1H, s), 7.41 (1H, dd), 7.53 (1H, d), 7.57 (2H, d), 7.69 (1H, d), 7.86 (2H, d), 8.70 (1H, d), 9.19 (2H, s), 9.33 (2H, s), 9.50 (1H, s)

Example 192

Synthesis of methyl 2-acetamido-3-[4-amidino-2-[(2R)-3-ethoxycarbonyl-2-[4-(piperidyl-4-oxy)benzoylamino]propoxy]phenyl]acrylate bistrifluoroacetate Synthesis of ethyl 2-acetamido-3-[4-amidino-2-[(2R)-3-ethoxycarbonyl-2-[4-(piperidyl-4-oxy)benzoylamino]propoxy]phenyl]acrylate bistrifluoroacetate Step 1

Synthesis of ethyl 4-(1-t-butoxycarbonyl-4-piperidyloxy)benzoate 1.7 g (10.2 mmol) of ethyl 4-hydroxybenzoate, 1.76 g (9.3 mmol) of 1-t-butoxycarbonyl-4-hydroxypiperidine, and 2.44 g (9.3 mmol) of triphenyl phosphine were dissolved in 40 ml of tetrahydrofuran, and 1.62 g (9.3 mmol) of diethyl azodicarboxylic acid was added thereto, and they were stirred at room temperature overnight. It was treated in an ordinary manner by treatment with ethyl acetate as the extractant to obtain the crude product. Then, it was purified by silica gel column chromatography to obtain the title compound.
Yield: 1.57 g (4.5 mmol) (44%)
1H-NMR (CDCl 3) δ: 1.38 (3H, t), 1.50 (9H, s) 1.70-1.80 (2H, m), 1.90-2.00 (2H, m), 3.30-3.41 (2H, m), 3.63-3.75 (2H, m), 4.35 (2H, q), 4.55 (1H, m), 6.90 (2H, d), 8.00 (2H, d)

Step 2

Synthesis of 4-(1-t-butoxycarbonyl-4-piperidyloxy)benzoic acid 847 mg (2.43 mmol) of ethyl 4-(1-t-butoxycarbonyl-4-piperidyloxy)benzoate was dissolved in 50 ml of ethanol, and 5 ml of 1 N sodium hydroxide was added thereto, and they were stirred for 3 days. The reaction solution was concentrated and treated in an ordinary manner with ethyl acetate as the extractant to obtain the title compound.
Yield: 697 mg (2.2 mmol) (92%)
1H-NMR (CDCl 3) δ: 1.50 (9H, s), 1.70-2.00 (4H, m), 3.30-3.40 (2H, m), 3.65-3.75 (2H, m), 4.60 (1H, s), 6.95 (2H, d), 8.05 (2H, d)

Step 3

Synthesis of methyl 2-acetamido-3-[4-amidino-2-[(2R)-3-ethoxycarbonyl-2-[4-(piperidyl-4-oxy)benzoylamino]propoxy]phenyl]acrylate bistrifluoroacetate 1.33 g (2.81 mmol) of (1R)-1-benzyloxycarbonylmethyl-2-(5-cyano-2-iodophenoxy)ethylammonium chloride, 1.10 g (3.10 mmol) of 4-(1-t-butoxycarbonyl-4-piperidyloxy)benzoic acid, 419 mg (3.10 mmol) of 1-hydroxybenzotriazole and 0.86 ml (6.19 mmol) of triethylamine were dissolved in 30 ml of dichloromethane. 593 mg (3.10 mmol) of 1-(3-dimethylaminopropyl)-3-ethylcarbodiimide hydrochloride was added to the solution under cooling with ice, and they were stirred for 10 minutes and then at room temperature for 16 hours. The reaction was terminated by the addition of water. After the treatment with dichloromethane as the extractant in an ordinary manner, the crude product was obtained. This product was dissolved in 15 ml of acetonitrile. 1.21 g (8.43 mmol) of methyl 2-acetamidoacrylate, 513 mg (1.69 mmol) of tris(2-methylphenyl)phosphine, 1.17 ml (8.43 mmol) of triethylamine and 0.5 ml of dimethylformamide were added to the solution. Then 69 mg (0.28 mmol) of palladium acetate was added to the resultant mixture at room temperature. After stirring at 100° C. for one hour, 30 mg (0.12 mmol) of palladium acetate was added thereto, and they were stirred at 100° C. for 4 hours. The solvent was distilled off, and the residue was purified by the silica gel column chromatography (volume ratio of chloroform:methanol=30:1) and dissolved in 5 ml of ethanol. 30 ml of 4 N solution of hydrogen chloride in dioxane was added to the solution, and they were stirred at room temperature for 20 hours. Then the solvent was distilled off, and the residue was dissolved in 20 ml of ethanol. 4.0 g (41.63 mmol) of ammonium carbonate was added to the solution, and they were stirred at room temperature for 58 hours. The solvent was distilled off, and the residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.
Yield: 514 mg (0.61 mmol) (22%)
1H-NMR (DMSO-d6) δ: 1.16 (3H, t), 1.72-1.89 (2H, m), 1.95 (3H, s), 2.04-2.17 (2H, m), 2.79 (2H, d), 3.03-3.18 (2H, m), 3.20-3.32 (2H, m), 3.66 (3H, s), 4.04 (2H, q), 4.23 (2H, d), 4.66-4.79 (1H, m), 7.06 (2H, d), 7.28 (1H, s), 7.44 (1H, dd), 7.53 (1H, d), 7.73 (1H, d), 7.81 (2H, d), 8.46 (1H, d), 9.18 (2H, s), 9.34 (2H, s), 9.67 (1H, brs)

Ethyl 2-acetamido-3-[4-amidino-2-[(2R)-3-ethoxycarbonyl-2-[4-(piperidyl-4-oxy)benzoylamino]propoxy]phenyl]acrylate bistrifluoroacetate was also obtained.

Yield: 104 mg (0.12 mmol) (4%)

1H-NMR (DMSO-d6) δ: 1.16 (3H, t), 1.19 (3H, t), 1.72-1.89 (2H, m), 1.96 (3H, s), 2.04-2.17 (2H, m), 2.78 (2H, d), 3.03-3.18 (2H, m), 3.20-3.32 (2H, m), 3.66 (3H, s), 4.08 (2H, q), 4.11 (2H, q), 4.22 (2H, d), 4.66-4.79 (1H, m), 7.06 (2H, d), 7.29 (1H, s), 7.44 (1H, dd), 7.52 (1H, d), 7.75 (1H, d), 7.82 (2H, d), 8.46 (1H, d), 9.20 (2H, s), 9.33 (2H, s), 9.65 (1H, brs)

Example 193

Synthesis of (3R)-4-[5-amidino-2-(2-carboxy-2-oxoethyl)phenoxy]-3-[4-(1-(1-iminoethyl)piperidyl-4-oxy)benzoylamino]butanoic acid bistrifluoroacetate 510 mg (0.61 mmol) of methyl 2-acetamido-3-[4-amidino-2-[(2R)-3-ethoxycarbony-2-[4-(piperidyl-4-oxy)benzoylamino]propoxy]phenyl]acrylate bistrifluoroacetate was dissolved in 10 ml of ethanol. 1.70 ml (12.18 mmol) of triethylamine and 752 mg (6.09 mmol) of ethyl acetimidate hydrochloride were added to the solution, and they were stirred at room temperature for 19 hours. The solvent was distilled off, and the residue was dissolved in 14 ml of 6 N hydrochloric acid, and the solution was stirred at 70° C. for 4 hours. The solvent was distilled off, and the residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 325 mg (0.48 mmol) (78%)

MS (ESI, M/Z) 568 (MH+)

1H-NMR (DMSO-d6) δ: 1.70-1.87 (2H, m), 2.02-2.15 (2H, m), 2.29 (3H, s), 2.68 (1H, d), 2.74 (1H, d), 3.48-3.58 (2H, m), 4.11-4.28 (2H, m), 4.60-4.72 (1H, m), 4.81 (1H, brs), 6.80 (1H, s), 7.07 (2H, d), 7.45 (1H, d), 7.48 (1H, s), 7.82 (2H, d), 8.33 (1H, d), 8.62 (1H, s), 9.14 (2H, s), 9.17 (1H, s), 9.26 (2H, s)

Example 194

Synthesis of methyl 2-acetamido-3-[4-amidino-2-[(2R)-3-ethoxycarbonyl-2-[4-(pyrrolidine-1-sulfonyl)benzoylamino]propoxy]phenyl]acrylate trifluoroacetate Synthesis of ethyl 2-acetamido-3-[4-amidino-2-[(2R)-3-ethoxycarbonyl-2-[4-(pyrrolidine-1-sulfonyl)benzoylamino]propoxy]phenyl]acrylate trifluoroacetate Step 1

Synthesis of 4-(pyrrolidine-1-sulfonyl)benzoic acid 1.0 ml (12 mmol) of pyrrolidine was dissolved in 33 ml of piperidine. 2.21 g (10 mmol) of 4-chlorosulfobenzoic acid was added to the solution under cooling with ice, and they were stirred for 30 minutes and then at room temperature for 30 minutes. The solvent was distilled off, and the residue was suspended in 30 ml of 3 N aqueous hydrochloric acid solution. After the treatment with dichloromethane as the extractant in an ordinary manner, the title compound was obtained.

Yield: 2.33 g (9.13 mmol) (91%).

1H-NMR (DMSO-d6) δ: 1.04-1.11 (4H, m), 2.55-2.64 (4H, m), 7.34 (2H, d), 7.55 (2H, d)

Step 2

Synthesis of methyl 2-acetamido-3-[4-amidino-2-[(2R)-3-ethoxycarbonyl-2-[4-(pyrrolidine-1-sulfonyl)benzoylamino]propoxy]phenyl]acrylate trifluoroacetate 1.50 g (3.17 mmol) of (1R)-1-benzyloxycarbonylmethyl-2-(5-cyano-2-iodophenoxy)ethyl ammonium chloride, 891 mg (3.49 mmol) of 4-(pyrrolidine-1-sulfonyl)benzoic acid, 472 mg (3.49 mmol) of 1-hydroxybenzotriazole, and 0.97 ml (6.98 mmol) of triethylamine were dissolved in 31 ml of dichloromethane, and 669 mg (3.49 mmol) of 1-(3-dimethylaminopropyl)-3-ethyl carbodiimide hydrochloride was added thereto, and they were stirred under cooling with ice for 10 minutes and then stirred at room temperature for 17 hours. The reaction was stopped by adding water, and the crude product was obtained in an ordinary manner by treatment with dichloromethane as the extractant. It was dissolved in 12 ml of acetonitrile, and 1.36 g (9.51 mmol) of methyl 2-acetamide acrylate, 579 mg (1.90 mmol) of tris(2-methylphenyl)phosphine, 1.33 ml (9.51 mmol) of triethylamine, and 0.5 ml of dimethylformamide were added thereto. Then, 78 mg (0.32 mmol) of palladium acetate was added thereto, and they were stirred at 100° C. for 1 hour, and 35 mg (0.14 mmol) of palladium acetate was further added thereto, and they were stirred at 100° C. for 3 hours. 700 mg (4.89 mmol) of methyl 2-acetamide acrylate, 250 mg (0.82 mmol) of tris(2-methylphenyl)phosphine, 3 ml (21.5 mmol) of triethylamine, and 33 ml (0.13 mmol) of palladium acetate were added again thereto, and they were further stirred at 100° C. for 2.5 hours. The solvent was distilled off, and the residue was purified by silica gel column chromatography (chloroform methanol=30:1, v/v) and dissolved in 3 ml of ethanol, and 30 ml of a dioxane solution containing 4 N hydrogen chloride was added thereto, and they were stirred at room temperature for 22 hours. Then, the solvent was distilled off, and the resulting residue was dissolved in 30 ml of ethanol, and 2.0 g (20.82 mmol) of ammonium carbonate was added thereto, and they were stirred at room temperature for 39 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 486 mg (0.64 mmol) (20%)

1H-NMR (DMSO-d6) δ: 1.17 (3H, t), 1.61-1.68 (4H, m), 1.94 (3H, s), 2.81 (2H, d), 3.12-3.29 (4H, m), 4.08 (2H, q), 4.21 (1H, dd), 4.28 (1H, dd), 4.76 (1H, brs), 7.29 (2H, s), 7.44 (1H, dd), 7.53 (1H, d), 7.72 (1H, d), 7 90 (2H, d), 8.00 (2H, d), 8.86 (1H, d), 9.11 (2H, s), 9.33 (2H, s), 9.67 (1H, brs)

Ethyl 2-acetamido-3-[4-amidino-2-[(2R)-3-ethoxycarbonyl-2-[4-(pyrrolidine-1-sulfonyl)benzoylamino]propoxy]phenyl]acrylate trifluoroacetate was also obtained.

Yield: 207 mg (0.27 mmol) (8%)

1H-NMR (DMSO-d6) δ: 1.15 (3H, t), 1.17 (3H, t), 1.61-1.68 (4H, m), 1.95 (3H, s), 2.82 (2H, d), 3.12-3.29 (4H, m), 4.08 (4H, q), 4.21 (1H, dd), 4.29 (1H, dd), 4.76 (1H, brs), 7.29

(2H, s), 7.43 (1H, dd), 7.51 (1H, d), 7.74 (1H, d), 7 90 (2H, d), 8.01 (2H, d), 8.87 (1H, d), 9.08 (2H, s), 9.33 (2H, s), 9.64 (1H, brs)

Example 195

Synthesis of (3R)-4-[5-amidino-2-(2-carboxy-2-oxo-ethyl)phenoxy]-3-[4-(pyrrolidine-1-sulfonyl)benzoylamino]butanoic acid trifluoroacetate 269 mg (0.35 mmol) of methyl 2-acetamide-3-[4-amidino-2-[(2R)-3-ethoxycarbonyl-2-[4-(pyrrolidine-1-sulfonyl)benzoylamino]propoxy]phenyl]acrylate trifluoroacetate was dissolved in 14 ml of 6 N hydrochloric acid and stirred at 70° C. for 4 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.
Yield: 146 mg (0.22 mmol) (62%)
MS (ESI, M/Z) 561 (MH+)
1H-NMR (DMSO-d6) δ: 1.58-1.70 (4H, m), 2.71 (1H, dd), 2.75 (1H, dd), 3.12-3.20 (4H, m), 4.20-4.30 (2H, m), 4.64-4.75 (1H, m), 6.80 (1H, s), 7.46 (1H, d), 7.47 (1H, s), 7.90 (2H, d), 8.02 (2H, d), 8.33 (1H, d), 9.03 (2H, s), 9.27 (2H, s)

Example 196

Synthesis of N-[4-[1-acetimidoyl-4-piperidyloxy]phenyl]-N-[2-(3-amidinophenoxy)ethyl]sulfamoylacetic acid bistrifluoroacetate Step 1

Synthesis of 1-t-butoxycarbonyl-4-(4-nitrophenoxy)piperidine 3.02 g (15.0 mmol) of 1-t-butoxycarbonyl-4-hydroxypiperidine, obtained by the t-butoxycarbonylation of 4-hydroxypiperidine with di-t-butyl dicarbonate in an ordinary manner, 2.09 g (15.0 mmol) of 4-nitrophenol and 4.72 g (18.0 mmol) of triphenylphosphine were dissolved in 50 ml of tetrahydrofuran. 7.84 g (18.0 mmol) of diethyl azodicarboxylate (40% solution in toluene) was added to the solution at room temperature, and they were stirred at room temperature overnight. After the treatment with ethyl acetate as extractant in an ordinary manner, the crude product was obtained. This product was purified by the silica gel column chromatography to obtain the title compound.
Yield: 2.74 g (8.5 mmol) (57%).
1H-NMR (CDCl3) δ 1.50 (9H, s), 1.75-1.86 (2H, m), 1.92-2.03 (2H, m), 3.36-3.43 (2H, m), 3.67-3.75 (2H, m), 4.58-4.64 (1H, m), 6.98 (2H, d), 8.20 (2H, d)

Step 2

Synthesis of 1-t-butoxycarbonyl-4-(4-aminophenoxy)piperidine 2.74 g (8.5 mmol) of 1-t-butoxycarbonyl-4-(4-nitrophenoxy)piperidine was dissolved in 20 ml of ethanol. 20 mg of 10% palladium/carbon was added to the solution, and they were stirred at room temperature in 1 atm. hydrogen atmosphere for 3 hours. Palladium/carbon was removed by the suction filtration. The filtrate was once concentrated and then treated with dichloromethane as extractant in an ordinary manner to obtain the title compound.
Yield: 2.59 g (8.02 mmol) (94%).
1H-NMR (CDCl3) δ 1.47 (9H, s), 1.63-1.75 (2H, m), 1.82-1.93 (2H, m), 3.22-3.32 (2H, m), 3.68-3.78 (2H, m), 4.71-4.80 (1H, m), 6.63 (2H, d), 6.76 (2H, d)

Step 3

Synthesis of 3-(2-bromoethoxy)benzonitrile 0.71 ml (10.0 mmol) of 2-bromoethanol, 1.43 g (12.0 mmol) of 3-cyanophenol and 3.15 g (12.0 mmol) of triphenylphosphine were dissolved in 100 ml of tetrahydrofuran. 5.22 g (12.0 mmol) of diethyl azodicarboxylate (40% solution in toluene) was added to the solution at room temperature, and they were stirred overnight. After the treatment with ethyl acetate as the extractant in an ordinary manner, the crude product was obtained. This product was purified by the silica gel column chromatography to obtain the title compound.
Yield: 1.63 g (7.2 mmol) (72%).
1H-NMR (CDCl3) δ 3.67 (2H, t), 4.32 (2H, t), 7.14-7.19 (2H, m), 7.28 (1H, d), 7.40 (1H, dd)

Step 4

Synthesis of 3-[2-[[4-(1-t-butoxycarbonyl-4-piperidyloxy)phenyl]amino]ethoxy]benzonitrile 616 mg (1.91 mmol) of 1-t-butoxycarbonyl-4-(4-aminophenoxy)piperidine, 432 ml (1.91 mmol) of 3-(2-bromoethoxy)benzonitrile and 634 mg (3.82 mmol) of potassium iodide were dissolved in 20 ml of dimethylformamide. 2.64 g (19.1 mmol) of potassium carbonate was added to the solution, and they were stirred at room temperature for 14 hours. The solvent was distilled off under reduced pressure. After the treatment with ethyl acetate as extractant in an ordinary manner, the crude product was obtained. This product was purified by the silica gel column chromatography to obtain the title compound.
Yield: 334 mg (0.76 mmol) (40%).
H-NMR (CDCl3) δ 1.48 (9H, s), 1.63-1.78 (2H, m), 1.81-1.96 (2H, m), 3.22-3.32 (2H, m), 3.52 (2H, t), 3.66-3.76 (2H, t), 4.17 (2H, t), 4.23-4.31 (1H, m), 6.63 (2H, d), 6.82 (2H, d), 7.14 (1H, dd), 7.16 (1H, d), 7.26 (1H, dt), 7.38 (1H, dd)

Step 5

Synthesis of Ethyl Sulfoacetate 2.21 g (15.8 mmol) of sulfoacetic acid was suspended in 30 ml of ethanol, and the suspension was heated at 80° C. under reflux for 5 hours. The solvent was distilled off to obtain the title compound.
Yield: 2.15 g (12.8 mmol) (81%)
H-NMR (CDCl3) δ 1.33 (3H, t), 4.07 (2H, s), 4.27 (2H, q)

Step 6

Synthesis of Ethyl Chlorosulfonyl Acetate 1.43 g (8.50 mmol) of ethyl sulfoacetate was added to 4.6 ml (51.02 mol) of phosphorus oxychloride, and they were heated at 100° C. under reflux for 5 hours. The solvent was distilled off to obtain the title compound.
Yield: 1.50 g (8.04 mmol) (95%)
H-NMR (CDCl3) δ 1.38 (3H, t), 4.38 (2H, q), 4.60 (2H, s)

Step 7

Synthesis of ethyl N-[4-(1-t-butoxycarbonyl-4-piperidyloxy)phenyl]-N-[2-(3-cyanophenoxy)ethyl]sulfamoylacetate 334 mg (0.76 mmol) of 3-[2-[[4-(1-t-butoxycarbonyl-4-piperidyloxy)phenyl]amino]ethoxy]benzonitrile and 2.79 ml (20 mmol) of triethylamine were dissolved in a mixed solvent of 10 ml of dichloromethane and 10 ml of pyridine. 1.50 g (8.04 mmol) of ethyl chlorosulfonylacetate was added to the solution under cooling with ice, and they were stirred at room temperature for 15 hours. After the treatment with dichloromethane as the extractant in an ordinary manner, the crude product was obtained. This product was purified by the silica gel column chromatography to obtain the title compound.

Yield: 299 mg (0.51 mmol) (67%).

H-NMR (CDCl3) δ 1.34 (3H, t), 1.47 (9H, s), 1.69-1.81 (2H, m), 1.87-1.99 (2H, m), 3.35 (2H, ddd), 3.69 (2H, ddd), 3.98 (2H, s), 4.06 (2H, t), 4.09 (2H, t), 4.30 (2H, q), 4.44-4.52 (1H, m), 6.92 (2H, d), 7.01 (1H, t), 7.06 (1H, ddd), 7.24 (1H, dt), 7.34 (1H, d), 7.39 (2H, d)

Step 8

Synthesis of N-[4-[1-acetimidoyl-4-piperidyloxy]phenyl]-N-[2-(3-amidinophenoxy)ethyl]sulfamoylacetic acid bistrifluoroacetate 299 mg (0.51 mmol) of ethyl N-[4-(1-t-butoxycarbonyl-4-piperidyloxy)phenyl]-N-[2-(3-cyanophenoxy)ethyl]sulfamoyl acetate was dissolved in 3 ml of ethanol, and 10 ml of a dioxane solution containing 4 N hydrogen chloride was added thereto, and the mixture was stirred at room temperature for 20 hours. Then, the solvent was distilled off, and the resulting residue was dissolved in 15 ml of ethanol, and 1.5 g (15.6 mmol) of ammonium carbonate was added thereto, and the mixture was stirred at room temperature for 55 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended amidino derivative was freeze-dried. The resulting solid was dissolved in 15 ml of ethanol, and 0.84 ml (6.0 mmol) of triethylamine and 370 mg (3.0 mmol) of ethyl acetoimidate hydrochloride were added successively thereto, and the mixture was stirred at room temperature for 18 hours. Then, the solvent was distilled off, and the resulting residue was dissolved in 14 ml of 6 N hydrochloric acid, and the mixture was stirred at 40° C. for 5 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 144 mg (0.19 mmol) (38%)

MS (ESI, m/z) 518 (MH+)

H-NMR (DMSO-d6) δ 1.70-1.85 (2H, m), 2.01-2.14 (2H, m), 2.29 (3H, s), 3.45-3.57 (2H, m), 3.69-3.83 (2H, m), 4.04 (4H, dd), 4.18 (2H, s), 4.72 (1H, brs), 7.05 (2H, d), 7.20 (1H, dd), 7.31 (1H, t), 7.35 (2H, d), 7.39 (1H, dd), 7.50 (1H, t), 8.62 (1H, s), 9.16 (1H, s), 9.22 (2H, s), 9.28 (2H, s)

Example 197

Synthesis of benzyl (3R)-3-(3-amidinophenylcarbamoyl)-3-(4-dimethylcarbamoylbenzoylamino)propionate trifluoroacetate 1.7 g (5.2 mmol) of N-t-butoxycarbonyl-D-aspartate-β-benzyl ester and 1.2 g (5.7 mmol) of 3-aminobenzamidine dihydrochloride were dissolved in 35 ml of pyridine, and 1.2 g (6.2 mmol) of 1-(3-dimethylaminopropyl)-3-ethyl carbodiimide hydrochloride was added thereto under cooling with ice and stirred at room temperature for 17 hours. The solvent was distilled off, and the resulting residue was purified by silica gel column chromatography, then dissolved in 30 ml of a dioxane solution containing 4 N hydrogen chloride, stirred at 0° C. for 1 hour and then at room temperature for 3 hours. The solvent was distilled off, and the resulting oily residue was dissolved in a mixed solvent of 30 ml of pyridine and 30 ml of dimethylformamide, and 995 mg (5.2 mmol) of 4-dimethylcarbamoylbenzoic acid (the compound in step 1 in Example 56) and 1.2 g (6.2 mmol) of 1-(3-dimethylaminopropyl)-3-ethyl carbodiimide hydrochloride were successively added thereto and stirred at room temperature for 18 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 642 mg (1.03 mmol) (20%)

H-NMR (DMSO-d6) δ 2.89 (3H, s), 2.94-3.02 (2H, m), 3.00 (3H, s), 5.05 (1H, dd), 5.13 (1H, d), 5.17 (1H, d), 7.28-7.38 (5H, m), 7.44 (1H, d), 7.51 (2H, d), 7.57 (1H, dd), 7.88 (1H, d), 7.93 (2H, d), 8.11 (1H, s), 8.99 (1H, d), 9.05 (2H, s), 9.32 (2H, s)

Example 198

Synthesis of benzyl (3R)-3-(3-amidinophenylcarbamoyl)-3-[4-(pyrrolidine-1-carbonyl)benzoylamino]propionate trifluoroacetate 1.7 g (5.2 mmol) of N-t-butoxycarbonyl-D-aspartate-β-benzyl ester and 1.2 g (5.7 mmol) of 3-aminobenzamidine dihydrochloride were dissolved in 35 ml of pyridine, and 1.2 g (6.2 mmol) of 1-(3-dimethylaminopropyl)-3-ethyl carbodiimide hydrochloride was added thereto under cooling with ice, and the mixture was stirred at room temperature for 17 hours. The solvent was distilled off, and the resulting residue was purified by silica gel column chromatography, then dissolved in 30 ml of a dioxane solution containing 4 N hydrogen chloride, stirred at 0° C. for 1 hour and then at room temperature for 3 hours. The solvent was distilled off, and the resulting oily-residue was dissolved in a mixed solvent of 30 ml of pyridine and 30 ml of dimethylformamide, and 1.13 g (5.2 mmol) of 4-(pyrrolidine-1-carbonyl)benzoic acid (Example ● ● ●) and 1.2 g (6.2 mmol) of 1-(3-dimethylaminopropyl)-3-ethyl carbodiimide were successively added thereto and stirred at room temperature for 18 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 109 mg (0.17 mmol) (3%)

H-NMR (DMSO-d6) δ 1.79-1.97 (4H, m), 2.94-3.02 (2H, m), 3.34-3.39 (2H, m), 3.44-3.52 (2H, m), 5.07 (1H, dd), 5.18 (2H, s), 7.29-7.38 (7H, m), 7.44 (1H, d), 7.59 (1H, dd), 7.87 (1H, d), 8.00 (2H, d), 8.11 (1H, s), 9.03 (2H, s), 9.08 (1H, d), 9.32 (2H, s)

Example 199

Synthesis of (3R)-3-(3-amidinophenylcarbamoyl)-3-[4-pyrrolidine-1-carbonyl)benzoylamino]propionic acid trifluoroacetate 101 mg (0.16 mmol) of benzyl (3R)-3-(3-amidinophenylcarbamoyl)-3-(4-dimethylcarbamoylbenzoylamino)propionate trifluoroacetate was dissolved in 4 ml conc. hydrochloric acid and stirred at 40° C. for 5 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 41 mg (0.08 mmol) (47%)

MS (ESI, m/z) 426 (MH+)

H-NMR (DMSO-d6) δ 2.89 (3H, s), 2.98 (1H, dd), 3.00 (3H, s), 3.27 (1H, dd), 4.86 (1H, ddd), 7.54 (2H, d), 7.67 (1H, dd), 7.72 (1H, dd), 7.80 (1H, d d), 7.87 (1H, dd), 7.93 (2H, d), 9.16 (2H, s), 9.47 (2H, s), 9.49 (1H, d)

Example 200

Synthesis of (3R)-3-(4-carboxybenzylamino)-4-(3-amidinophenoxy)butanoic acid trifluoroacetate 466 mg (0.73 mmol) of ethyl (3R)-3-(4-amidinobenzoylamino)-4-(3-amidinophenoxy)butyrate ditrifluoroacetate (the byproduct in Example 119) was dissolved in 10 ml conc. hydrochloric acid and stirred at 40° C. for 6 hours. The hydrogen chloride was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 17 mg (0.034 mmol) (5%)

MS (ESI, m/z) 386 (MH+)

H-NMR (DMSO-d6) δ 2.75 (2H, d), 4.12 (1H, dd), 4.24 (1H, dd), 4.62-4.77 (1H, m), 7.32-7.42 (3H, m), 7.54 (1H, dd), 7.93 (2H, d), 8.02 (2H, d), 9.17 (2H, s), 9.28 (2H, s)

Example 201

Synthesis of 3-[4-amidino-2-[2-[4-[2-(pyridine-4-yl)ethyl]benzoylamino]ethoxy]phenyl]-2-oxopropionic acid bistrifluoroacetate Step 1

Synthesis of 4-[2-(pyridine-4-yl)ethyl]benzoic acid hydrochloride 4.80 g (16.8 mmol) of methyl 4-(diethoxyphosphorylmethyl)benzoate (compound of step 1 in Example 42) was dissolved in 100 ml of tetrahydrofuran. 620 mg (15.5 mmol) of sodium hydride was added to the solution under cooling with ice, and they were stirred for 30 minutes and then at room temperature for 30 minutes. 1.38 g (12.9 mmol) of pyridine-4-aldehyde was added to the reaction mixture, and they were stirred for 20 hours. After the treatment with ethyl acetate as the extractant in an ordinary manner, the obtained crude product was dissolved in 30 ml of methanol. 300 mg of 10% palladium/carbon was added to the solution, and they were stirred in the presence of hydrogen for 20 hours. After the filtration through Celite, the solvent was distilled off. The residue was dissolved in 30 ml of concentrated hydrochloric acid, and the solution was stirred at 40° C. overnight. The solvent was distilled off to obtain the crude title compound.

Yield: 2.7 g (0.008 mmol) (92%).

Step 2

Synthesis of methyl 2-acetamido-3-[4-cyano-2-[2-[4-[2-(pyridine-4-yl)ethyl]benzoylamino]ethoxy]phenyl]acrylate trifluoroacetate 1.5 g (4.41 mmol) of methyl 2-acetamide-3-[4-cyano-2-(2-aminoethoxy)phenyl]acrylate was dissolved in 50 ml of dimethylformamide, and 1.84 ml (13.2 mmol) of triethylamine, 655 mg (4.85 mmol) of 1-hydroxybenzotriazole, 930 mg (4.85 mmol) of 1-(3-dimethylaminopropyl)-3-ethyl carbodiimide hydrochloride, and 1.10 g (4.85 mmol) of 4-[2-(pyridine-4-yl)ethyl]benzoate hydrochloride were added thereto and stirred at room temperature overnight. The reaction mixture was treated in an ordinary manner with dichloroethane as the extractant to obtain the crude product. The resulting crude product was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 800 mg (1.56 mmol) (35%)

H-NMR (DMSO-d6) δ 1.96 (3H, s), 2.82-2.98 (4H, m), 3.76 (3H, s), 3.78 (2H, dt), 4.30 (2H, t), 7.02 (2H, dd), 7.10 (2H, d), 7.17 (2H, d), 7.32 (1H, d), 7.42 (2H, br), 7.63 (2H, d), 8.42 (2H, d)

Step 3

Synthesis of 3-[4-amidino-2-[2-[4-[2-(pyridine-4-yl)ethyl]benzoylamino]ethoxy]phenyl]-2-oxopropionic acid bistrifluoroacetate 800 mg (1.56 mmol) of methyl 2-acetamide-3-[4-cyano-2-[2-[4-[2-(pyridine-4-yl)ethyl]benzoylamino]ethoxy]phenyl acrylate trifluoroacetate was dissolved in 1 ml of methanol and 5 ml of an dioxane solution containing 4 N hydrogen chloride, and they were stirred for 3 nights. The solvent was distilled off, and the residue was dissolved in 5 ml ethanol, and 443 mg of ammonium carbonate was added thereto, and the mixture was stirred overnight. After the solvent was distilled off, the residue was dissolved in 20 ml of conc. hydrochloric acid and stirred at 40° C. for 3 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 70 mg (0.10 mmol) (13%)

MS (ESI, m/z) 475 (MH+)

H-NMR (DMSO-d6) δ 2.90-3.29 (4H, m), 3.69 (2H, dt), 4.25 (2H, s, keto form), 4.27 (2H, t), 6.82 (1H, s, enol form), 7.33 (2H, d), 7.37-7.49 (2H, m), 7.66 (2H, d), 7.78 (2H, d), 8.33 (1H, d), 8.67 (2H, d), 8.71 (1H, t), 9.08 (2H, br), 9.27 (2H, br)

Example 202

Synthesis of ethyl 2-(2R)-(4-amidinobenzoylamino)-5-(3-amidinophenoxy)pentanoate bistrifluoroacetate Step 1

Synthesis of benzyl 2-(2R)-t-butoxycarbonylamino-5-hydroxypentanoate 5 g (15 mmol) of α-benzyl N-t-butoxycarbonyl-D-glutamate and 2.1 g (15 mmol) of triethylamine were dissolved in 75 ml of tetrahydrofuran. 1.43 ml (15 mmol) of ethyl chloroformate was added to the solution under cooling with ice, and they were stirred for 20 minutes. A precipitate thus formed was removed by the suction filtration. 5 g of ice and 0.57 g (15 mmol) of sodium borohydride were added to the filtrate under cooling with ice, and they were stirred for 1.5 hours. 30 ml of 1 N hydrochloric acid was added to the reaction mixture and they were stirred at room temperature for additional one hour. After the treatment with ethyl acetate as the extractant in an ordinary manner, the solvent was distilled off. The residue was purified by the silica gel column chromatography to obtain the title compound.

Yield: 1.67 g (5.2 mmol) (35%).
H-NMR (CDCl3) δ 1.40 (9H, s), 1.60-2.10 (4H, m), 3.60 (2H, t), 4.40 (1H, m), 5.20 (3H, m), 7.40 (5H, m).

Step 2

Synthesis of benzyl 2-(2R)-t-butoxycarbonylamino-5-(3-cyanophenoxy)pentanoate 6.77 g (21 mmol) of benzyl 2-(2R)-t-butoxycarbonylamino-5-hydroxypentanoate was dissolved in 105 ml of tetrahydrofuran. 2.74 g (23 mmol) of 3-cyanophenol, 6.6 g (25 mmol) of triphenylphosphine and 10 g (23 mmol) of diethyl azodicarboxylate (40% solution in toluene) were added to the solution, and they were stirred at room temperature for one hour. The solvent was distilled off, and the residue was treated with ethyl acetate as the extractant in an ordinary manner. The solvent was distilled off, and the residue was purified by the silica gel column chromatography to obtain the title compound.

Yield: 4.79 g (11.3 mmol) (54%)
H-NMR (CDCl3) δ 1.42 (9H, s), 1.70-2.10 (4H, m), 3.95 (2H, t), 4.40 (1H, m), 5.10 (1H, br), 5.20 (2H, m), 7.06-7.10 (2H, m), 7.23 (1H, d), 7.35 (5H, m)

Step 3

Synthesis of ethyl 2-(2R)-(4-amidinobenzoylamino)-5-(3-amidinophenoxy)pentanoate bistrifluoroacetate 4.79 g (11.3 mmol) of benzyl 2-(2R)-t-butoxycarbonylamino-5-(3-cyanophenoxy)pentanoate was dissolved in 48 ml of a dioxane solution containing 4 N hydrogen chloride, and they were stirred at room temperature for 2 hours. The solvent was distilled off, and the resulting de-t-butoxycarbonyl product was stirred in 57 ml of dichloromethane, and 1.6 g (11.3 mmol) of 4-cyanobenzoic acid, 1.68 g (12.4 mmol) of 1-hydroxybenzotriazole (hydrate), and 3.5 ml (24.8 mmol) of triethylamine were added thereto. 2.4 g (12.4 mmol) of 1-(3-dimethylaminopropyl)-3-ethyl carbodiimide hydrochloride was added thereto and stirred overnight. The crude condensate product was obtained in an ordinary manner by treatment with ethyl acetate as the extractant. 5 ml of dioxane, 4 ml of ethanol containing 30% (W/V) hydrogen chloride, and 40 ml of a dioxane solution containing 4 N hydrogen chloride were added thereto, and the mixture was stirred overnight. After the solvent was distilled off, the residue was stirred at room temperature overnight in 50 ml of an ethanol solution containing 10% (w/v) ammonia. The solvent was distilled off, and 25% of the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 187 mg (0.29 mmol) (18.2%)
MS (ESI, m/z) 426 (MH+), 424 (MH−).
H-NMR (DMSO-d6) δ 1.20 (3H, t), 1.80-2.10 (4H, m), 4.10-4.20 (4H, m), 4.50 (1H, m), 7.30 (1H, d), 7.40 (2H, m), 7.55 (1H, t) 7.95 (2H, d), 8.05 (2H, d), 9.10 (1H, d), 9.20 (2H, br), 9.30 (2H, br), 9.38 (2H, br), 9.45 (2H, br).

Example 203

Synthesis of ethyl 2-(2R)-(4-amidinobenzoylamino)-5-(3-amidinophenoxy)pentanoate bistrifluoroacetate Step 1

Synthesis of ethyl 2-(2R)-(4-amidinobenzoylamino)-5-(3-amidinophenoxy)pentanoate ditrifluoroacetate 1.9 g (4.46 mmol) of ethyl 2-(2S)-(4-amidino-benzoylamino)-5-(3-amidinophenoxy)pentanoate ditrifluoroacetate was stirred at 40° C. for 4 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 347 mg (0.55 mmol) (20%)
MS (ESI, m/z) 398 (MH+), 396 (MH−).
H-NMR (DMSO-d6) δ 1.80-2.10 (4H, m), 4.13 (2H, t), 4.50 (1H, m), 7.30 (1H, d), 7.40 (1H, d), 7.40 (1H, s), 7.52 (1H, t), 7.95 (2H, d), 8.10 (2H, d), 9.00 (1H, d), 9.20 (2H, br), 9.38 (2H, br), 9.40 (2H, br), 9.52 (2H, br).

Example 204

Synthesis of 4-(3-amidinophenoxy)-3-[[1-(pyridine-4-yl)-piperidine-4-carbonyl]amino]butyric acid bistrifluoroacetate Step 1

Synthesis of 1-(pyridine-4-yl)-piperidine-4-carboxylate chloride 7 g (34 mmol) of 1-(pyridine-4-yl)-piperidine-4-carboxylate hydrochloride was stirred in 340 ml of dichloromethane, and 1 ml of dimethylformamide and 10.4 ml (109 mmol) of oxalyl dichloride were added thereto and stirred at room temperature for 1 hour. The solvent was distilled off, and the residue was dried with a vacuum pump to obtain the title compound.

Yield: 7.9 g (35 mmol)

Step 2

Synthesis of benzyl 4-(3-cyanophenoxy)-3-[[1-pyridine-4-yl)-piperidine-4-carbonyl]amino]butyrate 3.7 g (16.5 mmol) of 1-(pyridine-4-yl)-piperidine-4-carboxylate chloride and 4 g (12 mmol) of benzyl (3R)-3-amino-4-(3-cyanophenoxy)butyrate were stirred in 60 ml of dichloromethane, and 5.95 ml (42.7 mmol) of triethylamine, 1 ml of dimethylformamide and 50 mg of 4-dimethylaminopyridine were added thereto and stirred overnight. The reaction solution was extracted with dichloromethane, then washed with 1 N sodium hydroxide and saturated saline and dried magnesium sulfate anhydride, and the solvent was distilled off. The residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid. The solvent of the fraction of the intended product was distilled off, and 1 N sodium hydroxide was added thereto, and the product was treated in an ordinary manner with dichloromethane as the extractant to obtain the title compound.

Yield: 1.58 g (3.17 mmol) (19%)

Step 3

Synthesis of 4-(3-amidinophenoxy)-3-[[1-(pyridine-4-yl)-piperidine-4-carbonyl]amino]butyrate ditrifluoroacetate 1.58 g (3.17 mmol) of benzyl 4-(3-cyanophenoxy)-3-[[1-(pyridine-4-yl)-piperidine-4-carbonyl]amino]butyrate and 1.6 ml of ethanol were stirred overnight in 16 ml of a dioxane solution containing 4 N hydrogen chloride. The solvent was distilled off, and 10 ml of ethanol and 0.5 g of ammonium carbonate were added thereto and stirred overnight, and the solvent was distilled off. The resulting residue was stirred in 3 ml of conc. hydrochloric acid at 40° C. for 4 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 594 mg (0.91 mmol) (29%)

MS (ESI, m/z) 426 (MH+)

H-NMR (DMSO-d6) δ1.50-1.61 (2H, m), 1.70-1.90 (2H, m), 2.50-2.85 (3H, m), 3.15-3.30 (2H, m), 4.00-4.20 (2H, m), 4.15-4.30 (2H, m), 4.40 (1H, m), 7.20 (2H, d), 7.30 (1H, d), 7.41 (1H, s), 7.42 (1H, d), 7.53 (1H, t), 8.17 (1H, d), 8.22 (2H, d), 9.29 (2H, br), 9.38 (2H, br).

Example 205

Synthesis of 3-[4-amidino-2-[2-[4-(pyrrolidine-1-carbonyl)benzoylamino]ethoxy]phenyl]-2-oxopropionic acid trifluoroacetate

Step 1

Synthesis of methyl 2-acetamido-3-[4-cyano-2-[2-[4-(pyrrolidine-1-carbonyl)benzoylamino]ethoxy]phenyl]acrylate 2.5 g (7.4 mmol) of methyl 2-acetamide-3-[4-cyano-2-(2-aminoethoxy)phenyl]acrylate was dissolved in dimethyl formaldehyde, and 1.56 g (8.1 mmol) of 4-(pyrrolidine-1-carbonyl)benzoic acid, 1.1 g (8.1 mmol) of 1-hydroxybenzotriazole, 1.53 ml of triethylamine, and 1.55 g (8.1 mmol) of 1-(3-dimethylaminopropyl)-3-ethyl carbodiimide hydrochloride were added thereto and stirred at room temperature overnight. The solvent was distilled off, and the resulting residue was treated in an ordinary manner with ethyl acetate as the extractant, and the solvent was distilled off, and the resulting residue was washed with hexane and dried to obtain the title compound.

Yield: 1.80 g (3.68 mmol) (50%)

H-NMR (DMSO-d6) δ 1.78-1.90 (4H, m), 1.95 (3H, s), 3.30-3.50 (4H, m), 3.60-3.65 (3H, s), 3.70 (2H, dt), 4.30 (2H, t), 7.20 (1H, s), 7.41 (1H, d), 7.55-7.70 (4H, m), 7.85 (2H, d), 8.75 (1H, t), 9.65 (1H, s).

Step 2

Synthesis of 3-[4-amidino-2-[2-[4-(pyrrolidine-1-carbonylbenzoylamino)ethoxy]phenyl]-2-oxopropionic acid trifluoroacetate 1.80 g (3.68 mmol) of methyl 2-acetamide-3-[4-cyano-2-[2-[4-(pyrrolidine-1-carbonyl)benzoylamino]ethoxy]phenyl]acrylate and 1 ml of ethanol were stirred for 2 nights in 20 ml of a dioxane solution containing 4 N hydrogen chloride. After the solvent was distilled off, 20 ml of ethanol and 1.0 g of ammonium carbonate were added thereto and stirred overnight. After the solvent was distilled off, 20 ml of 6 N hydrochloric acid was added thereto and the mixture was heated under reflux at 80° C. for 1.5 hours. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 345 mg (0.59 mmol) (16%)

MS (ESI, m/z) 467 (MH+)

H-NMR (DMSO-d6) δ 1.75-1.95 (4H, m), 3.30-3.50 (4H, m), 3.72 (2H, dt), 4.30 (2H, t), 4.25 (2H, s, keto form), 6.81 (1H, s, enol form), 7.35-7.50 (2H, m), 7.60 (2H, d), 7.89 (2H, d), 8.33 (1H, d), 8.85 (1H, br), 9.01 (2H, br), 9.27 (2H, br), 9.80 (1H, br, enol form)

Example 206

Synthesis of 3-[4-amidino-2-[2-[[1-(pyridine-4-yl) piperidine-4-carbonyl]amino]ethoxy]phenyl]-2-oxopropionic acid bistrifluoroacetate

Step 1

Synthesis of methyl 2-acetamido-3-[4-cyano-2-[2-[[1-(pyridine-4-yl)piperidine-4-carbonyl]amino] ethoxy]phenyl]acrylate trifluoroacetate 1.0 g (2.94 mmol) of methyl 2-acetamido-3-[4-cyano-2-(2-aminoethoxy)phenyl]acrylate hydrochloride, 0.79 g (3.24 mmol) of 1-(pyridine-4-yl)piperidine-4-carboxylic acid hydrochloride and 1.64 ml of triethylamine were stirred in dimethylformamide. 1.51 g (3.24 mmol) of bromotripyrrolidinophosphonium hexafluorophosphate was added to the resultant mixture under cooling with ice, and they were stirred at room temperature overnight. The solvent was distilled off under reduced pressure, and the residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 360 mg (0.73 mmol) (25%).

H-NMR (DMSO-d6) δ 1.50-1.70 (2H, m), 1.75-1.90 (2H, m), 1.95 (3H, s), 2.50 (1H, m), 3.15-3.30 (2H, m), 3.42 (2H, dt), 3.65 (3H, s), 4.10-4.22 (4H, m), 7.15-7.21 (3H, m), 7.44 (1H, d), 7.58 (1H, s), 7.68 (1H, d), 8.09 (1H, t), 8.21 (2H, d), 9.65 (1H, s)

Step 2

Synthesis of 3-[4-amidino-2-[2-[[1-(pyridine-4-yl) piperidine-4-carbonyl]amino]ethoxy]phenyl]-2-oxopropionic acid bistrifluoroacetate 360 mg (0.73 mmol) of methyl 2-acetamido-3-[4-cyano-2-[2-[[1-(pyridine-4-yl)piperidine-4-carbonyl]amino] ethoxy]phenyl]acrylate trifluoroacetate and 0.5 ml of ethanol were stirred in 10 ml of 4 N solution of hydrogen chloride in dioxane for two nights. The solvent was distilled off. 5 ml of ethanol and 0.21 g of ammonium carbonate were added to the residue, and they were stirred at room temperature overnight. The solvent was distilled off, and 10 ml of 6 N hydrochloric acid was added to the residue. After heating under reflux at 80° C. for 1.5 hours, the solvent was distilled off. The residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 205 mg (0.30 mmol) (41%).

MS (ESI, m/z) 454 (MH+)

H-NMR (DMSO-d6) δ 1.50-1.70 (2H, m), 1.80-1.95 (2H, m), 2.60 (1H, m), 3.18-3.30 (2H, m), 3.43-3.60 (2H, m), 4.10-4.30 (4H, m), 6.80 (1H, s, enol form), 7.18 (2H, d), 7.35-7.48 (2H, m), 8.22 (2H, d), 8.34 (1H, d) 9.15 (2H, br), 9.30 (2H, br), 9.80 (1H, br, enol form).

Example 207

Synthesis of N-[2-(3-amidinophenoxy)ethyl]-4-(4-methoxybenzoyl)benzamide trifluoroacetate

Step 1

Synthesis of methyl 4-(4-methoxybenzoyl)benzoate 2.1 g (16 mmol) of aluminum chloride and 2.4 g (12 mmol) of 4-chlorocarbonyl benzoic acid monomethyl ester were stirred in 15 ml of dichloromethane under stirring under cooling with ice. 1.0 g (9.3 mmol) of anisole was added to the resultant mixture. Two hours after, the temperature was elevated to room temperature, and the mixture was stirred overnight. After the treatment with dichloromethane as the extractant in an ordinary manner, the solvent was distilled off. The residue was purified by the silica gel column chromatography to obtain the title compound.

Yield: 610 mg (2.3 mmol) (25%)

H-NMR (CDCl3) δ 3.90 (3H, s), 3.98 (3H, s), 6.89 (2H, d), 7.79 (2H, d), 7.81 (2H, d), 8.14 (2H, d)

Step 2

Synthesis of 4-(4-methoxybenzoyl)benzoate 610 mg (2.3 mmol) of methyl 4-(4-methoxybenzoyl)benzoate was stirred in 40 ml of ethanol, and 6 ml of 1 N aqueous sodium hydroxide was added thereto, and the mixture was stirred for 3 days. The reaction solution was distilled off, and 1 N hydrochloric acid was added to the residue which was then treated in an ordinary manner with ethyl acetate as the extractant to obtain the title compound.

Yield: 313 mg (1.22 mmol) (53%)

H-NMR (DMSO-d6) δ: 3.88 (3H, s), 7.11 (2H, d), 7.78 (2H, d), 7.78 (2H, d), 8.09 (2H, d).

Step 3

Synthesis of N-[2-(3-amidinophenoxy)ethyl]-4-(4-methoxybenzoyl)benzamide trifluoroacetate 150 mg (0.59 mmol) of 4-(4-methoxybenzoyl)benzoic acid, 128 mg (0.64 mmol) of 3-(2-aminoethoxy)benzonitrile hydrochloride, 87 mg (0.64 mmol) of 1-hydroxybenzotriazole, 0.1 ml of triethylamine, 123 mg (0.64 mmol) of 1-(3-dimethylaminopropyl)-3-ethyl carbodiimide hydrochloride were stirred in dichloromethane overnight. The reaction mixture was treated in an ordinary manner with dichloromethane as the extractant. After addition of 1 ml ethanol, the resulting crude condensate product was stirred 2 nights in 10 ml of dioxane containing 4 N hydrogen chloride. The solvent was distilled off, and 0.2 g of ammonium carbonate and 10 ml of ethanol were added thereto, and the mixture was stirred overnight. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 103 mg (0.19 mmol) (32%)

MS (ESI, m/z) 418 (MH+)

H-NMR (DMSO-d6) δ 3.70 (2H, dt), 3.85 (3H, s), 4.25 (2H, t), 7.10 (2H, d), 7.30-7.43 (3H, m), 7.54 (1H, t), 7.76 (2H, d), 7.76 (2H, d), 8.01 (2H, d), 8.95 (1H, t), 9.10 (2H, br), 9.30 (2H, br).

Example 208

Synthesis of ethyl (2S)-2-(4-dimethylcarbamoylbenzoylamino)-4-(3-amidinophenoxy)butyrate trifluoroacetate The title compound was obtained in the same manner as in step 6 in Example 1 by treating benzyl (2S)-2-t-butoxycarbonylamino-4-(3-cyanophenoxy)butyrate (the compound in step 1 in Example 91) and benzyl (2S)-2-(4-dimethylcarbamoylbenzoylamino)-4-(3-cyanophenoxy)butyrate obtained in the same manner as in step 2 in Example 91 from 4-dimethylcarbamoylbenzoic acid as the starting material.

MS (ESI, m/z) 441 (MH+)
H-NMR (DMSO-d6) δ 1.20 (3H, t), 2.25 (2H, m), 2.83 (3H, s), 3.00 (3H, s), 4.10-4.30 (4H, m), 4.70 (1H, m), 7.30 (1H, d), 7.35 (1H, s), 7.37 (1H, d), 7.50 (2H, d), 7.51 (1H, t), 7.92 (2H, d), 8.92 (1H, d), 9.05 (2H, br), 9.30 (2H, br).

Example 209

Synthesis of ethyl (2S)-2-(4-amidinobenzoylamino)-4-(3-amidinophenoxy)butyrate bistrifluoroacetate The title compound was obtained by treating benzyl (2S)-2-(4-cyanobenzoylamino)-4-(3-cyanophenoxy)butyrate (the compound in step 2 in Example 91) in the same manner as in step 6 in Example 1.

MS (ESI, m/z) 412 (MH+)
H-NMR (DMSO-d6) δ 1.20 (3H, t), 2.22-2.40 (2H, m), 4.10-4.30 (4H, m), 4.70 (1H, m), 7.31 (1H, d), 7.37 (1H, s), 7.39 (1H, d), 7.53 (1H, t), 7.92 (2H, d), 8.07 (2H, d), 9.12 (1H, d), 9.20 (2H, br), 9.28 (2H, br), 9.33 (2H, br), 9.43 (2H, br).

Example 210

Synthesis of (2S)-2-(4-carbamoylbenzoylamino)-4-(3-amidinophenoxy)butyrate trifluoroacetate The title compound was obtained as the byproduct in step 3 in Example 91.

MS (ESI, m/z) 385 (MH+)
H-NMR (DMSO-d6) δ 2.20-2.40 (2H, m), 4.20 (2H, m), 4.65 (1H, m), 7.26-7.40 (3H, m), 7.51 (1H, br), 7.52 (1H, t), 7.95 (4H, s), 8.10 (1H, br), 8.87 (1H, d), 9.06 (2H, br), 9.29 (2H, br).

Example 211

Synthesis of 4-(3-amidinophenoxy)-3-(3R)-[4-(pyrrolidine-1-carbonyl)benzoylamino]butyrate trifluoroacetate

Step 1

Synthesis of 4-(1-pyrrolidylcarbonyl)benzoic acid 29.0 g (0.146 mol) of 4-chlorocarbonyl benzoic acid monomethyl ester, 14.2 g (200 mmol) of pyrrolidine and 21.0 g (208 mmol) of triethylamine were reacted in 350 ml of dichloromethane. After the treatment in an ordinary manner, methyl 4-(1-pyrrolidylcarbonyl)benzoate was obtained. 29.0 g of this ester compound was hydrolyzed with 12.0 g of sodium hydroxide in a mixed solvent comprising 70 ml of water, 70 ml of methanol and 70 ml of tetrahydrofuran. After the completion of the reaction, the solvent was distilled off. After the addition of 1 N hydrochloric acid followed by the treatment with dichloromethane as the extractant in an ordinary manner, the title compound was obtained.

Yield: 23.7 g (108 mmol)
1H-NMR (DMSO-6) δ: 1.75-1.90 (4H, m), 3.30-3.50 (4H, m), 7.62 (2H, d), 7.99 (2H, d), 13.14 (1H, br)

Step 2

Synthesis of benzyl 4-(3-cyanophenoxy)-3-(3R)-[4-(pyrrolidine-1-carbonyl)benzoylamino]butyrate 1.8 g (5.2 mmol) of benzyl (3R)-3-amino-4-(3-cyanophenoxy)butyrate hydrochloride (the compound in step 2 in Example 52), 703 mg (5.2 mmol) of 1-hydroxybenzotriazole (hydrate), 997 mg (5.2 mmol) of 1-(3-dimethylaminopropyl)-3-ethyl carbodiimide hydrochloride, 526 mg (5.2 mmol) of triethylamine, and 1.14 g (5.2 mmol) of 4-(1-pyrrolidyl carbonyl)benzoic acid were stirred in dichloromethane overnight. The reaction solution was washed with 1 N hydrochloric acid, 1 N aqueous sodium hydroxide and saturated saline and dried over sulfate magnesium anhydride, and the solvent was distilled off. The resulting residue was purified by silica gel chromatography (ethyl acetate) to obtain the title compound.

Yield: 1.82 g (3.56 mmol) (69%)
1H-NMR (CDCl3) δ: 1.85-2.05 (4H, m), 2.80-3.00 (2H, m), 3.35 (2H, t), 3.65 (2H, t), 4.10-4.25 (2H, m), 4.85 (1H, m), 5.20 (2H, s), 7.10 (1H, s), 7.12 (1H, d), 7.24-7.40 (7H, m), 7.54 (2H, d), 7.76 (2H, d)

Step 3

Synthesis of 4-(3-cyanophenoxy)-3-(3R)-[4-(pyrrolidine-1-carbonyl)benzoylamino]butyric acid trifluoroacetate 1.82 g (3.56 mmol) of benzyl 4-(3-cyanophenoxy)-(3R)-[4-(pyrrolidine-1-carbonyl)benzoylamino]butyrate and 3 ml of ethanol were stirred in dioxane containing 4 N hydrogen chloride for 2 days. The solvent was distilled off. 20 ml of ethanol and 1.0 g of ammonium carbonate (purity: 30% as ammonia) were added to the residue, and they were stirred overnight. The solvent was distilled off. 20 ml of concentrated hydrochloric acid was added to the residue, and they were stirred at 40° C. overnight. The solvent was distilled off. The residue was treated by the reversed phase high-performance liquid chromatography with silica gel, having octadodecyl group chemically bonded thereto, as the filler. After the elution with a mixed solvent of water and acetonitrile containing 0.1% (v/v) of trifluoroacetic acid, the fraction of the intended product was freeze-dried to obtain the title compound.

Yield: 913 mg (1.65 mmol) (46%).
MS (ESI, m/z) 439 (MH+)
1H-NMR (DMSO-d6) δ: 1.70-1.90 (4H, m), 2.75 (2H, d), 3.35 (2H, t), 3.50 (2H, t), 4.05-4.30 (2H, m), 4.70 (1H, m), 7.32-7.43 (3H, m), 7.54 (1H, t), 7.60 (2H, d), 7.88 (2H, d), 8.64 (1H, d), 9.10 (2H, br), 9.28 (2H, br)

Example 212

Synthesis of ethyl 4-(3-amidinophenoxy)-3-(3R)-(4-dimethylcarbamoylbenzoylamino)butyrate trifluoroacetate 1.87 g (3.98 mmol) of benzyl 4-(3-cyanophenoxy)-(3R)-3-(4-dimethylcarbamoyl-benzoylamino)butyrate (the compound in step 2 in Example 56) and 3 ml of ethanol were stirred for 2 days in dioxane containing 4 N hydrogen chloride. The solvent was distilled off, and to the resulting residue was added 20 ml of ethanol and 1.1 g ammonium carbonate (30% purity as ammonia), and the mixture was stirred overnight. The solvent was distilled off, and the resulting residue was purified by reverse phase high performance liquid chromatography in the same manner as in step 3 in Example 211 whereby the title compound was obtained.

Yield: 895 mg (1.61 mmol) (41%)

MS (ESI, m/z) 441 (MH+)

1H-NMR (DMSO-d6) δ: 1.15 (3H, t), 2.80 (2H, d), 2.90 (3H, s), 3.00 (3H, s), 4.10 (2H, q), 4.00-4.25 (2H, m), 4.70 (1H, m), 7.30-7.40 (3H, m), 7.50 (2H, d), 7.54 (1H, t), 7.87 (2H, d), 8.65 (1H, d), 9.04 (2H, br), 9.27 (2H, br)

Example 213

Synthesis of 3-[4-amidino-2-[2-[4-(N,N-dimethylamidino)benzoylamino]ethoxy]phenyl]-2-oxopropionic acid bistrifluoroacetate Step 1

Synthesis of t-butyl [2-(5-cyano-2-iodophenoxy)ethyl]carbamate

The title compound was obtained from 3-hydroxy-4-iodobenzonitrile (compound of step 2 in Example 79) and t-butyl (2-chloroethyl) carbamate (obtained from 2-chloroethylamine hydrochloride in the same manner as that of step 1 in Example 1) in the same manner as that of step 2 in Example 1.

1H-NMR (CDCl3) δ: 1.45 (9H, s), 3.62 (2H, dt), 4.10 (2H, t), 5.05 (1H, br), 6.96-7.06 (2H, m), 7.90 (1H, d)

Step 2

Synthesis of methyl 2-acetamido-3-[2-(2-t-butoxycarbonylamino-ethoxy)-4-cyanophenyl]acrylate 15.3 g (39.5 mmol) of t-butyl [2-(5-cyano-2-iodophenoxy)ethyl]carbamate, 9.05 g (63.2 mmol) of methyl 2-acetamidoacrylate, 11 ml (79 mmol) of triethylamine, 1.3 g of palladium (II) acetate and 7.30 g of tris(2-methylphenyl)phosphine were stirred in 150 ml of acetonitrile overnight. The solvent was distilled off, and the residue was treated by the silica gel chromatography (ethyl acetate/hexane) to obtain the crude product, which was washed with hexane and a mixed solvent of hexane/ethyl acetate, and then vacuum-dried to obtain the title compound.

Yield: 10.23 g (25.4 mmol) (64%).

1H-NMR (DMSO-d6) δ: 1.38 (9H, s), 1.95 (3H, s), 3.35 (2H, dt), 3.70 (3H, s), 4.10 (2H, t), 7.03 (1H, t), 7.20 (1H, s), 7.43 (1H, d), 7.55 (1H, s), 7.68 (1H, d), 9.65 (1H, s)

Step 3

Synthesis of methyl 2-acetamido-3-[2-(2-aminoethoxy)-4-cyanophenyl]acrylate hydrochloride 30 ml of dioxane was added to 7.75 g (19.2 mmol) of methyl 2-acetamido-3-[2-(2-t-butoxycarbonylamino-ethoxy)-4-cyanophenyl]acrylate. After stirring, 80 ml of dioxane containing 4 N hydrogen chloride was added to the obtained mixture, and they were stirred at room temperature for one hour. The solvent was distilled off, and the residue was suspended in ethyl acetate. The obtained suspension was filtered to obtain the title compound.

Yield: 4.38 g (12.9 mmol) (67%).

1H-NMR (DMSO-d6) δ: 1.95 (3H, s), 3.25 (2H, dt), 3.70 (3H, s), 4.30 (2H, t), 7.28 (1H, s), 7.48 (1H, d), 7.62 (1H, s), 7.70 (1H, d), 8.20 (3H, br), 9.75 (1H, s)

Step 4

Synthesis of 4-(N,N-dimethylamidino)benzoate hydrochloride

Ethyl 4-(N,N-dimethylamidino)benzoate (compound of step 1 in Example 7) was heated under reflux in 6 N hydrochloric acid for 6 hours, and then the solvent was distilled off to obtain the title compound.

1H-NMR (DMSO-d6) δ: 2.95 (3H, s), 3.25 (3H, s), 7.75 (2H, d), 8.15 (2H, d), 9.25 (1H, br), 9.50 (1H, br)

Step 5

Synthesis of methyl 2-acetamido-3-[4-cyano-2-[4-(N,N-dimethylamidino)benzoylamino]ethoxy]phenyl]acrylate trifluoroacetate 3.54 g (10.4 mmol) of methyl 2-acetamido-3-[2-(2-aminoethoxy)-4-cyanophenyl]acrylate hydrochloride, 2.62 g (11.5 mmol) of 4-(N,N-dimethylamidino)benzoic acid hydrochloride, 3.5 ml (19.6 mmol) of diisopropylethylamine and 6.19 g (13.3 mmol) of bromotripyrrolidinophosphonium hexafluorophosphate were stirred in dimethylformamide at room temperature overnight. Dimethylformamide was distilled off under reduced pressure. After the extraction with ethyl acetate, the extract was washed with 1 N aqueous sodium hydroxide solution and saturated aqueous common salt solution and then dried over anhydrous magnesium sulfate. The solvent was distilled off, and the residue was treated by the reversed phase high-performance liquid chromatography in the same manner as in the purification process in step 3 of Example 211 to obtain the title compound.

Yield: 1.0 g (1.73 mmol) (17%).

1H-NMR (DMSO-d6) δ: 1.95 (3H, s), 2.98 (3H, s), 3.22 (3H, s), 3.65 (3H, s), 3.70 (2H, dt), 4.30 (2H, t), 7.21 (1H, s), 7.44 (1H, d), 7.62-0.74 (4H, m), 8.03 (2H, d), 8.88 (1H, t), 8.96 (1H, s), 9.35 (1H, s), 9.67 (1H, s)

Step 6

Synthesis of 3-[4-amidino-2-[2-[4-(N,N-dimethylamidino)benzoylamino]ethoxy]phenyl]-2-oxo-propionic acid bistrifluoroacetate 1.0 g (1.73 mmol) of methyl 2-acetamido-3-[4-cyano-2-[2-[4-(N,N-dimethylamidino)benzoylamino]ethoxy]phenyl] acrylate trifluoroacetate and 1.0 ml of ethanol were stirred in 20 ml of dioxane containing 4 N hydrogen chloride at room temperature for 2 days. The solvent was distilled off. 20 ml of ethanol and 510 mg of ammonium carbonate were added to the residue, and they were stirred at room temperature for 9 hours. The solvent was distilled off. 30 ml of 6 N hydrochloric acid was added to the residue, and they were stirred at 80° C. for 1.5 hours. The solvent was distilled off, and the residue was treated by the reversed phase high-performance liquid chromatography in the same manner as in the purification process in step 3 of Example 211 to obtain the title compound.

Yield: 397 mg (0.59 mmol) (34%).

MS (ESI, m/z) 440 (MH+)

1H-NMR (DMSO-d6) δ: 2.95 (3H, s), 3.25 (3H, s), 3.75 (2H, dt), 4.35 (2H, t), 4.20 (2H, s, keto form), 6.80 (1H, s, enol form), 7.38-7.48 (2H, m), 7.69 (2H, d), 8.04 (2H, d), 8.33 (1H, d), 8.95-9.40 (7H, m), 9.80 (1H, br, enol form)

Example 214

Synthesis of N-[2-(3-amidinophenoxy)ethyl]-4-[(4,5-dihydro-1H-imidazole-2-yl)amino]benzamide bis-trifluoroacetate Step 1

Synthesis of imidazoline-2-sulfonic acid 3.32 g (32.5 mmol) of 2-imidazolinethion, 250 mg (1.03 mmol) of sodium molybdate dihydrate and 750 mg of sodium chloride were stirred in 15 ml of water under cooling with ice. 25 ml of 30% aqueous hydrogen peroxide solution was slowly dropped into the resultant mixture while the inner temperature is kept at 4° C. or below. After the completion of the dropping, the reaction mixture was stirred under cooling with ice for 2 hours. The reaction liquid was filtered to obtain the precipitate, which was washed with cold water and then dried in vacuo to obtain the title compound.
Yield: 1.47 g (9.81 mmol) (30%)
1H-NMR (DMSO-d6) δ: 3.85 (4H, s), 10.35 (1H, br)

Step 2

Synthesis of ethyl 4-[(4,5-dihydro-1H-imidazole-2-yl)amino]benzoate trifluoroacetate 991 mg (6.0 mmol) of ethyl 4-aminobenzoate, 1.0 g (6.66 mmol) of imidazoline-2-sulfonic acid and 1.35 g (13.3 mmol) of triethylamine were heated under reflux in 30 ml of acetonitrile overnight. The solvent was distilled off. After the extraction of the product from the residue with ethyl acetate, the extract was washed with 1 N aqueous sodium hydroxide solution and saturated aqueous common salt solution, and then dried over anhydrous magnesium sulfate. The solvent was distilled off, and the residue was treated by the reversed phase high-performance liquid chromatography in the same manner as in the purification process in step 3 of Example 211 to obtain the title compound.
Yield: 86 mg (0.25 mmol) (4%).
1H-NMR (CD3OD) δ: 1.40 (3H, t), 3.80 (4H, s), 4.38 (2H, q), 7.38 (2H, d), 8.10 (2H, d)

Step 3

Synthesis of N-[2-(3-cyanophenoxy)ethyl]-4-[(4,5-dihydro-1H-imidazole-2-yl)amino]benzamide trifluoroacetate 80 mg (0.23 mmol) of ethyl 4-[(4,5-dihydro-1H-imidazole-2-yl)amino]benzoate trifluoroacetate was heated under reflux in 10 ml of 6 N hydrochloric acid for 5 hours, and the solvent was distilled off whereby 4-[(4,5-dihydro-1H-imidazole-2-yl)amino]benzoate hydrochloride was obtained.

4-[(4,5-dihydro-1H-imidazole-2-yl)amino]benzoate hydrochloride

1H-NMR (DMSO-d6) δ: 3.70 (4H, s), 7.40 (2H, d), 8.00 (2H, d), 8.60 (2H, s)

2 ml of dimethylformamide, 50 mg (0.25 mmol) of 3-(2-aminoethoxy)benzonitrile hydrochloride (the compound in step 3 in Example 1, H-NMR (DMSO-d6) δ: 3.20 (2H, t), 4.25 (2H, t), 7.34 (1H, d), 7.46 (1H, d), 7.47 (1H, s), 7.54 (1H, t), 8.09 (3H, br)), 34 mg (0.25 mmol) of 1-hydroxybenzotriazole (hydrate), 48 mg (0.25 mmol) of 1-(3-dimethylaminopropyl)-3-ethyl carbodiimide hydrochloride, and 25 mg (0.25 mmol) of triethylamine were added thereto, and they were stirred at room temperature overnight. The solvent was distilled off under reduced pressure, and 1 N aqueous sodium hydroxide was added to the residue which was then extracted with ethyl acetate. The extract was washed with saturated saline and dried over magnesium sulfate anhydride, and the solvent was distilled off. The residue was purified by reverse phase high performance liquid chromatography in the same manner as in step 3 in Example 211 whereby the title compound was obtained.
Yield: 67 mg (0.14 mmol) (61%)
1H-NMR (DMSO-d6) δ: 3.65 (2H, dt), 3.70 (4H, s), 4.20 (2H, t), 7.30-7.52 (6H, m), 7.95 (2H, d), 8.50 (2H, s), 8.75 (1H, t)

Step 4

Synthesis of N-[2-(3-amidinophenoxy)ethyl]-4-[(4,5-dihydro-1H-imidazole-2-yl)amino]benzamide bis-trifluoroacetate 66 mg (0.14 mmol) of N-[2-(3-cyanophenoxy)ethyl]-4-[(4,5-dihydro-1H-imidazole-2-yl)amino]benzamide trifluoroacetate and 0.5 ml of ethanol were stirred for 3 days in 10 ml of dioxane containing 4 N hydrogen chloride. The solvent was distilled off, and 10 ml of ethanol and 45 mg of ammonium carbonate were added to the residue which was stirred for 2 days and the solvent was distilled off. The residue was purified by reverse phase high performance liquid chromatography in the same manner as in step 3 in Example 211 whereby the title compound was obtained.
Yield: 58 mg (0.10 mmol) (71%)
MS (ESI, m/z) 367 (MH+)
1H-NMR (DMSO-d6) δ: 3.70 (2H, dt), 3.70 (4H, s), 4.20 (2H, t), 7.30-7.42 (5H, m), 7.54 (1H, t), 7.95 (2H, d), 8.60 (2H, s), 8.80 (1H, t), 9.19 (2H, br), 9.30 (2H, br), 10.90 (1H, s)

Example 215

Synthesis of 4-(3-amidinophenoxy)-3-(3R)-[4-(N,N-dimethylamidino)benzoylamino]butyric acid bistrifluoroacetate Step 1

Synthesis of 4-(3-cyanophenoxy)-3-(3R)-[4-(N,N-dimethylamidino)benzoylamino]butyrate trifluoroacetate 3.7 g (9.0 mmol) of benzyl (3R)-3-t-butoxycarbonylamino-4-(3-cyanophenoxy)butyrate (the compound in step 1 in Example 52) was stirred in 20 ml of dioxane, and 10 ml of dioxane containing 4 N hydrogen chloride was added thereto, and they were stirred at room temperature. After stirring at room temperature for 2 hours, the solvent was distilled off, and 20 ml of dimethylformamide, 2.47 g (10.8 ml) of 4-(N,N-dimethylamidino)benzoate hydrochloride, 1.46 g (10.8 mmol) of 1-hydroxybenzotriazole (hydrate), 2.07 g (10.8 mmol) of 1-(3-dimethylaminopropyl)-3-ethyl carbodiimide hydrochloride, and 3.76 ml (27 mmol) of triethylamine were added thereto, and they were stirred at room temperature overnight. Ethyl acetate was added to the reaction solution which was then washed with 1 N aqueous sodium hydroxide and saturated saline and dried over magnesium sulfate anhydride, and the solvent was distilled off. The resulting residue was purified by reverse phase high performance liquid chromatography in the same manner as in step 3 in Example 211 whereby the title compound was obtained.

Yield: 2.0 g (3.34 mmol) (37%)

1H-NMR (DMSO-d6) δ: 2.85 (2H, d), 3.00 (3H, s), 3.25 (3H, s), 4.20 (2H, m), 4.75 (1H, m), 5.10 (2H, s), 7.28-7.52 (9H, m), 7.70 (2H, d), 8.02 (2H, d), 8.82 (1H, d), 9.06 (1H, br), 9.39 (1H, br)

Step 2

Synthesis of 4-(3-amidinophenoxy)-3-(3R)-[4-(N,N-dimethylamidino)benzoylamino]butyrate ditrifluoroacetate The title compound was obtained from 518 mg (0.87 mmol) of 4-(3-cyanophenoxy)-3-(3R)-[4-(N,N-dimethylamidino)benzoylamino]butyrate trifluoroacetate in the same manner as in step 3 in Example 211.

Yield: 205 mg (0.32 mmol) (37%)

MS (ESI, m/z) 412 (MH+)

1H-NMR (DMSO-d6) δ: 2.75 (2H, d), 2.95 (3H, s), 3.25 (3H, s), 4.10-4.30 (2H, m), 4.70 (1H, m), 7.32-7.43 (3H, m), 7.54 (1H, t), 7.71 (2H, d), 8.04 (2H, d), 8.80 (1H, d), 9.00 (1H, br), 9.15 (2H, br), 9.30 (2H, br), 9.35 (1H, br)

Example 216

Synthesis of 3-(3R)-[N-benzyl-N-(4-amidinobenzoyl)amino]-4-(3-amidinophenoxy)butyric acid bis-trifluoroacetate Step 1

Synthesis of benzyl 3-(3R)-benzylamino-4-(3-cyanophenoxy)butyrate 1N aqueous sodium hydroxide solution was added to benzyl (3R)-3-amino-4-(3-cyanophenoxy)butyrate. After the extraction with dichloromethane, the extract was washed with saturated aqueous common salt solution and dried over anhydrous magnesium sulfate. The solvent was distilled off to obtain benzyl (3R)-3-amino-4-(3-cyanophenoxy)butyrate. 240 mg (0.77 mmol) of this product was stirred in methanol. 106 mg (1.0 mmol) of benzaldehyde and 58 mg (0.92 mmol) of sodium cyanoborohydride were added to the resultant mixture, and they were stirred at room temperature overnight. 1N hydrochloric acid was added to the mixture. Methanol was distilled off under reduced pressure. 1 N aqueous sodium hydroxide solution was added to the residue. After the extraction with ethyl acetate, the extract was washed with saturated aqueous common salt solution. The product was dried over anhydrous magnesium sulfate, and the solvent was distilled off to obtain the title compound.

Yield: 196 mg (0.49 mmol) (64%)

1H-NMR (CDCl3) δ2.70 (2H, d), 3.45 (1H, m), 3.85 (2H, d), 4.00 (2H, m), 5.15 (2H, s), 7.00-7.10 (2H, m), 7.20-7.40 (12H, m)

Step 2

Synthesis of benzyl 3-(3R)-[N-benzyl-N-(4-cyanobenzoyl)amino]-4-(3-cyanophenoxy)butyrate 190 mg (0.47 mmol) of benzyl 3-(3R)-benzylamino-4-(3-cyanophenoxy)butyrate and 153 mg of triethylamine were stirred in 5 ml of dimethylformamide, and 70 mg (0.47 mmol) of 4-cyanobenzoyl chloride was added thereto under cooling with ice and stirred for 3 hours. 1 N hydrochloric acid was added thereto, followed by extraction with ethyl acetate. The extract was washed with 1 N sodium hydroxide and saturated saline and dried over magnesium sulfate anhydride, and the solvent was distilled off and the residue was purified by silica gel column chromatography (ethyl acetate-hexane) to obtain the title compound.

Yield: 148 mg (0.28 mmol) (59%)

1H-NMR (CDCl3) δ2.50-3.30 (2H, br), 3.70-4.80 (5H, br), 5.15 (2H, br), 6.80-7.70 (18H, br)

Step 3

Synthesis of 3-(3R)-[N-benzyl-N-(4-amidinobenzoyl)amino]-4-(3-amidinophenoxy)butyric acid bis-trifluoroacetate 178 mg (0.38 mmol) of benzyl 3-(3R)-[N-benzyl-N-(4-cyanobenzoyl)amino]-4-(3-cyanophenoxy)butyrate and 1 ml of ethanol were stirred in 5 ml of dioxane containing 4 N hydrogen chloride for 4 days. The solvent was distilled off, and 10 ml of ethanol containing 10% (w/v) ammonia was added thereto and the mixture was stirred at room temperature for 5 days. The solvent was distilled off, and the residue was stirred in 10 ml of conc. hydrochloric acid at 40° C. overnight. The solvent was distilled off, and the resulting residue was purified by reverse phase high performance liquid chromatography in the same manner as in step 3 in Example 211 to obtain the title compound.

Yield: 48 mg (0.07 mmol) (18%)

MS (ESI, m/z) 474 (MH+)

1H-NMR (DMSO-d6) δ: 2.60-3.00 (2H, m), 3.80-4.70 (5H, m), 7.10-8.00 (13H, m), 9.10-9.50 (8H, br)

Example 217

Synthesis of N-[2-(3-amidinophenoxy)ethyl]-3-(E)-(4-chlorophenyl)acrylamide trifluoroacetate Step 1

Synthesis of N-[2-(3-cyanophenoxy)ethyl]-3-(E)-(4-chlorophenyl)acrylamide 109 mg (0.55 mmol) of 3-(2-aminoethoxy)benzonitrile hydrochloride, 85 mg (0.55 mmol) of 1-hydroxybenzotriazole (hydrate), 105 mg (0.55 mmol) of 1-(3-dimethylaminopropyl)-3-ethyl carbodiimide hydrochloride, 61 mg (0.6 mmol) of triethylamine, and 100 mg (0.55 mmol) of p-chlorocinnamic acid were used, and the title compound was obtained in the same manner as in step 1 in Example 211.

Yield: 170 mg (0.52 mmol) (95%)

1H-NMR (CDCl3) δ 3.80 (2H, dt), 4.15 (2H, t), 6.05 (1H, br), 6.40 (1H, d), 7.15 (1H, d), 7.16 (1H, s), 7.27 (1H, d), 7.32-7.45 (5H, m), 7.61 (1H, d)

Step 2

Synthesis of N-[2-(3-amidinophenoxy)ethyl]-3-(E)-(4-chlorophenyl)acrylamide trifluoroacetate 165 mg (0.52 mmol) of N-[2-(3-cyanophenoxy)ethyl]-3-(E)-(4-chlorophenyl)acrylamide was used and the title compound was obtained in the same manner as in step 6 in Example 1.

Yield: 108 mg (0.24 mmol) (46%)
MS (ESI, m/z) 344 (MH+)
1H-NMR (DMSO-d6) δ: 3.60 (2H, dt), 4.15 (2H, t), 6.70 (1H, d), 7.30-7.62 (9H, m), 8.40 (1H, t), 9.05 (2H, br), 9.30 (2H, br)

Example 218

Synthesis of N-[2-(3-amidinophenoxy)ethyl]-N-methyl-4-carbamoyl-benzamide trifluoroacetate The title compound was obtained as the byproduct in step 2 in Example 115.

Yield: 21 mg (0.05 mmol) (8%)
MS (ESI, m/z) 341 (MH+)
1H-NMR (DMSO-d6) δ: 3.00 (3H, br), 3.60-4.40 (4H, br), 7.20-8.10 (10H, br), 9.30 (4H, br)

Example 219

Synthesis of 1-(4-amidinobenzoyl)-(2R)-2-[(3-amidinophenoxy)methyl]pyrrolidine bistrifluoroacetate

Step 1

Synthesis of 1-t-butoxycarbonyl-(2R)-2-chloromethylpyrrolidine 500 mg (5 mmol) of (2R)-2-hydroxymethyl-pyrrolidine, 1.1 g (5 mmol) of di-t-butyl dicarbonate and 500 mg (5 mmol) of triethylamine were stirred in dichloromethane at room temperature overnight. The reaction liquid was washed with 0.5 N hydrochloric acid and saturated aqueous common salt solution, and then dried over anhydrous magnesium sulfate. The solvent was distilled off, and the residue was dissolved in 20 ml of dichloromethane. 760 mg (7.5 mmol) of triethylamine and 860 mg (7.5 mmol) of mesyl chloride were added to the solution at 0° C. The obtained mixture was stirred at room temperature for 5 hours. The product was treated with dichloromethane as the extractant in an ordinary manner, and the residue was dissolved in 5 ml of dimethylformamide. 1.06 g (25 mmol) of lithium chloride was added to the solution, and the resultant mixture was stirred at 65° C. overnight. The product was treated with ethyl acetate as the extractant in an ordinary manner to obtain the title compound.

Yield: 426 mg (1.94 mmol) (39%)
1H-NMR (CDCl 3) δ 1.50 (9H, s), 1.75-2.05 (4H, m), 3.30-3.80 (4H, m), 4.00 (1H, m)

Step 2

Synthesis of 1-t-butoxycarbonyl-(2R)-2-[(3-cyanophenoxy)methyl]pyrrolidine 430 mg (2 mmol) of 1-t-butoxycarbonyl-(2R)-2-chloromethyl pyrrolidine was dissolved in 5 ml of dimethylamide, and 238 mg (2 mmol) of 3-hydroxy benzonitrile, 500 mg (3 mmol) of potassium iodide, and 414 mg (3 mmol) of potassium carbonate were added thereto and stirred at 90° C. for 3 days. The reaction mixture was treated in an ordinary manner with ethyl acetate as the extractant, and the resulting residue was purified by silica gel column chromatography to obtain the title compound.

Yield: 73 mg (0.24 mmol) (12%)
1H-NMR (CDCl3) δ 1.45 (9H, s), 1.82-2.08 (4H, m), 3.40 (2H, br), 3.90 (1H, m), 4.18 (2H, br), 7.10-7.30 (3H, m), 7.35 (1H, t)

Step 3

Synthesis of 1-(4-cyanobenzoyl)-(2R)-2-[(3-cyanophenoxy)methyl]pyrrolidine 70 mg (0.23 mmol) of 1-t-butoxycarbonyl-(2R)-2-[(3-cyanophenoxy)methyl]pyrrolidine was dissolved in a dioxane solution containing 4 N hydrogen chloride and then stirred at room temperature for 3 hours. The solvent was distilled off to obtain the crude de-t-butoxycarbonyl product. 38 mg (0.25 mmol) of 4-cyano-benzoic acid was dissolved in 3 ml of dimethylformamide, and 100 mg (1 mmol) of N-methyl morpholine and 25 mg (0.23 mmol) of ethyl chloroformate were added thereto and stirred at 0° C. for 5 minutes, and the crude de-t-butoxycarbonyl product was added thereto and stirred at room temperature for 2 hours. The reaction solution was treated in an ordinary manner with ethyl acetate as the extractant to obtain the title compound.

Yield: 69.6 mg (0.21 mmol) (91%)
1H-NMR (CDCl 3) δ: 1.82-2.22 (4H, m), 3.38-3.55 (2H, m), 4.10-4.63 (3H, m), 7.18-7.30 (3H, m), 7.39 (1H, t), 7.58 (2H, d), 7.73 (2H, d)

Step 4

Synthesis of 1-(4-amidinobenzoyl)-(2R)-2-[(3-amidinophenoxy)methyl]pyrrolidine bistrifluoroacetate The title compound was obtained from 69 mg (0.21 mmol) of 1-(4-cyanobenzoyl)-(2R)-2-[(3-cyanophenoxy)methyl] pyrrolidine as the starting material in the same operation as in step 6 in Example 1.

Yield: 22.7 mg (0.038 mmol) (18%)
MS (ESI, m/z) 366 (MH+)
1H-NMR (DMSO-d6) δ: 1.80-2.20 (4H, m), 3.30-3.55 (2H, m), 4.20-4.55 (3H, m), 7.36-7.58 (4H, m), 7.70 (2H, d), 7.89 (2H, d), 9.27-9.47 (8H, m)

Example 220

Synthesis of N-[2-(3-amidinophenoxy)ethyl]-6-(pyrrolidine-1-yl)nicotinamide trifluoroacetate

Step 1

Synthesis of 5-bromo-2-(pyrrolidine-1-yl)pyridine 4.95 g (28.6 mmol) of 2-amino-5-bromopyridine was dissolved in 40 ml of toluene. 9.95 ml (57.2 mmol) of diisopropylethylamine, 6.15 g (28.6 mmol) of 1,4-dibromobutane and 100 mg (0.82 mmol) of 4-(dimethylamino)pyridine were added to the solution, and they were stirred for three nights. After the treatment with dichloromethane as the extractant in an ordinary manner, the crude product was obtained, which was purified by the silica gel column chromatography to obtain the title compound.

Yield: 2.6 g (11.1 mmol) (39%)

1H-NMR (CDCl3) δ: 1.91-2.05 (4H, m), 3.32-3.46 (4H, m), 6.22 (1H, d), 7.44 (1H, dd), 8.12 (1H, d)

Step 2

Synthesis of methyl 6-(pyrrolidine-1-yl)nicotinate 2.6 g (11.1 mmol) of 5-bromo-2-(pyrrolidine-1-yl)pyridine was dissolved in 30 ml of dimethylformamide. 8.9 ml (220 mmol) of methanol, 3.06 ml (22 mmol) of triethylamine, 124 mg (0.5 mmol) of palladium (II) acetate and 2.7 g (11.1 mmol) of triphenylphosphine were added to the solution, and they were stirred in the presence of carbon monoxide at 70° C. overnight. After the treatment with ethyl acetate as the extractant in an ordinary manner, the crude product was obtained, which was purified by the silica gel column chromatography to obtain the title compound.

Yield: 1.0 g (4.85 mmol) (44%)

1H-NMR (CDCl3) δ 1.94-2.07 (4H, m), 3.40-3.56 (4H, m), 3.82 (3H, s), 6.29 (1H, d), 7.94 (1H, dd), 8.77 (1H, d)

Step 3

Synthesis of 6-(pyrrolidine-1-yl)nicotinic acid 1.0 g (4.85 mol) of methyl 6-(pyrrolidine-1-yl)nicotinoate was dissolved in 10 ml of conc. hydrochloric acid and stirred at 40° C. overnight. The solvent was distilled off whereby the hydrochloride of the title compound was obtained.

Yield: 1.0 g (4.39 mmol) (90%)

Step 4

Synthesis of N-[2-(3-amidinophenoxy)ethyl]-6-(pyrrolidine-1-yl)nicotinamide trifluoroacetate 396 mg (1.74 mmol) of 6-(pyrrolidine-1-yl)nicotic acid was dissolved in 10 ml of dichloromethane, and 0.86 ml (6.18 mmol) of triethylamine, 306 mg (2.27 mmol) of 1-hydroxybenzotriazole, 433 mg (2.27 mmol) of 1-(3-dimethylaminopropyl)-3-ethyl carbodiimide hydrochloride, and 449 mg (2.27 mmol) of 3-(2-aminoethoxy)benzonitrile hydrochloride were added thereto and stirred at room temperature overnight. It was treated in an ordinary manner with dichloromethane as the extractant to obtain the crude condensate product. The resulting crude product was dissolved in 1 ml of ethanol and 5 ml of a dioxane solution containing 4 N hydrogen chloride and stirred for 3 nights. The solvent was distilled off, and the residue was dissolved in 5 ml of ethanol, and 661 mg (8.49 mmol) of ammonium carbonate was added thereto, and the mixture was stirred overnight. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 430 mg (0.74 mmol) (43%)

MS (ESI, m/z) 354 (MH+)

1H-NMR (DMSO-d6) δ: 1.91-2.05 (4H, m), 3.44-3.58 (4H, m), 3.63 (2H, dt), 4.33 (2H, t), 6.80 (1H, d), 7.29-7.42 (3H, m), 7.54 (1H, dd), 8.12 (1H, dd), 8.51 (1H, d), 8.73 (1H, t), 9.20 (2H, br), 9.29 (2H, br)

Example 221

Synthesis of (3R)-4-(3-amidinophenoxy)-3-[4-[(1-acetimidoylpiperidine-4-yl)methyl]benzoylamino]butyric acid bistrifluoroacetate 10 mg (0.02 mmol) of ethyl (3R)-4-(3-amidinophenoxy)-3-[4-[(piperidine-4-yl)methyl]benzoylamino]butyrate ditrifluoroacetate (JP2 52-3) was dissolved in 1 ml of ethanol, and 10 mg (0.08 mmol) of ethylacetoimidate hydrochloride and 0.5 ml (3.3 mmol) of triethylamine were added thereto and stirred at room temperature overnight. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 6 mg (0.008 mmol) (57%)

MS (ESI, m/z) 480 (MH+)

1H-NMR (DMSO-d6) δ: 1.10-1.35 (2H, m), 1.58-1.75 (2H, m), 1.82-1.97 (1H, m), 2.23 (3H, s), 2.58 (2H, d), 2.70 (2H, d), 2.95-3.21 (2H, m), 3.62-3.92 (1H, m), 3.98-4.13 (2H, m), 4.24 (1H, dd), 4.68 (1H, ddt), 7.27 (2H, d), 7.32-7.43 (3H, m), 7.53 (1H, dd), 7.80 (2H, d), 8.47-8.65 (2H, m), 9.05 (1H, br), 9.21 (2H, br), 9.27 (2H, br)

Example 222

Synthesis of (3R)-4-(3-amidinophenoxy)-3-[[4-[imino(pyrrolidine-1-yl)methyl]benzoyl]amino]butylic acid dihydrochloride Step 1

Synthesis of 4-[imino(pyrrolidine-1-yl)methyl]benzoic acid hydrochloride 15.2 g (103 mmol) of 4-cyano-benzoic acid was added to 200 ml of an ethyl acetate solution containing 4 N hydrogen chloride and 50 ml of ethanol, and they were stirred for 5 days. The solvent was distilled off under reduced pressure, and 100 ml of ethyl acetate was added to the resulting solid, and the mixture was stirred for 30 minutes, and the solid was collected by filtration. The resulting solid was reacted with 15.0 g (211 mmol) of pyrrolidine and 10.0 g (98.8 mmol) of triethylamine for 2 days in 100 ml ethanol as the solvent. The solvent was distilled off, and 40 ml of 6 N hydrochloric acid was added to the residue, and it was reacted at 85° C. for 4 hours. The solvent was distilled off, and 50 ml of 1 N hydrochloric acid was added to the residue which was then stilled for 30 minutes, and the solid was collected by filtration and washed with 20 ml of ice-cold water. It was dried under reduced pressure to obtain the title compound.

Yield: 7.67 g (30.1 mmol) (29.2%)

MS (ESI, m/z) 479 (MH+)

1H-NMR (DMSO-d6) δ: 1.78-1.92 (2H, m), 1.98-2.12 (2H, m), 3.23-3.43 (2H, m), 3.58-3.62 (2H, m), 7.78 (2H, d), 8.15 (2H, d), 9.18 (1H, bs), 9.45 (1H, bs) 13.41 (1H, bs)

Step 2

Synthesis of (3R)-4-(3-amidinophenoxy)-3-[[4-[imino(pyrrolidine-1-yl)methyl]benzoyl]amino]butyric acid bistrifluoroacetate 3.52 g (8.58 mmol) of benzyl (3R)-3-t-butoxycarbonylamino-4-(3-cyanophenoxy)butyrate (JP2 52-1) was dissolved in 50 ml of an ethyl acetate solution containing 4 N hydrogen chloride, and the mixture was stirred at room temperature for 4 hours. The solvent was distilled off, and the resulting solid was dissolved in a mixed solvent of 95 ml of dimethylformamide and 20 ml of dimethyl sulfoxide, and 1.74 g (6.83 mmol) of 4-[imino-(pyrrolidine-1-yl)-methyl]benzoate hydrochloride, 2.71 g (5.81 mmol) of bromo-tris-pyrrolidinophosphonium hexafluoroborate and 3.85 (8.26 mmol) of di-isopropyl ethyl amine were added thereto, and the mixture was stirred at room temperature overnight. 400 ml of ethyl acetate was added thereto, and the reaction solution was washed with 200 ml of 1 N aqueous sodium hydroxide, and the organic layer was partitioned and dried over magnesium sulfate. The solvent was distilled off, and the resulting crude product was applied to reverse phase chromatography and eluted with a mixed solvent of water and acetonitrile containing 0.1% (v/v) trifluoroacetic acid, and the fraction of the intended product was freeze-dried to obtain the condensate. This condensate was reacted overnight with 35 ml of a dioxane solution containing 4 N hydrogen chloride and 7 ml of ethanol. The solvent was distilled off, and the resulting residue was dissolved in 20 ml of ethanol, and 620 mg (6.59 mmol) of ammonium carbonate was added thereto and the mixture was reacted overnight. Further, the solvent was distilled off and the resulting residue was reacted in the presence of 6 N hydrochloride at 40° C. overnight. The solvent was distilled off, and the resulting residue was applied to reverse phase chromatography and eluted with a mixed solvent of water and acetonitrile containing 0.1% (v/v) trifluoroacetic acid. The fraction of the intended product was freeze-dried, and 25 ml of dioxane containing 4 N hydrogen chloride was added thereto, and the mixture was stirred for 30 minutes. The solvent was distilled off, and 25 ml of water was added thereto, followed by freeze-drying to obtain the title compound.

Yield: 301 mg (0.590 mmol) (6.9%)
MS (ESI, m/z) 438 (MH+)
1H-NMR (DMSO-d6) δ: 1.80-1.91 (2H, m), 2.02-2.11 (2H, m), 2.73 (2H, d) 3.35 (2H, t), 3.57 (2H, d), 4.13 (1H, dd), 4.22 (1H, dd), 4.70 (1H, ddt), 7.34 (1H, d), 7.38-7.45 (2H, m), 7.53 (1H, dd), 7.74 (2H, d), 8.04 (2H, d), 8.83 (1H, d), 8.93 (1H, bs), 9.32 (2H, bs), 9.34 (2H, bs), 9.38 (1H, bs), 12.42 (1H, bs)

Example 223

Synthesis of N-[(1R)-2-(3-amidinophenoxy)-1-benzylethyl]-4-(pyrrolidine-1-carbonyl)benzamide trifluoroacetate

Step 1

Synthesis of t-butyl N-[(1R)-1-benzyl-2-chloroethyl]carbamate 6.01 g (36.4 mmol) of D-phenylalanine was dissolved in a solution comprising 5.35 g (53.0 mmol) of triethylamine, 50 ml of tetrahydrofuran and 50 ml of water. 7.52 g (34.5 mmol) of di-t-butyl dicarbonate was added to the solution, and they were stirred at room temperature overnight to conduct the N-t-butoxycarbonylation. After the treatment in an ordinary manner, the obtained solid was dissolved in 80 ml of THF, and reduced with 3.97 g (36.6 mmol) of ethyl chloroformate, 6.47 g (50.1 mmol) of diisopropylethylamine and 2.12 g (56.0 mmol) of sodium borohydride. The reaction product was then reacted with 4.17 g (36.4 mmol) of methanesulfonyl chloride and 6.47 g (50.1 mmol) of diisopropylethylamine in 80 ml of dimethylformamide as the solvent. After the treatment in an ordinary manner, the obtained residue was reacted with 8.42 g (199 mmol) of lithium chloride and 120 ml of dimethylformamide at 40° C. overnight also in an ordinary manner to obtain the title compound.

Yield: 8.52 g (31.6 mmol) (86.8%)
1H-NMR (CDCl3) δ: 2.82-2.94 (2H, m), 3.45 (1H, dd), 3.61 (1H, dd), 4.02-4.20 (1H, m), 4.85 (1H, d), 7.15-7.38 (5H, m)

Step 2

Synthesis of t-butyl N-[(1R)-1-benzyl-2-(3-cyanophenoxy)ethyl]carbamate 8.52 g (31.6 mmol) of t-butyl N-[(1R)-1-benzyl-2-chloroethyl]carbamate, 12.1 g (87.5 mmol) of potassium carbonate and 5 g (41.9 mmol) of 3-cyanophenol were reacted in 120 ml of dimethylformamide as the solvent at 70° C. overnight. After the treatment in an ordinary manner followed by the silica gel column chromatography, the title compound was obtained.

Yield: 5.28 g (15.0 mmol) (47.5%)
1H-NMR (CDCl3) δ: 1.42 (9H, s), 2.95-3.02 (2H, m), 3.90 (2H, t), 4.85 (1H, d), 7.08-7.41 (9H, m)

Step 3

Synthesis of N-[(1R)-2-(3-amidinophenoxy)-1-benzylethyl]-4-(pyrrolidine-1-carbonyl)benzamide trifluoroacetate 630 mg (1.79 mmol) of t-butyl N-[(1R)-1-benzyl-2-(3-cyanophenoxy)ethyl]carbamate was treated with 10 ml of a dioxane solution containing 4 N hydrogen chloride to obtain the de-protected product. Condensation was conducted in dimethylformamide by use of 720 mg (3.28 mmol) of 4-(pyrrolidine-1-carbonyl)benzoic acid, 1.55 g (8.09 mmol) of 1-(3-dimethylaminopropyl)-3-ethyl carbodiimide hydrochloride, 1.21 g (8.95 mmol) of 1-hydroxybenzotriazole and 1.48 g (11.5 mmol) of di-isopropyl ethylamine, and 52 mg of 4-dimethylaminopyridine. Further, the condensate was reacted for 6 days with 20 ml of a dioxane solution containing 4 N hydrogen chloride and 2 ml of ethanol. The solvent was distilled off, and the resulting residue was dissolved in 20 ml of ethanol, and 1.0 g (10.6 mmol) of ammonium carbonate was added thereto and allowed to react for 4 days. The solvent was distilled off, and the residue was applied to reverse phase chromatography and eluted with a mixed solvent of water and acetonitrile containing 0.1% (v/v) of trifluoroacetic acid, and the fraction of the intended product was freeze-dried to obtain the title compound.

Yield: 325 mg (0.556 mmol) (31.1%)
1H-NMR (DMSO-d6) δ: 1.75-1.93 (4H, m), 2.92-3.15 (2H, m), 3.35 (2H, t), 3.44 (2H, t), 4.05-4.12 (2H, m), 4.48-4.60 (1H, m), 7.18-7.55 (9H, m), 7.58 (2H, d), 7.82 (2H, d), 8.62 (1H, d), 9.15 (2H, bs), 9.27 (2H, bs)

Example 224

Synthesis of N-[(1R)-2-(3-amidinophenoxy)-1-benzylethyl]-4-(N,N-dimethylcarbamoyl)benzamide trifluoroacetate 630 mg (1.79 mmol) of t-butyl N-[(1R)-1-benzyl-2-(3-cyanophenoxy)ethyl]carbamate and 4-(N,N-dimethylcarbamoyl)benzoic acid were used, and the title compound was obtained in the same manner as in step 3 in Example 223.

Yield: 417 mg (0.747 mmol) (41.7%)

1H-NMR (DMSO-d6) δ: 2.84 (3H, s), 3.00 (3H, s), 2.95-3.10 (2H, m), 3.10-3.22 (2H, m), 4.50-4.62 (1H, m), 7.18-7.60 (9H, m), 7.46 (2H, d), 7.82 (2H, d), 8.62 (1H, d), 9.15 (2H, bs), 9.27 (2H, bs)

Example 225

Synthesis of N-[2-(3-amidinophenoxy)ethyl]-1-(dimethylaminocarbonyl)piperidine-4-carboxyamide trifluoroacetate

Step 1

Synthesis of N-[2-(3-cyanophenoxy)ethyl]-1-(dimethylaminocarbonyl)piperidine-4-carboxyamide 430 mg (1.58 mmol) of N-[2-(3-cyanophenoxy)ethyl]-piperidine-4-carboxyamide (JP2 19-1) was dissolved in 1.6 ml of dimethylformamide, and 0.3 ml (2.06 mmol) of triethylamine and 0.16 ml (1.74 mmol) of dimethyl carbamoyl chloride were added thereto at 0° C. and stirred at room temperature for 2 hours. It was treated in an ordinary manner with ethyl acetate as the extractant to obtain the title compound.

Yield: 206 mg (0.60 mmol) (38%)

Step 2

Synthesis of N-[2-(3-amidinophenoxy)ethyl]-1-(dimethylcarbamoyl)piperidine-4-carboxyamide trifluoroacetate 206 mg (0.60 mmol) of N-[2-(3-cyanophenoxy)ethyl]-1-(dimethylaminocarbonyl)piperidine-4-carboxyamide was stirred in 3 ml of dioxane containing 4 N hydrogen chloride, and 3 ml of ethanol containing hydrogen chloride was added thereto and stirred at room temperature for 1 day, and the solvent was distilled off under reduced pressure, and the resulting residue was dissolved in 5 ml of an ethanol solution containing 10% (w/v) ammonia and stirred at room temperature for 1 day. The solvent was distilled off, and the resulting residue was applied to reverse phase high performance liquid chromatography with silica gel having octadodecyl group chemically bonded thereto as the filler, and eluted with a mixed solvent of water and acetonitrile containing 0.1% (v/v) of trifluoroacetic acid, and the fraction of the intended product was freeze-dried to obtain the title compound.

Yield: 160 mg (0.34 mmol) (56%)

MS (ESI, m/z) 362 (MH+)

1H-NMR (DMSO-d6) δ: 1.50 (2H, ddd), 1.65 (2H, dd), 2.30 (1H, tt), 2.65 (2H, d), 2.70 (6H, s), 3.47 (2H, dd), 3.52 (2H, d), 4.08 (2H, t), 7.30 (1H, d), 7.36 (1H, s), 7.38 (1H, d), 7.53 (1H, t), 8.09 (1H, t), 9.24 (4H, d)

Example 226

The activity of inhibiting the activated blood coagulation factor X was determined in the same manner as that of Example 93, and the activity of inhibiting thrombin was determined in the same manner as that of Example 94.

The blood anticoagulating activity was determined in the same manner as that of Example 184. The results are summarized in Table 3.

TABLE 3

| | Activity of inhibiting activated blood coagulation factor X (pIC$_{50}$) | Thrombin inhibiting activity (pIC$_{50}$) | Blood anticoagulating activity (PT2) |
|---|---|---|---|
| Compound of Ex. 186 | 7.7 | 3.6 | 5.9 |
| Compound of Ex. 188 | 8.1 | 3.4 | 5.7 |
| Compound of Ex. 191 | 8.4 | 3.7 | 6.0 |
| Compound of Ex. 193 | 7.9 | 3.4 | 6.2 |
| Compound of Ex. 195 | 7.5 | 4.5 | 5.9 |

In Table 3, the compound of Example 181 was (3R)-4-[5-amidino-2-(2-carboxy-2-oxoethyl)phenoxy]-3-[4-(pyrrolidine-1-carbonyl)benzoylamino]butanoic acid trifluoroacetate.

It is apparent from the results that the benzamidine derivatives of the present invention have a high activity of specifically inhibiting the activated blood coagulation factor X.

The structural formulae of the compounds of the present invention used in Example 185 and thereafter are given below.

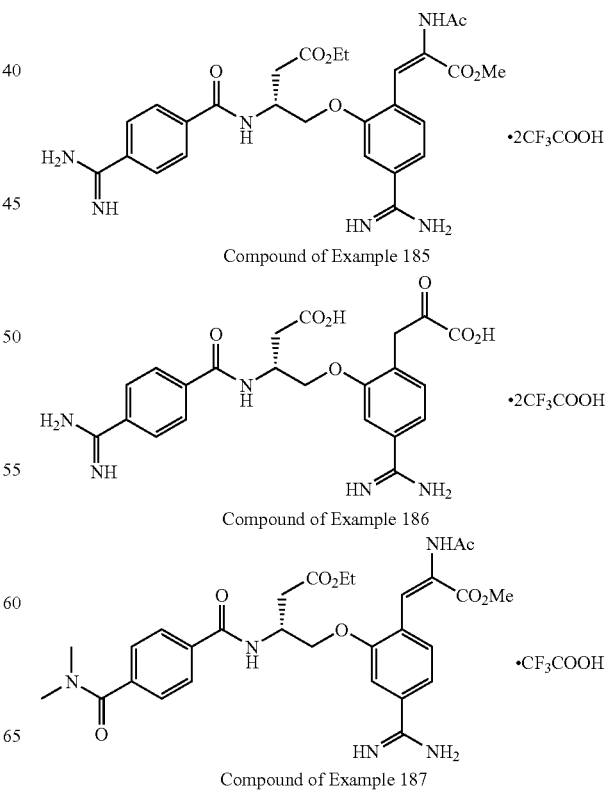

Compound of Example 185

Compound of Example 186

Compound of Example 187

-continued

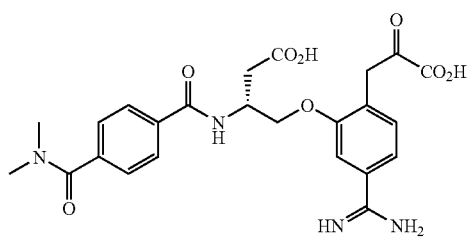

Compound of Example 188

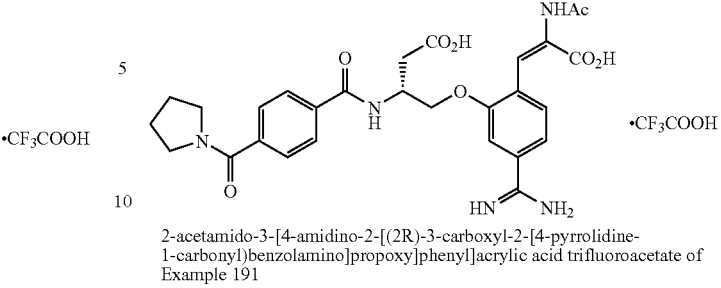

2-acetamido-3-[4-amindino-2-[(2R)-3-carboxyl-2-[4-pyrrolidine-1-carbonyl)benzolamino]propoxy]phenyl]acrylic acid trifluoroacetate of Example 191

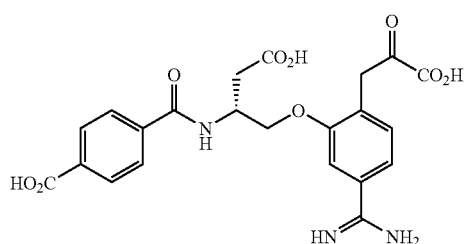

Compound of Example 189

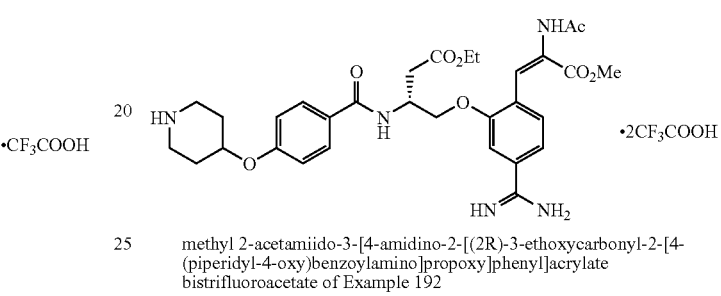

methyl 2-acetamiido-3-[4-amidino-2-[(2R)-3-ethoxycarbonyl-2-[4-(piperidyl-4-oxy)benzoylamino]propoxy]phenyl]acrylate bistrifluoroacetate of Example 192

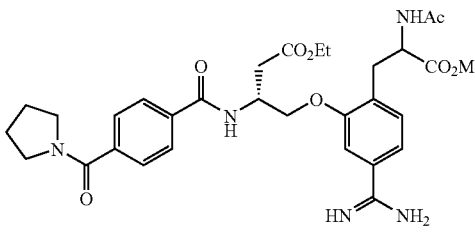

Compound of Example 190

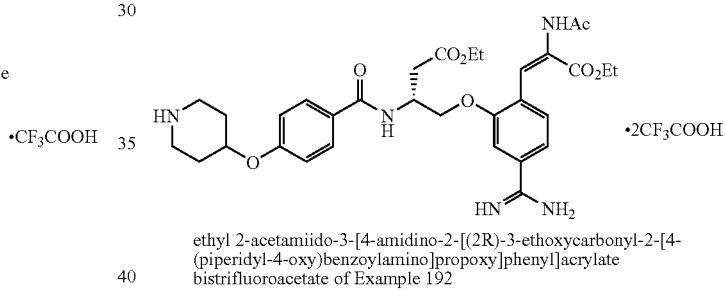

ethyl 2-acetamiido-3-[4-amidino-2-[(2R)-3-ethoxycarbonyl-2-[4-(piperidyl-4-oxy)benzoylamino]propoxy]phenyl]acrylate bistrifluoroacetate of Example 192

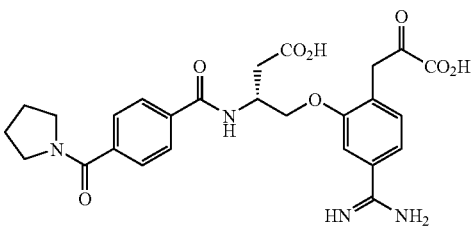

(3-R)-4-[5-amindino-2-(carboxy-2-oxoethyl)phenoxy]-3-[4-(pyrrolidine-1-carbonyl)benzoylamino]butanoic acid trifluoroacetate of Example 191

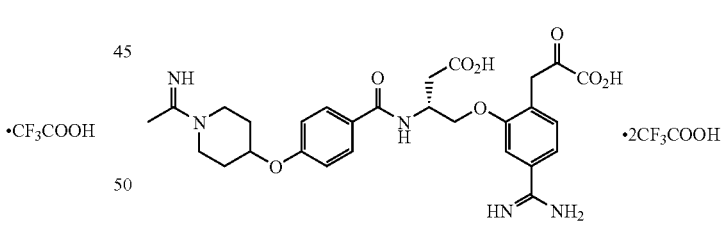

Compound of Example 193

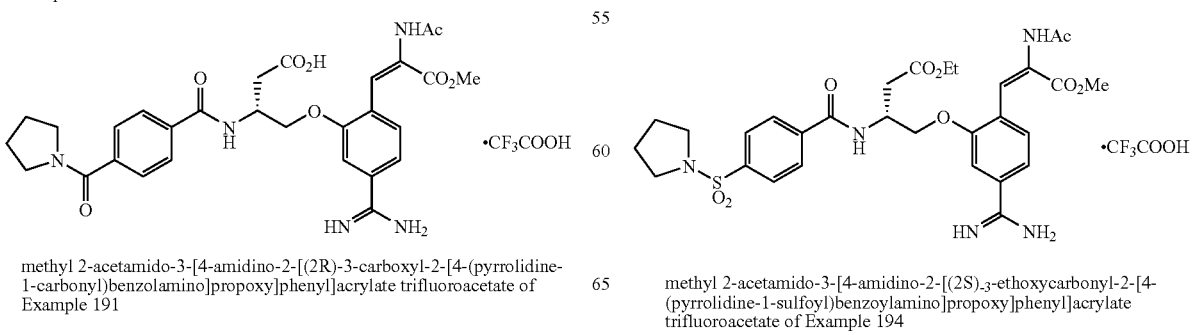

methyl 2-acetamido-3-[4-amidino-2-[(2R)-3-carboxy-2-[4-(pyrrolidine-1-carbonyl)benzolamino]propoxy]phenyl]acrylate trifluoroacetate of Example 191 methyl 2-acetamido-3-[4-amidino-2-[(2S)-3-ethoxycarbonyl-2-[4-(pyrrolidine-1-sulfoyl)benzoylamino]propoxy]phenyl]acrylate trifluoroacetate of Example 194

-continued
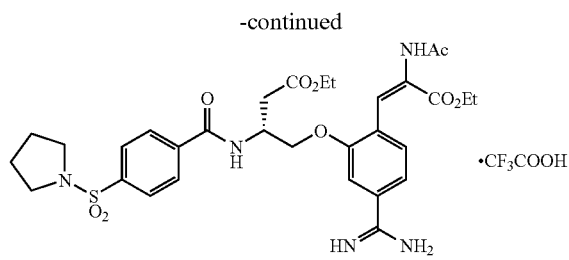
ethyl 2-acetamido-3-[4-amidino-2-[(2S)-3-ethoxycarbonyl-2-[4-(pyrrolidine-1-sulfoyl)benzoylamino]propoxy]phenyl]acrylate trifluoroacetate of Example 194
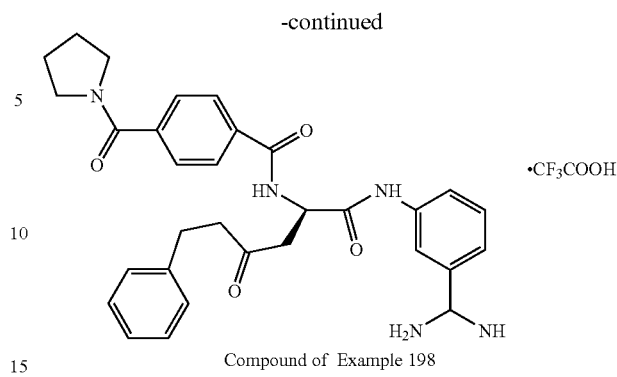
Compound of Example 198
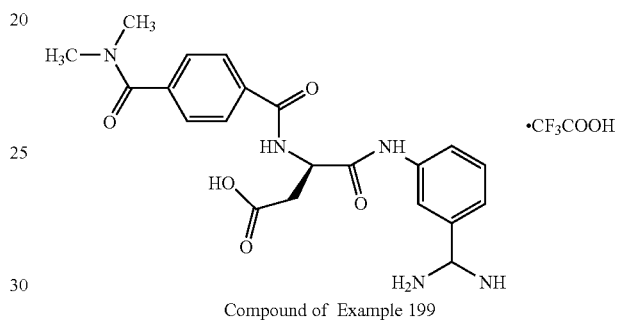
Compound of Example 199
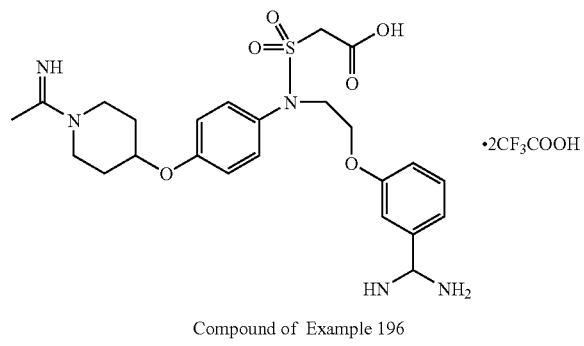
Compound of Example 195
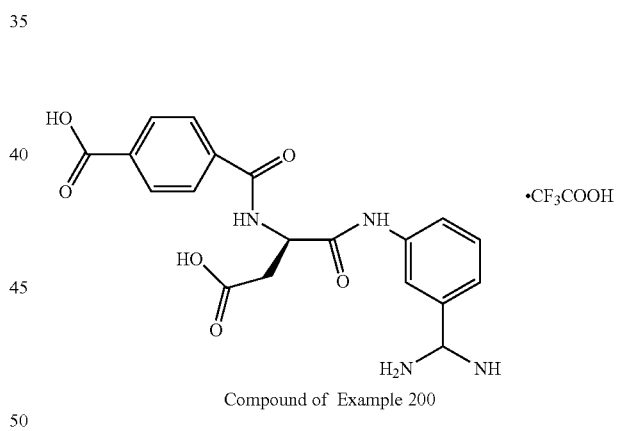
Compound of Example 200
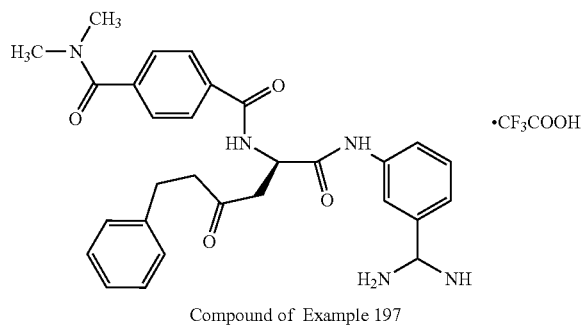
Compound of Example 196
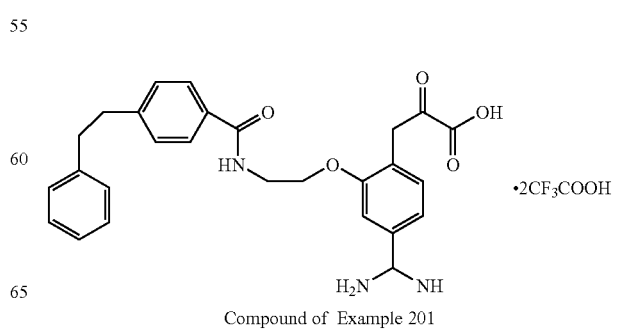
Compound of Example 201
Compound of Example 197

-continued
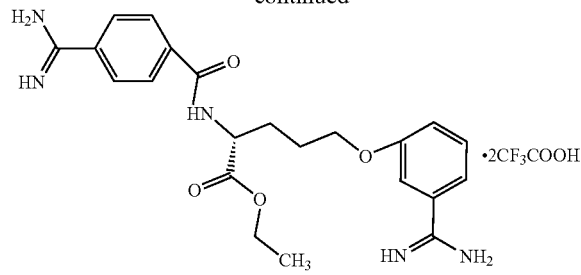
Compound of Example 202
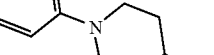
Compound of Example 206
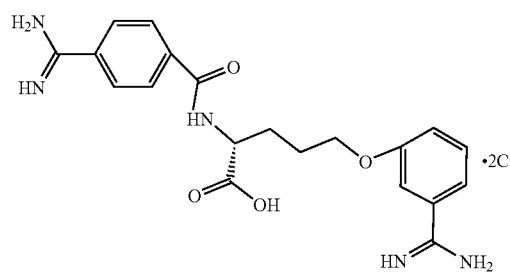
Compound of Example 203
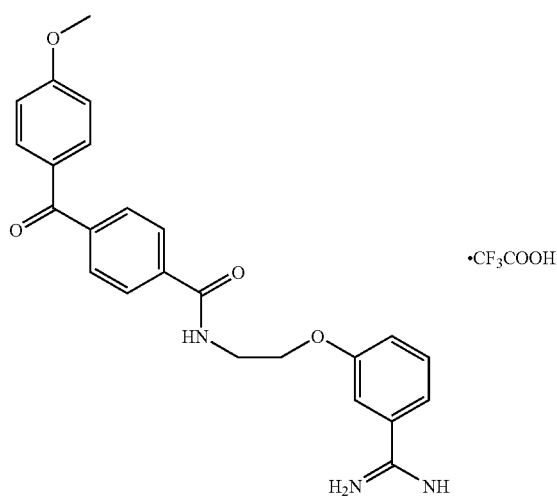
Compound of Example 207
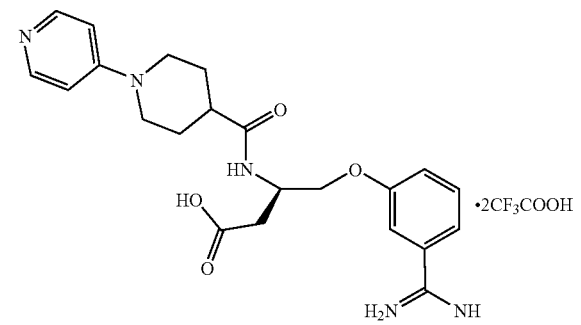
Compound of Example 204
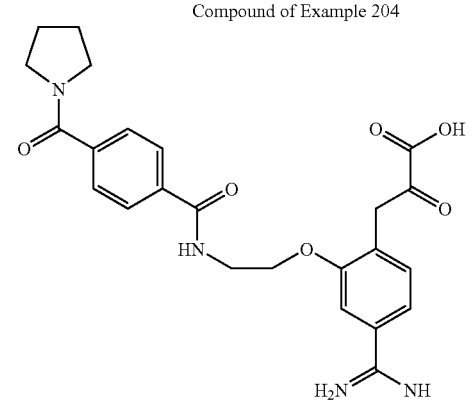
Compound of Example 205
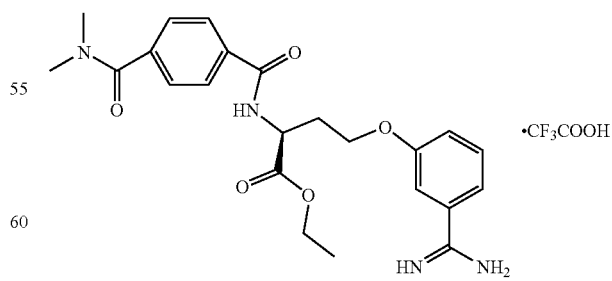
Compound of Example 208

-continued
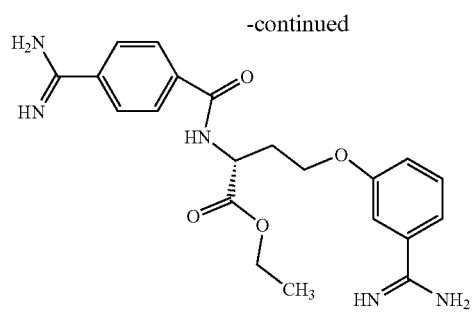
•2CF₃COOH
Compound of Example 209
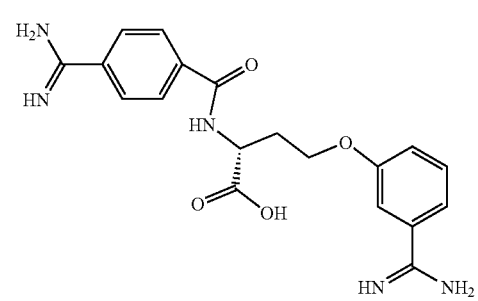
•CF₃COOH
Compound of Example 210
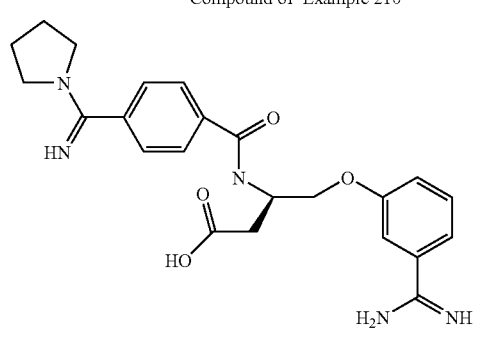
•CF₃COOH
Compound of Example 211
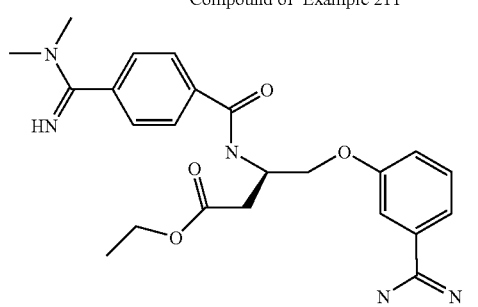
•CF₃COOH
Compound of Example 212
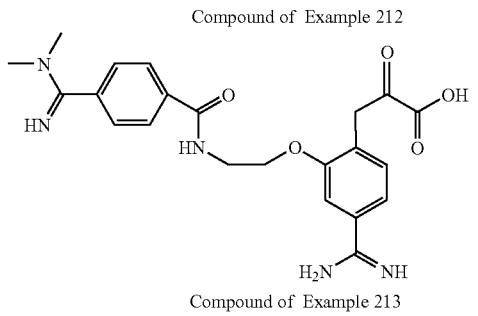
•2CF₃COOH
Compound of Example 213
-continued
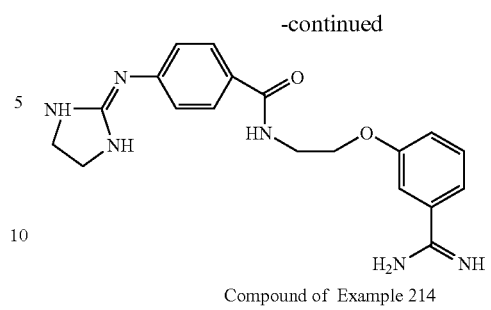
•2CF₃COOH
Compound of Example 214
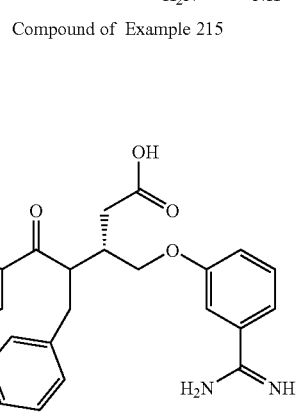
•2CF₃COOH
Compound of Example 215
•2CF₃COOH
Compound of Example 216
•CF₃COOH
Compound of Example 217
•CF₃COOH
Compound of Example 218

-continued

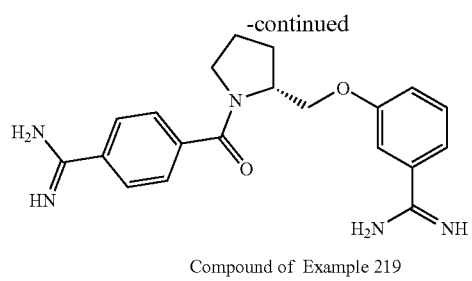
Compound of Example 219

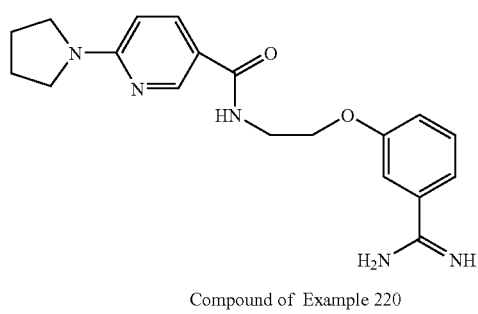
Compound of Example 220

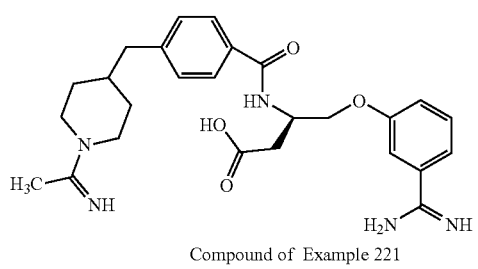
Compound of Example 221

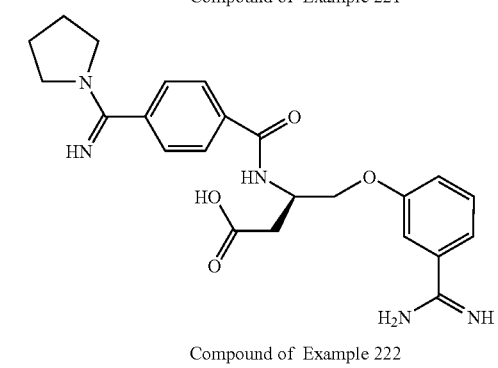
Compound of Example 222

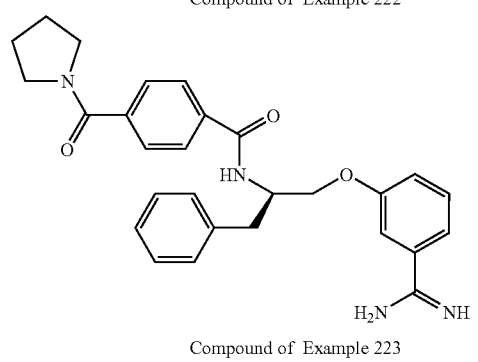
Compound of Example 223

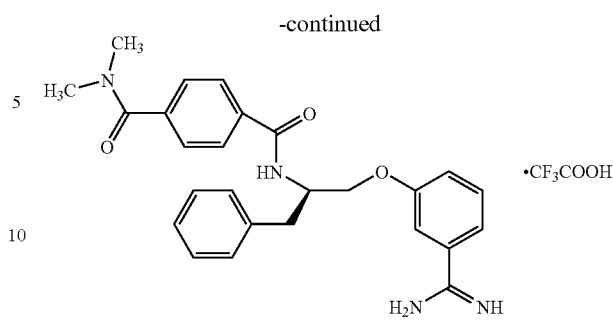
Compound of Example 224

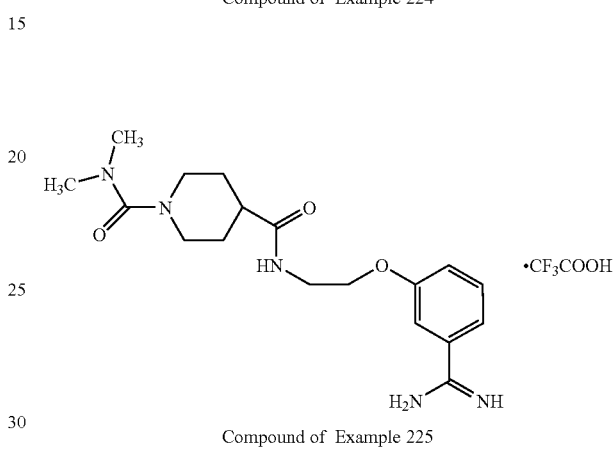
Compound of Example 225

The anticoagulants containing a compound or a salt thereof of the present invention have a blood-anticoagulant effect based on the excellent effect of inhibiting activated blood coagulation factor X. Therefore, the compounds of the present invention are usable for preventing and treating cerebrovascular disorders such as cerebral infarction, cerebral thrombosis, cerebral embolism, transient ischemic attack (TIA) and subarachnoidal hemorrhage (vasospasma); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; generalized intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

What is claimed is:

1. A benzamidine compound of the formula (1) or a pharmaceutically acceptable salt thereof:

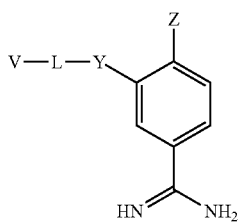

(1)

wherein L represents a group of formula (2):

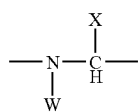

(2)

wherein:
- W in formula (2) represents hydrogen or alkyl having 1 to 6 carbon atoms;
- X in formula (2) represents hydrogen methyl substituted by carboxyl;
- V represents phenyl or benzoyl, each of which is substituted;
- wherein the substituent for V is selected from the group consisting of carboxyl, carbamoyl, mono- or dialkylcarbamoyl having 2 to 7 carbon atoms, amidino, mono- or dialkylamidino having 2 to 7 carbon atoms, piperidyloxy, iminoalkylpiperidyloxy having 7 to 10 carbon atoms, pyrrolidyloxy, piperidylalkyl having 6 to 9 carbon atoms, pyrrolidinyl, pyrrolidinylcarbonyl, pyrrolidinylsulfonyl, and pyridinylethyl;
- Y represents a group of any of the following formulae (7), (8), (9), (10) and (11):

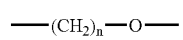 (7)

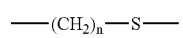 (8)

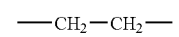 (9)

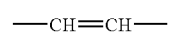 (10)

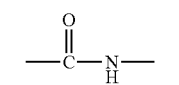 (11)

wherein n in formula (7) and (8) represents an integer of 1 to 3; and
Z represents a group of formula (12-2):

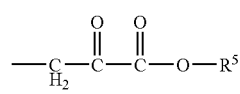

(12-2)

wherein $R^5$ represents hydrogen or alkyl having 1 to 6 carbon atoms.

2. The benzamidine compound or pharmaceutically acceptable salt thereof of claim 1, wherein V represents benzoyl having a substituent; and
Y represents a group of any formulae (7), (8), (9), (10) and (11); and n in formula (7) represents 1 or 2; and n in formula (8) represents 1.

3. The benzamidine compound or pharmaceutically acceptable salt thereof of claim 2, wherein the substituent for V is selected from the group consisting of carboxyl, dimethylcarbamoyl, amidino, and 1-pyrrolidinecarbonyl.

4. The benzamidine compound or pharmaceutically acceptable salt thereof of claim 2, wherein W is hydrogen or methyl.

5. The benzamidine compound or pharmaceutically acceptable salt thereof of claim 1, wherein Z in the formula (1) is 2-carboxy-2-oxoethyl.

6. The benzamidine compound or pharmaceutically acceptable salt thereof of claim 1, wherein
X represents hydrogen;
V represents benzoyl having a substituent;
Y represents a group of formulae (7), (8), (9), (10) and (11), and n in formula (7) represents 1 or 2, and n in formula (8) represents 1.

7. The benzamidine compound or pharmaceutically acceptable salt thereof of claim 6, wherein the substituent for V is selected from the group consisting of carboxyl, and amidino.

8. The benzamidine compound or pharmaceutically acceptable salt thereof of claim 6, wherein W is hydrogen or methyl.

9. The benzamidine compound or pharmaceutically acceptable salt thereof of claim 6, wherein Z in the formula (1) is 2-carboxy-2-oxoethyl.

10. The benzamidine compound or pharmaceutically acceptable salt thereof of claim 1, wherein
X represents hydrogen,
V represents benzoyl, having a substituent which is selected from the group consisting of carboxyl, mono- or dialkylcarbamoyl having 2 to 7 carbon atoms, amidino, mono- or dialkylamidino having 2 to 7 carbon atoms, and iminoalkylpiperidyloxy having 7 to 10 carbon atoms;
Y represents a group of the formula (7) wherein n represents an integer of 1; and
Z represents a group of formula (12-2-1):

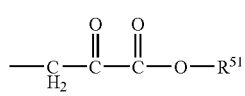

(12-2-1)

wherein $R^{51}$ represents hydrogen or alkyl having 1 to 6 carbon atoms.

11. The benzamidine compound or pharmaceutically acceptable salt thereof of claim 10, wherein
V represents benzoyl, having a substituent which is selected from the group consisting of mono- or dialkylcarbamoyl having 2 to 7 carbon atoms, amidino, mono- or dialkylamidino having 2 to 7 carbon atoms, and iminoalkylpiperidyloxy having 7 to 10 carbon atoms.

12. The benzamidine compound or pharmaceutically acceptable salt thereof of claim 10, wherein W represents hydrogen or methyl; and
V represents benzoyl having a substituent which is selected from the group consisting of dialkylcarbamoyl having 3 to 7 carbon atoms, dialkylamidino having 3 to 7 carbon atoms, and iminoalkylpiperidyloxy having 7 to 10 carbon atoms.

13. The benzamidine compound or pharmaceutically acceptable salt thereof of claim 10, wherein W represents hydrogen; and V represents benzoyl having a substituent at the p-position.

14. The benzamidine compound or pharmaceutically acceptable salt thereof of claim 1, wherein W represents hydrogen;

V represents benzoyl, having a substituent at the m- or p-position, which substituent is selected from the group consisting of mono- or dialkylamidino having 2 to 7 carbon atoms, carboxyl, amidino, dialkylaminocarbonyl having 3 to 6 carbon atoms, and iminoalkylpiperidyloxy having 7 to 10 carbon atoms;

Y represents a group of the formula (7) wherein n represents an integer of 1; and Z represents a group of formula (12-2-1):

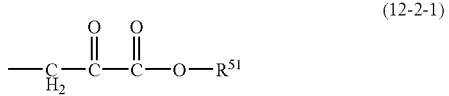

wherein $R^{51}$ represents hydrogen or alkyl having 1 to 6 carbon atoms.

15. The benzamidine compound or pharmaceutically acceptable salt thereof of claim 14, wherein Z in the formula (1) is 2-carboxy-2-oxoethyl.

16. The benzamidine compound or pharmaceutically acceptable salt thereof of claim 14, wherein V represents benzoyl, having a substituent at the p-position, which substituent is selected from the group consisting of amidino, carboxyl, and dimethylaminocarbonyl.

17. The benzamidine compound or pharmaceutically acceptable salt thereof of claim 1, wherein W represents hydrogen;

and

Y represents a group of the formula (7) wherein n represents an integer of 1.

18. A benzamidine compound or pharmaceutically acceptable salt thereof, which is selected from the group consisting of (3R)-3-(4-amidinobenzoylamino)-4-[5-amidino-2-(2-carboxy-2-oxoethyl)phenoxy]butanoic acid;

(3R)-4-[5-amidino-2-(2-carboxy 2-oxoethyl)phenoxy]-3-(4-dimethylcarbamoylbenzoylamino)butanoic acid;

(3R)-4-[5-amidino-2-(2-carboxy-2-oxoethyl)phenoxy]-3-(4-carboxybenzoylamino)butanoic acid;

(3R)-4-[5-amidino-2-(2-carboxy-2-oxoethyl)phenoxy]-3-[4-(pyrrolidine-1-carbonyl)benzoylamino]butanoic acid;

(3R)-4-[5-amidino-2-(2-carboxy-2-oxoethyl)phenoxy]-3-[4-(1-(1-iminoethyl)piperidyl-4-oxy)benzoylamino]butanoic acid;

(3R)-4-[5-amidino-2-(2-carboxy-2-oxoethyl)phenoxy]-3-[4-pyrrolidine-1-sulfonyl)benzoylamino]butanoic acid; and pharmaceutically acceptable salts thereof.

19. A composition, which comprises a benzamide compound or a pharmaceutically acceptable salt thereof as claimed in claim 1 as an active ingredient, and a pharmaceutically acceptable carrier.

20. A compound of the formula 3-[4-amidino-2-[2-[4-(1-acetimidoyl-4-piperidyloxy)benzoylamino]ethoxy]phenyl]-2-oxopropionic acid or a pharmaceutically acceptable salt thereof.

21. A composition, which comprises a benzamide compound or a pharmaceutically acceptable salt thereof as claimed in claim 18 as an active ingredient, and a pharmaceutically acceptable carrier.

22. A composition, which comprises a benzamide compound or a pharmaceutically acceptable salt thereof as claimed in claim 20 as an active ingredient, and a pharmaceutically acceptable carrier.

23. A benzamidine compound of the formula (1) or a pharmaceutically acceptable salt thereof:

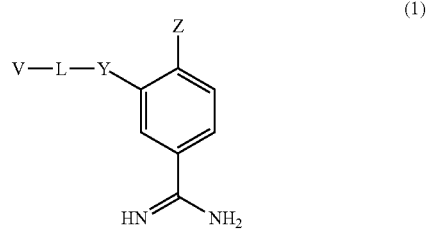

wherein L represents a group of formula (2):

wherein:

W in formula (2) represents hydrogen or alkyl having 1 to 6 carbon atoms;

X in formula (2) represents hydrogen;

V represents benzoyl, which is substituted;

wherein the substituent for V is selected from the group consisting of carboxyl, carbamoyl, mono- or dialkylcarbamoyl having 2 to 7 carbon atoms, amidino, mono- or dialkylamidino having 2 to 7 carbon atoms, piperidyloxy, iminoalkylpiperidyloxy having 7 to 10 carbon atoms, piperidylalkyl having 6 to 9 carbon atoms, pyrrolidinyl, pyrrolidinylcarbonyl pyrrolidinylsulfonyl, and pyridinylethyl;

Y represents a group of the formula —CH$_2$—O—; and

Z represents a group of formula (12-2):

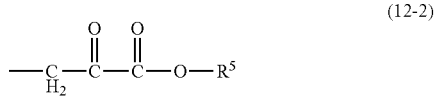

wherein $R^5$ represents hydrogen or alkyl having 1 to 6 carbon atoms.

24. A composition, which comprises a benzamide compound or a pharmaceutically acceptable salt thereof as claimed in claim 23 as an active ingredient, and a pharmaceutically acceptable carrier.

25. The benzamidine compound or pharmaceutically acceptable salt thereof of claim 23, wherein the substituent for V is selected from the group consisting of carboxyl, dimethylcarbamoyl, and amidino.

26. A composition, which comprises a benzamide compound or a pharmaceutically acceptable salt thereof as claimed in claim 25 as an active ingredient, and a pharmaceutically acceptable carrier.

27. The benzamidine compound or pharmaceutically acceptable salt thereof of claim 23, wherein the substituent for V is selected from the group consisting of carboxyl and amidino, acetyl, bromine, amino, methylamino, t-butoxycarbonylamino, aminomethyl, (methylamino)methyl, (N-t-butoxycarbonyl-N-methylamino)methyl, 4-piperidyloxy, 1-acetimidoyl-4-piperidyloxy, 3-pyrrolidyloxy; 1-t-butoxycarbonyl-3-pyrrolidyloxy, 2-carboxylethenyl, and 2-(ethoxycarbonyl)ethenyl.

28. A composition, which comprises a benzamide compound or a pharmaceutically acceptable salt thereof as claimed in claim 27 as an active ingredient, and a pharmaceutically acceptable carrier.

29. The benzamidine compound or pharmaceutically acceptable salt thereof of claim 23, wherein V represents benzoyl having a substituent at the p-position, which substituent is selected from the group consisting of dimethylcarbamoyl, (pyrrolidine-1-yl)carbonyl, N,N-dimethylamidino, and 4-pyridylethyl.

30. A composition, which comprises a benzamide compound or a pharmaceutically acceptable salt thereof as claimed in claim 29 as an active ingredient, and a pharmaceutically acceptable carrier.

31. The benzamidine compound or pharmaceutically acceptable salt thereof of claim 23, wherein V represents benzoyl, having a substituent at the p-position, which substituent is selected from the group consisting of amidino, carboxyl, and dimethylaminocarbonyl.

32. A composition, which comprises a benzamide compound or a pharmaceutically acceptable salt thereof as claimed in claim 31 as an active ingredient, and a pharmaceutically acceptable carrier.

* * * * *